US012502402B2

(12) United States Patent
Powers et al.

(10) Patent No.: US 12,502,402 B2
(45) Date of Patent: Dec. 23, 2025

(54) COMPOUNDS AND METHODS FOR MODULATING GFAP

(71) Applicant: Ionis Pharmaceuticals, Inc., Carlsbad, CA (US)

(72) Inventors: Berit Elissa Powers, Carlsbad, CA (US); Frank Rigo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 18/243,156

(22) Filed: Sep. 7, 2023

(65) Prior Publication Data

US 2024/0285669 A1 Aug. 29, 2024

Related U.S. Application Data

(63) Continuation of application No. 16/938,826, filed on Jul. 24, 2020, now Pat. No. 11,786,546.

(60) Provisional application No. 62/878,998, filed on Jul. 26, 2019.

(51) Int. Cl.

| | |
|---|---|
| ***A61K 31/712*** | (2006.01) |
| ***A61K 31/7125*** | (2006.01) |
| ***A61P 25/28*** | (2006.01) |
| ***C07H 21/02*** | (2006.01) |
| ***C12N 15/113*** | (2010.01) |

(52) U.S. Cl.

CPC ........ *A61K 31/712* (2013.01); *A61K 31/7125* (2013.01); *A61P 25/28* (2018.01); *C07H 21/02* (2013.01); *C12N 15/113* (2013.01); *C12N 2310/315* (2013.01); *C12N 2310/321* (2013.01); *C12N 2310/341* (2013.01)

(58) Field of Classification Search

CPC . C07H 21/02; C12N 15/113; C12N 2310/341
See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,458,066 | A | 7/1984 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,668,777 | A | 5/1987 | Caruthers et al. |
| 4,725,677 | A | 2/1988 | Koster et al. |
| 4,845,205 | A | 7/1989 | Huynh Dinh et al. |
| 4,973,679 | A | 11/1990 | Caruthers et al. |
| 4,981,957 | A | 1/1991 | Lebleu et al. |
| 5,013,830 | A | 5/1991 | Ohutsuka et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,132,418 | A | 7/1992 | Caruthers et al. |
| 5,134,066 | A | 7/1992 | Rogers et al. |
| RE34,036 | E | 8/1992 | McGeehan |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,185,444 | A | 2/1993 | Summerton et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,216,141 | A | 6/1993 | Benner |
| 5,220,007 | A | 6/1993 | Pederson et al. |
| 5,223,618 | A | 6/1993 | Cook et al. |
| 5,235,033 | A | 8/1993 | Summerton et al. |
| 5,256,775 | A | 10/1993 | Froehler |
| 5,264,423 | A | 11/1993 | Cohen et al. |
| 5,264,562 | A | 11/1993 | Matteucci |
| 5,264,564 | A | 11/1993 | Matteucci |
| 5,276,019 | A | 1/1994 | Cohen et al. |
| 5,278,302 | A | 1/1994 | Caruthers et al. |
| 5,286,717 | A | 2/1994 | Cohen et al. |
| 5,319,080 | A | 6/1994 | Leumann |
| 5,321,131 | A | 6/1994 | Agrawal et al. |

(Continued)

FOREIGN PATENT DOCUMENTS

| | | |
|---|---|---|
| WO | WO 2006/006948 | 1/2006 |
| WO | WO 2013/022984 | 2/2013 |

(Continued)

OTHER PUBLICATIONS

Abdelhak et al., "Blood GFAP as an emerging biomarker in brain and spinal cord disorders" Nature Reviews Neurology (2022) 18: 158-172.

(Continued)

*Primary Examiner* — Eric Olson

(74) *Attorney, Agent, or Firm* — Arnold & Porter Kaye Scholer LLP

(57) ABSTRACT

Provided are compounds, methods, and pharmaceutical compositions for reducing the amount or activity of GFAP RNA in a cell or subject, and in certain instances reducing the amount of GFAP in a cell or subject. Such compounds, methods, and pharmaceutical compositions are useful to ameliorate at least one symptom or hallmark of a leukodystrophy. Such symptoms and hallmarks include motor delays, cognitive delays, paroxysmal deterioration, seizures, vomiting, swallowing difficulties, ataxic gait, palatal myoclonus, autonomic dysfunction, and presence of intra-astrocytic inclusions called Rosenthal fibers. Such leukodystrophies include Alexander Disease.

42 Claims, No Drawings

Specification includes a Sequence Listing.

(56) References Cited

U.S. PATENT DOCUMENTS

| | | | |
|---|---|---|---|
| 5,359,044 | A | 10/1994 | Cook et al. |
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |
| 5,399,676 | A | 3/1995 | Froehler |
| 5,403,711 | A | 4/1995 | Walder et al. |
| 5,405,938 | A | 4/1995 | Sumerton et al. |
| 5,405,939 | A | 4/1995 | Suhadolnik et al. |
| 5,432,272 | A | 7/1995 | Benner |
| 5,434,257 | A | 7/1995 | Matteucci |
| 5,446,137 | A | 8/1995 | Maag et al. |
| 5,453,496 | A | 9/1995 | Caruthers et al. |
| 5,455,233 | A | 10/1995 | Spielvogel et al. |
| 5,457,187 | A | 10/1995 | Gmelner et al. |
| 5,457,191 | A | 10/1995 | Cook et al. |
| 5,459,255 | A | 10/1995 | Cook et al. |
| 5,466,677 | A | 11/1995 | Baxter et al. |
| 5,466,786 | A | 11/1995 | Burh et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,491,133 | A | 2/1996 | Walder et al. |
| 5,502,177 | A | 3/1996 | Matteucci et al. |
| 5,508,270 | A | 4/1996 | Baxter et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,711 | A | 6/1996 | Hawkins et al. |
| 5,527,899 | A | 6/1996 | Froehler |
| 5,536,821 | A | 7/1996 | Agrawal et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,555 | A | 10/1996 | Froehler et al. |
| 5,567,811 | A | 10/1996 | Mistura et al. |
| 5,571,799 | A | 11/1996 | Tkachuk et al. |
| 5,576,427 | A | 11/1996 | Cook et al. |
| 5,587,361 | A | 12/1996 | Cook et al. |
| 5,587,469 | A | 12/1996 | Cook et al. |
| 5,587,470 | A | 12/1996 | Cook et al. |
| 5,591,722 | A | 1/1997 | Montgomery et al. |
| 5,594,121 | A | 1/1997 | Froehler et al. |
| 5,596,086 | A | 1/1997 | Matteucci |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bishofberger et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci |
| 5,652,355 | A | 7/1997 | Metelev et al. |
| 5,652,356 | A | 7/1997 | Agrawal |
| 5,663,312 | A | 9/1997 | Chaturvedula |
| 5,670,633 | A | 9/1997 | Cook et al. |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,698,685 | A | 12/1997 | Summerton et al. |
| 5,700,920 | A | 12/1997 | Altmann et al. |
| 5,700,922 | A | 12/1997 | Cook |
| 5,721,218 | A | 2/1998 | Froehler |
| 5,750,692 | A | 5/1998 | Cook et al. |
| 5,763,588 | A | 6/1998 | Matteucci et al. |
| 5,792,608 | A | 8/1998 | Swaminathan et al. |
| 5,792,847 | A | 8/1998 | Burh et al. |
| 5,801,154 | A | 9/1998 | Baracchini et al. |
| 5,808,027 | A | 9/1998 | Cook et al. |
| 5,830,653 | A | 11/1998 | Froehler et al. |
| 5,859,221 | A | 1/1999 | Cook et al. |
| 5,948,903 | A | 9/1999 | Cook et al. |
| 5,994,517 | A | 11/1999 | Ts'O |
| 6,005,087 | A | 12/1999 | Cook et al. |
| 6,005,096 | A | 12/1999 | Matteucci et al. |
| 6,166,199 | A | 12/2000 | Cook et al. |
| 6,268,490 | B1 | 7/2001 | Imanishi et al. |
| 6,300,319 | B1 | 10/2001 | Manoharan |
| 6,426,220 | B1 | 7/2002 | Bennett et al. |
| 6,525,191 | B1 | 2/2003 | Ramasamy |
| 6,531,584 | B1 | 3/2003 | Cook et al. |
| 6,582,908 | B2 | 6/2003 | Fodor et al. |
| 6,600,032 | B1 | 7/2003 | Manoharan et al. |
| 6,660,720 | B2 | 12/2003 | Manoharan |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 6,906,182 | B2 | 6/2005 | Ts'o et al. |
| 7,015,315 | B1 | 3/2006 | Cook et al. |
| 7,034,133 | B2 | 4/2006 | Wengel et al. |
| 7,053,207 | B2 | 5/2006 | Wengel et al. |
| 7,101,993 | B1 | 9/2006 | Cook et al. |
| 7,262,177 | B2 | 8/2007 | Ts'o et al. |
| 7,399,845 | B2 | 7/2008 | Seth et al. |
| 7,427,672 | B2 | 9/2008 | Imanishi et al. |
| 7,491,805 | B2 | 2/2009 | Vargeese et al. |
| 7,547,684 | B2 | 6/2009 | Seth et al. |
| 7,569,686 | B1 | 8/2009 | Bhat et al. |
| 7,572,582 | B2 | 8/2009 | Wengel et al. |
| 7,666,854 | B2 | 2/2010 | Seth et al. |
| 7,696,345 | B2 | 4/2010 | Allerson et al. |
| 7,723,509 | B2 | 5/2010 | Manoharan et al. |
| 7,741,457 | B2 | 6/2010 | Swayze et al. |
| 7,750,131 | B2 | 7/2010 | Seth et al. |
| 7,875,733 | B2 | 1/2011 | Bhat et al. |
| 7,888,497 | B2 | 2/2011 | Bentwich et al. |
| 7,939,677 | B2 | 5/2011 | Bhat et al. |
| 8,022,193 | B2 | 9/2011 | Swayze et al. |
| 8,030,467 | B2 | 10/2011 | Seth et al. |
| 8,034,909 | B2 | 10/2011 | Wengel et al. |
| 8,080,644 | B2 | 12/2011 | Wengel et al. |
| 8,088,746 | B2 | 1/2012 | Seth et al. |
| 8,088,904 | B2 | 1/2012 | Swayze et al. |
| 8,090,542 | B2 | 1/2012 | Khvorova et al. |
| 8,106,022 | B2 | 1/2012 | Manoharan et al. |
| 8,124,745 | B2 | 2/2012 | Allerson et al. |
| 8,153,365 | B2 | 4/2012 | Wengel et al. |
| 8,268,980 | B2 | 9/2012 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,372,808 | B2 | 2/2013 | Messing et al. |
| 8,440,803 | B2 | 5/2013 | Swayze et al. |
| 8,501,805 | B2 | 8/2013 | Seth et al. |
| 8,530,640 | B2 | 9/2013 | Seth et al. |
| 8,546,556 | B2 | 10/2013 | Seth et al. |
| RE44,779 | E | 2/2014 | Imanishi et al. |
| 8,828,956 | B2 | 9/2014 | Manoharan et al. |
| 9,005,906 | B2 | 4/2015 | Swayze et al. |
| 9,012,421 | B2 | 4/2015 | Migawa et al. |
| 9,127,276 | B2 | 9/2015 | Prakash et al. |
| 9,290,760 | B2 | 3/2016 | Rajeev et al. |
| 9,550,988 | B2 | 1/2017 | Swayze |
| 11,786,546 | B2 | 10/2023 | Powers et al. |
| 2001/0053519 | A1 | 12/2001 | Fodor et al. |
| 2003/0082807 | A1 | 5/2003 | Wengel |
| 2003/0158403 | A1 | 8/2003 | Manoharan et al. |
| 2003/0175906 | A1 | 9/2003 | Manoharan et al. |

(56) References Cited

U.S. PATENT DOCUMENTS

2003/0207841 A1 11/2003 Kaneko et al.
2003/0224377 A1 12/2003 Wengel et al.
2003/0228597 A1 12/2003 Cowsert et al.
2004/0143114 A1 7/2004 Imanishi et al.
2004/0171570 A1 9/2004 Allerson et al.
2004/0192918 A1 9/2004 Imanishi et al.
2005/0130923 A1 6/2005 Bhat et al.
2005/0255487 A1 11/2005 Khvorova et al.
2006/0148740 A1 7/2006 Platenburg
2007/0031844 A1 2/2007 Khvorova et al.
2008/0039618 A1 2/2008 Allerson et al.
2008/0113351 A1 5/2008 Naito et al.
2010/0190837 A1 7/2010 Migawa et al.
2010/0197762 A1 8/2010 Swayze et al.
2011/0123520 A1 5/2011 Manoharan et al.
2013/0130378 A1 5/2013 Manoharan et al.
2013/0203836 A1 8/2013 Rajeev et al.
2013/0237585 A1 9/2013 Bennett et al.
2014/0107330 A1 4/2014 Freier et al.
2015/0018540 A1 1/2015 Prakash et al.
2015/0184153 A1 7/2015 Freier et al.
2015/0191727 A1 7/2015 Migawa et al.
2015/0267195 A1 9/2015 Seth et al.
2015/0275212 A1 10/2015 Albaek et al.
2021/0038629 A1 2/2021 Powers et al.

FOREIGN PATENT DOCUMENTS

WO WO 2013/173635 11/2013
WO WO 2019/089692 5/2019
WO WO 2021/021673 2/2021

OTHER PUBLICATIONS

Austin et al., "The neuro-immune balance in neuropathic pain: Involvement of inflammatory immune cells, immune-like glial cells and cytokines" J Neurol (2010) 229: 26-50.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Crooke, ST., et al., "Antisense Drug Technology" Second Edition, CRC Press (2008) Chapters 1-28.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
European Search Report for 20846055.0 dated Oct. 13, 2022.
Gautschi et al., "Activity of a novel bel-2/bcl-xLbispecific antisense oligonucleotide against tumors of diverse histologic origins" J. Natl. Cancer Inst. (2001) 93:463-471.
Hagemann et al., "Antisense suppression of glial fibrillary acidic protein as a treatment for Alexander disease" Ann Neurol (2018) 83: 27-39.
International Search Report for PCT/US20/043602 dated Dec. 15, 2020.
Kanski et al., "Histone Acetylation in Astrocytes Suppresses GFAP and Stimulates a Reorganization of the Intermediate Filament Network" J. Cell Sci (2014) 127: 4368-4380.
Kim et al., "Profiling of dynamically changed gene expression in dorsal root ganglia post peripheral nerve injury and a critical role of injury-induced glial fibrillary acetic protein in maintenance of pain behaviors" Pain (2009) 143: 114-122.
Kimura et al., "Clinical characteristics of autoimmune GFAP astrocytopathy" J Neurology (2019) 332: 91-98.
Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.
Messing et al., "Strategies for treatment in Alexander disease" Neurotherapeutics (2010) 7: 507-515.
Messing et al., "Fatal encephalopathy with astrocyte inclusions in GFAP transgenic mice" Am J Pathol (1998) 152: 391-398.
Messing et al., "GFAP at 50" ASN Neurology (2020) 1-23.
Middeldorp et al., "GFAP in health and disease" Progress in Neurology (2011) 93: 421-443.
New England Biolabs 1998/99 Catalog (cover page and pp. 121 and 284).
Powers et al., "Antisense Oligonucleotides (ASOs) Targeting Mouse Gfap Reverse Pathology in a Model of Alexander Disease" Poster for SfN 46th Annual Meeting—Neuroscience 2016: San Diego, CA (Nov. 12-16, 2016).
Powers et al., "Antisense Oligonucleotide Therapy Elicits Rapid, Sustained Pathology Reversal in a Mouse Model of Alexander Disease" Poster for SfN 47th Annual Meeting—Neuroscience 2017: Washington D.C. (Nov. 11-15, 2017).
Prust et al., "GFAP mutations, age at onset, and clinical subtypes in Alexander disease" Neurology (2011) 77: 1287-1294.
Quinlan et al., "GFAP and its role in Alexander disease" Experimental Cell Res (2007) 313: 2077-2087.
Reynolds et al., "Rational siRNA design for RNA interference" Nature Biotechnology (2004) 22(3):326-330.
Rothstein et al., "Knockout of Glutamate Transporters Reveals a Major Role for Astroglial Transport in Excitotoxicity and Clearance of Glutamate" Neuron (1996) 16: 675-686.
Sanghvi et al., "Heterocyclic Base Modifications in Nucleic Acids and Their Applications in Antisense Oligonucleotides" Antisense Research and Applications (1993) pp. 273-288.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Smith et al., "Therapeutic Oligonucleotides: State of the Art" Ann Rev Pharmacol Toxicol (2019) 59: 605-630.
Woolf et al., "Specificity of antisense oligonucleotides in vivo" PNAS (1992) 89: 7305-7309.
Yu et al., Astrogliosis in Culture: I. The Model and the Effect of Antisense Oligonucleotides on Glial Fibrillary Acidic Protein Synthesis J. Nuerosci. Res (1993) 34: 295-303.
Yu et al. (1993) Biology and Pathology of Astrocyte-Neuron Interactions. New York, NY: Penum Press. pp. 313-325.

COMPOUNDS AND METHODS FOR MODULATING GFAP

SEQUENCE LISTING

This application incorporates by reference a 2,616,122 byte xml file named "BIOL0353SEQ.xml," created on Sep. 5, 2023, which is the sequence listing for this application.

FIELD

Provided are compounds, methods, and pharmaceutical compositions for reducing the amount or activity of GFAP RNA in a cell or subject, and in certain instances reducing the amount of glial fibrillary acidic protein (GFAP) in a cell or subject. Such compounds, methods, and pharmaceutical compositions are useful to ameliorate at least one symptom or hallmark of a leukodystrophy. Such symptoms and hallmarks include motor delays, cognitive delays, paroxysmal deterioration, seizures, vomiting, swallowing difficulties, ataxic gait, palatal myoclonus, autonomic dysfunction, and intra-astrocytic inclusions called Rosenthal fibers. Such leukodystrophies include Alexander Disease.

BACKGROUND

Alexander Disease (AxD) is a rare developmental disorder that affects ~1/1,000,000 live births and is caused by a number of different autosomal dominant mutations in the gene encoding glial fibrillary acidic protein, GFAP. AxD is a typically fatal leukodystrophy with early onset (<age 4, Type I) or later onset (>age 4 Type II) forms (Prust et al., (2011) GFAP mutations, age at onset, and clinical subtypes in Alexander disease. Neurol 77; 1287-1294). Symptoms include motor and cognitive delays, paroxysmal deterioration, seizures, encephalopathy, macrocephaly, and intra-astrocytic inclusions called Rosenthal fibers.

There are no specific therapies for AxD, with current treatments being limited to supportive treatments for individual symptoms (e.g., antiepileptics to prevent seizures; Messing, et. al., "Strategies for treatment in Alexander Disease", *Neurotherapeutics: The Journal of the Am. Soc. For Expt. NeuroTher.,* 2016).

Currently there is a lack of acceptable options for treating leukody strophies such as AxD. It is therefore an object herein to provide compounds, methods, and pharmaceutical compositions for the treatment of such diseases.

SUMMARY OF THE INVENTION

Provided herein are compounds, methods and pharmaceutical compositions for reducing the amount or activity of GFAP RNA, and in certain embodiments reducing the expression of glial fibrillary acidic protein in a cell or subject. In certain embodiments, the subject has a leukodystrophy. In certain embodiments, the subject has Alexander Disease (AxD). In certain embodiments, compounds useful for reducing the amount or activity of GFAP RNA are oligomeric compounds. In certain embodiments, compounds useful for reducing the amount or activity of GFAP RNA are modified oligonucleotides. In certain embodiments, compounds useful for decreasing expression of glial fibrillary acidic protein are oligomeric compounds. In certain embodiments, compounds useful for decreasing expression of glial fibrillary acidic protein are modified oligonucleotides.

Also provided are methods useful for ameliorating at least one symptom or hallmark of a leukodystrophy. In certain embodiments, the leukodystrophy is Alexander Disease. In certain embodiments, the symptom or hallmark includes motor delays, cognitive delays, paroxysmal deterioration, seizures, vomiting, swallowing difficulties, ataxic gait, palatal myoclonus, autonomic dysfunction, and presence of intra-astrocytic inclusions called Rosenthal fibers.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, treatises, and GenBank, ENSEMBL, and NCBI reference sequence records, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyfuranosylsugar moiety. In certain embodiments, a 2'-deoxy nucleoside is a 2'-β-Ddeoxynucleoside and comprises a 2'-β-D-deoxyribosyl sugar moiety, which has the β-D ribosyl configuration as found in naturally occurring deoxyribonucleic acids (DNA). In certain embodiments, a 2'-deoxynucleoside may comprise a modified nucleobase or may comprise an RNA nucleobase (uracil).

As used herein, "2'-MOE" or "2'-MOE sugar moiety" means a 2'-$OCH_2CH_2OCH_3$ group in place of the 2'-OH group of a furanosyl sugar moiety. A "2'-MOE sugar moiety" means a sugar moiety with a 2'-$OCH_2CH_2OCH_3$ group in place of the 2'-OH group of a furanosyl sugar moiety. Unless otherwise indicated, a 2'-MOE sugar moiety is in the β-D-ribosyl configuration. "MOE" means O-methoxyethyl.

As used herein, "2'-MOE nucleoside" means a nucleoside comprising a 2'-MOE sugar moiety.

As used herein, “2'-OMe” or “2'-O-methyl sugar moiety” means a 2'-$OCH_3$ group in place of the 2'-OH group of a furanosyl sugar moiety. A “2'-O-methyl sugar moiety” or “2'-OMe sugar moiety” means a sugar moiety with a 2'-$OCH_3$ group in place of the 2'-OH group of a furanosyl sugar moiety. Unless otherwise indicated, a 2'-OMe sugar moiety is in the β-D-ribosyl configuration.

As used herein, “2'-OMe nucleoside” means a nucleoside comprising a 2'-OMe sugar moiety.

As used herein, “2'-substituted nucleoside” means a nucleoside comprising a 2'-substituted sugar moiety. As used herein, “2'-substituted” in reference to a sugar moiety means a sugar moiety comprising at least one 2'-substituent group other than H or OH.

As used herein, “5-methylcytosine” means a cytosine modified with a methyl group attached to the 5 position. A 5-methylcytosine is a modified nucleobase.

As used herein, “administering” means providing a pharmaceutical agent to a subject.

As used herein, “antisense activity” means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, “antisense compound” means an oligomeric compound capable of achieving at least one antisense activity.

As used herein, “ameliorate” in reference to a treatment means improvement in at least one symptom or hallmark relative to the same symptom or hallmark in the absence of the treatment. In certain embodiments, amelioration is the reduction in the severity or frequency of a symptom or the delayed onset or slowing of progression in the severity or frequency of a symptom. In certain embodiments, the symptom or hallmark is motor delays, cognitive delays, paroxysmal deterioration, seizures, vomiting, swallowing difficulties, ataxic gait, palatal myoclonus, autonomic dysfunction, and presence of intra-astrocytic inclusions called Rosenthal fibers.

As used herein, “bicyclic nucleoside” or “BNA” means a nucleoside comprising a bicyclic sugar moiety.

As used herein, “bicyclic sugar” or “bicyclic sugar moiety” means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the furanosyl sugar moiety is a ribosyl moiety. In certain embodiments, the bicyclic sugar moiety does not comprise a furanosyl moiety.

As used herein, “cerebrospinal fluid” or “CSF” means the fluid filling the space around the brain and spinal cord. “Artificial cerebrospinal fluid” or “aCSF” means a prepared or manufactured fluid that has certain properties of cerebrospinal fluid.

As used herein, “cleavable moiety” means a bond or group of atoms that is cleaved under physiological conditions, for example, inside a cell, an animal, or a human.

As used herein, “complementary” in reference to an oligonucleotide means that at least 70% of the nucleobases of the oligonucleotide or one or more portions thereof and the nucleobases of another nucleic acid or one or more portions thereof are capable of hydrogen bonding with one another when the nucleobase sequence of the oligonucleotide and the other nucleic acid are aligned in opposing directions. As used herein, “complementary nucleobases” means nucleobases that are capable of forming hydrogen bonds with one another. Complementary nucleobase pairs include adenine (A) and thymine (T), adenine (A) and uracil (U), cytosine (C) and guanine (G), 5-methylcytosine ($^{m}$C) and guanine (G). Complementary oligonucleotides and/or target nucleic acids need not have nucleobase complementarity at each nucleoside. Rather, some mismatches are tolerated. As used herein, “fully complementary” or “100% complementary” in reference to an oligonucleotide, or a portion thereof, means that the oligonucleotide, or portion thereof, is complementary to another oligonucleotide or target nucleic acid at each nucleobase of the shorter of the two oligonucleotides, or at each nucleoside if the oligonucleotides are the same length.

As used herein, “conjugate group” means a group of atoms that is directly or indirectly attached to an oligonucleotide. Conjugate groups include a conjugate moiety and a conjugate linker that attaches the conjugate moiety to the oligonucleotide.

As used herein, “conjugate linker” means a single bond or a group of atoms comprising at least one bond that connects a conjugate moiety to an oligonucleotide.

As used herein, “conjugate moiety” means a group of atoms that is attached to an oligonucleotide via a conjugate linker.

As used herein, “contiguous” in the context of an oligonucleotide refers to nucleosides, nucleobases, sugar moieties, or internucleoside linkages that are immediately adjacent to each other. For example. “contiguous nucleobases” means nucleobases that are immediately adjacent to each other in a sequence.

As used herein, “constrained ethyl” or “cEt” or “cEt modified sugar moiety” means a 4' to 2' bridge in place of the 2'OH-group of a ribosyl sugar moiety, wherein the bridge has the formula of 4'-CH(CH)—O-2', and wherein the methyl group of the bridge is in the S configuration. A “cEt sugar moiety” is a bicyclic sugar moiety with a 4' to 2' bridge in place of the 2'OH-group of a ribosyl sugar moiety, wherein the bridge has the formula 4'-$CH(CH_3)$—O-2', and wherein the methyl group of the bridge is in the S configuration.

As used herein, “cEt nucleoside” means a nucleoside comprising a cEt sugar moiety.

As used herein, “chirally enriched population” means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, “chirally controlled” in reference to an internucleoside linkage means chirality at that linkage is enriched for a particular stereochemical configuration.

As used herein, “deoxy region” means a region of 5-12 contiguous nucleotides, wherein at least 70% of the nucleosides are 2'-β-D-deoxynucleosides. In certain embodiments, each nucleoside is selected from a 2'-β-D-deoxynucleoside, a bicyclic nucleoside, and a 2'-substituted nucleoside. In certain embodiments, a deoxy region supports RNase H activity. In certain embodiments, a deoxy region is the gap or internal region of a gapmer.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." The internal region is a deoxy region. The positions of the internal region or gap refer to the order of the nucleosides of the internal region and are counted starting from the 5'-end of the internal region. Unless otherwise indicated. "gapmer" refers to a sugar motif. Unless otherwise indicated, the sugar moiety of each nucleoside of the gap is a 2'-β-D-deoxynucleoside. In certain embodiments, the gap comprises one 2'-substituted nucleoside at position 1, 2, 3, 4, or 5 of the gap, and the remainder of the nucleosides of the gap ar 2'-β-D-deoxynucleosides. As used herein, the term "MOE gapmer" indicates a gapmer having a gap comprising 2'-β-D-deoxynucleosides and wings comprising 2'-MOE nucleosides. As used herein, the term "mixed wing gapmer" indicates a gapmer having wings comprising modified nucleosides comprising at least two different sugar modifications. Unless otherwise indicated, a gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid that is amenable to oligomeric compound-mediated reduction of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "internucleoside linkage" means the covalent linkage between contiguous nucleosides in an oligonucleotide. As used herein, "modified internucleoside linkage" means any internucleoside linkage other than a phosphodiester internucleoside linkage. "Phosphorothioate internucleoside linkage or "PS internucleoside linkage" is a modified internucleoside linkage in which one of the non-bridging oxygen atoms of a phosphodiester internucleoside linkage is replaced with a sulfur atom.

As used herein, "leukodystrophy" means a disorder due to abnormalities in the myelin sheath of neurons.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "motif" means the pattern of unmodified and/or modified sugar moieties, nucleobases, and/or internucleoside linkages, in an oligonucleotide.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. A "5-methylcytosine" is a modified nucleobase. A universal base is a modified nucleobase that can pair with any one of the five unmodified nucleobases. As used herein, "nucleobase sequence" means the order of contiguous nucleobases in a target nucleic acid or oligonucleotide independent of any sugar or internucleoside linkage modification.

As used herein, "nucleoside" means a compound, or a fragment of a compound, comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to a subject. Certain such carriers enable pharmaceutical compositions to be formulated as, for example, tablets, pills, dragees, capsules, liquids, gels, syrups, slurries, suspension and lozenges for the oral ingestion by a subject.

In certain embodiments, a pharmaceutically acceptable carrier or diluent is sterile water, sterile saline, sterile buffer solution or sterile artificial cerebrospinal fluid.

As used herein, "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein, "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein, "prodrug" means a therapeutic agent in a form outside the body that is converted to a different form within a subject or cells thereof. Typically, conversion of a prodrug within the subject is facilitated by the action of an enzymes (e.g., endogenous or viral enzyme) or chemicals present in cells or tissues and/or by physiologic conditions.

As used herein, "reducing the amount or activity" refers to a reduction or blockade of the transcriptional expression or activity relative to the transcriptional expression or activity in an untreated or control sample and does not necessarily indicate a total elimination of transcriptional expression or activity.

As used herein, "RNA" means an RNA transcript and includes pre-mRNA and mature mRNA unless otherwise specified.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "standard in vitroassay" means the assay described in Example 1 and reasonable variations thereof.

As used herein, "standard in vivo assay" means the assay described in Example 7 and reasonable variations thereof.

As used herein, "stereomndom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "subject" means a human or non-human animal.

As used herein, "sugar moiety" means an unmodified sugar moiety or a modified sugar moiety. As used herein, "unmodified sugar moiety" means a 2'-OH(H) β-D-ribosyl moiety, as found in RNA (an "unmodified RNA sugar moiety"), or a 2'-H(H) β-D-deoxyribosyl sugar moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "symptom or hallmark" means any physical feature or test result that indicates the existence or extent of a disease or disorder. In certain embodiments, a symptom is apparent to a subject or to a medical professional examining or testing said subject. In certain embodiments, a hallmark is apparent upon invasive diagnostic testing, including, but not limited to, post-mortem tests. In certain embodiments, a hallmark is apparent on a brain MRI scan.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to a subject. For example, a therapeutically effective amount improves a symptom or hallmark of a disease.

CERTAIN EMBODIMENTS

The present disclosure provides the following non-limiting numbered embodiments:

Embodiment 1: An oligomeric compound comprising a modified oligonucleotide consisting of 12 to 30 linked nucleosides wherein the nucleobase sequence of the modified oligonucleotide is at least 90% complementary to an equal length portion of a GFAP nucleic acid, and wherein the modified oligonucleotide comprises at least one modification selected from a modified sugar moiety and a modified internucleoside linkage.

Embodiment 2: An oligomeric compound comprising a modified oligonucleotide consisting of 12 to 30 linked nucleosides and having a nucleobase sequence comprising at least 12, at least 13, at least 14, at least 15, at least 16, at least 17, at least 18, at least 19, or 20 contiguous nucleobases of any of SEQ ID NOs: 20-2809 or 2813, wherein the modified oligonucleotide comprises at least one modification selected from a modified sugar moiety and a modified internucleoside linkage.

Embodiment 3: An oligomeric compound comprising a modified oligonucleotide consisting of 12 to 30 linked nucleosides and having a nucleobase sequence comprising at least 12, at least 13, at least 14, at least 15, at least 16, at least 17, or 18 contiguous nucleobases of any of SEQ ID NOs: 2816-2837, 2839-2846, 2850-2854, 2856, 2859, 2861-2863, 2866, 2873-2876, 2886-2888, 2891, wherein the modified oligonucleotide comprises at least one modification selected from a modified sugar moiety and a modified internucleoside linkage.

Embodiment 4: An oligomeric compound comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 contiguous nucleobases complementary to:

an equal length portion of nucleobases 9324-9348 of SEQ ID NO: 2;

an equal length portion of nucleobases 9459-9480 of SEQ ID NO: 2;

an equal length portion of nucleobases 9530-9580 of SEQ ID NO: 2;

an equal length portion of nucleobases 12006-12038 of SEQ ID NO: 2; or an equal length portion of nucleobases 13038-13058 of SEQ ID NO: 2.

wherein the modified oligonucleotide comprises at least one modification selected from a modified sugar moiety and a modified internucleoside linkage.

Embodiment 5: An oligomeric compound comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, or at least 18 contiguous nucleobases of a sequence selected from:

SEQ ID Nos: 21, 1177, 2321, 2398, 2808-2809, 2840-2842, 2853-2854;

SEQ ID Nos: 555, 2093, 2170, 2813;

SEQ ID Nos: 20, 88, 166, 1331, 1408, 1485, 1637, 1713, 1714, 1789, 1790, 1637, 1638, 1865, 1866, 1941, 2018, 2095, 2172, 2249, 2326, 2403, 2480, 2557, 2633, 2709, 2785, 2816-2818, 2859, 2861, 2886-2887;

SEQ ID Nos: 815, 893, 971, 1049, 1269, 1270, 1346, 1423, 1499, 1500, 1660, 1736, 2655, 2731: or

SEQ ID Nos: 825, 1973.

Embodiment 6: The oligomeric compound of any of embodiments 1-5, wherein the modified oligonucleotide has a nucleobase sequence that is at least 80%, at least 85%, at least 90%, at least 95%, or 100% complementary to the nucleobase sequence of SEQ ID NO: 1, SEQ ID NO: 2 or SEQ ID NO: 3 when measured across the entire nucleobase sequence of the modified oligonucleotide.

Embodiment 7: The oligomeric compound of any of embodiments 1-6, wherein the modified oligonucleotide comprises at least one modified sugar moiety.

Embodiment 8: The oligomeric compound of embodiment 7, wherein the modified oligonucleotide comprises at least one bicyclic sugar moiety.

Embodiment 9: The oligomeric compound of embodiment 8, wherein the bicyclic sugar moiety has a 4'-2' bridge, wherein the 4'-2' bridge is selected from $CH_2$—O—; and —$CH(CH_3)$—O.

Embodiment 10: The oligomeric compound of any of embodiments 1-9, wherein the modified oligonucleotide comprises at least one non-bicyclic modified sugar moiety.

Embodiment 11: The oligomeric compound of embodiment 10, wherein the non-bicyclic modified sugar moiety is a 2'-MOE sugar moiety or a 2'-OMe sugar moiety.

Embodiment 12: The oligomeric compound of any of embodiments 1-11, wherein the modified oligonucleotide comprises at least one sugar surrogate.

Embodiment 13: The oligomeric compound of embodiment 12, wherein the sugar surrogate is any of morpholino, modified morpholino, PNA, THP, and F-HNA.

Embodiment 14: The oligomeric compound of any of embodiments 1-7 or 10-13, wherein the modified oligonucleotide does not comprise a bicyclic sugar moiety.

Embodiment 15: The oligomeric compound of any of embodiments 1-14, wherein the modified oligonucleotide is a gapmer.

Embodiment 16: The oligomeric compound of any of embodiments 1-15, wherein the modified oligonucleotide comprises:

a 5'-region consisting of 1-6 linked nucleosides;

a central region consisting of 6-10 linked nucleosides; and a 3'-region consisting of 1-6 linked nucleosides; wherein each of the 5'-region nucleosides and each of the 3'-region nucleosides comprises a modified sugar moiety and at least one of the central region nucleosides comprises a 2'-deoxyribosyl sugar moiety.

Embodiment 17: The oligomeric compound of embodiment 16, wherein the modified oligonucleotide comprises a 5'-region consisting of 6 linked nucleosides:

a central region consisting of 10 linked nucleosides; and a 3'-region consisting of 4 linked nucleosides: wherein each of the 5'-region nucleosides and each of the 3'-region nucleosides comprises a 2'-MOE modified sugar moiety, and each of the central region nucleosides comprises a 2'-deoxyribosyl sugar moiety.

Embodiment 18: The oligomeric compound of embodiment 16, wherein the modified oligonucleotide comprises:

a 5'-region consisting of 5 linked nucleosides;

a central region consisting of 10 linked nucleosides; and a 3'-region consisting of 5 linked nucleosides; wherein each of the 5'-region nucleosides and each of the 3'-region nucleosides comprises a 2'-MOE modified sugar moiety, and each of the central region nucleosides comprises a 2'-deoxyribosyl sugar moiety.

Embodiment 19: The oligomeric compound of embodiment 16, wherein the modified oligonucleotide comprises:

a 5'-region consisting of 4 linked nucleosides;

a central region consisting of 10 linked nucleosides; and a 3'-region consisting of 6 linked nucleosides; wherein each of the 5'-region nucleosides and each of the 3'-region nucleosides comprises a 2'-MOE modified sugar moiety, and each of the central region nucleosides comprises a 2'-deoxyribosyl sugar moiety.

Embodiment 20: The oligomeric compound of embodiment 16, wherein the modified oligonucleotide comprises a 5'-region consisting of 5 linked nucleosides;

a central region consisting of 8 linked nucleosides; and a 3'-region consisting of 5 linked nucleosides; wherein each of the 5'-region nucleosides and each of the 3'-region nucleosides comprises a 2'-MOE modified sugar moiety, and each of the central region nucleosides comprises a 2'-deoxyribosyl sugar moiety.

Embodiment 21: The oligomeric compound of any of embodiments 1-20, wherein the modified oligonucleotide comprises at least one modified internucleoside linkage.

Embodiment 22: The oligomeric compound of embodiment 21, wherein each internucleoside linkage of the modified oligonucleotide is a modified internucleoside linkage.

Embodiment 23: The oligomeric compound of embodiments 21 or 22, wherein the modified internucleoside linkage is a phosphorothioate internucleoside linkage.

Embodiment 24: The oligomeric compound of any one of embodiments 1-21, wherein the modified oligonucleotide comprises at least one phosphodiester internucleoside linkage.

Embodiment 25: The oligomeric compound of any of embodiments 21, 23, or 24, wherein each internucleoside linkage is either a phosphodiester internucleoside linkage or a phosphorothioate internucleoside linkage.

Embodiment 26: The oligomeric compound of any one of embodiments 1-21 or 23-25, wherein the modified oligonucleotide has an internucleoside linkage motif selected from among: sooosssssssssssooss, sooooossssssssssoss, soooossssssssssooss, sooosssssssssooss, or sooossssssssssoooss: wherein, s=a phosphothioate internucleoside linkage and o=a phosphodiester internucleoside linkage.

Embodiment 27: The oligomeric compound of any of embodiments 1-26, wherein the modified oligonucleotide comprises at least one modified nucleobase.

Embodiment 28: The oligomeric compound of embodiment 27, wherein the modified nucleobase is a 5-methylcytosine.

Embodiment 29: The oligomeric compound of any of embodiments 1-28, wherein the modified oligonucleotide consists of 12-30, 12-22, 12-20, 14-18, 14-20, 15-17, 15-25, 16-20, 18-22 or 18-20 linked nucleosides.

Embodiment 30: The oligomeric compound of any of embodiments 1-29, wherein the modified oligonucleotide consists of 18 linked nucleosides.

Embodiment 31: The oligomeric compound of any of embodiments 1-30, wherein the modified oligonucleotide consists of 20 linked nucleosides.

Embodiment 32: The oligomeric compound of any of embodiments 1-31, consisting of the modified oligonucleotide.

Embodiment 33: An oligomeric duplex comprising an oligomeric compound of any of embodiments 1-31.

Embodiment 34: An antisense compound comprising or consisting of an oligomeric compound of any of embodiments 1-32 or an oligomeric duplex of embodiment 33.

Embodiment 35: A pharmaceutical composition comprising an oligomeric compound of any of embodiments 1-32 or an oligomeric duplex of embodiment 33 and a pharmaceutically acceptable carrier or diluent.

Embodiment 36: The pharmaceutical composition of embodiment 35, wherein the pharmaceutically acceptable diluent is artificial cerebral spinal fluid.

Embodiment 37: The pharmaceutical composition of embodiment 36, wherein the pharmaceutical composition consists of the modified oligonucleotide and phosphate buffered saline.

Embodiment 38: A method comprising administering to a subject a pharmaceutical composition of any of embodiments 35-37.

Embodiment 39: A method of treating a disease associated with GFAP comprising administering to an individual having or at risk for developing a disease associated with GFAP a therapeutically effective amount of a compound of any one of embodiments 1-34 or a pharmaceutical composition according to any of embodiments 35-37; and thereby treating the disease associated with GFAP.

Embodiment 40: The method of embodiment 39, wherein the GFAP-associated disease is Alexander Disease.

Embodiment 41: The method of any of embodiments 38-40, wherein at least one symptom or hallmark of the GFAP-associated disease is ameliorated.

Embodiment 42: The method of embodiment 41, wherein the symptom or hallmark is motor delays, cognitive delays, paroxysmal deterioration, seizures, vomiting, swallowing difficulties, ataxic gait, palatal myoclonus, autonomic dysfunction, or the presence of intra-astrocytic inclusions called Rosenthal fibers.

Embodiment 43: The method of any of embodiments 38-42, wherein GFAP levels in the individual are reduced.

Embodiment 44: A modified oligonucleotide according to the following chemical structure:

(SEQ ID NO: 2905)

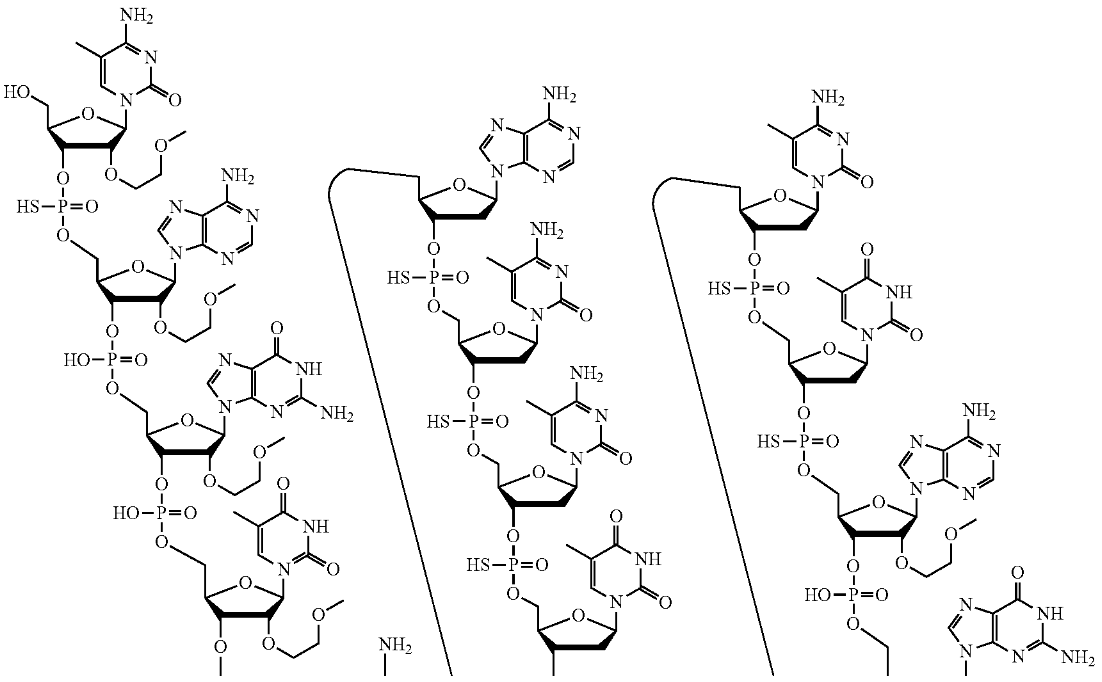

-continued
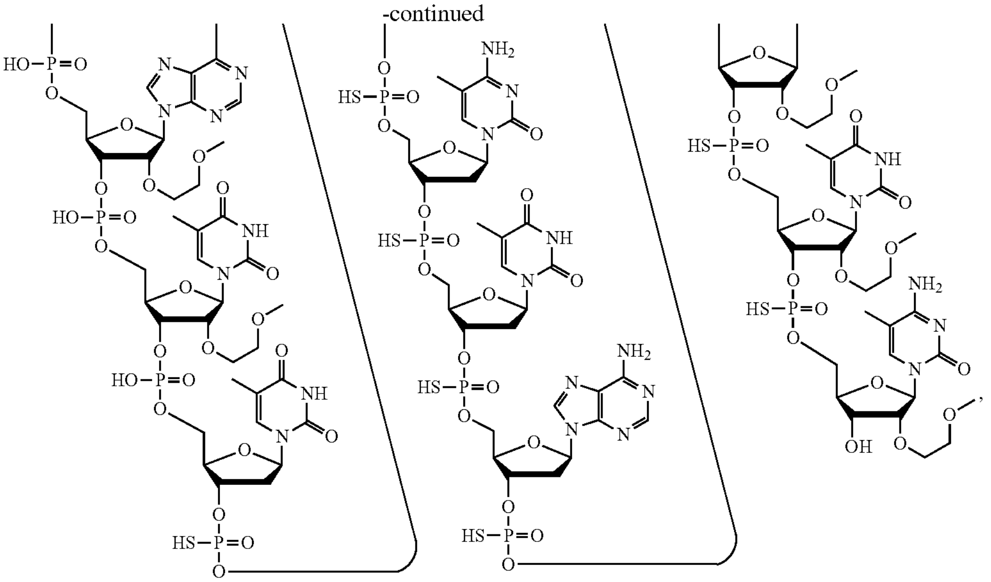
or a salt thereof.
Embodiment 45: A modified oligonucleotide according to the following chemical structure:
(SEQ ID NO: 2905)
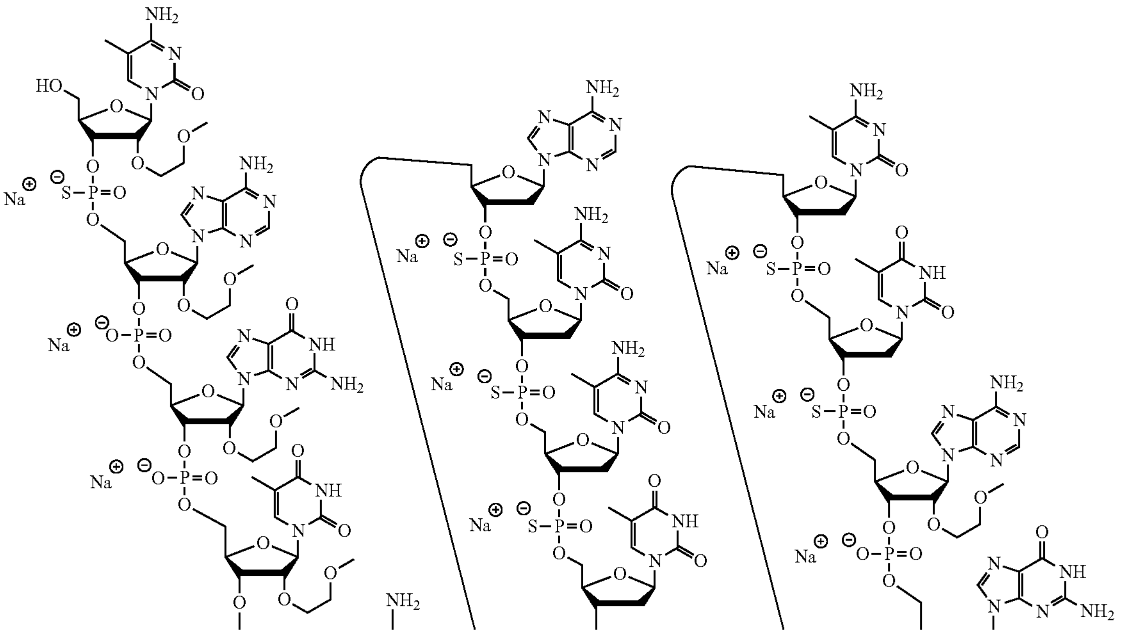

-continued
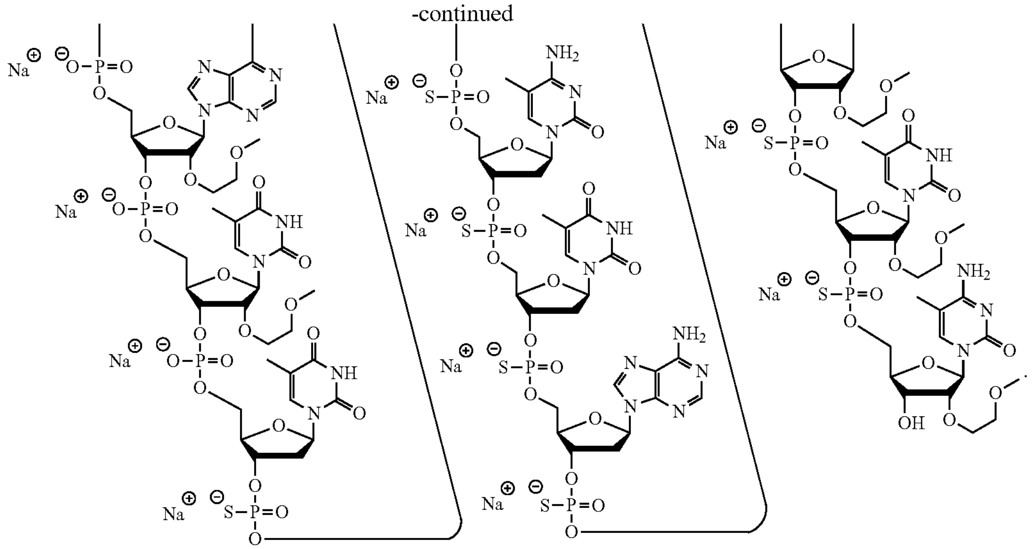
Embodiment 40: A modified oligonucleotide according to the following chemical structure:
(SEQ ID NO: 2904)
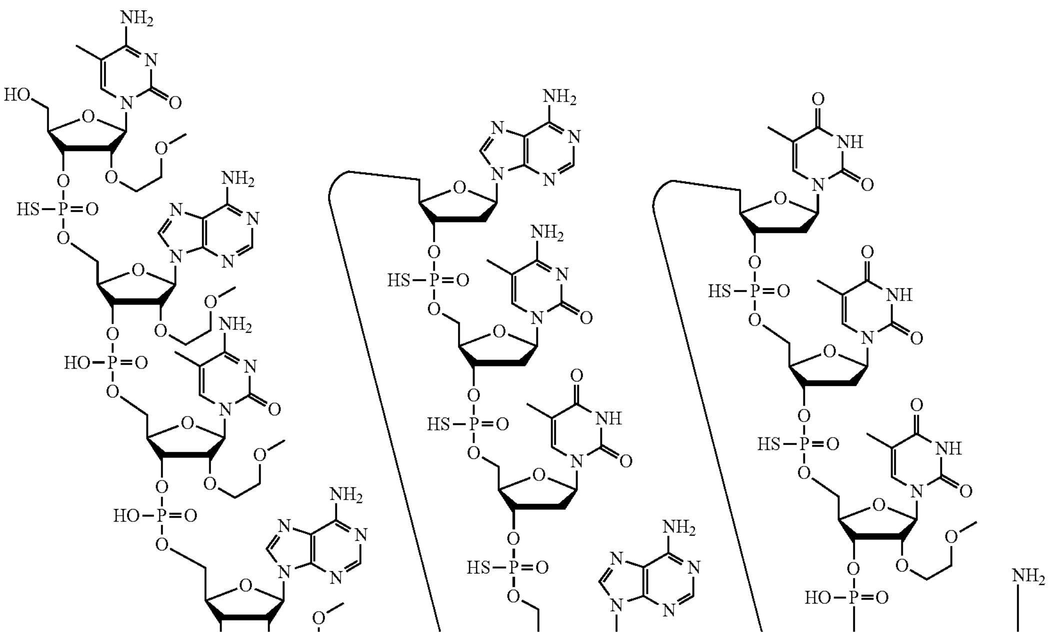

-continued
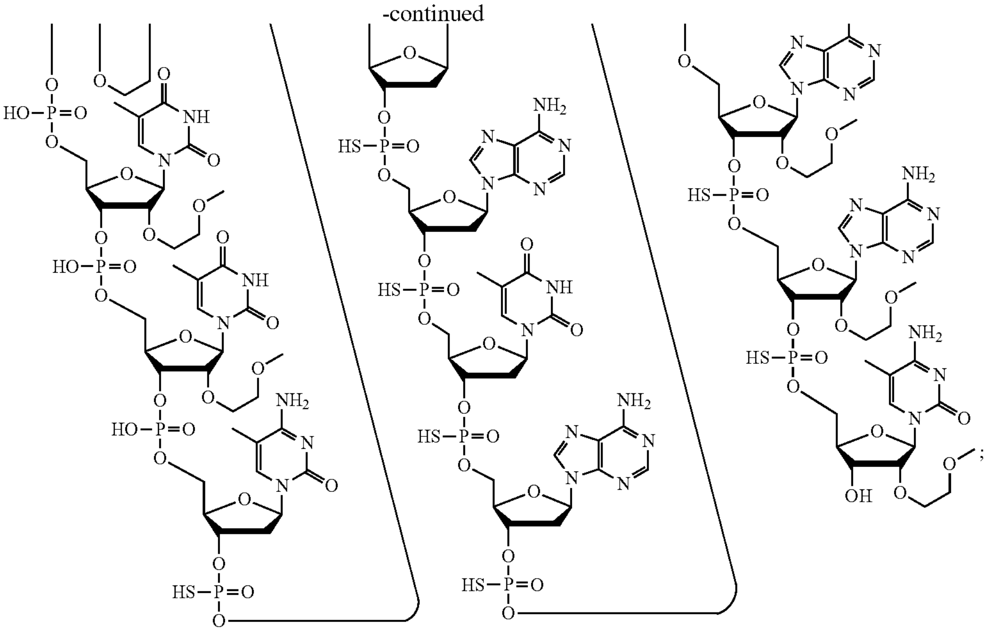
or a salt thereof.
Embodiment 47: A modified oligonucleotide according to the following chemical structure:
(SEQ ID NO: 2904)
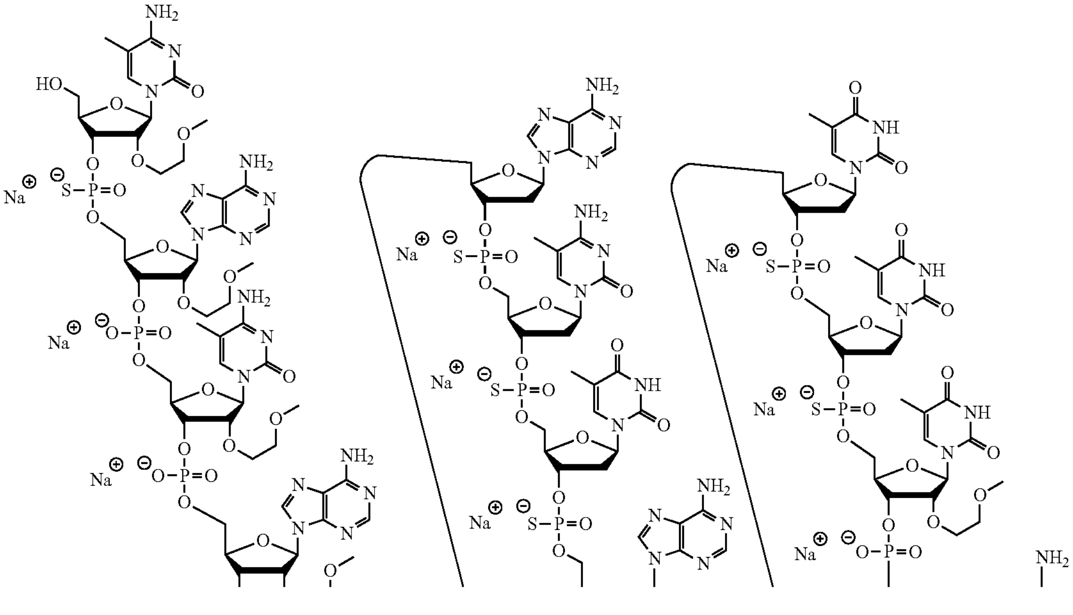

-continued
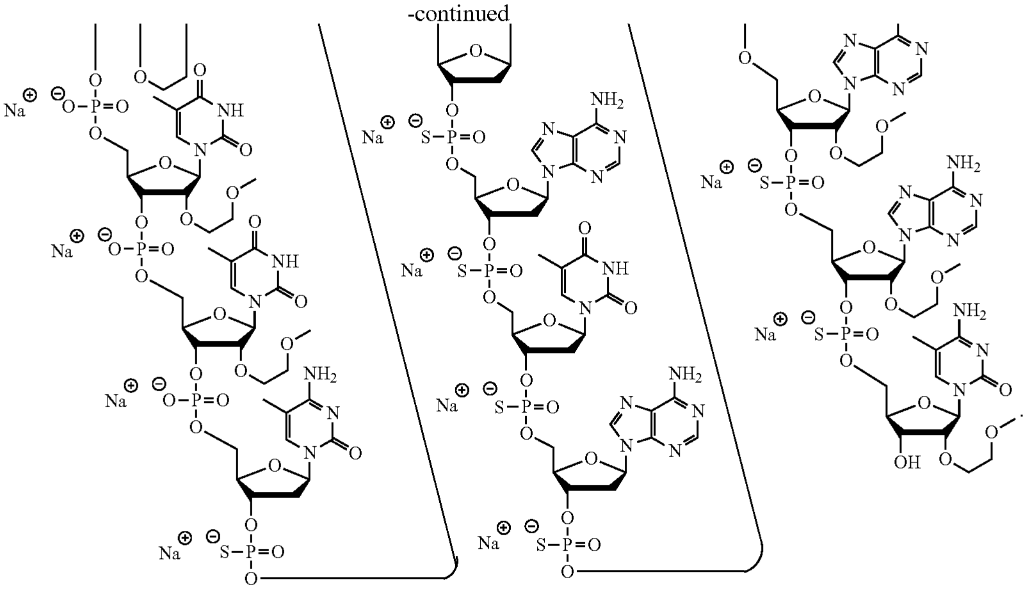
Embodiment 48: A modified of oligonucleotide according to the Mowing chemical structure:
(SEQ ID NO: 2903)
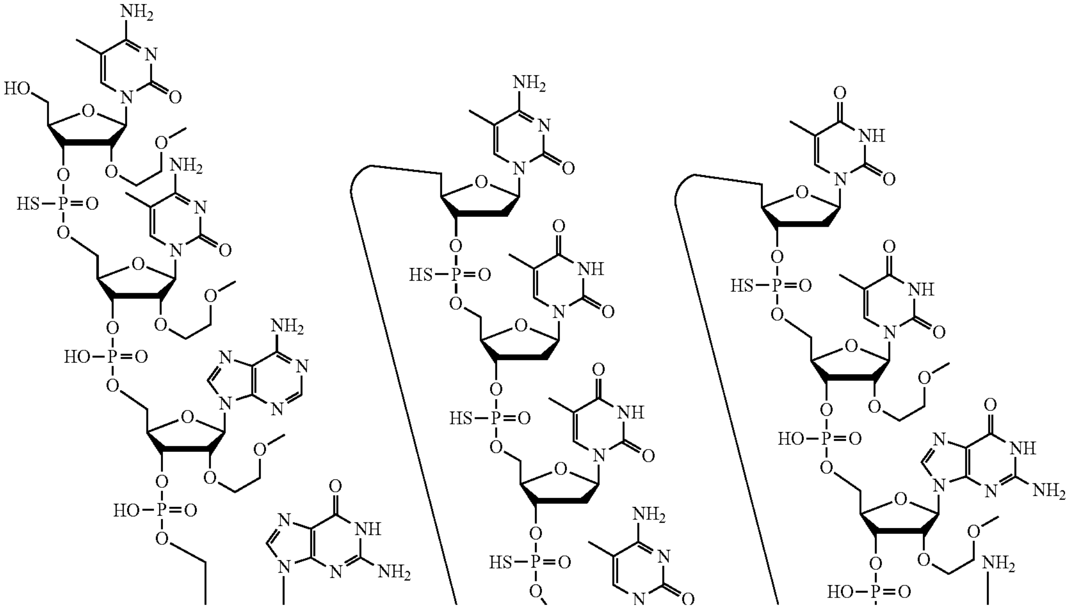

-continued
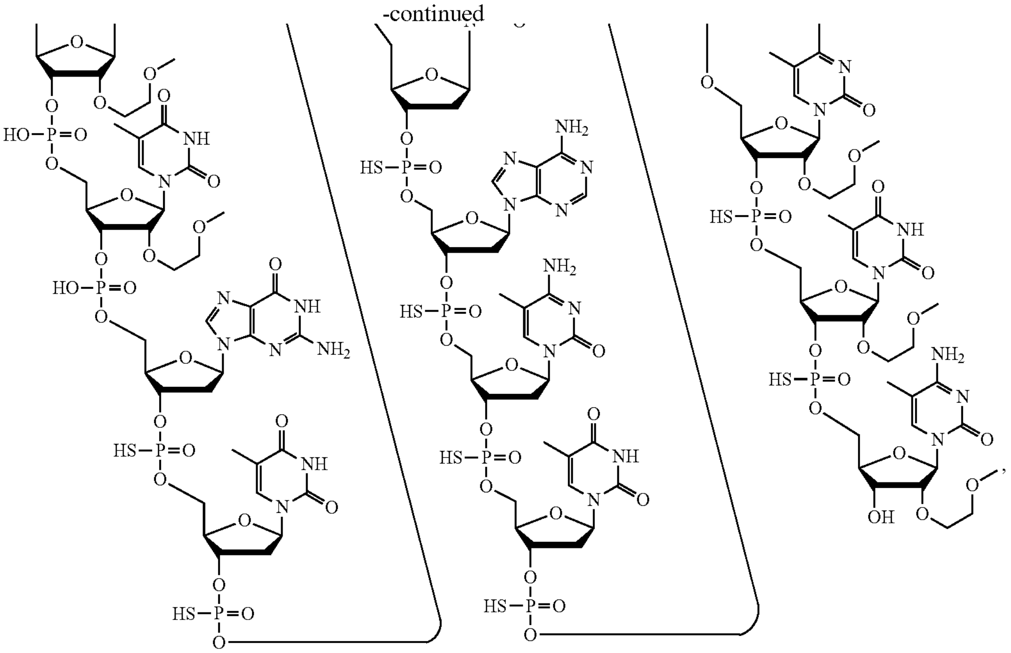
or a salt thereof.
Embodiment 49: A modified oligonucleotide according to the following chemical structure:
(SEQ ID NO: 2903)
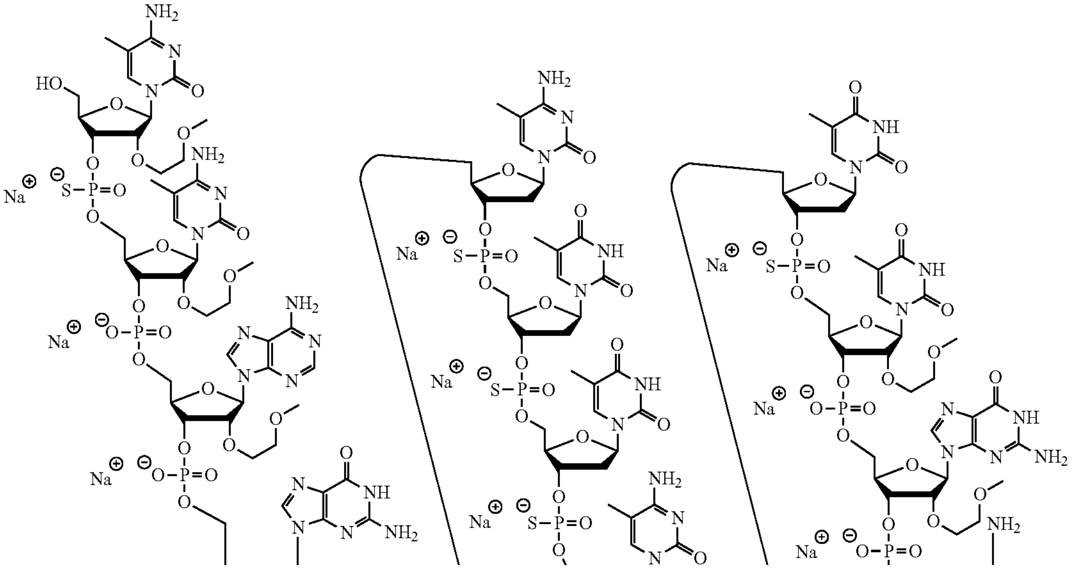

-continued
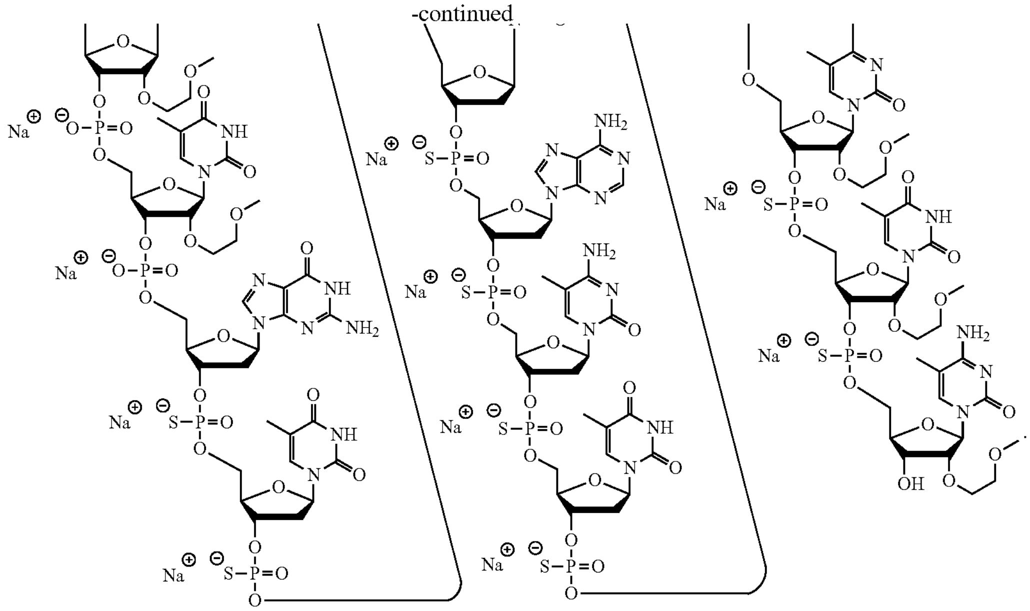
Embodiment 50: A modified oligonucleotide according to the following chemical structure:
(SEQ ID NO: 2902)
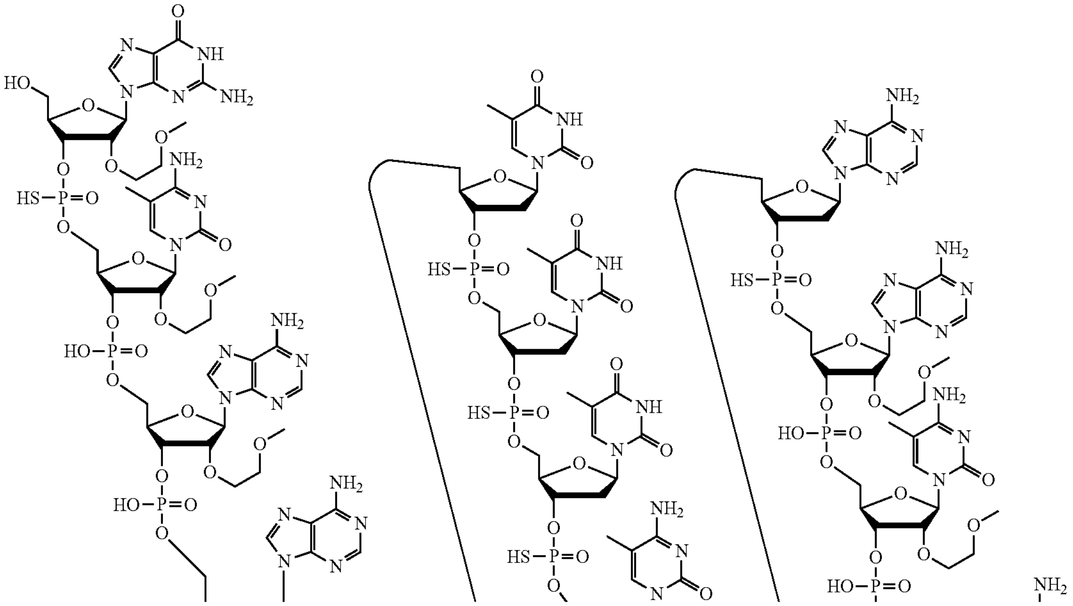

-continued
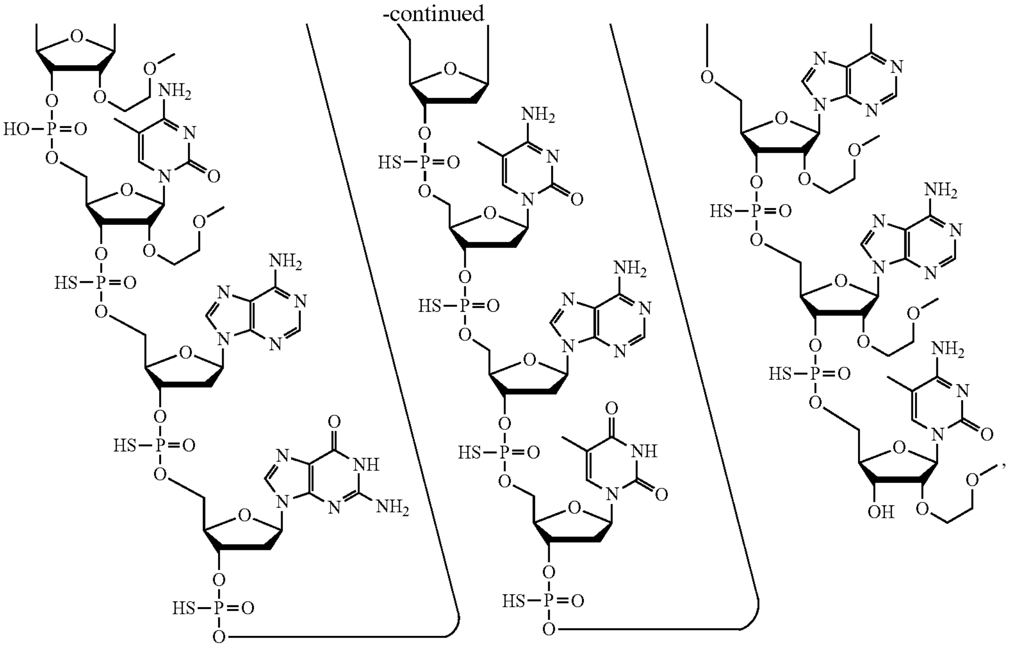
or a salt thereof.
Embodiment 51: A modified oligonucleotide according to the following chemical structure:
(SEQ ID NO: 2902)
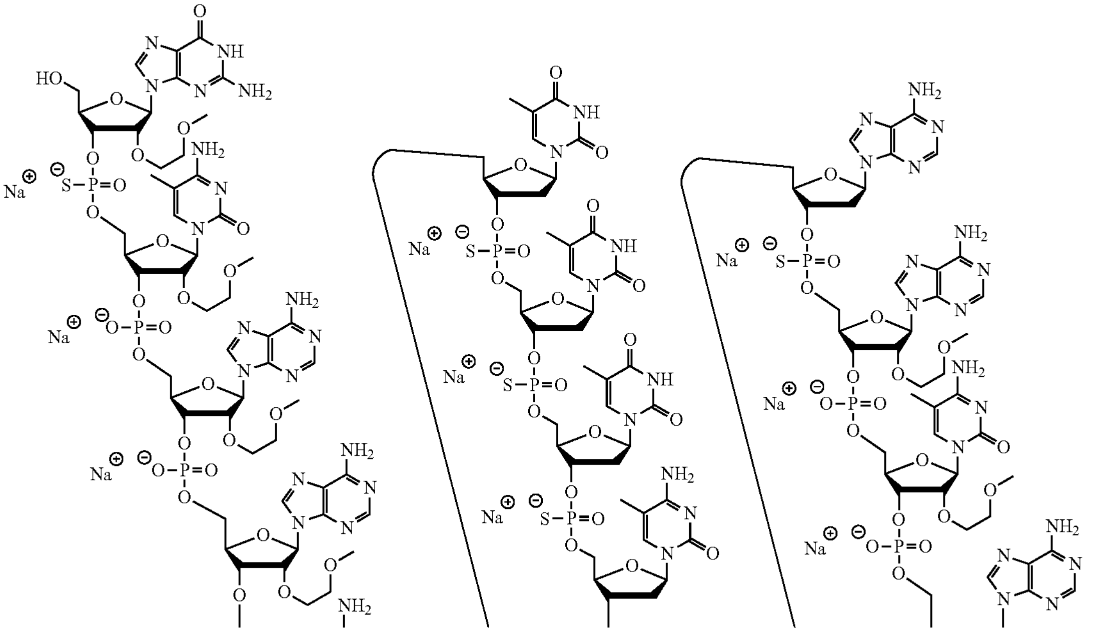

-continued
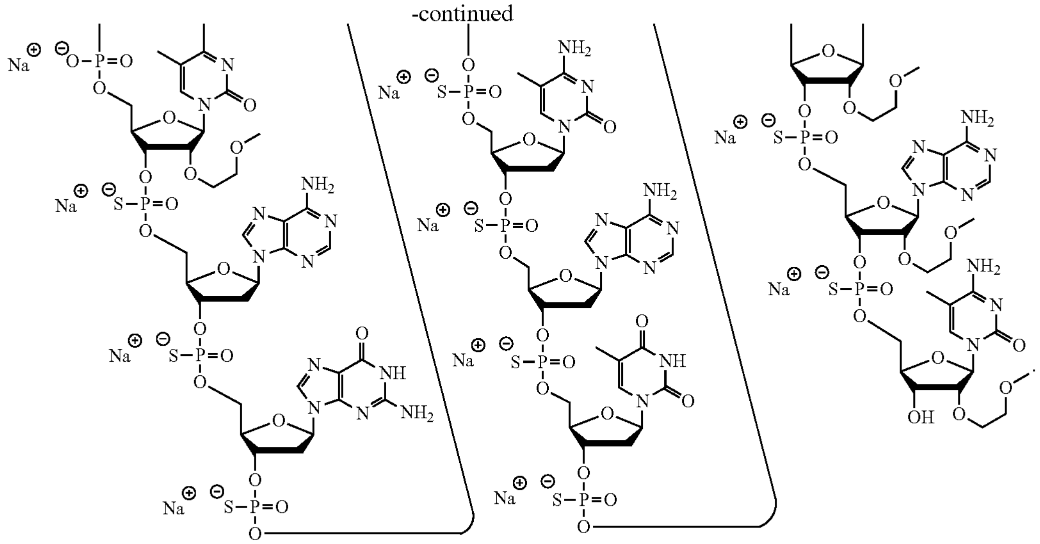
Embodiment 52: A modified oligonucleotide according to the following chemical structure:
(SEQ ID NO: 2906)
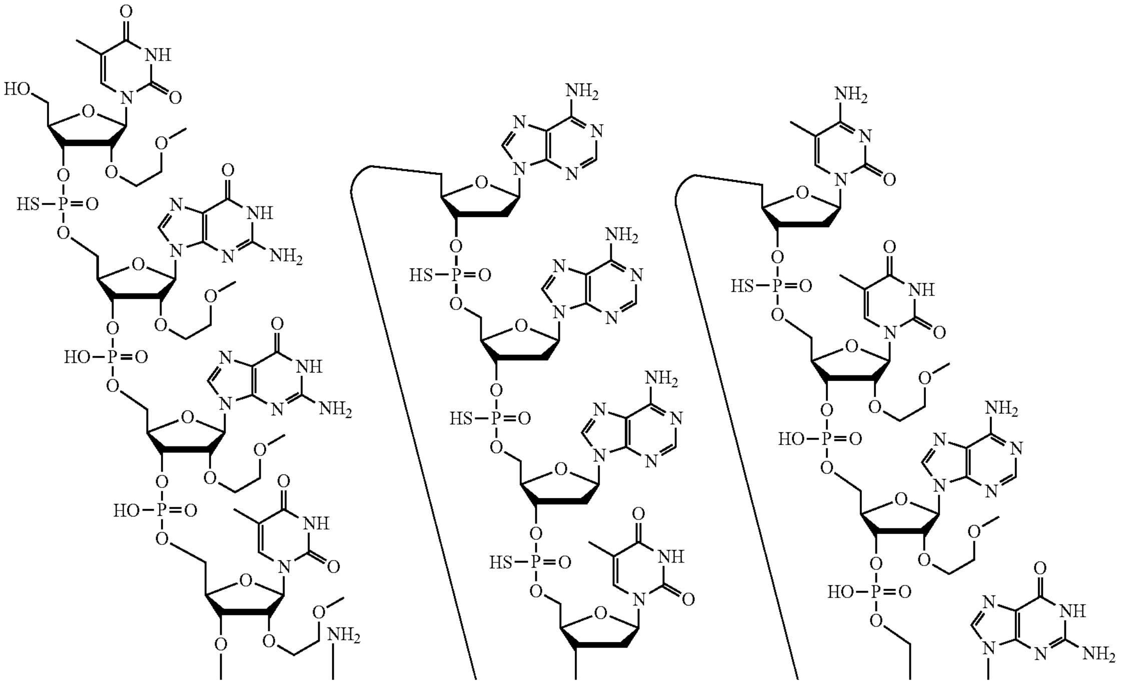

-continued
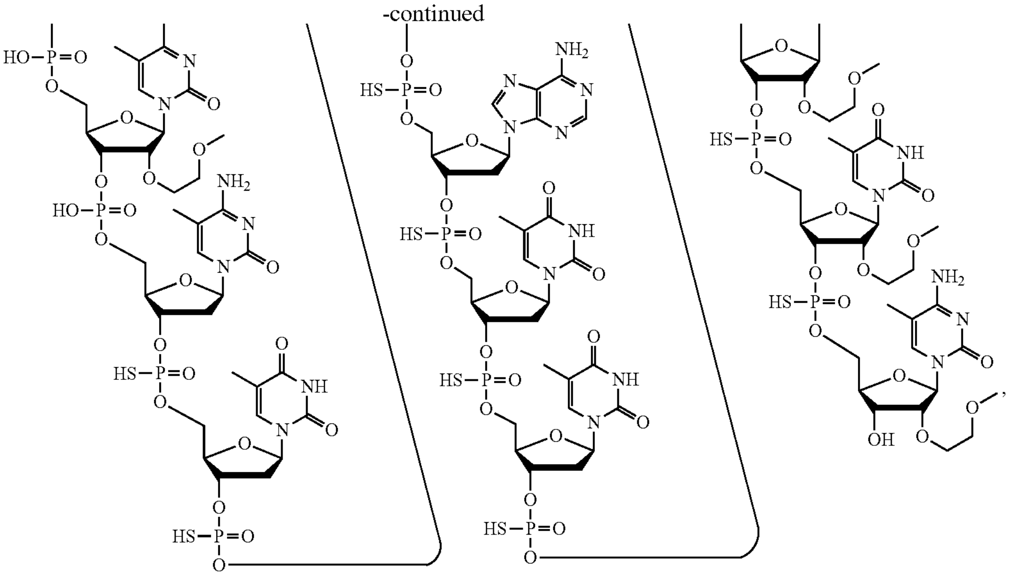
or a salt thereof.
Embodiment 53: A modified oligonucleotide according to the following chemical structure:
(SEQ ID NO: 2906)
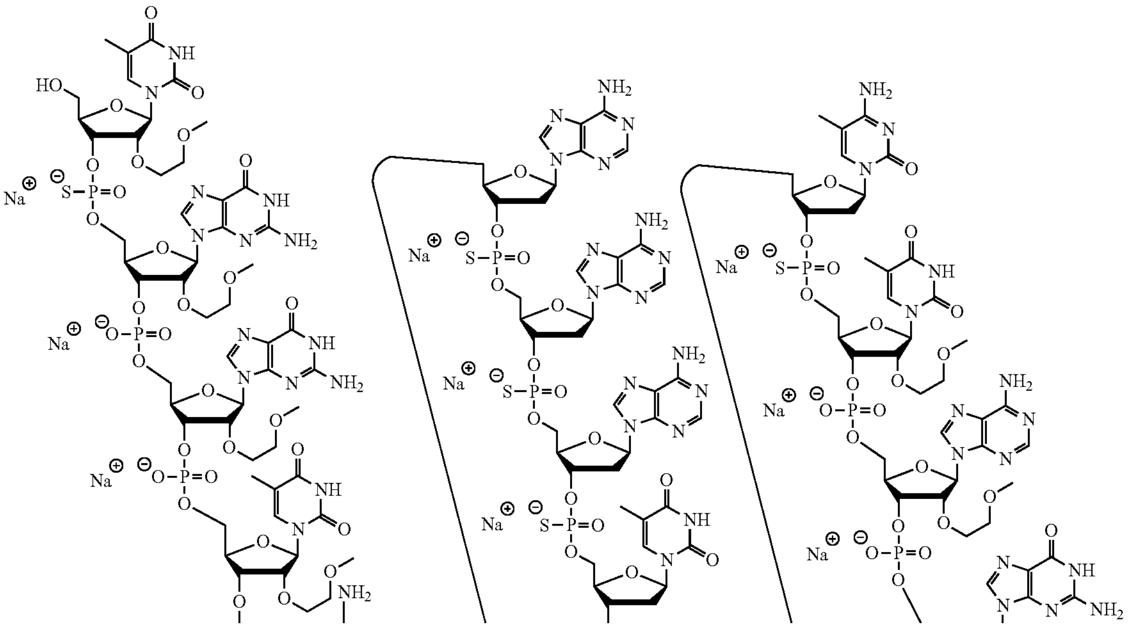

-continued
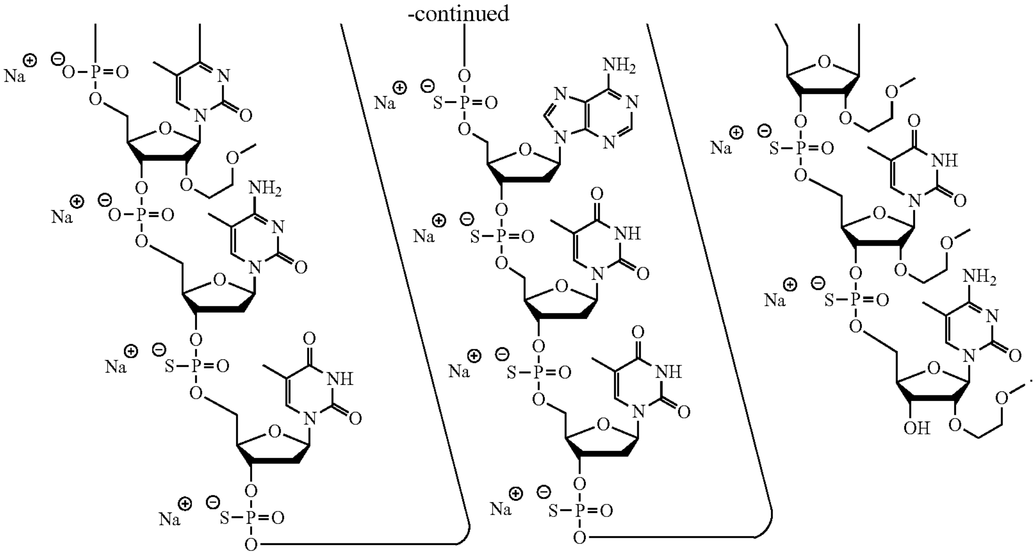
Embodiment 54: A modified oligonucleotide according to the following chemical structure:
(SEQ ID NO: 2901)
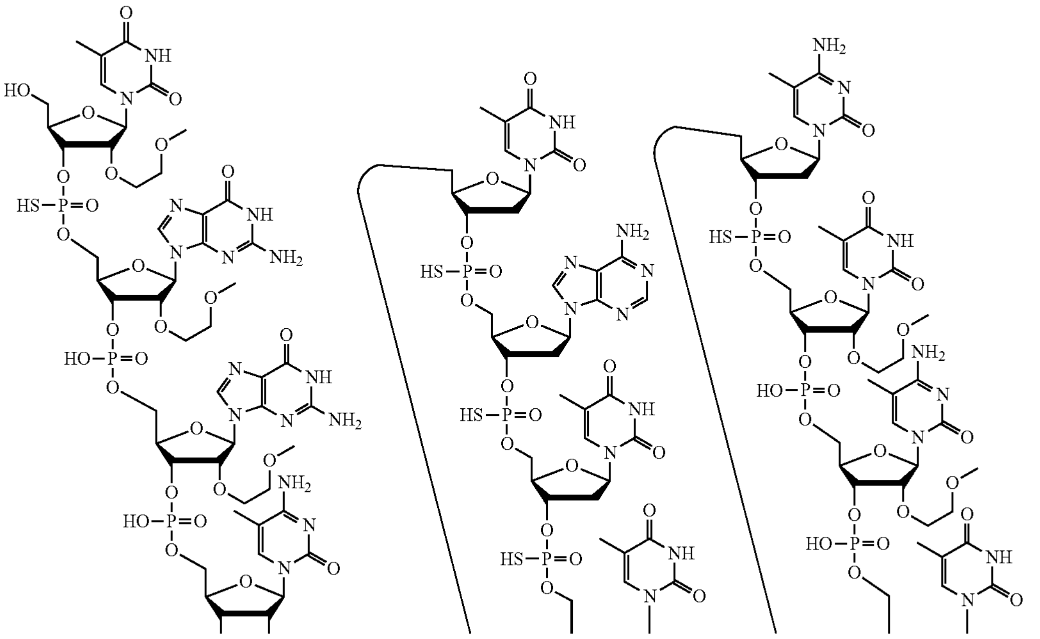

-continued
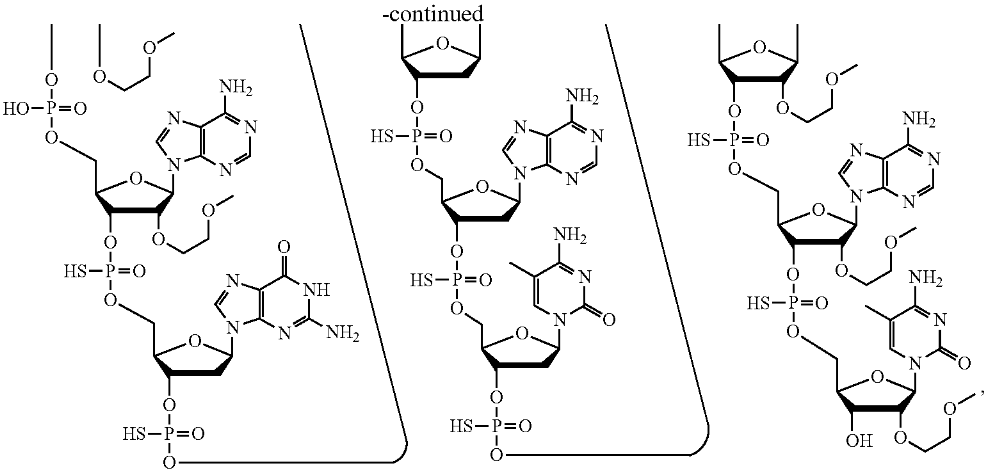
or a salt thereof.
Embodiment 55: A modified oligonucleotide according to the following chemical structure:
(SEQ ID NO: 2901)
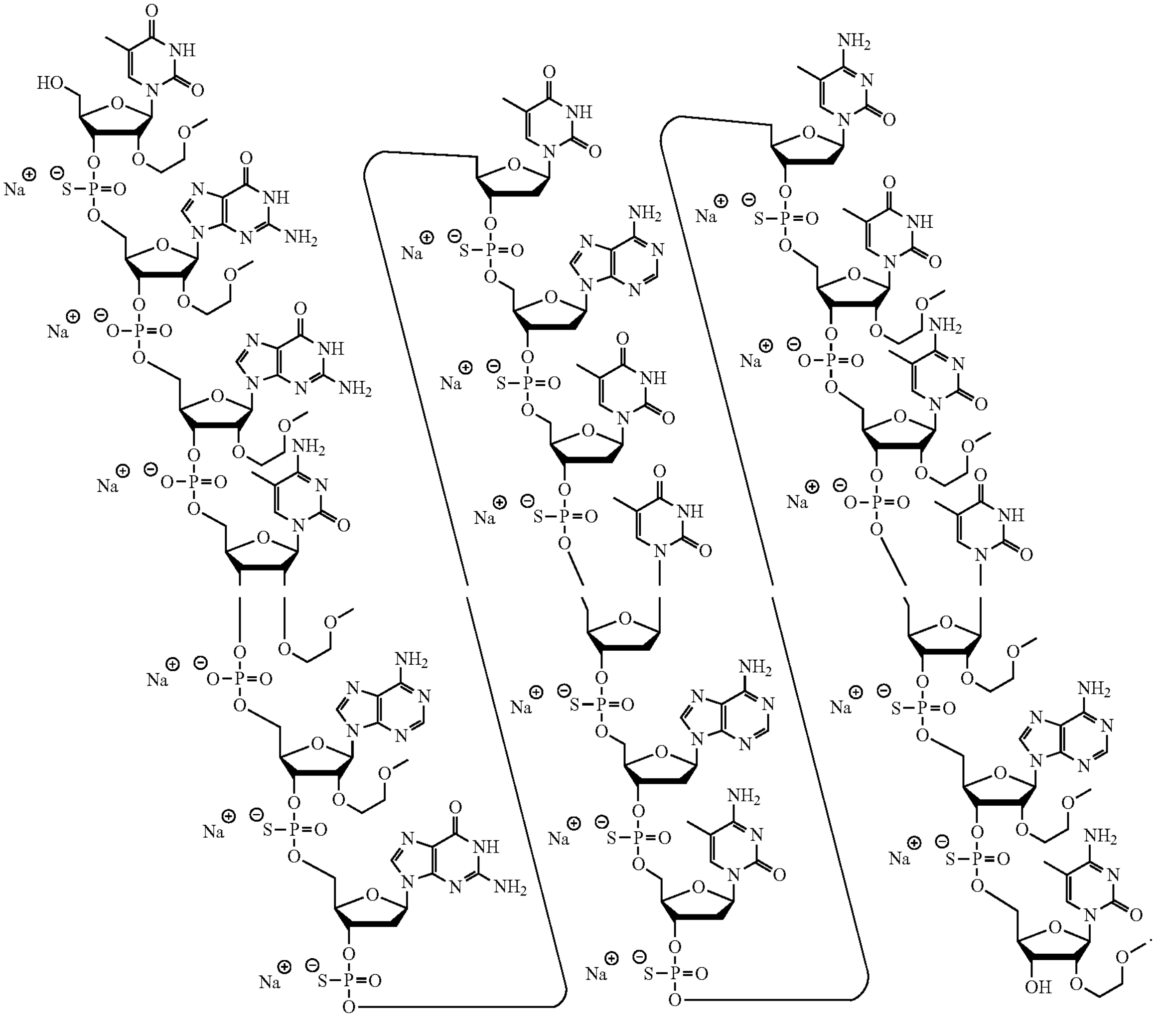

Embodiment 56: The modified oligonucleotide of any one of embodiments 44, 46, 48, 50, 52, and 54, which is the sodium salt or potassium salt of the chemical structure.

Embodiment 57: A pharmaceutical composition comprising the modified oligonucleotide ofany of embodiments 44-56 and a pharmaceutically acceptable carrier or diluent.

Embodiment 58: The pharmaceutical composition of embodiment 57, wherein the pharmaceutically acceptable diluent is artificial cerebrospinal fluid.

Embodiment 59: The pharmaceutical composition of embodiment 58, wherein the pharmaceutical composition consists of the modified oligonucleotide and artificial cerebrospinal fluid.

Embodiment 60: A compound comprising a modified oligonucleotide according to the following chemical notation: ${}^{m}C_{es}A_{eo}G_{eo}A_{eo}T_{eo}T_{ds}A_{ds}{}^{m}C_{ds}{}^{m}C_{ds}T_{ds}{}^{m}C_{ds}T_{ds}A_{ds}{}^{m}C_{ds}T_{ds}A_{eo}G_{es}T_{es}{}^{m}C_{e}$ (SEQ ID NO: 2905), wherein:

A=an adenine nucleobase, ${}^{m}C$=a 5-methylcytosine nucleobase,

G=a guanine nucleobase,

T=a thymine nucleobase, e=a 2'-β-D-MOE sugar moiety, d=a 2'-β-D-deoxyribosyl sugar moiety, s=a phosphorothioate internucleoside linkage, and o=a phosphodiester internucleoside linkage.

Embodiment 61: A compound comprising a modified oligonucleotide according to the following chemical notation: ${}^{m}C_{es}A_{eo}{}^{m}C_{eo}A_{eo}T_{eo}T_{eo}{}^{m}C_{ds}A_{ds}{}^{m}C_{ds}T_{ds}A_{ds}A_{ds}T_{ds}A_{ds}T_{ds}T_{ds}T_{eo}A_{es}A_{es}{}^{m}C_{e}$ (SEQ ID NO: 2904), wherein A=an adenine nucleobase, ${}^{m}C$=a 5-methylcytosine nucleobase, G=a guanine nucleobase, T=a thymine nucleobase, e=a 2'-β-D-MOE sugar moiety, d=a 2'-β-D-deoxyribosyl sugar moiety.

s=a phosphorothioate internucleoside linkage, and o=a phosphodiester internucleoside linkage.

Embodiment 62: A compound comprising a modified oligonucleotide according to the following chemical notation: ${}^{m}C_{es}{}^{m}C_{eo}A_{eo}G_{eo}T_{eo}G_{ds}T_{ds}{}^{m}C_{ds}T_{ds}T_{ds}{}^{m}C_{ds}A_{ds}{}^{m}C_{ds}T_{ds}T_{ds}T_{eo}G_{eo}{}^{m}C_{es}T_{es}{}^{m}C_{e}$ (SEQ ID NO: 2903), wherein:

A=an adenine nucleobase, ${}^{m}C$=a 5-methylcytosine nucleobase,

G=a guanine nucleobase,

T=a thymine nucleobase, e=a 2'-β-D-MOE sugar moiety, d=a 2'-β-D-deoxyribosyl sugar moiety, s=a phosphorothioate internucleoside linkage, and o=a phosphodiester internucleoside linkage.

Embodiment 63: A compound comprising a modified oligonucleotide according to the following chemical notation: $G_{es}{}^{m}C_{eo}A_{eo}A_{eo}{}^{m}C_{es}A_{ds}G_{ds}T_{ds}T_{ds}T_{ds}{}^{m}C_{ds}{}^{m}C_{ds}A_{ds}T_{ds}A_{ds}A_{eo}{}^{m}C_{eo}A_{es}A_{es}{}^{m}C_{e}$ (SEQ ID NO: 2902), wherein:

A=an adenine nucleobase.

${}^{m}C$=a 5-methylcytosine nucleobase,

G=a guanine nucleobase,

T=a thymine nucleobase, e=a 2'-β-D-MOE sugar moiety, d=a 2'-β-D-deoxyribosyl sugar moiety, s=a phosphorothioate internucleoside linkage, and o=a phosphodiester internucleoside linkage.

Embodiment 64: A compound comprising a modified oligonucleotide according to the following chemical notation: $T_{es}G_{eo}G_{eo}T_{eo}{}^{m}C_{eo}{}^{m}C_{ds}T_{ds}A_{ds}A_{ds}A_{ds}T_{ds}A_{ds}T_{ds}T_{ds}{}^{m}C_{ds}T_{eo}A_{eo}G_{es}T_{es}{}^{m}C_{e}$ (SEQ ID NO: 2906), wherein:

A=an adenine nucleobase.

${}^{m}C$=a 5-methylcytosine nucleobase,

G=a guanine nucleobase,

T=a thymine nucleobase, e=a 2'-β-D-MOE sugar moiety, d=a 2'-β-D-deoxyribosyl sugar moiety, s=a phosphorothioate internucleoside linkage, and o=a phosphodiester internucleoside linkage.

Embodiment 65: A compound comprising a modified oligonucleotide according to the following chemical notation: $T_{es}G_{eo}G_{eo}{}^{m}C_{eo}A_{es}G_{ds}T_{ds}A_{ds}T_{ds}T_{ds}T_{ds}A_{ds}{}^{m}C_{ds}{}^{m}C_{ds}T_{eo}{}^{m}C_{eo}T_{es}A_{es}{}^{m}C_{e}$ (SEQ ID NO: 2901), wherein:

A=an adenine nucleobase, ${}^{m}C$=a 5-methylcytosine nucleobase,

G=a guanine nucleobase,

T=a thymine nucleobase, e=a 2'-β-D-MOE sugar moiety, d=a 2'-β-D-deoxyribosyl sugar moiety.

s=a phosphorothioate internucleoside linkage, and o=a phosphodiester internucleoside linkage.

Embodiment 66: The compound of any of embodiments 60-65, comprising the modified oligonucleotide covalently linked to a conjugate group.

Embodiment 67: A pharmaceutical composition comprising a compound of any of embodiments 60-66, and a pharmaceutically acceptable diluent or carrier.

Embodiment 68: The pharmaceutical composition of embodiment 67, wherein the pharmaceutically acceptable diluent is artificial cerebrospinal fluid.

Embodiment 69: The pharmaceutical composition of embodiment 68, wherein the pharmaceutical composition consists of the compound and artificial cerebrospinal fluid.

Embodiment 70: A chirally enriched population of modified oligonucleotides of any of embodiments 60-65, wherein the population is enriched for modified oligonucleotides comprising at least one particular phosphorothioate internucleoside linkage having a particular stereochemical configuration.

Embodiment 71: The chirally enriched population of embodiment 70, wherein the population is enriched for modified oligonucleotides comprising at least one particular phosphorothioate internucleoside linkage having the (Sp) configuration.

Embodiment 72: The chirally enriched population of embodiment 70, wherein the population is enriched for modified oligonucleotides comprising at least one particular phosphorothioate internucleoside linkage having the (Sp) configuration.

Embodiment 73: The chirally enriched population of embodiment 70, wherein the population is enriched for modified oligonucleotides having a particular, independently selected stereochemical configuration at each phosphorothioate internucleoside linkage Embodiment 74: The chirally enriched population of embodiment 70, wherein the population is enriched for modified oligonucleotides having the (Sp) configuration at each phosphorothioate internucleoside linkage.

Embodiment 75: The chirally enriched population of embodiment 70, wherein the population is enriched for modified oligonucleotides having the (Rp) configuration at each phosphothioate internucleoside linkage.

Embodiment 76: The chirally enriched population of embodiment 70, wherein the population is enriched for modified oligonucleotides having the (Rp) configuration at one particular phosphorothioate internucleoside linkage and the (Sp) configuration at each of the remaining phosphorothioate internucleoside linkages.

Embodiment 77: The chirally enriched population of embodiment 70 or embodiment 73 wherein the population is enriched for modified oligonucleotides having at least 3 contiguous phosphorothioate internucleoside linkages in the Sp, Sp, and Rp configurations, in the 5' to 3' direction.

Embodiment 78: A chirally enriched population of modified oligonucleotides of any of embodiments 44-55, wherein all of the phosphorothioate internucleoside linkages of the modified oligonucleotide are stereorandom.

Embodiment 79: A method comprising administering to an individual the pharmaceutical composition of any of embodiments 56-58 and 67-69.

Embodiment 80: A method of treating a disease associated with GFAP, comprising administering to an individual having or at risk of having a disease associated with GFAP a therapeutically effective amount of the pharmaceutical composition of any one of embodiments 56-58 and 67-69, thereby treating the disease associated with GFAP.

Embodiment 81: A method of reducing GFAP protein in the CSF of an individual having or at risk of having a disease associated with GFAP a therapeutically effective amount of a pharmaceutical composition of any one of embodiments 56-58 and 67-69, thereby reducing GFAP protein in the CSF.

Embodiment 82: The method of embodiment 80 or embodiment 81, wherein the disease is a neurodegenerative disease.

Embodiment 83: The method of any of embodiments 80-82, wherein the disease is Alexander disease.

Embodiment 84: The method of any of embodiments 80-83, wherein at least one symptom or hallmark of the disease is ameliorated.

Embodiment 85: The method of embodiment 84, wherein the symptom or hallmark is any of motor delays, cognitive delays, paroxysmal deterioration, seizures, vomiting, swallowing difficulties, ataxic gait, palatal myoclonus, autonomic dysfunction, or the presence of intra-astrocytic inclusions called Rosenthal fibers.

Embodiment 86: The method of am of embodiments 79-85, wherein the pharmaceutical composition is administered to the central nervous system or systemically.

Embodiment 87: The method of embodiment 86, wherein the pharmaceutical composition is administered to the central nervous system and systemically.

Embodiment 88: The method of any of embodiments 80-87, wherein the pharmaceutical composition is administered any of intrathecally, systemically, subcutaneously, or intramuscularly.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-$OCH_3$ ("OMe" or "O-methyl"), and 2'-$O(CH_2)_2OCH$ ("MOE" or "O-methoxyethyl"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, O—$C_1$-$C_{10}$ alkyl, O—$C_1$-$C_{10}$ substituted alkyl, S-alkyl, $N(R_m)$-alkyl, O-alkenyl, S-alkenyl, $N(R_m)$-alkenyl. O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl, and the 2'-substituent groups described in Cook et al. U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted non-bicyclic modified nucleoside comprises a sugar moiety comprising a non-bridging 2'-substituent group selected from: F, $NH_2$, $N_3$, $OCF_3$. $OCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)—N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted non-bicycic modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_{20}N(CH_3)_2$, $O(CH_2)_2O(CH_2)_2N(CH_3)_2$, and $OCH_2C(=O)—N(H)CH_3$ ("NMA").

In certain embodiments, a 2'-substituted non-bicyclic modified nucleoside comprises a sugar moiety comprising a non-bridging 2'-substituent group selected from: F, OCH, and $OCH_2CH_2OCH_3$.

In certain embodiments, modified furanosyl sugar moieties and nucleosides incorporating such modified furanosyl sugar moieties are further defined by isomeric configuration.

For example, a 2'-deoxyfuranosyl sugar moiety may be in seven isomeric configurations other than the naturally occurring pi-D-deoxyribosyl configuration. Such modified sugar moieties are described in, e.g., WO 2019/157531, incorporated by reference herein. A 2'-modified sugar moiety has an additional stereocenter at the 2'-position relative to a 2'-deoxyfuranosyl sugar moiety; therefore, such sugar moieties have a total of sixteen possible isomeric configurations, 2'-modified sugar moieties described herein are in the 1-D-ribosyl isomeric configuration unless otherwise specified.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt"), 4'-$CH_2$—$CH_2$-2', 4'-$CH_2$—N(R)-2', 4'-CH $(CH_2OCH_3)$-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4'-$CH_2$—$N(OCH_3)$-2' and analogs thereof (see, e.g., Prakash et al., U.S. Pat. No. 8,278,425), 4'-$CH_2$—O—$N(CH_3)$-2' (see, e.g., Allerson et al., U.S. Pat. No. 7,696,345 and Allerson et al., U.S. Pat. No. 8,124,745), 4'-$CH_2$—$C(H)(CH_3)$-2' (see, e.g., Zhou, et al., *J. Org. Chem.,* 2009, 74, 118-134), 4'-$CH_2$—$C(=CH_2)$-2' and analogs thereof (see e.g., Seth et al., U.S. Pat. No. 8,278,426), 4'-$C(R_aR_b)$—N(R)—O-2', 4'-$C(R_aR_b)$—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —$[C(R_a)(R_b)]_n$—, —$[C(R_a)(R_b)]_n$—O—, —$C(R_a)$=$C(R_b)$C—, $C(R_a)$=N—, —C(=$NR_a$)—, —C(=O)—, —C(=S)—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$alicyclic radical, halogen, $OJ_1$, $NJ_1J_2$, $SJ_1$, $N_3$, $COOJ_1$, acyl (C(=O)—H), substituted acyl, CN, sulfonyl $(S(=O)_2$-$J_1)$, or sulfoxy (S(=O)-$J_1$); and each $J_1$ and $J_2$ is, independently. H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research,* 1997, 25(22), 44294443, Albaek et al., *J. Org. Chem.,* 2006, 71, 7731-7740, Singh et al. *Chem. Commun.,* 1998, 4, 455-456: Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039: Srivastava et al., *J. Am. Chem. Soc.,* 2007, 129, 8362-8379; Wengel et al. U.S. Pat. No. 7,053,207: Imanishi et al., U.S. Pat. No. 6,268,490; Imanishi et al. U.S. Pat. No. 6,770,748; Imanishi et al. U.S. RE44,779: Wengel et al., U.S. Pat. No. 6,794,499; Wengel et al., U.S. Pat. No. 6,670,461: Wengel et al., U.S. Pat. No. 7,034,133; Wengel et al., U.S. Pat. No. 8,080,644; Wengel et al., U.S. Pat. No. 8,034,909: Wengel et al. U.S. Pat. No. 8,153,365: Wengel et al., U.S. Pat. No. 7,572,582; Ramasamy et al. U.S. Pat. No. 6,525,191; Torsten et al., WO 2004/106356; Wengel et al., WO 1999/014226; Seth et al. WO 2007/134181; Seth et al., U.S. Pat. No. 7,547,684; Seth et al. U.S. Pat. No. 7,666,854; Seth et al., U.S. Pat. No. 8,088,746; Seth et al. U.S. Pat. No. 7,750,131: Seth et al., U.S. Pat. No. 8,030,467; Seth et al., U.S. Pat. No. 8,268,980: Seth et al., U.S. Pat. No. 8,546,556; Seth et al., U.S. Pat. No. 8,530,640; Migawa et al. U.S. Pat. No. 9,012,421: Seth et al. U.S. Pat. No. 8,501,805; and U.S. Patent Publication Nos. Allerson et al. US2008/0039618 and Migawa et al. US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

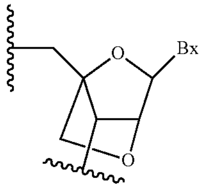

LNA (β-D-configuration) bridge = 4'-$CH_2$—O-2'

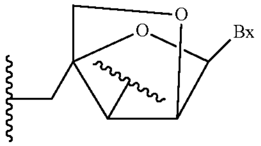

*α*-L-LNA (α-L-configuration) bridge = 4'-$CH_2$—O-2'

α-L-methyleneoxy (4'-$CH_2$—O-2') or α-L-LNA bicyclic nucleosides have been incorporated into oligonucleotides that showed antisense activity (Frieden et al., *Nucleic Acid Research,* 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see. e.g., Bhat et al. U.S. Pat. No. 7,875,733 and Bhat et al. U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

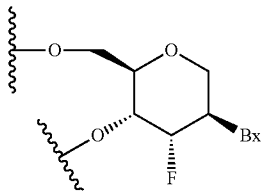

F-HNA ("F-HNA", see e.g. Swayze et al., U.S. Pat. No. 8,088,904; Swayze et al. U.S. Pat. No. 8,440,803; Swayze et al. U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

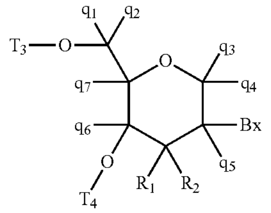

wherein, independently, for each of the modified THP nucleosides:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H.

In certain embodiments, at least one of $q_1$, $q_2$, $q_3$, $q_4$, $q_5$, $q_6$ and $q_7$ is other than H, In certain embodiments, at least one of $q_1$, $q_2$, $q_3$, $q_4$, $q_5$, $q_6$ and $q_7$ is methyl. In certain embodiments, modified THP nucleosides are provided wherein one of R, and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al. Biochemistry, 2002, 41, 45034510 and Summerton et al., U.S. Pat. No. 5,698,685; Summerton et al., U.S. Pat. No. 5,166,315; Summerton et al. U.S. Pat. No. 5,185,444; and Summerton et al., U.S. Pat. No. 5,034,506). As used here, the term "morpholino" means a sugar surrogate having the following structure:

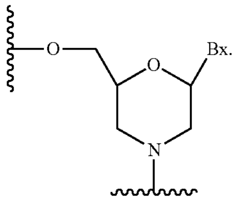

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleosides comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2. N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($-C\equiv C-CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrvlguanine, 4-N-benzoylcytosine, 4-N-benzoyluracil, 5-methyl 4-N-benzoylcytosine, 5-methyl 4-N-benzoylumcil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp).

Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz J. I., Ed., John Wiley & Sons, 1990, 858-859: Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442443.

Publications that teach the preparation of certain of the above noted modified nucleobases as well as other modified nucleobases include without limitation. Manoharan et al., US2003/0158403; Manoharan et al. US2003/0175906; Dinh et al., U.S. Pat. No. 4,845,205: Spielvogel et al., U.S. Pat. No. 5,130,302; Rogers et al. U.S. Pat. No. 5,134,066; Bischofberger et al., U.S. Pat. No. 5,175,273: Urdea et al., U.S. Pat. No. 5,367,066: Benner et al. U.S. Pat. No. 5,432, 272: Matteucci et al. U.S. Pat. No. 5,434,257: Gmeiner et al., U.S. Pat. No. 5,457,187; Cook et al., U.S. Pat. No. 5,459, 255; Froehler et al., U.S. Pat. No. 5,484,908; Matteucci et al., U.S. Pat. No. 5,502,177; Hawkins et al. U.S. Pat. No. 5,525,711; Haralambidis et al., U.S. Pat. No. 5,552,540; Cook et al., U.S. Pat. No. 5,587,469; Froehler et al. U.S. Pat. No. 5,594,121: Switzer et al. U.S. Pat. No. 5,596,091; Cook et al., U.S. Pat. No. 5,614,617; Froehler et al., U.S. Pat. No. 5,645,985: Cook et al., U.S. Pat. No. 5,681,941; Cook et al., U.S. Pat. No. 5,811,534: Cook et al., U.S. Pat. No. 5,750, 692; Cook et al., U.S. Pat. No. 5,948,903: Cook et al., U.S. Pat. No. 5,587,470; Cook et al., U.S. Pat. No. 5,457,191: Matteucci et al., U.S. Pat. No. 5,763,588: Froehler et al., U.S. Pat. No. 5,830,653; Cook et al., U.S. Pat. No. 5,808, 027: Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphodiesters, which contain a phosphodiester bond ("$P(O_2)=O$") (also referred to as unmodified or naturally occurring linkages), phosphotriesters, methylphosphonates, phosphoramidates, phosphorothioates ("$P(O_2)=S$"), and phosphorodithioates ("HS—P=S"). Representative non-phosphorus containing internucleoside linking groups include but are not limited to methylenemethylimino ($—CH_2—N(CH_3)—O—CH_2—$), thiodiester, thionocarbamate ($—O—C(=O)(NH)—S—$); siloxane ($—O—SiH_2—O—$); and N,N'-dimethylhydrazine ($—CH_2—N(CH_3)—N(CH_3)—$). Modified internucleoside linkages, compared to naturally occurring phosphodiester internucleoside linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate internucleoside linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate internucleoside linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkage in a particular, independently selected stereochemical configuration. In certain embodiments, the particular configuration of the particular phosphorothioate internucleoside linkage is present in at least 65% of the molecules in the population. In certain embodiments, the particular configuration of the particular phosphorothioate internucleoside linkage is present in at least 70% of the molecules in the population. In certain embodiments, the particular configuration of the particular phosphorthioate internucleoside linkage is present in at least 80% of the molecules in the population. In certain embodiments, the particular configuration of the particular phosphorothioate internucleoside linkage is present in at least 90% of the molecules in the population. In certain embodiments, the particular configuration of the particular phosphorothioate internucleoside linkage is present in at least 99% of the molecules in the population. Such chirally enriched populations of modified oligonucleotides can be generated using synthetic methods known in the art. e.g., methods described in Oka et al., *JACS* 125, 8307 (2003). Wan et al. *Nuc. Acid. Res.* 42, 13456 (2014), and WO 2017/015555. In certain embodiments, a population of modified oligonucleotides is enriched for modified oligonucleotides having at least one indicated phosphoothioate in the (Sp) configuration. In certain embodiments, a population of modified oligonucleotides is enriched for modified oligonucleotides having at least one phosphothioate in the (Rp) configuration. In certain embodiments, modified oligonucleotides comprising (Rp) and/or (Sp) phosphorothioates comprise one or more of the following formulas, respectively, wherein "B" indicates a nucleobase:

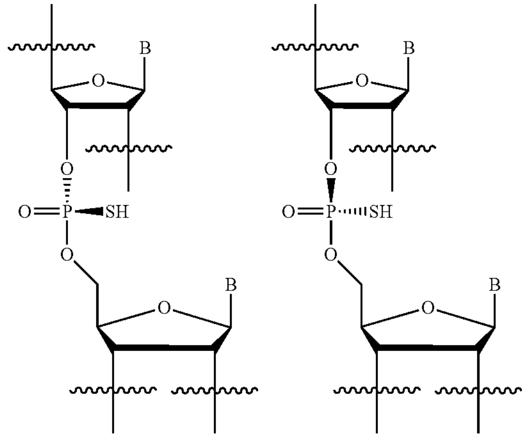

($R_p$) ($S_p$)

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates. MMI (3'-$CH_2$—$N(CH_3)$—O-5'), amide-3 (3'-$CH_2$—C(═O)—N(H)-5), amide 4 (3'-$CH_2$—N(H)—C(═O)-5'), formacetal (3'-O—$CH_2$—O-5'), methoxypropyl (MOP), and thioformacetal (3'-S—$CH_2$—O-5'). Further neutral internucleoside linkages include nonionic linkages comprising siloxane (di alkylsiloxane), carboxylate ester, carboxamide, sulfide, sulfonate ester and amides (see for example: *Carbohydrate Modifications in Antisense Research*; Y. S. Sanghvi and P. D. Cook, Eds., ACS Symposium Series 580: Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or portion thereof in a defined pattern or sugar motif. In certain instances, such sugar motifs include but are not limited to any of the sugar modifications discussed herein.

In certain embodiments, modified oligonucleotides have a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap.

Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-6 nucleosides. In certain embodiments, each nucleoside of each wing of a gapmer comprises a modified sugar moiety. In certain embodiments, at least one nucleoside of each wing of a gapmer comprises a modified sugar moiety. In certain embodiments, at least two nucleosides of each wing of a gapmer comprises a modified sugar moiety. In certain embodiments, at least three nucleosides of each wing of a gapmer comprises a modified sugar moiety. In certain embodiments, at least four nucleosides of each wing of a gapmer comprises a modified sugar moiety. In certain embodiments, at least five nucleosides of each wing of a gapmer comprises a modified sugar moiety.

In certain embodiments, the gap of a gapmer comprises 7-12 nucleosides. In certain embodiments, each nucleoside of the gap of a gapmer comprises a 2-deoxyribosyl sugar moiety. In certain embodiments, each nucleoside of the gap of a gapmer comprises a 2'-β-D-deoxyribosyl sugar moiety. In certain embodiments, at least one nucleoside of the gap of a gapmer comprises a modified sugar moiety. In certain embodiments, at least one nucleoside of the gap of a gapmer comprises a 2'-OMe sugar moiety.

In certain embodiments, the gapmer is a deoxy gapmer. In certain embodiments, the nucleosides on the gap side of each wing/gap junction comprise 2'-β-D-deoxyribosyl sugar moieties and the nucleosides on the wing sides of each wing/gap junction comprise modified sugar moieties. In certain embodiments, each nucleoside of the gap comprises a 2-deoxyribosyl sugar moiety. In certain embodiments, each nucleoside of each wing of a gapmer comprises a modified sugar moiety. In certain embodiments, one nucleoside of the gap comprises a modified sugar moiety and each remaining nucleoside of the gap comprises a 2-deoxyribosyl sugar moiety.

In certain embodiments, modified oligonucleotides comprise or consist of a portion having a fully modified sugar motif. In such embodiments, each nucleoside of the fully modified portion of the modified oligonucleotide comprises a modified sugar moiety. In certain embodiments, each nucleoside of the entire modified oligonucleotide comprises a modified sugar moiety. In certain embodiments, modified oligonucleotides comprise or consist of a portion having a fully modified sugar motif, wherein each nucleoside within the fully modified portion comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprises a 2'-β-D-deoxyribosyl sugar moiety. Thus, a 5-10-5 MOE gapmer consists of 5 linked 2'-MOE nucleosides in the 5'-wing, 10 linked 2'-β-D-deoxynucleosides in the gap, and 5 linked 2'-MOE nucleosides in the 3'-wing. A 3-10-3 cEt gapmer consists of 3 linked cEt nucleosides in the 5'-wing, 10 linked 2'-β-D-deoxynucleosides in the gap, and 3 linked cEt nucleosides in the 3'-wing. A 5-8-5 gapmer consists of 5 linked nucleosides comprising a modified sugar moiety in the 5'-wing, 8 linked 2'-deoxynucleosides in the gap, and 5 linked nucleosides comprising a modified sugar moiety in the 3'-wing. A mixed wing gapmer has at least two different modified sugars in the 5' and/or 3' wing. A 5-8-5 or 5-8-4 mixed wing gapmer has at least two different modified sugar moieties in the 5'- and/or the 3'-wing.

In certain embodiments, modified oligonucleotides are 5-10-5 MOE gapmers. In certain embodiments, modified oligonucleotides are 4-10-6 MOE gapmers. In certain embodiments, modified oligonucleotides are 6-10-4 MOE gapmers. In certain embodiments, modified oligonucleotides are 5-8-5 MOE gapmers. In certain embodiments, modified oligonucleotides are X-Y-Z MOE gapmers, wherein X and Z are independently selected from 1, 2, 3, 4, 5, or 6 and Y is 7, 8, 9, 10, or 11.

In certain embodiments, modified oligonucleotides have the following sugar motif (5' to 3'): meeemddddddddddnmmmmm, wherein 'd' represents a 2'-deoxyribosyl sugar moiety, 'e' represents a 2'-MOE sugar moiety, and 'in' represents a 2'-OMe sugar moiety.

2. Certain Nucleobase Motifs

In certain embodiments, oligonucleotides comprise modified and/or unmodified nucleobases arranged along the oligonucleotide or portion thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines. In certain embodiments, all of the cytosine nucleobases are 5-methylcytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of the nucleoside is a 2'-deoxyribosyl sugar moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P═O). In certain embodiments, each internucleoside linking group of a modified oligonucleotide is a phosphorothioate internucleoside linkage (P═S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester internucleoside linkage is not a terminal internucleoside linkage, and the remaining internucleoside linkages are phosphorothioate internucleoside linkages. In certain such embodiments, all of the phosphorothioate internucleoside linkages are stereorandom. In certain embodiments, all of the phosphorothioate internucleoside linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

In certain embodiments, modified oligonucleotides have an internucleoside linkage motif of sooosssssssssssooss, wherein each "s" represents a phosphorothioate internucleoside linkage and each "o" represents a phosphodiester internucleoside linkage. In certain embodiments, modified oligonucleotides have an internucleoside linkage motif of (5' to 3'): sooooossssssssssoss, wherein each "s" represents a phosphorothioate internucleoside linkage and each "o" represents a phosphodiester internucleoside linkage. In certain embodiments, modified oligonucleotides have an internucleoside linkage motif of (5' to 3'): soooossssssssssooss, wherein each "s" represents a phosphorothioate internucleoside linkage and each "o" represents a phosphodiester internucleoside linkage. In certain embodiments, modified oligonucleotides have an internucleoside linkage motif of (5' to 3'):sooosssssssssooss, wherein each "s" represents a phosphorothioate internucleoside linkage and each "o" represents a phosphodiester internucleoside linkage.

In certain embodiments, modified oligonucleotides have an internucleoside linkage motif of (5' to 3'): sooossssssssssoooss, wherein each "s" represents a phosphorothioate internucleoside linkage and each "o" represents a phosphodiester internucleoside linkage. In certain embodiments, modified oligonucleotides have an internucleoside linkage motif of (5' to 3'): sooosssssssssssssss, wherein each "s" represents a phosphorothioate internucleoside linkage and each "o" represents a phosphodiester internucleoside linkage.

C. Certain Lengths

It is possible to increase or decrease the length of an oligonucleotide without eliminating activity. For example, in Woolf et al. Proc. Natl. Acad. Sci. USA 89:7305-7309, 1992) a series of oligonucleotides 13-25 nucleobases in length were tested for their ability to induce cleavage of a target nucleic acid in an oocyte injection model. Oligonucleotides 25 nucleobases in length with 8 or 11 mismatch bases near the ends of the oligonucleotides were able to direct specific cleavage of the target nucleic acid, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50: provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

D. Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for i-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a portion of an oligonucleotide has a nucleobase sequence that is complementary to a second oligonucleotide or an identified reference nucleic acid, such as a target nucleic acid. In certain embodiments, the nucleobase sequence of a portion or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, abasic nucleosides, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc.

Natl. Acad. Sci. USA, 1989, 86, 6553-6556), cholic acid (Manoharan et al., *Bioorg. Med Chem. Lett.,* 1994, 4, 1053-1060), a thioether, e.g., hexyl-S-tritylthiol (Manoharan et al., *Ann. N.Y. Acad Sci.,* 1992, 660, 306-309: Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoards et al., *EMBO J.*, 1991, 10, 1111-1118; Kabanov et al., *FEBS Lett.*, 1990, 259, 327-330; Svinarchuk et al. *Biochimie*, 1993, 75, 49-54), a phospholipid, e.g., di-hexadecyl-rac-glycerol or triethyl-ammonium 1,2-di-O-hexadecyl-mc-glycero-3-H-phosphonate (Manoharan et al. *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al. *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

In certain embodiments, conjugate groups may be selected from any of a C22 alkyl, C20 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, C5 alkyl, C22 alkenyl, C20 alkenyl, C16 alkenyl, C10 alkenyl, C21 alkenyl, C19 alkenyl, C18 alkenyl, C15 alkenyl, C14 alkenyl, C13 alkenyl, C12 alkenyl, C11 alkenyl, C9 alkenyl, C8 alkenyl, C7 alkenyl, C6 alkenyl, or C5 alkenyl.

In certain embodiments, conjugate groups may be selected from any of C22 alkyl, C20 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, and C5 alkyl, where the alkyl chain has one or more unsaturated bonds.

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, lipophilic groups, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active dung substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties. e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate or phosphodiester internucleoside linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphodiester internucleoside linkage and covalently attached to the remainder of the conjugate linker or conjugate moiety by a phosphate or phosphorothioate internucleoside linkage. In certain such embodiments, the cleavable moiety is 2'-deoxyadenosine.

3. Cell-Targeting Moieties

In certain embodiments, a conjugate group comprises a cell-targeting moiety. In certain embodiments, a conjugate group has the general formula:

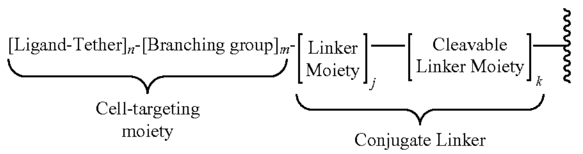

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

B. Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphonates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a portion complementary to a target nucleic acid and a second oligomeric compound having a portion complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybrdization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or subject.

V. Certain Target Nucleic Acids

In certain embodiments, oligomeric compounds comprise or consist of an oligonucleotide comprising a portion that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target nucleic acid is a mature mRNA. In certain embodiments, the target nucleic acid is a pre-mRNA. In certain embodiments, the target region is entirely within an intron. In certain embodiments, the target region spans an intron/exon junction. In certain embodiments, the target region is at least 50% within an intron.

A. Complementarity/Mismatches to the Target Nucleic Acid

It is possible to introduce mismatch bases without eliminating activity. For example, Gautschi et al (J. Natl. Cancer Inst, 93:463471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28- and 42-nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a portion that is 00%, or fully complementary to a target nucleic acid. In certain embodiments, the portion of full complementarity is 6, 7, 8, 9, 10, 11, 12, 13, 14, 15, 16, 17, 18, 19, 20, 21, 22, 23, or 24 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, 8, 9, 10, or 11 from the 5'-end of the gap region. In certain embodiments, the mismatch is at position 1, 2, 3, 4, 5, or 6 from the 5'-end of the 5' wing region or the 3' wing region.

B. GFAP

In certain embodiments, oligomeric compounds comprise or consist of an oligonucleotide that is complementary to a target nucleic acid, wherein the target nucleic acid is a GFAP nucleic acid. In certain embodiments, GFAP nucleic acid has the sequence set forth in SEQ ID NO: 1 (GENBANK Accession No. NM_002055.4), SEQ ID NO: 2 (GENBANK Accession No. NC_000017.11 truncated from nucleotides 44903001 to 44919000), or SEQ ID NO: 3 (GENBANK Accession No. NM_001131019.2).

In certain embodiments, contacting a cell with an oligomeric compound complementary to any of SEQ ID NO: 1-3 reduces the amount of GFAP RNA and in certain embodiments reduces the amount of GFAP protein. In certain embodiments, the oligomeric compound consists of a modified oligonucleotide. In certain embodiments, contacting a cell with an oligomeric compound complementary to any of SEQ ID NO: 1-3 reduces the amount of GFAP RNA in a cell, and in certain embodiments reduces the amount of GFAP protein in a cell. In certain embodiments, the cell is in vitro. In certain embodiments, the cell is in a subject. In certain embodiments, the oligomeric compound consists of a modified oligonucleotide. In certain embodiments, contacting a cell in a subject with an oligomeric compound complementary to any of SEQ ID NO: 1-3 ameliorates one or more symptom or hallmark of a leukodystrophy. In certain embodiments, the leukodystrophy is AxD. In certain embodiments, the symptom or hallmark is selected from motor delays, cognitive delays, paroxysmal deterioration, seizures, vomiting, swallowing difficulties, ataxic gait, palatal myoclonus, autonomic dysfunction, and presence of intra-astrocytic inclusions called Rosenthal fibers.

In certain embodiments, an oligomeric compound complementary to any of SEQ ID NO: 1-3 is capable of reducing the detectable amount of GFAP RNA in vitro by at least 10%, at least 20%, at least 30%, at least 40%, at least 50%, at least 60%, at least 70%, at least 80%, or at least 90% when administered according to the standard cell assay. In certain embodiments, an oligomeric compound complementary to SEQ ID NO: 1, SEQ ID NO: 2915, or SEQ ID NO: 2916 is capable of decreasing the amount of GFAP in vitro by at least 10%, at least 20%, at least 30%, at least 40%, at least 50%, at least 60%, at least 70%, at least 80%, or at least 90% when administered according to the standard in vitro assay. In certain embodiments, an oligomeric compound complementary to SEQ ID NO: 1. SEQ ID NO: 2, or SEQ ID NO: 3 is capable of reducing the detectable amount of GFAP RNA in the CSF of a subject by at least 10%, at least 20%, at least 30%, at least 40%, at least 50%, at least 60%, at least 70%, at least 80%, or at least 90%. In certain embodiments, an oligomeric compound complementary to SEQ ID NO: 1, SEQ ID NO: 2, or SEQ ID NO: 3 is capable of decreasing the detectable amount of GFAP in the CSF of a subject by at least 10%, at least 20%, at least 30%, at least 40%, at least 50%, at least 60%, at least 70%, at least 80%, or at least 90%.

C. Certain Target Nucleic Acids in Certain Tissues

In certain embodiments, oligomeric compounds comprise or consist of an oligonucleotide comprising a portion that is complementary to a target nucleic acid, wherein the target nucleic acid is expressed in a pharmacologically relevant tissue. In certain embodiments, the pharmacologically relevant tissues are the cells and tissues that comprise the central nervous system (CNS). Such tissues include the brain and spinal cord. In certain embodiments, the pharmacologically relevant tissues include white matter tracts across the brain and spinal cord, such tissues include the corpus callosum, cortex, cerebellum, hippocampus, brain stem, striatum, and spinal cord. In certain embodiments, the pharmacologically relevant tissues include the cortex, cerebellum, hippocampus, brain stem, and spinal cord. In certain embodiments, the pharmacologically relevant cells are oligodendrocytes and oligodendrocyte progenitor cells. In certain embodiments, the pharmacologically relevant cells are Schwann cells or Schwann cell progenitors.

VI. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid ("artificial CSF" or "aCSF"). In certain embodiments, the artificial cerebrospinal fluid is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to a subject, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents comprising an oligomeric compound provided herein to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzil alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™: the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), intraneural, perineural, etc.). In certain of such embodiments, a pharmaceutical composition comprises a carrier and is formulated in aqueous solution, such as water or physiologically compatible buffers such as Hanks's solution. Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form. e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, or ionized and in association with a cation (salt) form, aqueous solutions of such compounds exist in equilibrium among such forms. For example, a phosphate linkage of an oligonucleotide in aqueous solution exists in equilibrium among free acid, anion and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or salt thereof" expressly includes all such forms that may be fully or partially protonated/de-protonated/in association with a cation. In certain instances, one or more specific cation is identified.

In certain embodiments, modified oligonucleotides or oligomeric compounds are in aqueous solution with sodium. In certain embodiments, modified oligonucleotides or oligomeric compounds are in aqueous solution with potassium. In certain embodiments, modified oligonucleotides or oligomeric compounds are in PBS. In certain embodiments, modified oligonucleotides or oligomeric compounds are in water. In certain such embodiments, the pH of the solution is adjusted with NaOH and/or HCl to achieve a desired pH.

Herein, certain specific doses are described. A dose may be in the form of a dosage unit. For clarity, a dose (or dosage unit) of a modified oligonucleotide or an oligomeric compound in milligrams indicates the mass of the free acid form of the modified oligonucleotide or oligomeric compound. As described above, in aqueous solution, the free acid is in equilibrium with anionic and salt forms. However, for the purpose of calculating dose, it is assumed that the modified oligonucleotide or oligomeric compound exists as a solvent-free, sodium-acetate free, anhydrous, free acid. For example, where a modified oligonucleotide or an oligomeric compound is in solution comprising sodium (e.g., saline), the modified oligonucleotide or oligomeric compound may be partially or fully de-protonated and in association with Na+ ions. However, the mass of the protons are nevertheless counted toward the weight of the dose, and the mass of the Na+ ions are not counted toward the weight of the dose. Thus, for example, a dose, or dosage unit, of 10 mg of Compound No. 1362458, equals the number of fully protonated molecules that weighs 10 mg. This would be equivalent to 10.47 mg of solvent-free, sodium acetate-free, anhydrous sodiated Compound No. 1362458. When an oligomeric compound comprises a conjugate group, the mass of the conjugate group is included in calculating the dose of such oligomeric compound. If the conjugate group also has an acid, the conjugate group is likewise assumed to be fully protonated for the purpose of calculating dose.

VII. Certain Compositions

1. Compound No. 1166998

In certain embodiments, Compound No. 1166998 is characterized as a 6-104 MOE gapmer having a sequence (from 5' to 3') of CAGTATTACCTCTACTAGTC (SEQ ID NO: 2905), wherein each of nucleosides 1-6 and 17-20 (from 5' to 3') are 2'-β-D-MOE nucleosides and each of nucleosides 7-16 are 2'-β-D-deoxynucleosides, wherein the internucleoside linkages between nucleosides 2 to 3, 3 to 4, 4 to 5, 5 to 6, 6 to 7, and 17 to 18 are phosphodiester internucleoside linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methylcytosine.

In certain embodiments, Compound No. 1166998 is represented by the following chemical notation: ${}^{m}C_{es}A_{eo}G_{eo}T_{eo}A_{eo}T_{eo}T_{ds}A_{ds}{}^{m}C_{ds}{}^{m}C_{ds}T_{ds}{}^{m}C_{ds}T_{ds}A_{ds}{}^{m}C_{ds}T_{ds}A_{eo}G_{es}T_{es}{}^{m}C_{e}$ (SEQ ID NO: 2905), wherein:

A=an adenine nucleobase, ${}^{m}C$=a 5-methylcytosine nucleobase,

G=a guanine nucleobase,

T=a thymine nucleobase, e=a 2'-β-D-MOE sugar moiety. d=a 2'-β-D-deoxyribosyl sugar moiety, s=a phosphorothioate internucleoside linkage, and o=a phosphodiester internucleoside linkage.

In certain embodiments, Compound No. 1166998 is represented by the following chemical structure:
(SEQ ID NO: 2905)
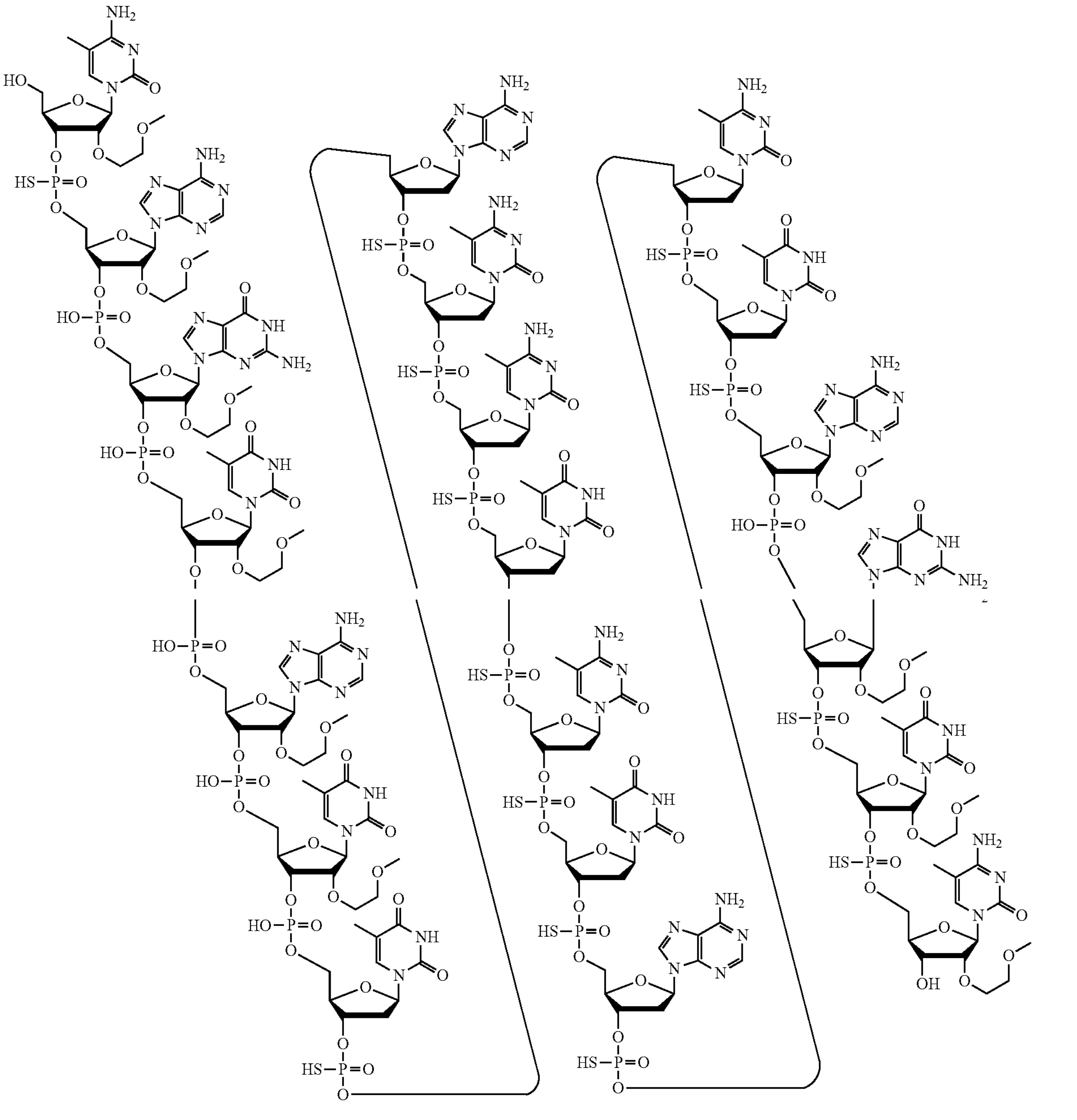

Structure 1. Compound No. 1166998
In certain embodiments, the sodium salt of Compound No. 1100998 is represented by the following chemical structure:
(SEQ ID NO: 2905)
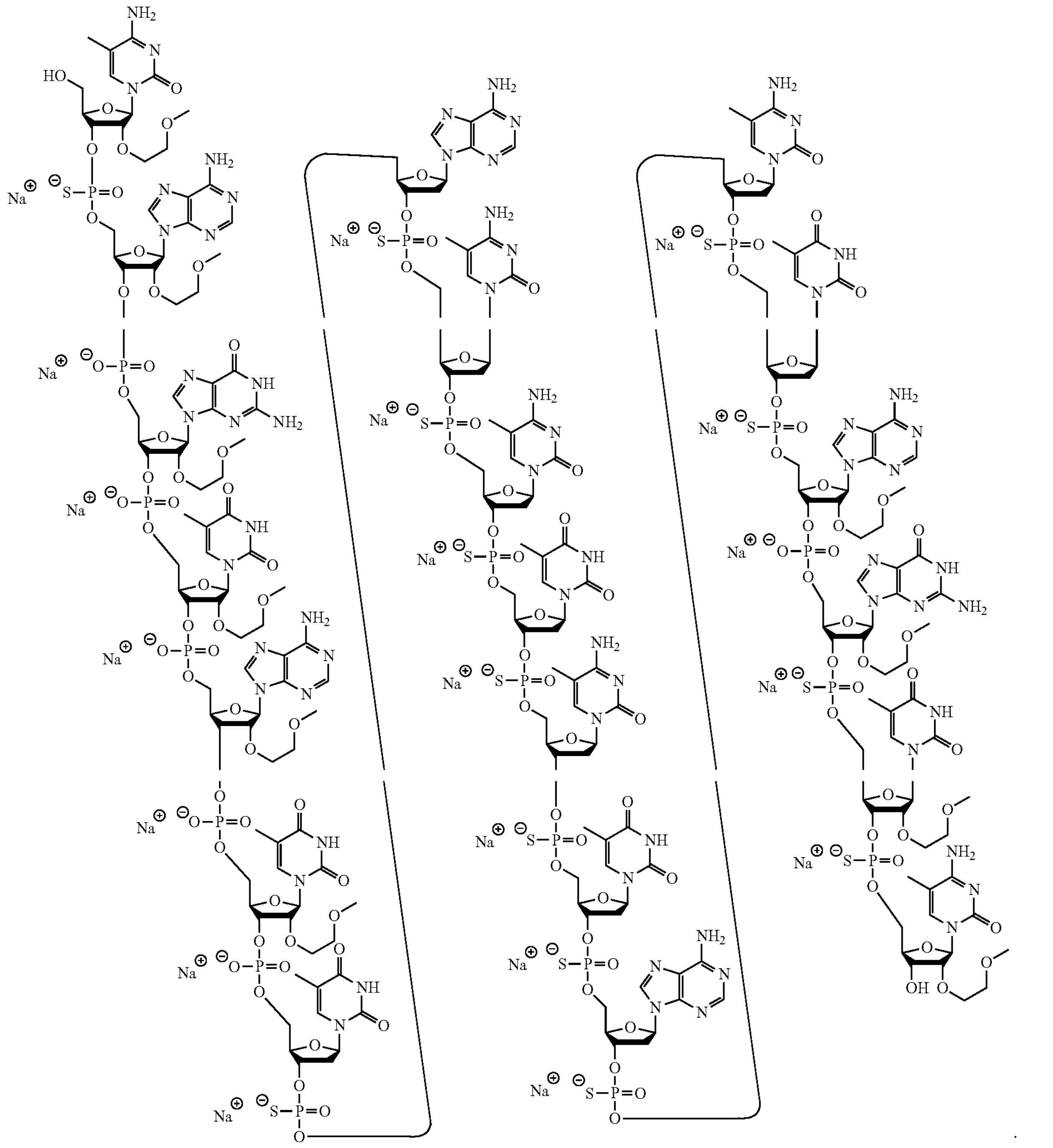

-continued

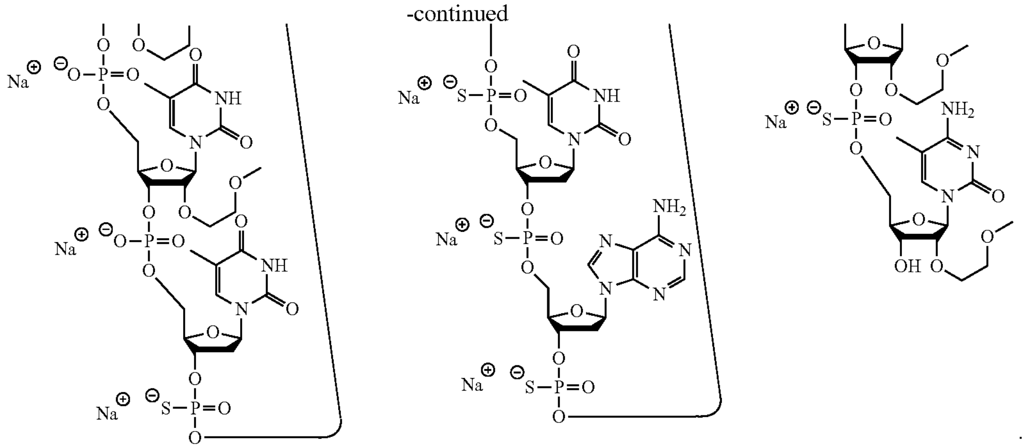

Structure 2. The sodium salt of Compound No. 1166998

2. Compound No. 1166985

In certain embodiments. Compound No. 1166985 is characterized as a 6-104 MOE gapmer having a sequence (from 5' to 3') of CACATTCACTAATATTTAAC (SEQ ID NO: 2904), wherein each of nucleosides 1-6 and 17-20 (from 5' to 3') are 2'-β-D-MOE nucleosides and each of nucleosides 7-16 are 2'-1-D-deoxynucleosides, wherein the internucleoside linkages between nucleosides 2 to 3, 3 to 4, 4 to 5, 5 to 6, 6 to 7, and 17 to 18 are phosphodiester internucleoside linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate internucleoside linkages, and wherein each cytosine is a 5-methylcytosine.

In certain embodiments, Compound No. 1166985 is represented by the following chemical notation: $^{m}C_{es}A_{eo}{}^{m}C_{eo}A_{eo}T_{eo}T_{eo}{}^{m}C_{ds}A_{ds}{}^{m}C_{ds}A_{ds}{}^{m}C_{ds}T_{ds}A_{ds}A_{ds}T_{ds}A_{ds}T_{ds}T_{ds}T_{ds}T_{eo}A_{es}A_{es}{}^{m}C_{e}$ (SEQ ID NO: 2904), wherein:

A=an adenine nucleobase.

$^{m}$C=a 5-methylcytosine nucleobase.

G=a guanine nucleobase,

T=a thymine nucleobase, e=a 2'-β-D-MOE sugar moiety, d=a 2'-β-D-deoxyribosyl sugar moiety, s=a phosphorothioate internucleoside linkage, and o=a phosphodiester internucleoside linkage.

In certain embodiments, Compound No. 1160985 is represented by the following chemical structure:

(SEQ ID NO: 2904)

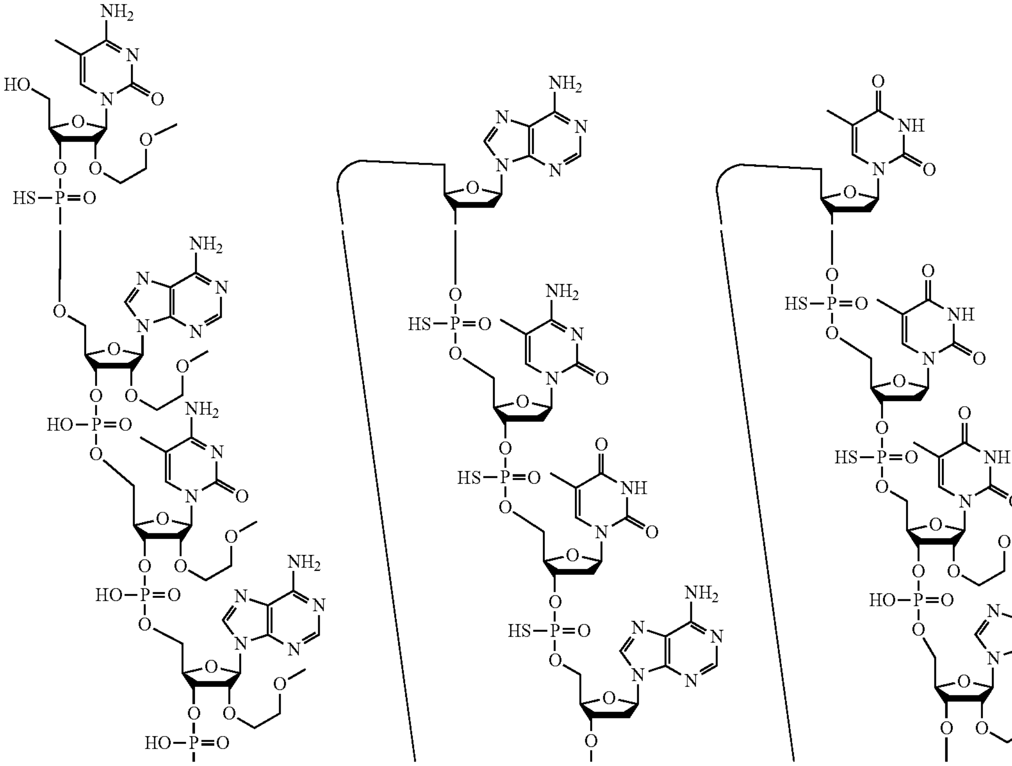

-continued
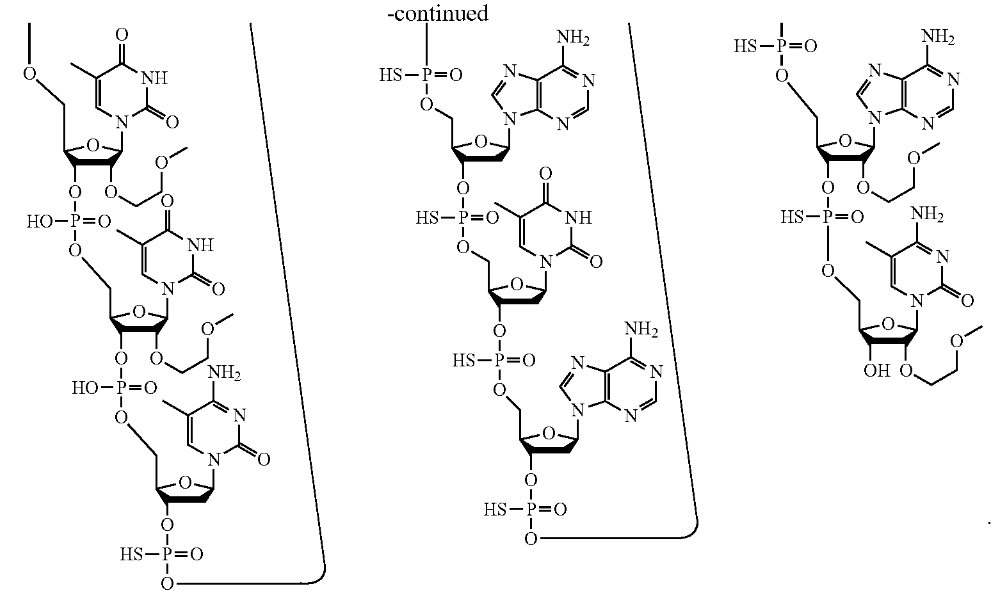
Structure 3. Compound No. 1166985
In certain embodiments, the sodium salt of Compound No. 1160985 is represented by the following chemical structure:
(SEQ ID NO: 2904)
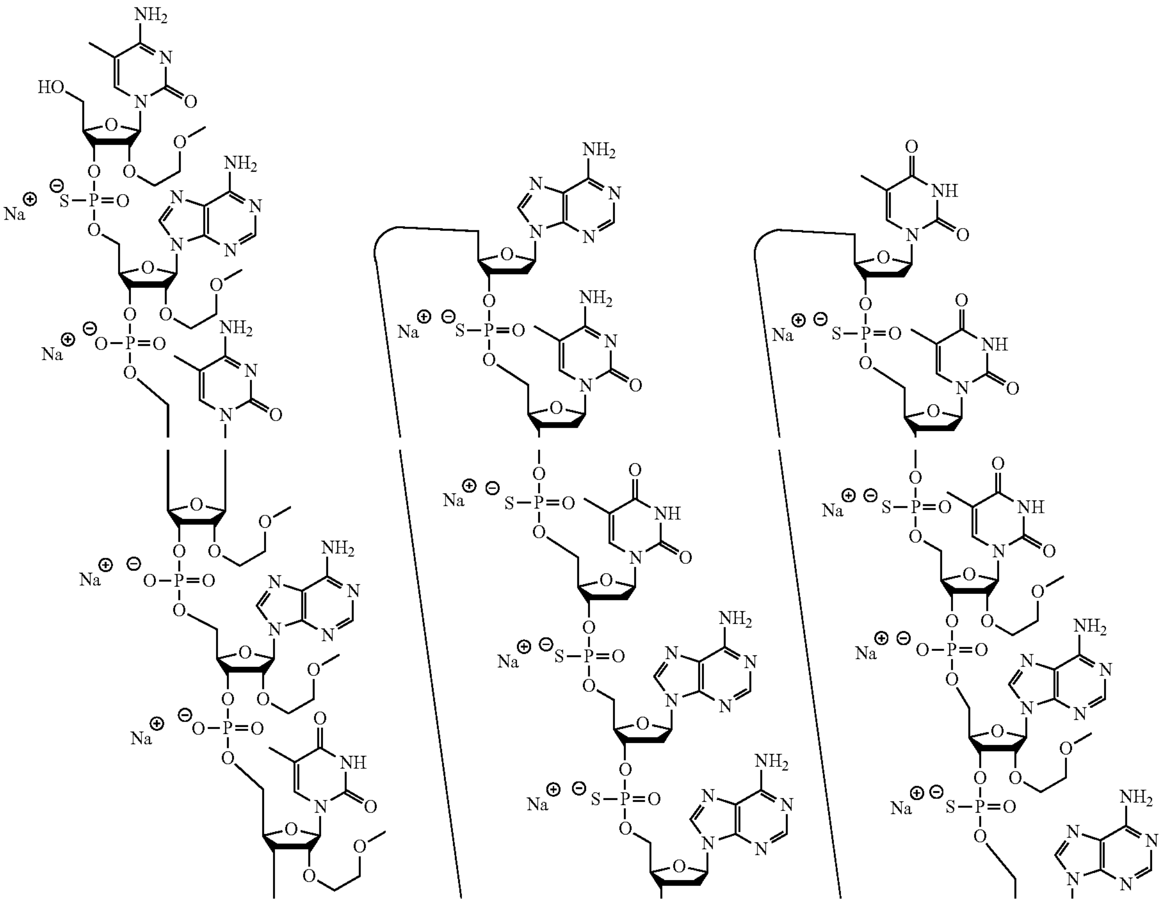

-continued

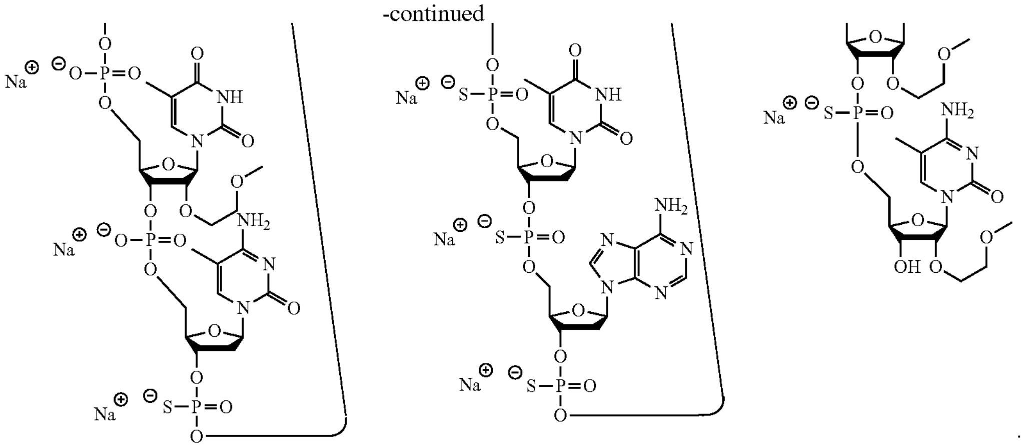

Structure 4. The sodium salt of Compound No. 1166985

3. Compound No. 1166954

In certain embodiments. Compound No. 1166954 is characterized as a 5-10-5 MOE gapmer having a sequence (from 5' to 3') of CCAGTGTCTTCACTTTGCTC (SEQ ID NO: 2903), wherein each of nucleosides 1-5 and 16-20 (from 5' to 3') are 2'-β-D-MOE nucleosides and each of nucleosides 6-15 are 2'-1-D-deoxynucleosides, wherein the internucleoside linkages between nucleosides 2 to 3, 3 to 4, 4 to 5, 5 to 6, 16 to 17, and 17 to 18 are phosphodiester internucleoside linkages and the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methylcytosine.

In certain embodiments, Compound No. 1166954 is represented by the following chemical notation: ${}^{m}C_{es}{}^{m}C_{eo}A_{eo}G_{eo}T_{eo}G_{ds}T_{ds}{}^{m}C_{ds}T_{ds}T_{ds}{}^{m}C_{ds}A_{ds}{}^{m}C_{ds}T_{ds}T_{ds}T_{eo}G_{eo}{}^{m}C_{es}T_{es}{}^{m}C_{e}$ (SEQ ID NO: 2903), wherein:

A=an adenine nucleobase, ${}^{m}C$=a 5-methylcytosine nucleobase,

G=a guanine nucleobase,

T=a thymine nucleobase, e=a 2'-β-D-MOE sugar moiety, d=a 2'-β-D-deoxyribosyl sugar moiety, s=a phosphorothioate internucleoside linkage, and o=a phosphodiester internucleoside linkage.

In certain embodiments, Compound No. 1160954 is represented by the following chemical structure:

(SEQ ID NO: 2903)

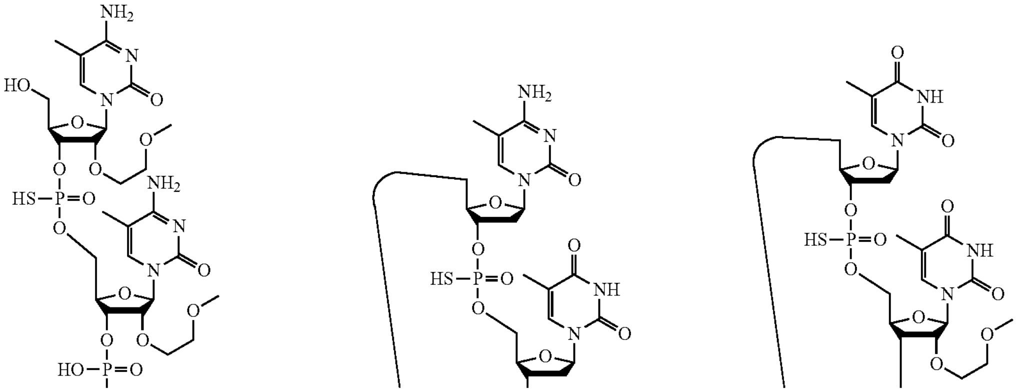

-continued
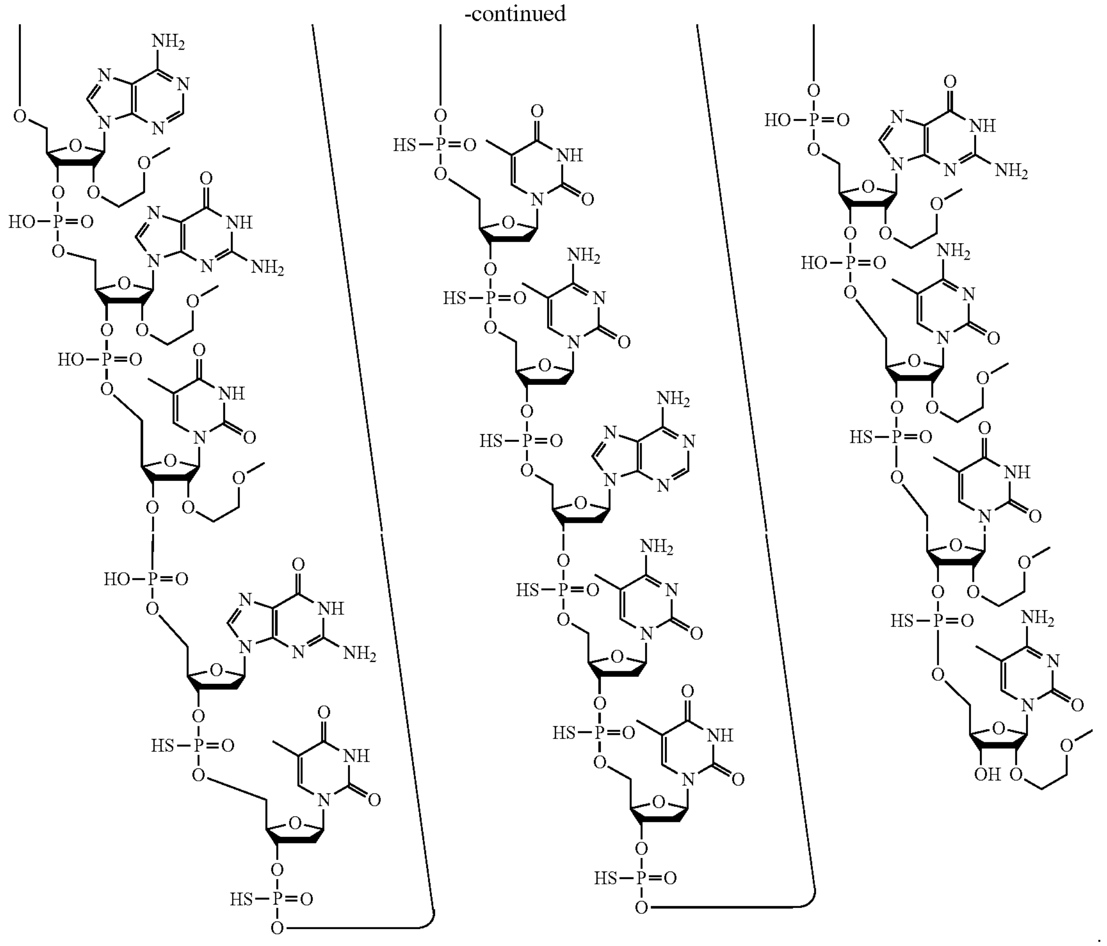
Structure 5: Compound No. 11669154
In certain embodiments, the sodium salt of Compound No. 1160954 is represented by the following chemical structure:
(SEQ ID NO: 2903)
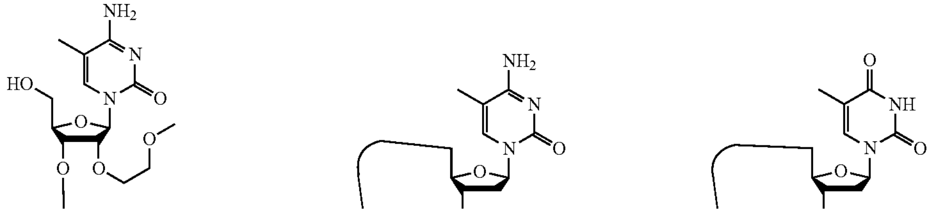

-continued

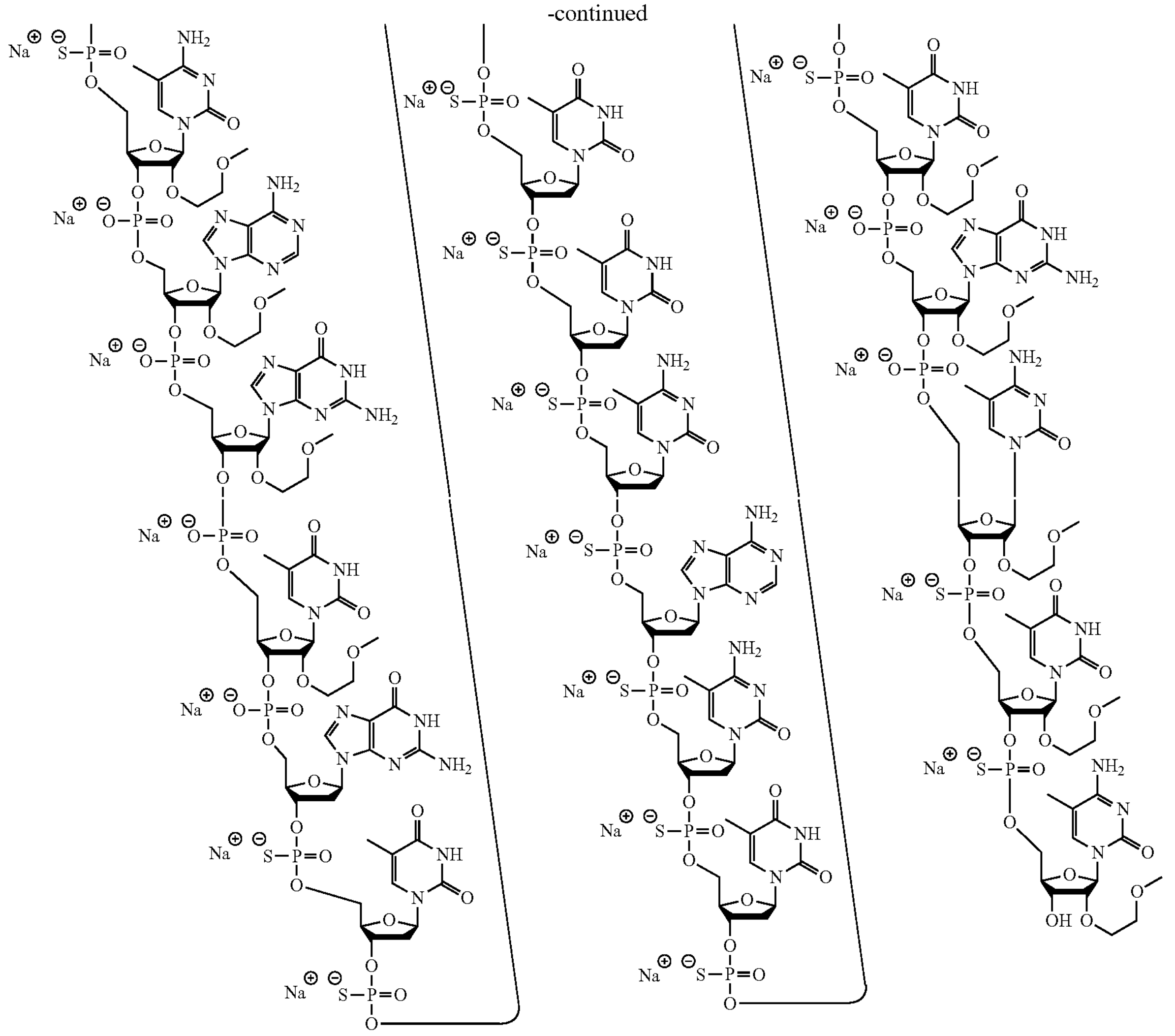

Structure 6: The sodium salt of Compound No. 1166914

4. Compound No. 1072813

In certain embodiments. Compound No. 1072813 is characterized as a 5-10-5 MOE gapmer having a sequence (from 5' to 3') of GCAACAGTTTCCATAACAAC (SEQ ID NO: 2902), wherein each of nucleosides 1-5 and 16-20 (from 5' to 3') are 2'-β-D-MOE nucleosides and each of nucleosides 6-15 are 2'-1-D-deoxynucleosides, wherein the internucleoside linkages between nucleosides 2 to 3, 3 to 4, 4 to 5, 16 to 17, and 17 to 18 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methylcytosine.

In certain embodiments, Compound No. 1072813 is represented by the following chemical notation: $G_{es}{}^{m}C_{eo}A_{eo}A_{eo}{}^{m}C_{es}A_{ds}G_{ds}T_{ds}T_{ds}T_{ds}{}^{m}C_{ds}{}^{m}C_{ds}A_{ds}T_{ds}A_{ds}A_{eo}{}^{m}C_{eo}A_{es}A_{es}{}^{m}C_{e}$ (SEQ ID NO: 2902), wherein:

A=an adenine nucleobase, $^{m}$C=a 5-methylcytosine nucleobase,

G=a guanine nucleobase,

T=a thymine nucleobase, e=a 2'-β-D-MOE sugar moiety, d=a 2'-β-D-deoxyribosyl sugar moiety, s=a phosphothioate internucleoside linkage, and o=a phosphodiester internucleoside linkage.

In certain embodiments, Compound No. 1072813 is represented by the following chemical structure:

(SEQ ID NO: 2902)
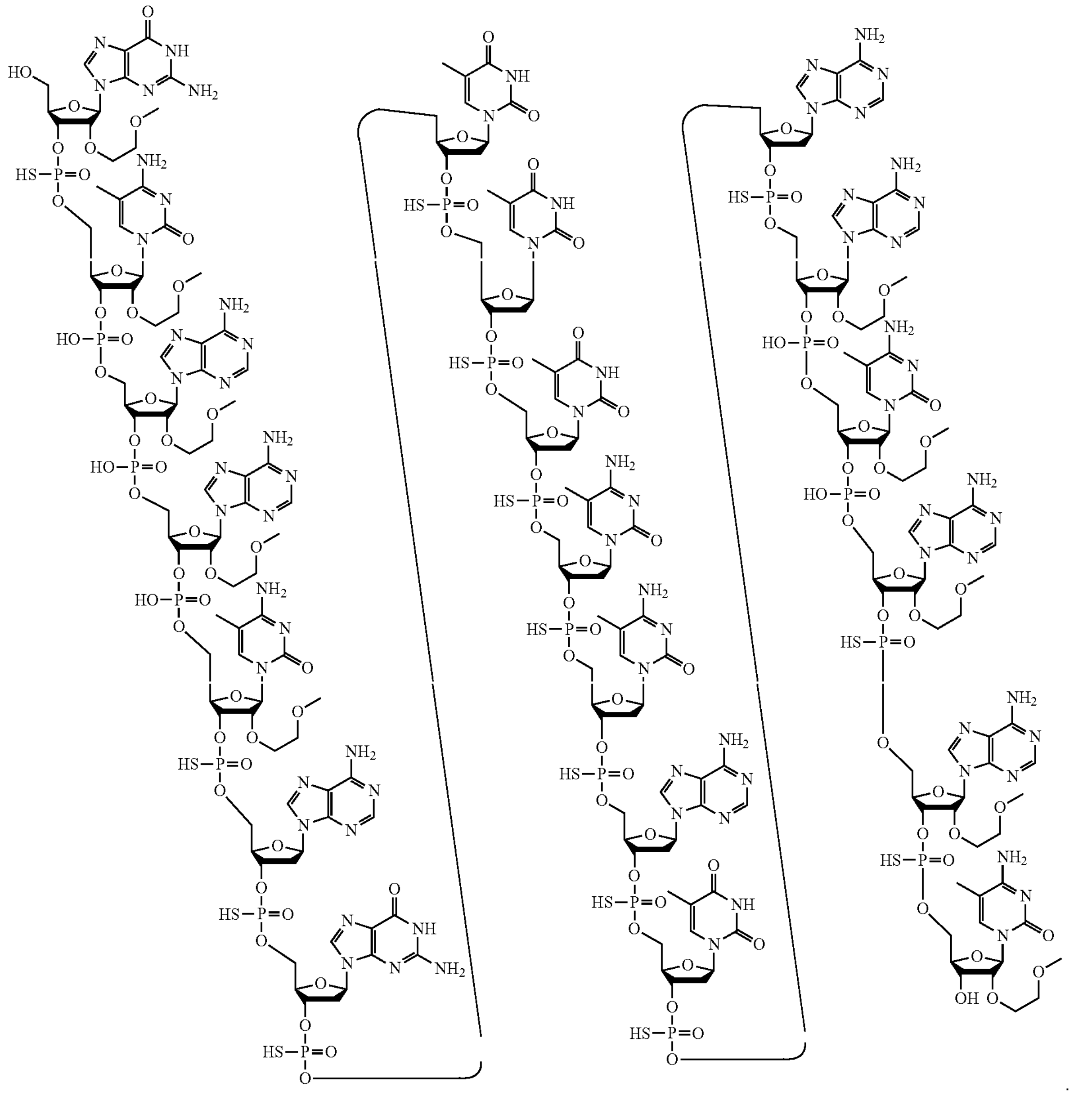
Structure 7: Compound No. 1072813
In certain embodiments, the sodium salt of Compound No. 1072813 is represented by the following chemical structure:

(SEQ ID NO: 2902)

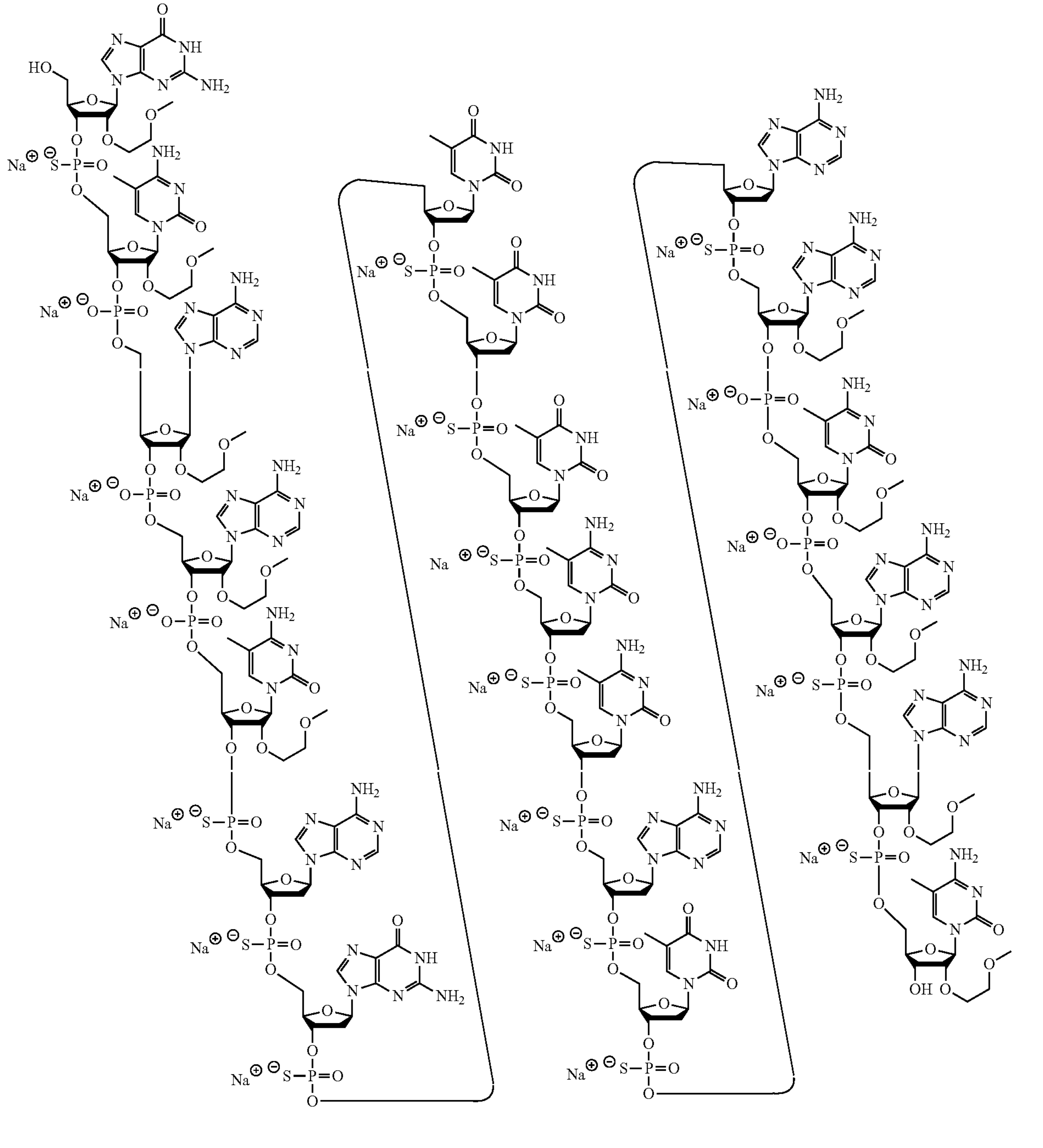

Structure 8: The sodium salt of Compound No. 1072813

5. Compound No. 1199983

In certain embodiments. Compound No. 1199983 is characterized as a 5-10-5 MOE gapmer having a sequence (from 5' to 3') of TGGTCCTAAATATTCTAGTC (SEQ ID NO: 2906), wherein each of nucleosides 1-5 and 16-20 (from 5' to 3') are 2'-β-D-MOE nucleosides and each of nucleosides 6-15 are 2'-1-D-deoxynucleosides, wherein the internucleoside linkages between nucleosides 2 to 3, 3 to 4, 4 to 5, 5 to 6, 16 to 17, and 17 to 18 are phosphodiester internucleoside linkages and the internucleoside linkages between nucleosides 1 to 2, 6 to 7, 7 to 8, 8 to 9, 9 to 10, 10 to 11, 11 to 12, 12 to 13, 13 to 14, 14 to 15, 15 to 16, 18 to 19, and 19 to 20 are phosphorothioate internucleoside linkages, and wherein each cytosine is a 5-methylcytosine.

In certain embodiments, Compound No. 1199983 is represented by the following chemical notation: $T_{es}G_{eo}G_{eo}$-$T_{eo}{}^{m}C_{eo}{}^{m}C_{ds}T_{ds}A_{ds}A_{ds}A_{ds}T_{ds}A_{ds}T_{ds}T_{ds}T_{ds}{}^{m}C_{ds}T_{eo}A_{e}$-${}_{o}G_{es}T_{es}{}^{m}C_{e}$ (SEQ ID NO: 2906), wherein:

A=an adenine nucleobase, ${}^{m}C$=a 5-methylcytosine nucleobase,

G=a guanine nucleobase,

T=a thymine nucleobase, e=a 2'-β-D-MOE sugar moiety, d=a 2'-β-D-deoxyribosyl sugar moiety, s=a phosphorothioate internucleoside linkage, and o=a phosphodiester internucleoside linkage.

In certain embodiments, Compound No. 1199983 is represented by the following chemical structure:
(SEQ ID NO: 2906)
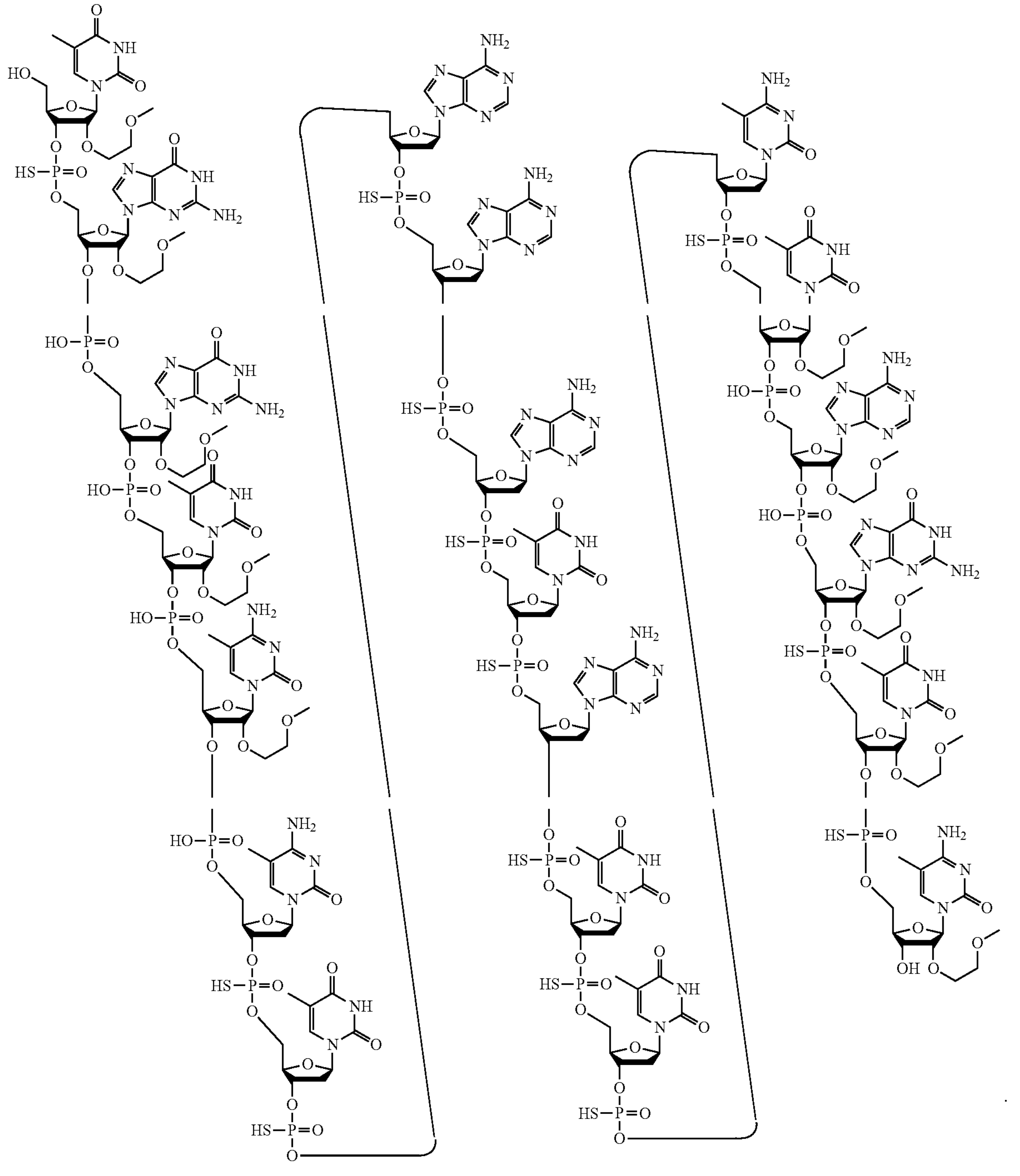

Structure 9: Compound No. 1199983

In certain embodiments, the sodium salt of Compound No. 1199983 is represented by the following chemical structure:

to 15 and 15 to 16 are phosphodiester internucleoside linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 16 to 17, and 17 to 18 are (SEQ ID NO: 2906)

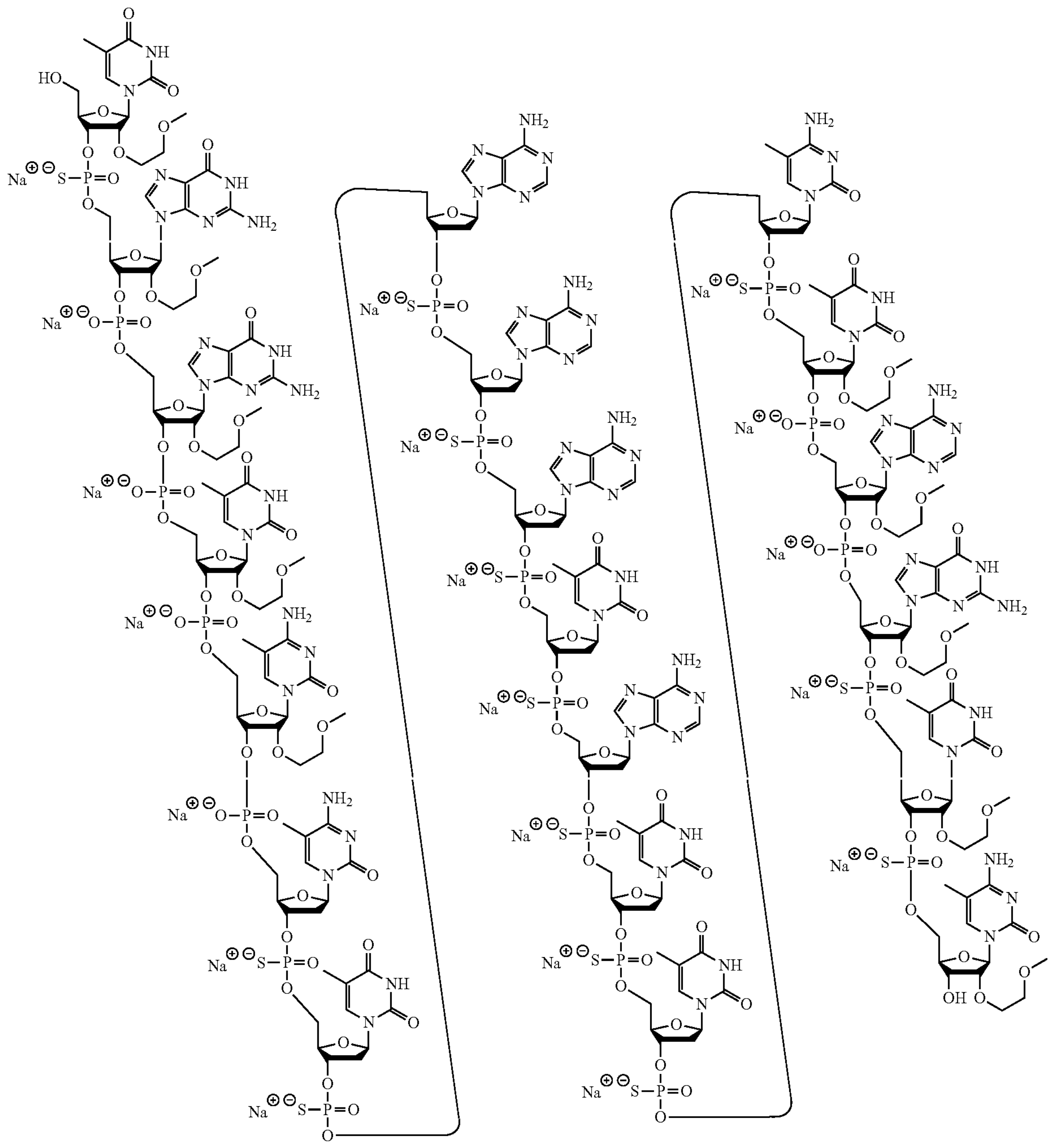

Structure 10: The sodium salt or Compound No. 1199993

6. Compound No. 1166721

In certain embodiments. Compound No. 1166721 is characterized as a 5-8-5 MOE gapmer having a sequence (from 5' to 3') of TGGTCCTAAATATTCTAGTC (SEQ ID NO: 2901), wherein each of nucleosides 1-5 and 14-18 (from 5' to 3') are 2'-β-D-MOE nucleosides and each of nucleosides 6-15 are 2'-1-D-deoxynucleosides, wherein the internucleoside linkages between nucleosides 2 to 3, 3 to 4, 4 to 5, 14 phosphorothioate internucleoside linkages, and wherein each cytosine is a 5-methylcytosine.

In certain embodiments, Compound No. 1166721 is represented by the following chemical notation: $T_{es}G_{eo}G_{eo}{}^{m}C_{eo}A_{ds}G_{ds}T_{ds}A_{ds}T_{ds}T_{ds}A_{ds}{}^{m}C_{ds}{}^{m}C_{ds}T_{eo}{}^{m}C_{eo}T_{es}A_{es}{}^{m}C_{e}$ (SEQ ID NO: 2901), wherein:

A=an adenine nucleobase, ${}^{m}$C=a 5-methylcytosine nucleobase,

G=a guanine nucleobase,
T=a thymine nucleobase,
e=a 2'-β-D-MOE sugar moiety,
d=a 2'-β-D-deoxyribosyl sugar moiety.

s=a phosphorothioate internucleoside linkage, and
o=a phosphodiester internucleoside linkage.

In certain embodiments, Compound No. 1160721 is represented by the following chemical structure:

(SEQ ID NO: 2901)

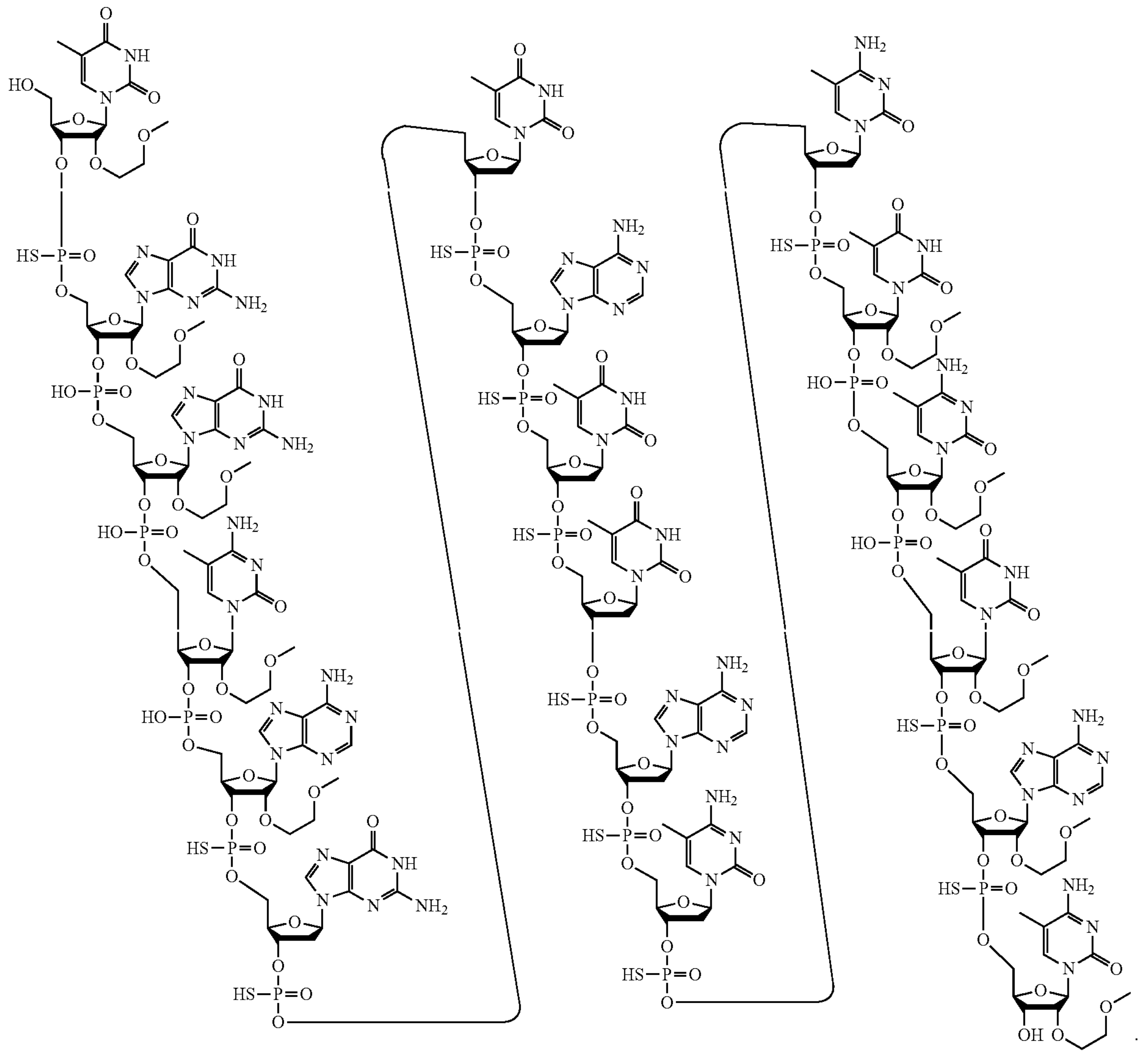

Structure 11: Compound No. 1166721

In certain embodiments, the sodium salt of Compound No. 1166721 is represented by the following chemical structure:

(SEQ ID NO: 2901)

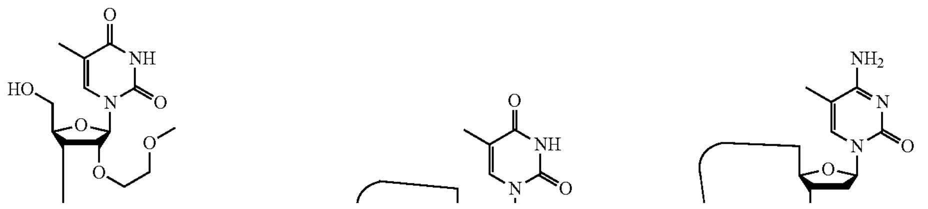

-continued

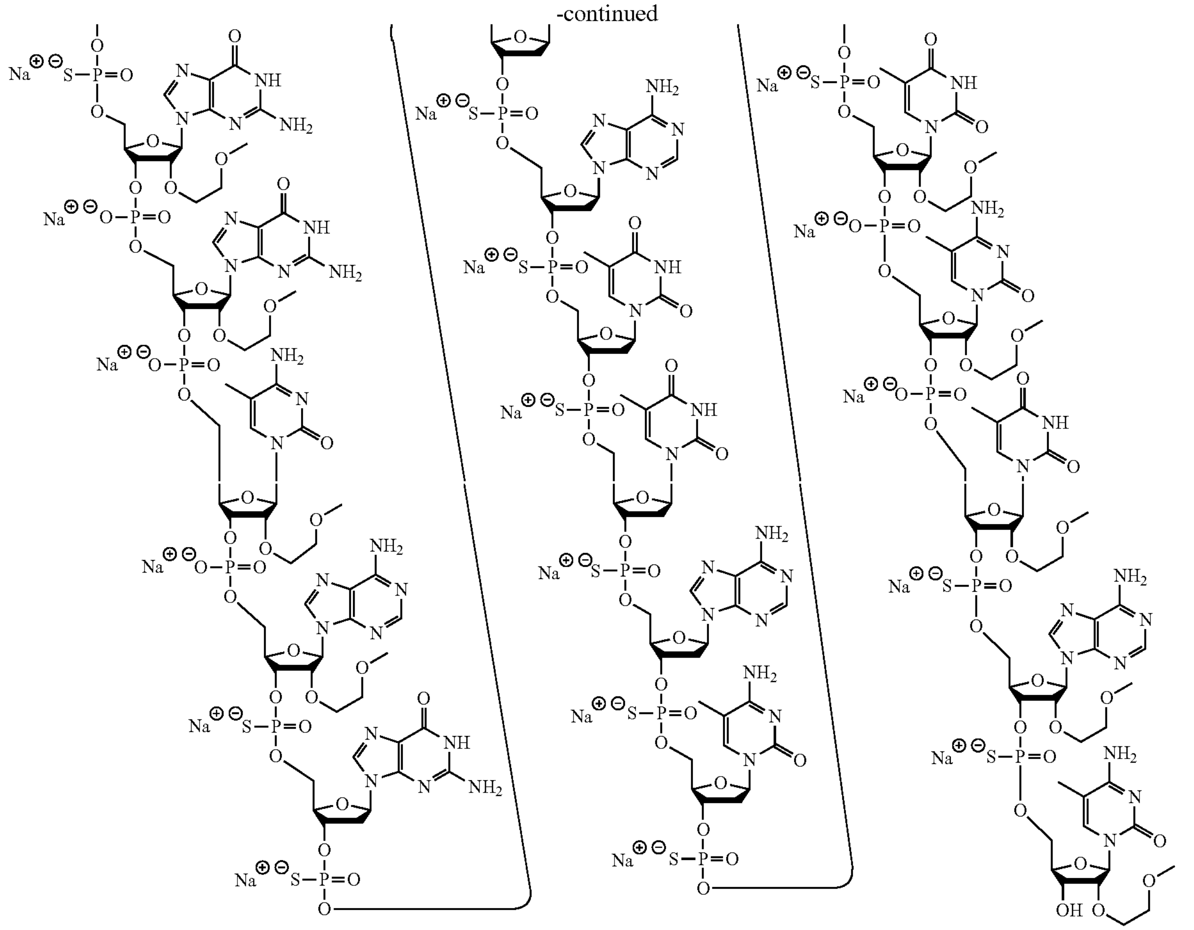

Structure 12: The sodium salt of Compound No. 1166721

VIII. Certain Hotspot Regions

In certain embodiments, nucleobases in the ranges specified below comprise a hotspot region of GFAP nucleic acid. In certain embodiments, modified oligonucleotides that are complementary to a hotspot region of GFAP nucleic acid achieve an average of more than 50% reduction of GFAP RNA in vitro in the standard cell assay. In certain embodiments, modified oligonucleotides that are complementary to a hotspot region of GFAP nucleic acid achieve an average of 75% or greater reduction of GFAP RNA in vivo in the standard in vivo assay.

1. Nucleobases 9324-9348 of SEQ ID NO: 2 In certain embodiments, nucleobases 9324-9348 of SEQ ID NO: 2 comprise a hotspot region. In certain embodiments, modified oligonucleotides are complementary to a portion of nucleobases 9324-9348 of SEQ ID NO: 2. In certain embodiments, modified oligonucleosides are 20 nucleobases in length. In certain embodiments, modified oligonucleotides are 18 nucleobases in length. In certain embodiments, modified oligonucleotides are gapmers. In certain embodiments, the gapmers are MOE gapmers. In certain embodiments, the internucleoside linkages of the modified oligonucleotides are phosphoothioate internucleoside linkages and phosphodiester internucleoside linkages. In certain embodiments, the phosphodiester ("o") and phosphorthioate ("s") internucleoside linkages are arranged in order from 5' to 3':

In certain embodiments, modified nucleotides have an internucleoside linkage motif of sooosssssssssssooss, soooosssssssssssoss, sooosssssssssssooss, sooossssssssooss, or sooosssssssssssoooss, wherein each "s" represents a phosphorothioate internucleoside linkage and each "o" represents a phosphodiester internucleoside linkage.

The nucleobase sequences of SEQ ID Nos: 21, 1177, 2321, 2398, 2808-2809, 2840-2842, and 2853-2854 are complementary to a portion of nucleobases 9324-9348 of SEQ ID NO: 2.

The nucleobase sequence of Compound Nos.: 1048181-1048182, 1104071-1104072, 1166746-1166748, 1166803-1166808, 1166894-1166899, 1166985-1166990, 1174016, and 1174018 are complementary to a portion of nucleobases 9324-9348 of SEQ ID NO: 2.

In certain embodiments, modified oligonucleotides complementary to a portion of nucleobases 9324-9348 of SEQ ID NO: 2 achieve at least 7% reduction of GFAP RNA in vitro in the standard cell assay. In certain embodiments, modified oligonucleotides complementary to a portion of nucleobases 9324-9348 of SEQ ID NO: 2 achieve an average of 42% reduction of GFAP RNA in vitro in the standard cell assay. In certain embodiments, modified oligonucleotides complementary to a portion of nucleobases 9324-9348 of SEQ ID NO: 2 achieve an average of 81% reduction of GFAP RNA in vivo in the standard in vivo assay.

2. Nucleobases 9459-9480 of SEO ID NO: 2

In certain embodiments, nucleobases 9459-9480 of SEQ ID NO: 2 comprise a hotspot region. In certain embodiments, modified oligonucleotides are complementary to a portion of nucleobases 9459-9480 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are gapmers. In certain embodiments, the gapmers are MOE gapmers. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': In certain embodiments, modified nucleotides have an internucleoside linkage motif of sooosssssssssssooss or soooosssssssssssooss, wherein each "s" represents a phosphorothioate internucleoside linkage and each "o" represents a phosphodiester internucleoside linkage.

The nucleobase sequences of SEQ ID Nos: 555, 2093, 2170, and 2813 are complementary to a portion of nucleobases 9459-9480 of SEQ ID NO: 2.

The nucleobase sequence of Compound Nos.: 1048190, 1104116-1104117, and 1199982-1199984 are complementary to a portion of nucleobases 9459-9480 of SEQ ID NO: 2.

In certain embodiments, modified oligonucleotides complementary to a portion of nucleobases 9459-9480 of SEQ ID NO: 2 achieve at least 26% reduction of GFAP RNA in vitro in the standard cell assay. In certain embodiments, modified oligonucleotides complementary to a portion of nucleobases 9459-9480 of SEQ ID NO: 2 achieve an average of 42% reduction of GFAP RNA in vitro in the standard cell assay. In certain embodiments, modified oligonucleotides complementary to a portion of nucleobases 9459-9480 of SEQ ID NO: 2 achieve an average of 91% reduction of GFAP RNA in vivo in the standard in vivo assay.

3. Nucleobases 9530-9580 of SEO ID NO: 2

In certain embodiments, nucleobases 9530-9580 of SEQ ID NO: 2 comprise a hotspot region. In certain embodiments, modified oligonucleotides are complementary to a portion of nucleobases 9530-9580 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are gapmers. In certain embodiments, the gapmers are MOE gapmers. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': In certain embodiments, modified nucleotides have an internucleoside linkage motif of sooosssssssssssooss, soooooosssssssssssoss, soooosssssssssssooss, sooossssssssssooss, or sooosssssssssssoooss, wherein each "s" represents a phosphorothioate internucleoside linkage and each "o" represents a phosphodiester internucleoside linkage.

The nucleobase sequences of SEQ ID Nos.: 20, 88, 166, 1331, 1408, 1485, 1637, 1713, 1714, 1789, 1790, 1637, 1638, 1865, 1866, 1941, 2018, 2095, 2172, 2249, 2326, 2403, 2480, 2557, 2633, 2709, 2785, 2816-2818, 2859, 2861, and 2886-2887 are complementary to a portion of nucleobases 9530-9580 of SEQ ID NO: 2.

The nucleobase sequence of Compound Nos.: 1048200-1048201, 1073062-1073064, 1104142-1104161, 1166719-1166721, 1166816-1166823, 1166826, 1166907-1166920, 1166998-1167011, 1174024, 1174026, and 1174029-1174030 are complementary to a portion of nucleobases 9530-9580 of SEQ ID NO: 2.

In certain embodiments, modified oligonucleotides complementary to a portion of nucleobases 9530-9580 of SEQ ID NO: 2 achieve at least 27% reduction of GFAP RNA in vitro in the standard cell assay. In certain embodiments, modified oligonucleotides complementary to a portion of nucleobases 9530-9580 of SEQ ID NO: 2 achieve an average of 52% reduction of GFAP RNA in vitro in the standard cell assay. In certain embodiments, modified oligonucleotides complementary to a portion of nucleobases 9530-9580 of SEQ ID NO: 2 achieve an average of 82% reduction of GFAP RNA in vivo in the standard in vivo assay.

4. Nucleobases 12006-12038 of SEO ID NO: 2

In certain embodiments, nucleobases 12006-12038 of SEQ ID NO: 2 comprise a hotspot region. In certain embodiments, modified oligonucleotides are complementary to a portion of nucleobases 12006-12038 of SEQ ID NO: 2.

In certain embodiments, modified oligonucleotides are 20 nucleobases in length. In certain embodiments, modified oligonucleotides are 18 nucleobases in length. In certain embodiments, modified oligonucleotides are gapmers. In certain embodiments, the gapmers are MOE gapmers. In certain embodiments, the internucleoside linkages of the modified oligonucleotides are phosphorothioate internucleoside linkages and phosphodiester internucleoside linkages. In certain embodiments, the phosphodiester ("o") and phosphorothioate ("s") internucleoside linkages are arranged in order from 5' to 3': In certain embodiments, modified nucleotides have an internucleoside linkage motif of sooosssssssssssooss, wherein each "s" represents a phosphoothioate internucleoside linkage and each "o" represents a phosphodiester internucleoside linkage.

The nucleobase sequences of SEQ ID Nos.: 815, 893, 971, 1049, 1269, 1270, 1346, 1423, 1499, 1500, 1660, 1736, 2655, and 2731 are complementary to a portion of nucleobases 12006-12038 of SEQ ID NO: 2.

The nucleobase sequence of Compound Nos.: 1047362-1047365, 1072813-1072818, and 1103276-1103279 are complementary to a portion of nucleobases 12006-12038 of SEQ ID NO: 2.

In certain embodiments, modified oligonucleotides complementary to a portion of nucleobases 12006-12038 of SEQ ID NO: 2 achieve at least 29% reduction of GFAP RNA in vitro in the standard cell assay. In certain embodiments, modified oligonucleotides complementary to a portion of nucleobases 12006-12038 of SEQ ID NO: 2 achieve an average of 52% reduction of GFAP RNA in vitro in the standard cell assay. In certain embodiments, modified oligonucleotides complementary to a portion of nucleobases 12006-12038 of SEQ ID NO: 2 achieve an average of 82% reduction of GFAP RNA in vivo in the standard in vivo assay.

5. Nucleobases 13038-13058 of SEO ID NO: 2

In certain embodiments, nucleobases 13038-13058 of SEQ ID NO: 2 comprise a hotspot region. In certain embodiments, modified oligonucleotides are complementary to a portion of nucleobases 13038-13058 of SEQ ID NO: 2. In certain embodiments, modified oligonucleotides are 20 nucleobases in length. In certain embodiments, modified oligonucleotides are 18 nucleobases in length. In certain embodiments, modified oligonucleotides are gapmers. In certain embodiments, the gapmers are MOE gapmers. In certain embodiments, the internucleoside linkages of the modified oligonucleotides are phosphorothioate internucleoside linkages and phosphodiester internucleoside linkages.

In certain embodiments, the phosphodiester ("o") and phosphorothioate ("s") internucleoside linkages are arranged in order from 5' to 3': In certain embodiments, modified nucleotides have an internucleoside linkage motif of sooossssssssssooss, soooooossssssssssoss, or soooosssssssssssooss, wherein each "s" represents a phosphorothioate internucleoside linkage and each "o" represents a phosphodiester internucleoside linkage.

The nucleobase sequences of SEQ ID Nos.: 825 and 1973 are complementary to a portion of nucleobases 13038-13058 of SEQ ID NO: 2.

The nucleobase sequence of Compound Nos.: 1047522, 1166954, and 1167046 are complementary to a portion of nucleobases 13038-13058 of SEQ ID NO: 2.

In certain embodiments, modified oligonucleotides complementary to a portion of nucleobases 13038-13058 of SEQ ID NO: 2 achieve at least 27% reduction of GFAP RNA in vitro in the standard cell assay. In certain embodiments, modified oligonucleotides complementary to a portion of nucleobases 13038-13058 of SEQ ID NO: 2 achieve an average of 41% reduction of GFAP RNA in vitro in the standard cell assay. In certain embodiments, modified oligonucleotides complementary to a portion of nucleobases 13038-13058 of SEQ ID NO: 2 achieve an average of 84% reduction of GFAP RNA in vivo in the standard in vivo assay.

6. Additional Hotspot Regions

In certain embodiments, the ranges described in the Table below comprise hotspot regions. Each hotspot region begins with the nucleobase of SEQ ID NO: 2 identified in the "Start Site SEQ ID NO: 2" column and ends with the nucleobase of SEQ ID NO: 2 identified in the "Stop Site SEQ ID NO: 2" column. In certain embodiments, modified oligonucleotides are complementary within any of the hotspot regions 1-14, as defined in the table below. In certain embodiments, modified oligonucleotides are 18 nucleobases in length. In certain embodiments, modified oligonucleotides are 20 nucleobases in length. In certain embodiments, modified oligonucleotides are gapmers. In certain embodiments, modified oligonucleotides are 5-8-5, 5-10-3, 4-10-6, 6-104, or 5-10-5 MOE gapmers.

The nucleobase sequence of compounds listed in the "Compound No, in range" column in the table below are complementary to SEQ ID NO: 2 within the specified hotspot region. The nucleobase sequence of the oligonucleotides listed in the "SEQ ID NO: in range" column in the table below are complementary to the target sequence. SEQ ID NO: 2, within the specified hotspot region.

In certain embodiments, modified oligonucleotides complementary to nucleobases within the hotspot region achieve at least "Min. % Red, in vitro" (minimum % reduction, relative to untreated control cells) of GFAP RNA in vitro in the standard cell assay, as indicated in the table below. In certain embodiments, modified oligonucleotides complementary to nucleobases within the hotspot region achieve an average of "Avg. % Red, in vitro" (average % reduction, relative to untreated control cells) of GFAP RNA in vitro in the standard cell assay, as indicated in the table below. In certain embodiments, modified oligonucleotides complementary to nucleobases within the hotspot region achieve a maximum of "Max. % Red, in vitro" (maximum % reduction, relative to untreated control cells) of GFAP RNA in vitro in the standard cell assay, as indicated in the table below. In certain embodiments, modified oligonucleotides complementary to nucleobases within the hotspot region achieve an average of "Avg. % Red, in vivo" (average % reduction, relative to PBS-treated animals) of GFAP RNA in vivo in the standard in vivo assay, as indicated in the table below.

TABLE 1

GFAP Hotspots

| Hotspot ID | Start Site SEQ ID NO: 2 | Start Site SEQ ID NO: 2 | Min. % Red. in vitro | Max. % Red. In vitro | Avg. % Red. in vitro | Avg. % Red. in vivo | Compound No. in Range | SEQ ID NOs: in Range |
|---|---|---|---|---|---|---|---|---|
| 1 | 9324 | 9348 | 7 | 78 | 42 | 81 | 1048181-1048182, 1104071-1104072, 1166746-1166748, 1166803-1166808, 1166894-1166899, 1166985-1166990, 1174016, 1174018 | 21, 1177, 2321, 2398, 2808-2809, 2840-2842, 2853-2854 |
| 2 | 9459 | 9480 | 26 | 65 | 42 | 91 | 1048190, 1104116-1104117, 1199982-1199984 | 555, 2093, 2170, 2813 |
| 3 | 9530 | 9580 | 18 | 82 | 52 | 82 | 1048199-1048201, 1073062-1073064, 1104142-1104161, 1166719-1166721, 1166816-1166823, 1166826, 1166907-1166920, 1166998-1167011, 1174024, 1174026, 1174029-1174030 | 20, 88, 166, 1331, 1408, 1485, 1637, 1713, 1714, 1789, 1790, 1637, 1638, 1865, 1866, 1941, 2018, 2095, 2172, 2249, 2326, 2403, 2480, 2557, 2633, 2709, 2785, 2816-2818, 2859, 2861, 2886-2887 |
| 4 | 12006 | 12038 | 29 | 75 | 52 | 82 | 1047362-1047365, 1072813-1072818, 1103276-1103279 | 815, 893, 971, 1049 1269, 1270, 1346, 1423, 1499, 1500, 1660, 1736, 2655, 2731 |
| 5 | 13038 | 13058 | 27 | 56 | 41 | 84 | 1047522, 1166954, 1167046 | 825, 1973 |
| 6 | 8530 | 8557 | 14 | 79 | 52 | 89 | 1047706-1047708, 1103567-1103571 | 213, 291, 369, 1601, 1753, 1829, 1905, 1982 |

TABLE 1-continued

| GFAP Hotspots | | | | | | | | |
|---|---|---|---|---|---|---|---|---|
| Hotspot ID | Start Site SEQ ID NO: 2 | Start Site SEQ ID NO: 2 | Min. % Red. in vitro | Max. % Red. In vitro | Avg. % Red. in vitro | Avg. % Red. in vivo | Compound No. in Range | SEQ ID NOs: in Range |
| 7 | 8731 | 8754 | 44 | 64 | 53 | 88 | 1047733-1047735, 1103591, 1103592, 1174050, 1174051, 1174056, 1174058, 1174062, 1174063 | 1072, 1149, 1227, 2291, 2368 |
| 8 | 8749 | 8807 | 25 | 92 | 52 | 75 | 1047601-1047610, 1072854-1072868, 1103462-1103472, 1166738-1166740, 1166742, 1166744, 1166793-1166795, 1166798-1166800, 1166885-1166890, 1166975, 1166982, 1174012-1174013 | 51, 129, 207, 752, 830, 908, 986, 1064, 1141, 1219, 1279, 1280-1282, 1356-1359, 1433-1436, 1510-1512, 1595, 1671, 1747, 2206, 2283, 2360, 2437, 2514, 2590, 2666, 2742, 2835-2837, 2839, 2850-2851, 2866 |
| 9 | 9511 | 9536 | 32 | 90 | 55 | 86 | 1048197, 1073060, 1104129-1104133, 1166749-1166751, 1166809-1166810, 1166812-1166813, 1166900-1166903, 1166991-1166994, 1174020 | 1100, 1484, 1864, 1940, 2017, 2094, 2171, 2819-2821, 2856 |
| 10 | 9565 | 9602 | 20 | 75 | 53 | 82 | 1048202-1048204, 1073065, 1104165-1104179, 1166757-1166760, 1166831, 1166835, 1166926-1166929, 1167012, 1167017, 1167018, 1174031, 1174034 | 244, 322, 400, 1562, 1639, 1715, 1791, 1867, 1943, 2020, 2173, 2250, 2327, 2404, 2481, 2558, 2634, 2710, 2786, 2873-2876, 2888, 2891 |
| 11 | 11155 | 11184 | 37 | 82 | 69 | 85 | 1073093-1073095, 1104307-1104312, 1167024-1167027, 1166761-1166763, 1166842-1166843, 1166845-1166847, 1166933-1166934, 1167024-1167027, 1174037 | 1339, 1569, 2028, 2105, 2182, 2259, 2336, 2413, 2822-2824, 2863 |
| 12 | 12044 | 12067 | 49 | 67 | 58 | 85 | 1047372-1047374, 1072824-1072825, 1166852, 1167033-1167036 | 348, 426, 504, 1425, 1502 |
| 13 | 12080 | 12108 | 45 | 88 | 68 | 79 | 1047384-1047388, 1072834-1072835, 1103284-1103285, 1166948, 1167040 | 37, 115, 193, 271, 349, 1274, 1351, 2041, 2118 |
| 14 | 13333 | 13367 | 53 | 93 | 75 | 89 | 1047579-104592, 1072849-1072850, 1166775-1166787, 1166867, 1166869-1166875, 1166877-1166878, 1167050-1167051, 1167053-1167060 | 50, 283, 361, 439, 517, 595, 673, 751, 829, 907, 985, 1063, 1140, 1218, 1278, 1508, 2825-2833, 2843-2846 |

NONLIMITING DISCLOSURE AND INCORPORATION BY REFERENCE

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar moiety (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases.

By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^{m}$CGAUCG," wherein $^{m}$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, all cis- and trans-isomers and tautomeric forms of the compounds herein are also included unless otherwise indicated. Oligomeric compounds described herein include chirally pure or enriched mixtures as well as racemic mixtures. For example, oligomeric compounds having a plurality of phosphorothioate internucleoside linkages include such compounds in which chirality of the phosphorothioate internucleoside linkages is controlled or is random. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}$H hydrogen atoms. Isotopic substitutions encompassed by the compounds herein include but are not limited to: $^{2}$H or $^{3}$H in place of $^{1}$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments.

Example 1: Effect of 5-10-5 MOE Gapmer Modified Oligonucleotides on Human GFAP RNA In Vitro, Single Dose Modified oligonucleotides complementary to human GFAP nucleic acid were designed and tested for their single dose effects on GFAP RNA in vitro. The modified oligonucleotides were tested in a series of experiments that had similar culture conditions.

The modified oligonucleotides in the tables below are 5-10-5 MOE gapmers with mixed PO/PS internucleoside linkages. The gapmers are 20 nucleosides in length, wherein the central gap segment consists of ten 2'-β-D-deoxynucleosides and the 5' and 3' wing segments each consists of five 2'-MOE modified nucleosides. The sugarmotif for the gapmers is (from 5' to 3'): eeeeedddddddddeecee; wherein 'd' represents a 2'-β-D-deoxyribosyl sugar moiety, and 'e' represents a 2'-MOE sugar moiety. The internucleoside linkage motif for the gapmers is (from 5' to 3'): sooosssssssssssooss; wherein each 'o' represents a phosphodiester internucleoside linkage and each 's' represents a phosphorothioate internucleoside linkage. Each cytosine residue is a 5-methylcytosine.

"Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. Each modified oligonucleotide listed in the Tables below is 100% complementary to SEQ ID NO: 1 (GENBANK Accession No. NM_002055.4), or SEQ ID NO: 2 (GENBANK Accession No. NC_000017.11 truncated from nucleotides 44903001 to 44919000). 'N/A' indicates that the modified oligonucleotide is not 100% complementary to that particular target nucleic acid sequence.

Cultured U251 cells were treated with modified oligonucleotide at a concentration of 4,000 nM using free uptake at a density of 10.000 cells per well. After a treatment period of approximately 48 hours, total RNA was isolated from the cells and GFAP RNA levels were measured by quantitative real-time RTPCR. GFAP RNA levels were measured by human GFAP primer probe set RTS37485 (forward sequence CTGGAGGTTGAGAGGGACA, designated herein as SEQ ID NO: 11; reverse sequence GCTTCATCTGCTTCCTGTCT, designated herein as SEQ ID NO: 12; probe sequence CTGGAGCTTCTGCCTCACAGTGG, designated herein as SEQ ID NO: 13). GFAP RNA levels were normalized to total RNA content, as measured by RIBOGREEN®. Reduction of GFAP RNA is presented in the tables below as percent GFAP RNA amount relative to untreated control cells. Each table represents results from an individual assay plate. The values marked with an asterisk (*) indicate that the modified oligonucleotide is complementary to the amplicon region of the primer probe set. Additional assays may be used to measure the potency and efficacy of the modified oligonucleotides complementary to the amplicon region.

TABLE 2

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047144 | 17 | 36 | 3465 | 3484 | CGAGGGCTTTATGAAGGAGT | 80 | 22 |
| 1047160 | 131 | 150 | 3579 | 3598 | GCCAGGAGCCAGGCCCCCCA | 67 | 23 |
| 1047176 | 248 | 267 | 3696 | 3715 | GGCCCGGGTCTCCTTGAAGC | 109 | 24 |
| 1047192 | 488 | 507 | 3936 | 3955 | GTCCTGTGCCAGATTGTCCC | 7* | 25 |
| 1047208 | 579 | 598 | N/A | N/A | CATCTGCTTCCTGTCTATAG | 6* | 26 |
| 1047224 | 649 | 668 | 5238 | 5257 | CTCAAGAACCGGATCTCCTC | 105 | 27 |
| 1047240 | 813 | 832 | 5699 | 5718 | ACTCTTCGGCTTCATGCATG | 69 | 28 |
| 1047256 | 1029 | 1048 | 7601 | 7620 | GCGCCTCCTGATAACTGGCC | 80 | 29 |
| 1047272 | 1251 | 1270 | 10865 | 10884 | CTTCTGACACAGACTTGGTG | 92 | 30 |
| 1047288 | 1298 | 1317 | 10912 | 10931 | ATCCCGCATCTCCACGGTCT | 90 | 31 |
| 1047304 | 1351 | 1370 | 11640 | 11659 | CTGCCTCACATCACATCCTT | 87 | 32 |
| 1047320 | 1416 | 1435 | 11705 | 11724 | CGGAGCAACTATCCTGCTTC | 102 | 33 |
| 1047336 | 1617 | 1636 | 11906 | 11925 | AAGCTGCTGGCCATGCCCCT | 87 | 34 |
| 1047352 | 1664 | 1683 | 11953 | 11972 | TGCCCCCCGCCCTCCTCCCC | 83 | 35 |
| 1047368 | 1736 | 1755 | 12025 | 12044 | GAGAGAACCTCCATCTCTGG | 47 | 36 |
| 1047384 | 1791 | 1810 | 12080 | 12099 | TCAGTTTTCCTCCAGCAGCC | 55 | 37 |
| 1047400 | 1854 | 1873 | 12143 | 12162 | GACAAAACAAGCCTCTGGCC | 66 | 38 |
| 1047416 | 2036 | 2055 | 12325 | 12344 | CGTCCCCACCCATCTTAGAC | 60 | 39 |
| 1047432 | 2180 | 2199 | 12469 | 12488 | GTGCTGAGAATCAAGCTCCC | 93 | 40 |
| 1047448 | 2237 | 2256 | 12526 | 12545 | CCCCCTCTATCCCTCCCAGC | 11 | 41 |
| 1047464 | 2280 | 2299 | 12569 | 12588 | CTGGGCTTGACCTCTCTGTA | 63 | 42 |
| 1047480 | 2379 | 2398 | 12668 | 12687 | TGGTCACCCACAACCCCTAC | 81 | 43 |
| 1047496 | 2457 | 2476 | 12746 | 12765 | CCCTTTCTCTCCTGTTTCAG | 79 | 44 |
| 1047512 | 2486 | 2505 | 12775 | 12794 | AAGTCATGCCCTGCCCCCAT | 45 | 45 |
| 1047528 | 2780 | 2799 | 13069 | 13088 | GCACCCGGCCTCCAGGCTGC | 76 | 46 |
| 1047544 | 2861 | 2880 | 13150 | 13169 | GGCACAGATCCCACCAGTCT | 106 | 47 |
| 1047560 | 2903 | 2922 | 13192 | 13211 | GAGAGGAGAACCCTGAAGTG | 72 | 48 |
| 1047576 | 3035 | 3054 | 13324 | 13343 | CCTCAGCGACTAAAGGCAGC | 77 | 49 |
| 1047592 | 3058 | 3077 | 13347 | 13366 | GCGCAGCATTTGTCTTTATT | 47 | 50 |
| 1047608 | N/A | N/A | 8777 | 8796 | GCTTTTGAGATATCTTGTGA | 8 | 51 |
| 1047624 | N/A | N/A | 9031 | 9050 | GTTTAATGTACAGTTACTCT | 71 | 52 |
| 1047640 | N/A | N/A | 9070 | 9089 | CCAAGGACTCACCACCTTTA | 75 | 53 |
| 1047656 | N/A | N/A | 9202 | 9221 | AGGGATGAAAGAATAAAGCA | 92 | 54 |
| 1047672 | N/A | N/A | 8381 | 8400 | CCTGCTGTACTGACCTCGAA | 94 | 55 |
| 1047688 | N/A | N/A | 8456 | 8475 | ATCCTCAGTCCCAGTCTGGA | 54 | 56 |
| 1047704 | N/A | N/A | 8504 | 8523 | CTGCAGTGTCACGAAGGCCC | 74 | 57 |

TABLE 2-continued

| Reduction of GFAP RNA by 5-10-5 MOE gapmers with mixed PO/PS internucleoside linkages in U251 cells | | | | | | | |
|---|---|---|---|---|---|---|---|
| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
| 1047720 | N/A | N/A | 8637 | 8656 | TGTCAAGCTCTCACCCAGTT | 77 | 58 |
| 1047736 | N/A | N/A | 8737 | 8756 | TTGGTGCTTTTGCCCCCTGT | 56 | 59 |
| 1047752 | N/A | N/A | 4093 | 4112 | GGATAGTGCCCCATCAAGAG | 109 | 60 |
| 1047768 | N/A | N/A | 4264 | 4283 | AGTCACAAAGCCCAGCCATG | 95 | 61 |
| 1047784 | N/A | N/A | 4322 | 4341 | GCTTCCAACTCCTCCTTTAT | 101 | 62 |
| 1047800 | N/A | N/A | 4359 | 4378 | CAGAATCCAATCTCCCTCAT | 106 | 63 |
| 1047816 | N/A | N/A | 4405 | 4424 | GCTTTGCGCCCAGACCTGCC | 68 | 64 |
| 1047832 | N/A | N/A | 4525 | 4544 | ATTCCTCTGATCCCAGGTAA | 52 | 65 |
| 1047848 | N/A | N/A | 4704 | 4723 | CCTTAACTCATTACTAAGGT | 69 | 66 |
| 1047864 | N/A | N/A | 4806 | 4825 | GAGACCACCCCCACCCAGGA | 70 | 67 |
| 1047880 | N/A | N/A | 4868 | 4887 | GTCCAGGCTCTTCTGAGGAC | 66 | 68 |
| 1047896 | N/A | N/A | 5007 | 5026 | GTGGCCATCAATCCTTTCCT | 103 | 69 |
| 1047912 | N/A | N/A | 5117 | 5136 | CCCCAGGCTCCTTCTCCCCA | 74 | 70 |
| 1047928 | N/A | N/A | 5388 | 5407 | TGTCTCTACCTGCCAATCTC | 100 | 71 |
| 1047944 | N/A | N/A | 5521 | 5540 | CTCAGGGTACAGGCCACAGC | 90 | 72 |
| 1047960 | N/A | N/A | 5791 | 5810 | ACCCTCCTTCCCCCATTCTC | 94 | 73 |
| 1047976 | N/A | N/A | 5934 | 5953 | AGCTACTACTAATAATAGCA | 98 | 74 |
| 1047992 | N/A | N/A | 6023 | 6042 | ACTTCGGCTCTCTCATCTGT | 75 | 75 |
| 1048008 | N/A | N/A | 6146 | 6165 | AACCCAAAACAGACTGGCAG | 79 | 76 |
| 1048024 | N/A | N/A | 6281 | 6300 | CCCACACTACATATAAGCTC | 105 | 77 |
| 1048040 | N/A | N/A | 6329 | 6348 | CCTGTCCTGCCTAGCCCAAA | 71 | 78 |
| 1048056 | N/A | N/A | 6417 | 6436 | GGGCCCTGCCTCTCTGTGCT | 81 | 79 |
| 1048072 | N/A | N/A | 6544 | 6563 | ATAGCCCTTTCTCCCCTGCC | 86 | 80 |
| 1048088 | N/A | N/A | 6959 | 6978 | AATCCAGAACCTTCCACACT | 114 | 81 |
| 1048104 | N/A | N/A | 7073 | 7092 | TGGGACTTTTCCCAACAACT | 93 | 82 |
| 1048120 | N/A | N/A | 7412 | 7431 | CGCCCTCGACCCAGGTCCTC | 57 | 83 |
| 1048136 | N/A | N/A | 7907 | 7926 | AGTGACTGCCTGCTATGTGT | 94 | 84 |
| 1048152 | N/A | N/A | 7989 | 8008 | TTGGAGGGTGACCCAAGTCC | 81 | 85 |
| 1048168 | N/A | N/A | 8235 | 8254 | ACGCCCTTTTCCTTGCCAGG | 74 | 86 |
| 1048184 | N/A | N/A | 9373 | 9392 | TAGCTCCCCCCTCCCCCCGC | 52 | 87 |
| 1048200 | N/A | N/A | 9534 | 9553 | GCAGTATTACCTCTACTAGT | 45 | 88 |
| 1048216 | N/A | N/A | 9610 | 9629 | CCTGTCCCCTTTCCTCTTTC | 74 | 89 |
| 1048232 | N/A | N/A | 9791 | 9810 | CCACCAACCAGCCACATGAC | 98 | 90 |
| 1048248 | N/A | N/A | 9826 | 9845 | ATCAGGAGACCAGAGCTCAA | 78 | 91 |
| 1048264 | N/A | N/A | 10622 | 10641 | GGCCTGGCTTCATTTCAGCC | 66 | 92 |

TABLE 2-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1048280 | N/A | N/A | 10734 | 10753 | AGTATGAGAACCTATGCAAC | 80 | 93 |
| 1048296 | N/A | N/A | 10793 | 10812 | GGGCATGAGCCATCCTCTCC | 35 | 94 |
| 1048312 | N/A | N/A | 10942 | 10961 | GACTGGGCCCAAATCCCTCC | 87 | 95 |
| 1048328 | N/A | N/A | 11063 | 11082 | CCTTGCTCTCCTCCAGAATT | 67 | 96 |
| 1048344 | N/A | N/A | 11227 | 11246 | GCTACTAACTTTAATTCTCT | 41 | 97 |
| 1048360 | N/A | N/A | 11321 | 11340 | CCTCTTCCCATTCCCCTGGT | 62 | 98 |
| 1048376 | N/A | N/A | 11488 | 11507 | GGTCTTACTTTTCTTGATAG | 72 | 99 |

TABLE 3

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047145 | 18 | 37 | 3466 | 3485 | GCGAGGGCTTTATGAAGGAG | 99 | 100 |
| 1047161 | 133 | 152 | 3581 | 3600 | CGGCCAGGAGCCAGGCCCCC | 82 | 101 |
| 1047177 | 267 | 286 | 3715 | 3734 | TCATCTCTGCCCGCTCACTG | 88 | 102 |
| 1047193 | 490 | 509 | 3938 | 3957 | AGGTCCTGTGCCAGATTGTC | 8* | 103 |
| 1047209 | 585 | 604 | N/A | N/A | TGGCTTCATCTGCTTCCTGT | 5* | 104 |
| 1047225 | 651 | 670 | 5240 | 5259 | TCCTCAAGAACCGGATCTCC | 37 | 105 |
| 1047241 | 821 | 840 | 5707 | 5726 | GCGGTACCACTCTTCGGCTT | 77 | 106 |
| 1047257 | 1051 | 1070 | 7623 | 7642 | CCCTCTTCCTCCAGCCGCGC | 35 | 107 |
| 1047273 | 1252 | 1271 | 10866 | 10885 | CCTTCTGACACAGACTTGGT | 86 | 108 |
| 1047289 | 1305 | 1324 | 10919 | 10938 | CCTCTCCATCCCGCATCTCC | 87 | 109 |
| 1047305 | 1352 | 1371 | 11641 | 11660 | CCTGCCTCACATCACATCCT | 66 | 110 |
| 1047321 | 1417 | 1436 | 11706 | 11725 | GCGGAGCAACTATCCTGCTT | 96 | 111 |
| 1047337 | 1631 | 1650 | 11920 | 11939 | CCTCATTCTAACGCAAGCTG | 58 | 112 |
| 1047353 | 1665 | 1684 | 11954 | 11973 | GTGCCCCCCGCCCTCCTCCC | 46 | 113 |
| 1047369 | 1739 | 1758 | 12028 | 12047 | TCCGAGAGAACCTCCATCTC | 72 | 114 |
| 1047385 | 1792 | 1811 | 12081 | 12100 | CTCAGTTTTCCTCCAGCAGC | 50 | 115 |
| 1047401 | 1876 | 1895 | 12165 | 12184 | TCCCACCTCATAAAAACCAA | 94 | 116 |
| 1047417 | 2059 | 2078 | 12348 | 12367 | GGTGACTGCCCCAGGTGGCA | 68 | 117 |
| 1047433 | 2181 | 2200 | 12470 | 12489 | AGTGCTGAGAATCAAGCTCC | 75 | 118 |
| 1047449 | 2238 | 2257 | 12527 | 12546 | CCCCCCTCTATCCCTCCCAG | 60 | 119 |
| 1047465 | 2310 | 2329 | 12599 | 12618 | GTCCCCTCCAGTCTGCACGG | 49 | 120 |
| 1047481 | 2380 | 2399 | 12669 | 12688 | CTGGTCACCCACAACCCCTA | 82 | 121 |

TABLE 3-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047497 | 2458 | 2477 | 12747 | 12766 | CCCCTTTCTCTCCTGTTTCA | 29 | 122 |
| 1047513 | 2491 | 2510 | 12780 | 12799 | GGACAAAGTCATGCCCTGCC | 85 | 123 |
| 1047529 | 2781 | 2800 | 13070 | 13089 | AGCACCCGGCCTCCAGGCTG | 86 | 124 |
| 1047545 | 2862 | 2881 | 13151 | 13170 | GGGCACAGATCCCACCAGTC | 65 | 125 |
| 1047561 | 2924 | 2943 | 13213 | 13232 | CCCTTCTTCGGCCTTAGAGG | 62 | 126 |
| 1047577 | 3040 | 3059 | 13329 | 13348 | TTTTTCCTCAGCGACTAAAG | 49 | 127 |
| 1047593 | 3060 | 3079 | 13349 | 13368 | GGGCGCAGCATTTGTCTTTA | 59 | 128 |
| 1047609 | N/A | N/A | 8778 | 8797 | GGCTTTTGAGATATCTTGTG | 13 | 129 |
| 1047625 | N/A | N/A | 9036 | 9055 | TGCCAGTTTAATGTACAGTT | 72 | 130 |
| 1047641 | N/A | N/A | 9072 | 9091 | ACCCAAGGACTCACCACCTT | 89 | 131 |
| 1047657 | N/A | N/A | 9212 | 9231 | ATGGAGCCTCAGGGATGAAA | 69 | 132 |
| 1047673 | N/A | N/A | 8382 | 8401 | CCCTGCTGTACTGACCTCGA | 91 | 133 |
| 1047689 | N/A | N/A | 8460 | 8479 | CCTGATCCTCAGTCCCAGTC | 82 | 134 |
| 1047705 | N/A | N/A | 8506 | 8525 | CGCTGCAGTGTCACGAAGGC | 63 | 135 |
| 1047721 | N/A | N/A | 8643 | 8662 | GGCAGATGTCAAGCTCTCAC | 83 | 136 |
| 1047737 | N/A | N/A | 3963 | 3982 | TCCTCACTTCTGCCTCACAG | 66 | 137 |
| 1047753 | N/A | N/A | 4095 | 4114 | AAGGATAGTGCCCCATCAAG | 69 | 138 |
| 1047769 | N/A | N/A | 4265 | 4284 | CAGTCACAAAGCCCAGCCAT | 64 | 139 |
| 1047785 | N/A | N/A | 4324 | 4343 | CCGCTTCCAACTCCTCCTTT | 49 | 140 |
| 1047801 | N/A | N/A | 4361 | 4380 | CCCAGAATCCAATCTCCCTC | 85 | 141 |
| 1047817 | N/A | N/A | 4419 | 4438 | AGGCAGTCACCTGTGCTTTG | 96 | 142 |
| 1047833 | N/A | N/A | 4526 | 4545 | GATTCCTCTGATCCCAGGTA | 63 | 143 |
| 1047849 | N/A | N/A | 4705 | 4724 | GCCTTAACTCATTACTAAGG | 82 | 144 |
| 1047865 | N/A | N/A | 4807 | 4826 | AGAGACCACCCCCACCCAGG | 91 | 145 |
| 1047881 | N/A | N/A | 4910 | 4929 | TGGTTTCATCCTGGAGCCTG | 60 | 146 |
| 1047897 | N/A | N/A | 5012 | 5031 | GGTGGGTGGCCATCAATCCT | 71 | 147 |
| 1047913 | N/A | N/A | 5168 | 5187 | CATCTGCTTCCTGGAGTGGC | 31 | 148 |
| 1047929 | N/A | N/A | 5400 | 5419 | TCTTTCATTTCCTGTCTCTA | 81 | 149 |
| 1047945 | N/A | N/A | 5561 | 5580 | CCCGAACCTCCTGACCAGGG | 117 | 150 |
| 1047961 | N/A | N/A | 5800 | 5819 | GCTTCCTCCACCCTCCTTCC | 75 | 151 |
| 1047977 | N/A | N/A | 5935 | 5954 | CAGCTACTACTAATAATAGC | 104 | 152 |
| 1047993 | N/A | N/A | 6040 | 6059 | TTAGTTAACCTCTCTGGACT | 79 | 153 |
| 1048009 | N/A | N/A | 6147 | 6166 | TAACCCAAAACAGACTGGCA | 101 | 154 |
| 1048025 | N/A | N/A | 6282 | 6301 | TCCCACACTACATATAAGCT | 83 | 155 |
| 1048041 | N/A | N/A | 6330 | 6349 | GCCTGTCCTGCCTAGCCCAA | 80 | 156 |

TABLE 3-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1048057 | N/A | N/A | 6464 | 6483 | GCCACTCACACTCCTCAGCT | 79 | 157 |
| 1048073 | N/A | N/A | 6548 | 6567 | TCTAATAGCCCTTTCTCCCC | 88 | 158 |
| 1048089 | N/A | N/A | 6961 | 6980 | AGAATCCAGAACCTTCCACA | 88 | 159 |
| 1048105 | N/A | N/A | 7074 | 7093 | CTGGGACTTTTCCCAACAAC | 86 | 160 |
| 1048121 | N/A | N/A | 7418 | 7437 | AGGCCCCGCCCTCGACCCAG | 95 | 161 |
| 1048137 | N/A | N/A | 7915 | 7934 | AAACATCTAGTGACTGCCTG | 87 | 162 |
| 1048153 | N/A | N/A | 8061 | 8080 | AAGGAGGCAGAAGAGATGGG | 59 | 163 |
| 1048169 | N/A | N/A | 8286 | 8305 | CTGGGACACCCCTAGGCTGG | 68 | 164 |
| 1048185 | N/A | N/A | 9374 | 9393 | TTAGCTCCCCCCTCCCCCCG | 84 | 165 |
| 1048201 | N/A | N/A | 9536 | 9555 | TGGCAGTATTACCTCTACTA | 43 | 166 |
| 1048217 | N/A | N/A | 9611 | 9630 | TCCTGTCCCCTTTCCTCTTT | 63 | 167 |
| 1048233 | N/A | N/A | 9792 | 9811 | GCCACCAACCAGCCACATGA | 89 | 168 |
| 1048249 | N/A | N/A | 10005 | 10024 | CTGTAATCCCCTTACTCGGG | 94 | 169 |
| 1048265 | N/A | N/A | 10636 | 10655 | CTGCTCTGTCTTCTGGCCTG | 65 | 170 |
| 1048281 | N/A | N/A | 10735 | 10754 | GAGTATGAGAACCTATGCAA | 53 | 171 |
| 1048297 | N/A | N/A | 10794 | 10813 | AGGGCATGAGCCATCCTCTC | 78 | 172 |
| 1048313 | N/A | N/A | 10944 | 10963 | CTGACTGGGCCCAAATCCCT | 95 | 173 |
| 1048329 | N/A | N/A | 11074 | 11093 | ACATTCAGTTTCCTTGCTCT | 89 | 174 |
| 1048345 | N/A | N/A | 11228 | 11247 | AGCTACTAACTTTAATTCTC | 82 | 175 |
| 1048361 | N/A | N/A | 11330 | 11349 | GCCAAATCCCCTCTTCCCAT | 19 | 176 |
| 1048377 | N/A | N/A | 11491 | 11510 | CCAGGTCTTACTTTTCTTGA | 85 | 177 |

TABLE 4

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047146 | 58 | 77 | 3506 | 3525 | CTCCTCTCCATCCTGCTCTG | 94 | 178 |
| 1047162 | 138 | 157 | 3586 | 3605 | GACGGCGGCCAGGAGCCAGG | 115 | 179 |
| 1047178 | 274 | 293 | 3722 | 3741 | AGCTCCATCATCTCTGCCCG | 117 | 180 |
| 1047194 | 495 | 514 | 3943 | 3962 | TGGCCAGGTCCTGTGCCAGA | 67* | 181 |
| 1047210 | 588 | 607 | 5177 | 5196 | GGGTGGCTTCATCTGCTTCC | 18* | 182 |
| 1047226 | 656 | 675 | 5245 | 5264 | GATCTTCCTCAAGAACCGGA | 62 | 183 |
| 1047242 | 822 | 841 | 5708 | 5727 | AGCGGTACCACTCTTCGGCT | 113 | 184 |
| 1047258 | 1052 | 1071 | 7624 | 7643 | CCCCTCTTCCTCCAGCCGCG | 16 | 185 |

TABLE 4-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047274 | 1253 | 1272 | 10867 | 10886 | GCCTTCTGACACAGACTTGG | 113 | 186 |
| 1047290 | 1309 | 1328 | N/A | N/A | ATGACCTCTCCATCCCGCAT | 108 | 187 |
| 1047306 | 1353 | 1372 | 11642 | 11661 | TCCTGCCTCACATCACATCC | 75 | 188 |
| 1047322 | 1499 | 1518 | 11788 | 11807 | GCAAGCTGACCTAGGGACAG | 68 | 189 |
| 1047338 | 1632 | 1651 | 11921 | 11940 | TCCTCATTCTAACGCAAGCT | 68 | 190 |
| 1047354 | 1666 | 1685 | 11955 | 11974 | GGTGCCCCCCGCCCTCCTCC | 90 | 191 |
| 1047370 | 1740 | 1759 | 12029 | 12048 | CTCCGAGAGAACCTCCATCT | 77 | 192 |
| 1047386 | 1793 | 1812 | 12082 | 12101 | TCTCAGTTTTCCTCCAGCAG | 33 | 193 |
| 1047402 | 1888 | 1907 | 12177 | 12196 | AGCATAGGGATATCCCACCT | 63 | 194 |
| 1047418 | 2063 | 2082 | 12352 | 12371 | GGCAGGTGACTGCCCCAGGT | 106 | 195 |
| 1047434 | 2182 | 2201 | 12471 | 12490 | AAGTGCTGAGAATCAAGCTC | 103 | 196 |
| 1047450 | 2239 | 2258 | 12528 | 12547 | GCCCCCCTCTATCCCTCCCA | 103 | 197 |
| 1047466 | 2329 | 2348 | 12618 | 12637 | CTCCTCCATCTCTACCAGCG | 52 | 198 |
| 1047482 | 2381 | 2400 | 12670 | 12689 | ACTGGTCACCCACAACCCCT | 79 | 199 |
| 1047498 | 2461 | 2480 | 12750 | 12769 | CATCCCCTTTCTCTCCTGTT | 74 | 200 |
| 1047514 | 2532 | 2551 | 12821 | 12840 | CGGCCTGGTATGACACAGCA | 91 | 201 |
| 1047530 | 2782 | 2801 | 13071 | 13090 | GAGCACCCGGCCTCCAGGCT | 80 | 202 |
| 1047546 | 2864 | 2883 | 13153 | 13172 | CTGGGCACAGATCCCACCAG | 107 | 203 |
| 1047562 | 2927 | 2946 | 13216 | 13235 | GGACCCTTCTTCGGCCTTAG | 69 | 204 |
| 1047578 | 3043 | 3062 | 13332 | 13351 | TTATTTTTCCTCAGCGACTA | 75 | 205 |
| 1047594 | 3062 | 3081 | 13351 | 13370 | AAGGGCGCAGCATTTGTCTT | 86 | 206 |
| 1047610 | N/A | N/A | 8782 | 8801 | GTGAGGCTTTTGAGATATCT | 33 | 207 |
| 1047626 | N/A | N/A | 9038 | 9057 | TCTGCCAGTTTAATGTACAG | 114 | 208 |
| 1047642 | N/A | N/A | 9078 | 9097 | CTGCGCACCCAAGGACTCAC | 96 | 209 |
| 1047658 | N/A | N/A | 9257 | 9276 | CCTGAGGGAAGAATCCTCTG | 86 | 210 |
| 1047674 | N/A | N/A | 8390 | 8409 | CCACGAGGCCCTGCTGTACT | 111 | 211 |
| 1047690 | N/A | N/A | 8461 | 8480 | CCCTGATCCTCAGTCCCAGT | 82 | 212 |
| 1047706 | N/A | N/A | 8534 | 8553 | CCCTGGTATGATAGGCTCTG | 62 | 213 |
| 1047722 | N/A | N/A | 8645 | 8664 | AGGGCAGATGTCAAGCTCTC | 110 | 214 |
| 1047738 | N/A | N/A | 3968 | 3987 | TCCCCTCCTCACTTCTGCCT | 91 | 215 |
| 1047754 | N/A | N/A | 4097 | 4116 | GCAAGGATAGTGCCCCATCA | 94 | 216 |
| 1047770 | N/A | N/A | 4268 | 4287 | CCACAGTCACAAAGCCCAGC | 84 | 217 |
| 1047786 | N/A | N/A | 4325 | 4344 | TCCGCTTCCAACTCCTCCTT | 107 | 218 |
| 1047802 | N/A | N/A | 4362 | 4381 | CCCCAGAATCCAATCTCCCT | 84 | 219 |
| 1047818 | N/A | N/A | 4477 | 4496 | CCACCGCTTCACAGCTGTGC | 77 | 220 |

TABLE 4-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047834 | N/A | N/A | 4528 | 4547 | GGGATTCCTCTGATCCCAGG | 93 | 221 |
| 1047850 | N/A | N/A | 4706 | 4725 | TGCCTTAACTCATTACTAAG | 64 | 222 |
| 1047866 | N/A | N/A | 4809 | 4828 | ACAGAGACCACCCCCACCCA | 63 | 223 |
| 1047882 | N/A | N/A | 4959 | 4978 | CTGACCTGTCTATAGGCAGC | 89* | 224 |
| 1047898 | N/A | N/A | 5085 | 5104 | GCCTTACCCCTCCTTCTGGG | 100 | 225 |
| 1047914 | N/A | N/A | 5268 | 5287 | TGCCCTGGCCTCACCTCCTC | 98 | 226 |
| 1047930 | N/A | N/A | 5401 | 5420 | GTCTTTCATTTCCTGTCTCT | 55 | 227 |
| 1047946 | N/A | N/A | 5562 | 5581 | TCCCGAACCTCCTGACCAGG | 117 | 228 |
| 1047962 | N/A | N/A | 5803 | 5822 | CCAGCTTCCTCCACCCTCCT | 137 | 229 |
| 1047978 | N/A | N/A | 5936 | 5955 | TCAGCTACTACTAATAATAG | 91 | 230 |
| 1047994 | N/A | N/A | 6077 | 6096 | AACTCTACCACTTAGGAGCT | 130 | 231 |
| 1048010 | N/A | N/A | 6148 | 6167 | GTAACCCAAAACAGACTGGC | 85 | 232 |
| 1048026 | N/A | N/A | 6283 | 6302 | CTCCCACACTACATATAAGC | 82 | 233 |
| 1048042 | N/A | N/A | 6331 | 6350 | TGCCTGTCCTGCCTAGCCCA | 72 | 234 |
| 1048058 | N/A | N/A | 6467 | 6486 | TCTGCCACTCACACTCCTCA | 95 | 235 |
| 1048074 | N/A | N/A | 6549 | 6568 | TTCTAATAGCCCTTTCTCCC | 83 | 236 |
| 1048090 | N/A | N/A | 6990 | 7009 | TCAGCAAGCGAATGAATGAA | 157 | 237 |
| 1048106 | N/A | N/A | 7075 | 7094 | GCTGGGACTTTTCCCAACAA | 91 | 238 |
| 1048122 | N/A | N/A | 7449 | 7468 | AGGCCCCGCCTCTAGCCCGG | 110 | 239 |
| 1048138 | N/A | N/A | 7920 | 7939 | TCATCAAACATCTAGTGACT | 91 | 240 |
| 1048154 | N/A | N/A | 8112 | 8131 | TCTATCTGAAGGAAGATGGA | 90 | 241 |
| 1048170 | N/A | N/A | 8329 | 8348 | GTGATCCTGAAAGAAAGCAG | 68 | 242 |
| 1048186 | N/A | N/A | 9375 | 9394 | TTTAGCTCCCCCCTCCCCCC | 126 | 243 |
| 1048202 | N/A | N/A | 9566 | 9585 | TGCTTTAGTGACCTGTGACT | 74 | 244 |
| 1048218 | N/A | N/A | 9614 | 9633 | CTTTCCTGTCCCCTTTCCTC | 134 | 245 |
| 1048234 | N/A | N/A | 9793 | 9812 | AGCCACCAACCAGCCACATG | 83 | 246 |
| 1048250 | N/A | N/A | 10006 | 10025 | CCTGTAATCCCCTTACTCGG | 92 | 247 |
| 1048266 | N/A | N/A | 10652 | 10671 | GCTGCCAGAGTCCTGGCTGC | 81 | 248 |
| 1048282 | N/A | N/A | 10742 | 10761 | CCATCATGAGTATGAGAACC | 88 | 249 |
| 1048298 | N/A | N/A | 10814 | 10833 | GAGGCCTCTCATGGACTTTC | 84 | 250 |
| 1048314 | N/A | N/A | 10953 | 10972 | AGCCAGAGCCTGACTGGGCC | 80 | 251 |
| 1048330 | N/A | N/A | 11080 | 11099 | GGAATTACATTCAGTTTCCT | 72 | 252 |
| 1048346 | N/A | N/A | 11268 | 11287 | CTCCCCATCCCCAACTGTGT | 107 | 253 |
| 1048362 | N/A | N/A | 11331 | 11350 | CGCCAAATCCCCTCTTCCCA | 106 | 254 |
| 1048378 | N/A | N/A | 11492 | 11511 | CCCAGGTCTTACTTTTCTTG | 80 | 255 |

TABLE 5

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047147 | 61 | 80 | 3509 | 3528 | CGTCTCCTCTCCATCCTGCT | 74 | 256 |
| 1047163 | 139 | 158 | 3587 | 3606 | AGACGGCGGCCAGGAGCCAG | 100 | 257 |
| 1047179 | 275 | 294 | 3723 | 3742 | GAGCTCCATCATCTCTGCCC | 116 | 258 |
| 1047195 | 500 | 519 | 3948 | 3967 | CACAGTGGCCAGGTCCTGTG | 70* | 259 |
| 1047211 | 589 | 608 | 5178 | 5197 | AGGGTGGCTTCATCTGCTTC | 37* | 260 |
| 1047227 | 657 | 676 | 5246 | 5265 | GGATCTTCCTCAAGAACCGG | 90 | 261 |
| 1047243 | 823 | 842 | 5709 | 5728 | GAGCGGTACCACTCTTCGGC | 83 | 262 |
| 1047259 | 1054 | 1073 | 7626 | 7645 | TGCCCCTCTTCCTCCAGCCG | 63 | 263 |
| 1047275 | 1254 | 1273 | 10868 | 10887 | GGCCTTCTGACACAGACTTG | 116 | 264 |
| 1047291 | 1311 | 1330 | N/A | N/A | TAATGACCTCTCCATCCCGC | 91 | 265 |
| 1047307 | 1354 | 1373 | 11643 | 11662 | GTCCTGCCTCACATCACATC | 88 | 266 |
| 1047323 | 1524 | 1543 | 11813 | 11832 | CCTGATACTGACGGAGCCTA | 56 | 267 |
| 1047339 | 1633 | 1652 | 11922 | 11941 | CTCCTCATTCTAACGCAAGC | 116 | 268 |
| 1047355 | 1668 | 1687 | 11957 | 11976 | TAGGTGCCCCCCGCCCTCCT | 68 | 269 |
| 1047371 | 1754 | 1773 | 12043 | 12062 | ACAGTTCCCAGATACTCCGA | 80 | 270 |
| 1047387 | 1794 | 1813 | 12083 | 12102 | GTCTCAGTTTTCCTCCAGCA | 12 | 271 |
| 1047403 | 1966 | 1985 | 12255 | 12274 | CCAATCTATAATCCCAGCTA | 89 | 272 |
| 1047419 | 2065 | 2084 | 12354 | 12373 | TGGGCAGGTGACTGCCCCAG | 110 | 273 |
| 1047435 | 2192 | 2211 | 12481 | 12500 | CAGATCCCCCAAGTGCTGAG | 87 | 274 |
| 1047451 | 2240 | 2259 | 12529 | 12548 | AGCCCCCCTCTATCCCTCCC | 97 | 275 |
| 1047467 | 2335 | 2354 | 12624 | 12643 | TGCCTCCTCCTCCATCTCTA | 72 | 276 |
| 1047483 | 2384 | 2403 | 12673 | 12692 | GCAACTGGTCACCCACAACC | 49 | 277 |
| 1047499 | 2462 | 2481 | 12751 | 12770 | ACATCCCCTTTCTCTCCTGT | 77 | 278 |
| 1047515 | 2675 | 2694 | 12964 | 12983 | TTTGTGTGTGAGTAAGAAGG | 49 | 279 |
| 1047531 | 2785 | 2804 | 13074 | 13093 | CCTGAGCACCCGGCCTCCAG | 80 | 280 |
| 1047547 | 2865 | 2884 | 13154 | 13173 | TCTGGGCACAGATCCCACCA | 85 | 281 |
| 1047563 | 2928 | 2947 | 13217 | 13236 | AGGACCCTTCTTCGGCCTTA | 70 | 282 |
| 1047579 | 3044 | 3063 | 13333 | 13352 | TTTATTTTTCCTCAGCGACT | 47 | 283 |
| 1047611 | N/A | N/A | 8826 | 8845 | TTCCATTTACAATCTGGTGA | 93 | 285 |
| 1047627 | N/A | N/A | 9040 | 9059 | GCTCTGCCAGTTTAATGTAC | 128 | 286 |
| 1047643 | N/A | N/A | 9079 | 9098 | ACTGCGCACCCAAGGACTCA | 77 | 287 |
| 1047659 | N/A | N/A | 9283 | 9302 | ACTTTATTCACTGCAAGAGC | 65 | 288 |
| 1047675 | N/A | N/A | 8398 | 8417 | TGCCCTTCCCACGAGGCCCT | 53 | 289 |
| 1047691 | N/A | N/A | 8462 | 8481 | GCCCTGATCCTCAGTCCCAG | 92 | 290 |
| 1047707 | N/A | N/A | 8535 | 8554 | ACCCTGGTATGATAGGCTCT | 46 | 291 |
| 1047723 | N/A | N/A | 8662 | 8681 | CTCAGGGATCTGCAGACAGG | 81 | 292 |

TABLE 5-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047739 | N/A | N/A | 3969 | 3988 | ATCCCCTCCTCACTTCTGCC | 85* | 293 |
| 1047755 | N/A | N/A | 4119 | 4138 | GTCCCTCCCATCATGTTGGG | 83 | 294 |
| 1047771 | N/A | N/A | 4270 | 4289 | GCCCACAGTCACAAAGCCCA | 68 | 295 |
| 1047787 | N/A | N/A | 4327 | 4346 | TCTCCGCTTCCAACTCCTCC | 109 | 296 |
| 1047803 | N/A | N/A | 4363 | 4382 | ACCCCAGAATCCAATCTCCC | 81 | 297 |
| 1047819 | N/A | N/A | 4503 | 4522 | ACCTTTTGAAATGAATTTTA | 65 | 298 |
| 1047835 | N/A | N/A | 4588 | 4607 | CTCCTGCACTTGAAGGCACA | 101 | 299 |
| 1047851 | N/A | N/A | 4707 | 4726 | TTGCCTTAACTCATTACTAA | 77 | 300 |
| 1047867 | N/A | N/A | 4811 | 4830 | TCACAGAGACCACCCCCACC | 97 | 301 |
| 1047883 | N/A | N/A | 4964 | 4983 | CCTCCCTGACCTGTCTATAG | 103* | 302 |
| 1047899 | N/A | N/A | 5086 | 5105 | TGCCTTACCCCTCCTTCTGG | 76 | 303 |
| 1047915 | N/A | N/A | 5270 | 5289 | TCTGCCCTGGCCTCACCTCC | 102 | 304 |
| 1047931 | N/A | N/A | 5403 | 5422 | TTGTCTTTCATTTCCTGTCT | 67 | 305 |
| 1047947 | N/A | N/A | 5563 | 5582 | TTCCCGAACCTCCTGACCAG | 131 | 306 |
| 1047963 | N/A | N/A | 5804 | 5823 | CCCAGCTTCCTCCACCCTCC | 58 | 307 |
| 1047979 | N/A | N/A | 5937 | 5956 | ATCAGCTACTACTAATAATA | 128 | 308 |
| 1047995 | N/A | N/A | 6078 | 6097 | CAACTCTACCACTTAGGAGC | 97 | 309 |
| 1048011 | N/A | N/A | 6150 | 6169 | CAGTAACCCAAAACAGACTG | 85 | 310 |
| 1048027 | N/A | N/A | 6284 | 6303 | GCTCCCACACTACATATAAG | 48 | 311 |
| 1048043 | N/A | N/A | 6352 | 6371 | CTTCTCTTCCTGTCCACAGC | 93 | 312 |
| 1048059 | N/A | N/A | 6471 | 6490 | GGCTTCTGCCACTCACACTC | 85 | 313 |
| 1048075 | N/A | N/A | 6550 | 6569 | GTTCTAATAGCCCTTTCTCC | 124 | 314 |
| 1048091 | N/A | N/A | 6991 | 7010 | GTCAGCAAGCGAATGAATGA | 85 | 315 |
| 1048107 | N/A | N/A | 7109 | 7128 | CAGCACCCCAGTTAACCCCA | 73 | 316 |
| 1048123 | N/A | N/A | 7450 | 7469 | CAGGCCCCGCCTCTAGCCCG | 88 | 317 |
| 1048139 | N/A | N/A | 7928 | 7947 | CCATTCAGTCATCAAACATC | 76 | 318 |
| 1048155 | N/A | N/A | 8120 | 8139 | GGCGCATGTCTATCTGAAGG | 76 | 319 |
| 1048171 | N/A | N/A | 8330 | 8349 | GGTGATCCTGAAAGAAAGCA | 103 | 320 |
| 1048187 | N/A | N/A | 9391 | 9410 | TGCAAGTAAAAAGTAATTTA | 69 | 321 |
| 1048203 | N/A | N/A | 9568 | 9587 | TGTGCTTTAGTGACCTGTGA | 31 | 322 |
| 1048219 | N/A | N/A | 9619 | 9638 | GGTCCCTTTCCTGTCCCCTT | 53 | 323 |
| 1048235 | N/A | N/A | 9794 | 9813 | TAGCCACCAACCAGCCACAT | 97 | 324 |
| 1048251 | N/A | N/A | 10007 | 10026 | ACCTGTAATCCCCTTACTCG | 89 | 325 |
| 1048267 | N/A | N/A | 10657 | 10676 | GTGCTGCTGCCAGAGTCCTG | 35 | 326 |
| 1048283 | N/A | N/A | 10750 | 10769 | CCCCCTCCCCATCATGAGTA | 100 | 327 |

TABLE 5-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1048299 | N/A | N/A | 10841 | 10860 | GGCTGGTTTCTGCAGATGTG | 87 | 328 |
| 1048315 | N/A | N/A | 10954 | 10973 | CAGCCAGAGCCTGACTGGGC | 188 | 329 |
| 1048331 | N/A | N/A | 11086 | 11105 | GGAAACGGAATTACATTCAG | 130 | 330 |
| 1048347 | N/A | N/A | 11269 | 11288 | CCTCCCCATCCCCAACTGTG | 99 | 331 |
| 1048363 | N/A | N/A | 11332 | 11351 | ACGCCAAATCCCCTCTTCCC | 93 | 332 |
| 1048379 | N/A | N/A | 11501 | 11520 | CCCCGACTTCCCAGGTCTTA | 91 | 333 |

TABLE 6

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047148 | 112 | 131 | 3560 | 3579 | ACCATCATCTCCCCTGAGGA | 116 | 334 |
| 1047164 | 150 | 169 | 3598 | 3617 | TGCCAGGACCCAGACGGCGG | 96 | 335 |
| 1047180 | 277 | 296 | 3725 | 3744 | TTGAGCTCCATCATCTCTGC | 123 | 336 |
| 1047196 | 503 | 522 | 3951 | 3970 | CCTCACAGTGGCCAGGTCCT | 27* | 337 |
| 1047212 | 615 | 634 | 5204 | 5223 | TCTTCCTCTCCAGATCCAGA | 77 | 338 |
| 1047228 | 658 | 677 | 5247 | 5266 | TGGATCTTCCTCAAGAACCG | 75 | 339 |
| 1047244 | 824 | 843 | 5710 | 5729 | GGAGCGGTACCACTCTTCGG | 74 | 340 |
| 1047260 | 1058 | 1077 | 7630 | 7649 | GCTCTGCCCCTCTTCCTCCA | 82 | 341 |
| 1047276 | 1255 | 1274 | 10869 | 10888 | TGGCCTTCTGACACAGACTT | 137 | 342 |
| 1047292 | 1312 | 1331 | N/A | N/A | TTAATGACCTCTCCATCCCG | 81 | 343 |
| 1047308 | 1356 | 1375 | 11645 | 11664 | GGGTCCTGCCTCACATCACA | 69 | 344 |
| 1047324 | 1526 | 1545 | 11815 | 11834 | GGCCTGATACTGACGGAGCC | 73 | 345 |
| 1047340 | 1634 | 1653 | 11923 | 11942 | CCTCCTCATTCTAACGCAAG | 63 | 346 |
| 1047356 | 1672 | 1691 | 11961 | 11980 | GTAGTAGGTGCCCCCCGCCC | 84 | 347 |
| 1047372 | 1755 | 1774 | 12044 | 12063 | CACAGTTCCCAGATACTCCG | 49 | 348 |
| 1047388 | 1795 | 1814 | 12084 | 12103 | AGTCTCAGTTTTCCTCCAGC | 24 | 349 |
| 1047404 | 1999 | 2018 | 12288 | 12307 | GGAGAACAACCCTCTGAGCT | 75 | 350 |
| 1047420 | 2101 | 2120 | 12390 | 12409 | CACTTGAGTCATCGCTCAGG | 107 | 351 |
| 1047436 | 2193 | 2212 | 12482 | 12501 | ACAGATCCCCCAAGTGCTGA | 73 | 352 |
| 1047452 | 2241 | 2260 | 12530 | 12549 | CAGCCCCCCTCTATCCCTCC | 88 | 353 |
| 1047468 | 2337 | 2356 | 12626 | 12645 | ATTGCCTCCTCCTCCATCTC | 93 | 354 |
| 1047484 | 2395 | 2414 | 12684 | 12703 | AGAGGCCAAGTGCAACTGGT | 80 | 355 |
| 1047500 | 2463 | 2482 | 12752 | 12771 | TACATCCCCTTTCTCTCCTG | 47 | 356 |

TABLE 6-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047516 | 2699 | 2718 | 12988 | 13007 | CACTACCTAGAATACTGGGT | 92 | 357 |
| 1047532 | 2794 | 2813 | 13083 | 13102 | CGTGTCAGCCCTGAGCACCC | 129 | 358 |
| 1047548 | 2866 | 2885 | 13155 | 13174 | CTCTGGGCACAGATCCCACC | 141 | 359 |
| 1047564 | 2931 | 2950 | 13220 | 13239 | GGAAGGACCCTTCTTCGGCC | 67 | 360 |
| 1047580 | 3045 | 3064 | 13334 | 13353 | CTTTATTTTTCCTCAGCGAC | 35 | 361 |
| 1047612 | N/A | N/A | 8827 | 8846 | GTTCCATTTACAATCTGGTG | 60 | 363 |
| 1047628 | N/A | N/A | 9053 | 9072 | TTACCACTAACAAGCTCTGC | 76 | 364 |
| 1047644 | N/A | N/A | 9081 | 9100 | CCACTGCGCACCCAAGGACT | 89 | 365 |
| 1047660 | N/A | N/A | 9290 | 9309 | ACATAAAACTTTATTCACTG | 74 | 366 |
| 1047676 | N/A | N/A | 8399 | 8418 | GTGCCCTTCCCACGAGGCCC | 176 | 367 |
| 1047692 | N/A | N/A | 8463 | 8482 | TGCCCTGATCCTCAGTCCCA | 81 | 368 |
| 1047708 | N/A | N/A | 8536 | 8555 | TACCCTGGTATGATAGGCTC | 60 | 369 |
| 1047724 | N/A | N/A | 8669 | 8688 | GTGCTTGCTCAGGGATCTGC | 56 | 370 |
| 1047740 | N/A | N/A | 3971 | 3990 | CCATCCCCTCCTCACTTCTG | 85* | 371 |
| 1047756 | N/A | N/A | 4120 | 4139 | GGTCCCTCCCATCATGTTGG | 76 | 372 |
| 1047772 | N/A | N/A | 4272 | 4291 | CTGCCCACAGTCACAAAGCC | 103 | 373 |
| 1047788 | N/A | N/A | 4328 | 4347 | TTCTCCGCTTCCAACTCCTC | 133 | 374 |
| 1047804 | N/A | N/A | 4364 | 4383 | CACCCCAGAATCCAATCTCC | 78 | 375 |
| 1047820 | N/A | N/A | 4507 | 4526 | AACCACCTTTTGAAATGAAT | 118 | 376 |
| 1047836 | N/A | N/A | 4596 | 4615 | CACATGTCCTCCTGCACTTG | 108 | 377 |
| 1047852 | N/A | N/A | 4708 | 4727 | TTTGCCTTAACTCATTACTA | 91 | 378 |
| 1047868 | N/A | N/A | 4812 | 4831 | GTCACAGAGACCACCCCCAC | 108 | 379 |
| 1047884 | N/A | N/A | 4965 | 4984 | ACCTCCCTGACCTGTCTATA | 83 | 380 |
| 1047900 | N/A | N/A | 5087 | 5106 | TTGCCTTACCCCTCCTTCTG | 102 | 381 |
| 1047916 | N/A | N/A | 5282 | 5301 | AGCTTTCCTCCCTCTGCCCT | 92 | 382 |
| 1047932 | N/A | N/A | 5405 | 5424 | GTTTGTCTTTCATTTCCTGT | 82 | 383 |
| 1047948 | N/A | N/A | 5564 | 5583 | GTTCCCGAACCTCCTGACCA | 103 | 384 |
| 1047964 | N/A | N/A | 5805 | 5824 | TCCCAGCTTCCTCCACCCTC | 78 | 385 |
| 1047980 | N/A | N/A | 5938 | 5957 | TATCAGCTACTACTAATAAT | 106 | 386 |
| 1047996 | N/A | N/A | 6079 | 6098 | CCAACTCTACCACTTAGGAG | 96 | 387 |
| 1048012 | N/A | N/A | 6151 | 6170 | TCAGTAACCCAAAACAGACT | 124 | 388 |
| 1048028 | N/A | N/A | 6285 | 6304 | GGCTCCCACACTACATATAA | 134 | 389 |
| 1048044 | N/A | N/A | 6353 | 6372 | TCTTCTCTTCCTGTCCACAG | 93 | 390 |
| 1048060 | N/A | N/A | 6473 | 6492 | GTGGCTTCTGCCACTCACAC | 129 | 391 |
| 1048076 | N/A | N/A | 6556 | 6575 | CCCTGGGTTCTAATAGCCCT | 89 | 392 |

TABLE 6-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1048092 | N/A | N/A | 6993 | 7012 | TGGTCAGCAAGCGAATGAAT | 81 | 393 |
| 1048108 | N/A | N/A | 7111 | 7130 | AGCAGCACCCCAGTTAACCC | 104 | 394 |
| 1048124 | N/A | N/A | 7451 | 7470 | CCAGGCCCCGCCTCTAGCCC | 89 | 395 |
| 1048140 | N/A | N/A | 7932 | 7951 | CCATCCATTCAGTCATCAAA | 70 | 396 |
| 1048156 | N/A | N/A | 8142 | 8161 | GGCTTGAGTGTTATCTGGGA | 74 | 397 |
| 1048172 | N/A | N/A | 8332 | 8351 | ATGGTGATCCTGAAAGAAAG | 87 | 398 |
| 1048188 | N/A | N/A | 9392 | 9411 | ATGCAAGTAAAAAGTAATTT | 61 | 399 |
| 1048204 | N/A | N/A | 9581 | 9600 | TCTGCCATTTATCTGTGCTT | 61 | 400 |
| 1048220 | N/A | N/A | 9621 | 9640 | TAGGTCCCTTTCCTGTCCCC | 60 | 401 |
| 1048236 | N/A | N/A | 9795 | 9814 | TTAGCCACCAACCAGCCACA | 106 | 402 |
| 1048252 | N/A | N/A | 10009 | 10028 | GCACCTGTAATCCCCTTACT | 76 | 403 |
| 1048268 | N/A | N/A | 10658 | 10677 | AGTGCTGCTGCCAGAGTCCT | 80 | 404 |
| 1048284 | N/A | N/A | 10751 | 10770 | CCCCCCTCCCCATCATGAGT | 82 | 405 |
| 1048300 | N/A | N/A | 10921 | 10940 | TACCTCTCCATCCCGCATCT | 109 | 406 |
| 1048316 | N/A | N/A | 10976 | 10995 | TGGCCTTGAGAATCCCTGGG | 99 | 407 |
| 1048332 | N/A | N/A | 11090 | 11109 | CTGAGGAAACGGAATTACAT | 83 | 408 |
| 1048348 | N/A | N/A | 11272 | 11291 | AGCCCTCCCCATCCCCAACT | 121 | 409 |
| 1048364 | N/A | N/A | 11333 | 11352 | TACGCCAAATCCCCTCTTCC | 92 | 410 |
| 1048380 | N/A | N/A | 11504 | 11523 | AGTCCCCGACTTCCCAGGTC | 116 | 411 |

TABLE 7

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047149 | 113 | 132 | 3561 | 3580 | CACCATCATCTCCCCTGAGG | 102 | 412 |
| 1047165 | 151 | 170 | 3599 | 3618 | GTGCCAGGACCCAGACGGCG | 120 | 413 |
| 1047181 | 279 | 298 | 3727 | 3746 | CATTGAGCTCCATCATCTCT | 92 | 414 |
| 1047197 | 525 | 544 | N/A | N/A | TGGTTTCATCCTGGAGCTTC | 39* | 415 |
| 1047213 | 617 | 636 | 5206 | 5225 | AATCTTCCTCTCCAGATCCA | 79 | 416 |
| 1047229 | 659 | 678 | 5248 | 5267 | GTGGATCTTCCTCAAGAACC | 83 | 417 |
| 1047245 | 825 | 844 | 5711 | 5730 | TGGAGCGGTACCACTCTTCG | 77 | 418 |
| 1047261 | 1060 | 1079 | 7632 | 7651 | AGGCTCTGCCCCTCTTCCTC | 78 | 419 |
| 1047277 | 1257 | 1276 | 10871 | 10890 | GGTGGCCTTCTGACACAGAC | 98 | 420 |
| 1047293 | 1313 | 1332 | N/A | N/A | CTTAATGACCTCTCCATCCC | 105 | 421 |

TABLE 7-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047309 | 1357 | 1376 | 11646 | 11665 | TGGGTCCTGCCTCACATCAC | 154 | 422 |
| 1047325 | 1529 | 1548 | 11818 | 11837 | GCAGGCCTGATACTGACGGA | 46 | 423 |
| 1047341 | 1635 | 1654 | 11924 | 11943 | TCCTCCTCATTCTAACGCAA | 53 | 424 |
| 1047357 | 1684 | 1703 | 11973 | 11992 | GTGGAGGGCGATGTAGTAGG | 42 | 425 |
| 1047373 | 1756 | 1775 | 12045 | 12064 | GCACAGTTCCCAGATACTCC | 33 | 426 |
| 1047389 | 1812 | 1831 | 12101 | 12120 | CTTCCCTTTCCTGTCTGAGT | 64 | 427 |
| 1047405 | 2003 | 2022 | 12292 | 12311 | TCTAGGAGAACAACCCTCTG | 160 | 428 |
| 1047421 | 2103 | 2122 | 12392 | 12411 | GACACTTGAGTCATCGCTCA | 63 | 429 |
| 1047437 | 2194 | 2213 | 12483 | 12502 | AACAGATCCCCCAAGTGCTG | 85 | 430 |
| 1047453 | 2242 | 2261 | 12531 | 12550 | GCAGCCCCCCTCTATCCCTC | 173 | 431 |
| 1047469 | 2341 | 2360 | 12630 | 12649 | CCCAATTGCCTCCTCCTCCA | 53 | 432 |
| 1047485 | 2407 | 2426 | 12696 | 12715 | TTCCCACAATCCAGAGGCCA | 101 | 433 |
| 1047501 | 2464 | 2483 | 12753 | 12772 | ATACATCCCCTTTCTCTCCT | 63 | 434 |
| 1047517 | 2701 | 2720 | 12990 | 13009 | GGCACTACCTAGAATACTGG | 73 | 435 |
| 1047533 | 2833 | 2852 | 13122 | 13141 | GTCTGCTCAGTCAAAGCAGA | 93 | 436 |
| 1047549 | 2877 | 2896 | 13166 | 13185 | CCCAGTCCCATCTCTGGGCA | 134 | 437 |
| 1047565 | 2932 | 2951 | 13221 | 13240 | GGGAAGGACCCTTCTTCGGC | 66 | 438 |
| 1047581 | 3046 | 3065 | 13335 | 13354 | TCTTTATTTTTCCTCAGCGA | 41 | 439 |
| 1047613 | N/A | N/A | 8828 | 8847 | CGTTCCATTTACAATCTGGT | 47 | 441 |
| 1047629 | N/A | N/A | 9056 | 9075 | CCTTTACCACTAACAAGCTC | 161 | 442 |
| 1047645 | N/A | N/A | 9086 | 9105 | CAGCTCCACTGCGCACCCAA | 85 | 443 |
| 1047661 | N/A | N/A | 9300 | 9319 | AGAGCAGGGAACATAAAACT | 69 | 444 |
| 1047677 | N/A | N/A | 8400 | 8419 | AGTGCCCTTCCCACGAGGCC | 85 | 445 |
| 1047693 | N/A | N/A | 8464 | 8483 | TTGCCCTGATCCTCAGTCCC | 117 | 446 |
| 1047709 | N/A | N/A | 8547 | 8566 | CCACCTAGAAGTACCCTGGT | 75 | 447 |
| 1047725 | N/A | N/A | 8688 | 8707 | GAAAACACTCAGAAGGGCAG | 101 | 448 |
| 1047741 | N/A | N/A | 3972 | 3991 | CCCATCCCCTCCTCACTTCT | 133 | 449 |
| 1047757 | N/A | N/A | 4122 | 4141 | CTGGTCCCTCCCATCATGTT | 136 | 450 |
| 1047773 | N/A | N/A | 4273 | 4292 | GCTGCCCACAGTCACAAAGC | 126 | 451 |
| 1047789 | N/A | N/A | 4334 | 4353 | TCAACCTTCTCCGCTTCCAA | 66 | 452 |
| 1047805 | N/A | N/A | 4369 | 4388 | TTCTTCACCCCAGAATCCAA | 123 | 453 |
| 1047821 | N/A | N/A | 4508 | 4527 | TAACCACCTTTTGAAATGAA | 75 | 454 |
| 1047837 | N/A | N/A | 4657 | 4676 | CTGCTCACACAGGCGCATCC | 97 | 455 |
| 1047853 | N/A | N/A | 4709 | 4728 | TTTTGCCTTAACTCATTACT | 142 | 456 |
| 1047869 | N/A | N/A | 4813 | 4832 | TGTCACAGAGACCACCCCCA | 87 | 457 |

TABLE 7-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047885 | N/A | N/A | 4968 | 4987 | TCCACCTCCCTGACCTGTCT | 84 | 458 |
| 1047901 | N/A | N/A | 5090 | 5109 | GCCTTGCCTTACCCCTCCTT | 86 | 459 |
| 1047917 | N/A | N/A | 5284 | 5303 | TGAGCTTTCCTCCCTCTGCC | 93 | 460 |
| 1047933 | N/A | N/A | 5417 | 5436 | TAGTGTCTTTCTGTTTGTCT | 82 | 461 |
| 1047949 | N/A | N/A | 5565 | 5584 | AGTTCCCGAACCTCCTGACC | 74 | 462 |
| 1047965 | N/A | N/A | 5806 | 5825 | CTCCCAGCTTCCTCCACCCT | 101 | 463 |
| 1047981 | N/A | N/A | 5939 | 5958 | GTATCAGCTACTACTAATAA | 137 | 464 |
| 1047997 | N/A | N/A | 6080 | 6099 | TCCAACTCTACCACTTAGGA | 112 | 465 |
| 1048013 | N/A | N/A | 6152 | 6171 | CTCAGTAACCCAAAACAGAC | 79 | 466 |
| 1048029 | N/A | N/A | 6287 | 6306 | CTGGCTCCCACACTACATAT | 86 | 467 |
| 1048045 | N/A | N/A | 6354 | 6373 | TTCTTCTCTTCCTGTCCACA | 92 | 468 |
| 1048061 | N/A | N/A | 6474 | 6493 | AGTGGCTTCTGCCACTCACA | 88 | 469 |
| 1048077 | N/A | N/A | 6557 | 6576 | ACCCTGGGTTCTAATAGCCC | 104 | 470 |
| 1048093 | N/A | N/A | 7008 | 7027 | ACCTAGCACAACACCTGGTC | 77 | 471 |
| 1048109 | N/A | N/A | 7318 | 7337 | GCGCTCACCGTGCCGCGCAG | 85 | 472 |
| 1048125 | N/A | N/A | 7497 | 7516 | GAGCCCCGACCCGACTTGGG | 55 | 473 |
| 1048141 | N/A | N/A | 7943 | 7962 | GTTGAATCCATCCATCCATT | 73 | 474 |
| 1048157 | N/A | N/A | 8195 | 8214 | AGCTTTTTCCCCAGCAGCCA | 91 | 475 |
| 1048173 | N/A | N/A | 8333 | 8352 | AATGGTGATCCTGAAAGAAA | 80 | 476 |
| 1048189 | N/A | N/A | 9415 | 9434 | AGCTAAGAATCATTTCAGGG | 77 | 477 |
| 1048205 | N/A | N/A | 9584 | 9603 | CTCTCTGCCATTTATCTGTG | 67 | 478 |
| 1048221 | N/A | N/A | 9622 | 9641 | ATAGGTCCCTTTCCTGTCCC | 67 | 479 |
| 1048237 | N/A | N/A | 9796 | 9815 | CTTAGCCACCAACCAGCCAC | 123 | 480 |
| 1048253 | N/A | N/A | 10010 | 10029 | CGCACCTGTAATCCCCTTAC | 97 | 481 |
| 1048269 | N/A | N/A | 10666 | 10685 | ATCCCAATAGTGCTGCTGCC | 79 | 482 |
| 1048285 | N/A | N/A | 10755 | 10774 | CGCACCCCCCTCCCCATCAT | 109 | 483 |
| 1048301 | N/A | N/A | 10925 | 10944 | TCCTTACCTCTCCATCCCGC | 106 | 484 |
| 1048317 | N/A | N/A | 10993 | 11012 | GGCTTTCCTCCATGGCCTGG | 93 | 485 |
| 1048333 | N/A | N/A | 11092 | 11111 | GACTGAGGAAACGGAATTAC | 86 | 486 |
| 1048349 | N/A | N/A | 11278 | 11297 | ATGGAAAGCCCTCCCCATCC | 86 | 487 |
| 1048365 | N/A | N/A | 11334 | 11353 | ATACGCCAAATCCCCTCTTC | 105 | 488 |
| 1048381 | N/A | N/A | 11505 | 11524 | AAGTCCCCGACTTCCCAGGT | 79 | 489 |

TABLE 8

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047150 | 115 | 134 | 3563 | 3582 | CCCACCATCATCTCCCCTGA | 93 | 490 |
| 1047166 | 156 | 175 | 3604 | 3623 | GGCGGGTGCCAGGACCCAGA | 79 | 491 |
| 1047182 | 358 | 377 | 3806 | 3825 | AGCTGGTTCAGCTCAGCAGC | 114 | 492 |
| 1047198 | 528 | 547 | 4913 | 4932 | GGTTGGTTTCATCCTGGAGC | 19* | 493 |
| 1047214 | 619 | 638 | 5208 | 5227 | TCAATCTTCCTCTCCAGATC | 115 | 494 |
| 1047230 | 680 | 699 | N/A | N/A | GAGTTCCCGAACCTCCTCCT | 85 | 495 |
| 1047246 | 838 | 857 | N/A | N/A | AGGTCTGCAAACTTGGAGCG | 90 | 496 |
| 1047262 | 1064 | 1083 | 7636 | 7655 | CTTGAGGCTCTGCCCCTCTT | 88 | 497 |
| 1047278 | 1258 | 1277 | 10872 | 10891 | AGGTGGCCTTCTGACACAGA | 94 | 498 |
| 1047294 | 1314 | 1333 | N/A | N/A | CCTTAATGACCTCTCCATCC | 154 | 499 |
| 1047310 | 1358 | 1377 | 11647 | 11666 | GTGGGTCCTGCCTCACATCA | 88 | 500 |
| 1047326 | 1530 | 1549 | 11819 | 11838 | GGCAGGCCTGATACTGACGG | 103 | 501 |
| 1047342 | 1636 | 1655 | 11925 | 11944 | TTCCTCCTCATTCTAACGCA | 66 | 502 |
| 1047358 | 1685 | 1704 | 11974 | 11993 | TGTGGAGGGCGATGTAGTAG | 50 | 503 |
| 1047374 | 1757 | 1776 | 12046 | 12065 | GGCACAGTTCCCAGATACTC | 40 | 504 |
| 1047390 | 1813 | 1832 | 12102 | 12121 | CCTTCCCTTTCCTGTCTGAG | 81 | 505 |
| 1047406 | 2004 | 2023 | 12293 | 12312 | GTCTAGGAGAACAACCCTCT | 96 | 506 |
| 1047422 | 2112 | 2131 | 12401 | 12420 | GTGGACTGAGACACTTGAGT | 54 | 507 |
| 1047438 | 2201 | 2220 | 12490 | 12509 | CGTACACAACAGATCCCCCA | 61 | 508 |
| 1047454 | 2243 | 2262 | 12532 | 12551 | GGCAGCCCCCCTCTATCCCT | 57 | 509 |
| 1047470 | 2342 | 2361 | 12631 | 12650 | TCCCAATTGCCTCCTCCTCC | 66 | 510 |
| 1047486 | 2413 | 2432 | 12702 | 12721 | CCTTAATTCCCACAATCCAG | 147 | 511 |
| 1047502 | 2465 | 2484 | 12754 | 12773 | GATACATCCCCTTTCTCTCC | 67 | 512 |
| 1047518 | 2702 | 2721 | 12991 | 13010 | GGGCACTACCTAGAATACTG | 43 | 513 |
| 1047534 | 2843 | 2862 | 13132 | 13151 | CTGCTCACCAGTCTGCTCAG | 97 | 514 |
| 1047550 | 2878 | 2897 | 13167 | 13186 | TCCCAGTCCCATCTCTGGGC | 106 | 515 |
| 1047566 | 2933 | 2952 | 13222 | 1324 | AGGGAAGGACCCTTCTTCGG | 71 | 516 |
| 1047582 | 3047 | 3066 | 13336 | 13355 | GTCTTTATTTTTCCTCAGCG | 9 | 517 |
| 1047614 | N/A | N/A | 8850 | 8869 | GCAGCTAACCGCGAGCCGGC | 132 | 519 |
| 1047630 | N/A | N/A | 9057 | 9076 | ACCTTTACCACTAACAAGCT | 89 | 520 |
| 1047646 | N/A | N/A | 9088 | 9107 | AGCAGCTCCACTGCGCACCC | 116 | 521 |
| 1047662 | N/A | N/A | 9311 | 9330 | ATTTAACATTAAGAGCAGGG | 45 | 522 |
| 1047678 | N/A | N/A | 8401 | 8420 | CAGTGCCCTTCCCACGAGGC | 110 | 523 |
| 1047694 | N/A | N/A | 8467 | 8486 | CCTTTGCCCTGATCCTCAGT | 77 | 524 |
| 1047710 | N/A | N/A | 8549 | 8568 | CCCCACCTAGAAGTACCCTG | 99 | 525 |
| 1047726 | N/A | N/A | 8689 | 8708 | AGAAAACACTCAGAAGGGCA | 169 | 526 |

TABLE 8-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1047742 | N/A | N/A | 3973 | 3992 | CCCCATCCCCTCCTCACTTC | 100 | 527 |
| 1047758 | N/A | N/A | 4124 | 4143 | TTCTGGTCCCTCCCATCATG | 77 | 528 |
| 1047774 | N/A | N/A | 4277 | 4296 | GCTCGCTGCCCACAGTCACA | 123 | 529 |
| 1047790 | N/A | N/A | 4338 | 4357 | GACATCAACCTTCTCCGCTT | 67 | 530 |
| 1047806 | N/A | N/A | 4375 | 4394 | CTCACTTTCTTCACCCCAGA | 156 | 531 |
| 1047822 | N/A | N/A | 4510 | 4529 | GGTAACCACCTTTTGAAATG | 91 | 532 |
| 1047838 | N/A | N/A | 4659 | 4678 | TTCTGCTCACACAGGCGCAT | 148 | 533 |
| 1047854 | N/A | N/A | 4712 | 4731 | GGCTTTTGCCTTAACTCATT | 72 | 534 |
| 1047870 | N/A | N/A | 4815 | 4834 | GCTGTCACAGAGACCACCCC | 93 | 535 |
| 1047886 | N/A | N/A | 4971 | 4990 | CCCTCCACCTCCCTGACCTG | 59 | 536 |
| 1047902 | N/A | N/A | 5092 | 5111 | CAGCCTTGCCTTACCCCTCC | 70 | 537 |
| 1047918 | N/A | N/A | 5285 | 5304 | TTGAGCTTTCCTCCCTCTGC | 80 | 538 |
| 1047934 | N/A | N/A | 5429 | 5448 | TTCCGTCTCCCTTAGTGTCT | 105 | 539 |
| 1047950 | N/A | N/A | 5566 | 5585 | GAGTTCCCGAACCTCCTGAC | 70 | 540 |
| 1047966 | N/A | N/A | 5813 | 5832 | GGATATTCTCCCAGCTTCCT | 90 | 541 |
| 1047982 | N/A | N/A | 5945 | 5964 | AGAACAGTATCAGCTACTAC | 106 | 542 |
| 1047998 | N/A | N/A | 6085 | 6104 | GGAAATCCAACTCTACCACT | 106 | 543 |
| 1048014 | N/A | N/A | 6153 | 6172 | GCTCAGTAACCCAAAACAGA | 96 | 544 |
| 1048030 | N/A | N/A | 6288 | 6307 | CCTGGCTCCCACACTACATA | 116 | 545 |
| 1048046 | N/A | N/A | 6356 | 6375 | CCTTCTTCTCTTCCTGTCCA | 133 | 546 |
| 1048062 | N/A | N/A | 6486 | 6505 | TGCTCAGACACCAGTGGCTT | 109 | 547 |
| 1048078 | N/A | N/A | 6567 | 6586 | GCCTGGCCTCACCCTGGGTT | 88 | 548 |
| 1048094 | N/A | N/A | 7023 | 7042 | CTGCCAGACCTCAGCACCTA | 81 | 549 |
| 1048110 | N/A | N/A | 7322 | 7341 | GGCCGCGCTCACCGTGCCGC | 109 | 550 |
| 1048126 | N/A | N/A | 7498 | 7517 | GGAGCCCCGACCCGACTTGG | 124 | 551 |
| 1048142 | N/A | N/A | 7944 | 7963 | GGTTGAATCCATCCATCCAT | 105 | 552 |
| 1048158 | N/A | N/A | 8196 | 8215 | TAGCTTTTTCCCCAGCAGCC | 89 | 553 |
| 1048174 | N/A | N/A | 8334 | 8353 | GAATGGTGATCCTGAAAGAA | 81 | 554 |
| 1048190 | N/A | N/A | 9462 | 9481 | AGTGGTCCTAAATATTCTAG | 66 | 555 |
| 1048206 | N/A | N/A | 9585 | 9604 | TCTCTCTGCCATTTATCTGT | 91 | 556 |
| 1048222 | N/A | N/A | 9623 | 9642 | CATAGGTCCCTTTCCTGTCC | 71 | 557 |
| 1048238 | N/A | N/A | 9799 | 9818 | CAACTTAGCCACCAACCAGC | 120 | 558 |
| 1048254 | N/A | N/A | 10576 | 10595 | GGCTTTCTGAAAACCCAGCA | 72 | 559 |
| 1048270 | N/A | N/A | 10673 | 10692 | CCCCCAAATCCCAATAGTGC | 117 | 560 |
| 1048286 | N/A | N/A | 10756 | 10775 | TCGCACCCCCCTCCCCATCA | 106 | 561 |

TABLE 8-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ NO ID |
|---|---|---|---|---|---|---|---|
| 1048302 | N/A | N/A | 10926 | 10945 | CTCCTTACCTCTCCATCCCG | 120 | 562 |
| 1048318 | N/A | N/A | 10994 | 11013 | AGGCTTTCCTCCATGGCCTG | 91 | 563 |
| 1048334 | N/A | N/A | 11110 | 11129 | TAGAACAGCCTATGGAGGGA | 52 | 564 |
| 1048350 | N/A | N/A | 11300 | 11319 | GTTTCCTTTTACCAAGCTGG | 34 | 565 |
| 1048366 | N/A | N/A | 11335 | 11354 | GATACGCCAAATCCCCTCTT | 94 | 566 |
| 1048382 | N/A | N/A | 11508 | 11527 | GGGAAGTCCCCGACTTCCCA | 92 | 567 |

TABLE 9

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047151 | 116 | 135 | 3564 | 3583 | CCCCACCATCATCTCCCCTG | 89 | 568 |
| 1047167 | 173 | 192 | 3621 | 3640 | CATTCGAGCCAGGGAGAGGC | 82 | 569 |
| 1047183 | 372 | 391 | 3820 | 3839 | GCTCCTTGGCCCGCAGCTGG | 147 | 570 |
| 1047199 | 529 | 548 | 4914 | 4933 | AGGTTGGTTTCATCCTGGAG | 47* | 571 |
| 1047215 | 620 | 639 | 5209 | 5228 | CTCAATCTTCCTCTCCAGAT | 93 | 572 |
| 1047231 | 683 | 702 | 5569 | 5588 | CTGGAGTTCCCGAACCTCCT | 113 | 573 |
| 1047247 | 943 | 962 | 7300 | 7319 | AGAGACTCCAGGTCGCAGGT | 104 | 574 |
| 1047263 | 1098 | 1117 | 7670 | 7689 | CCTGGTACTOCTGCAAGTGG | 139 | 575 |
| 1047279 | 1260 | 1279 | 10874 | 10893 | TGAGGTGGCCTTCTGACACA | 106 | 576 |
| 1047295 | 1319 | 1338 | N/A | N/A | GGACTCCTTAATGACCTCTC | 77 | 577 |
| 1047311 | 1370 | 1389 | 11659 | 11678 | AGAGGCCACCAGGTGGGTCC | 88 | 578 |
| 1047327 | 1531 | 1550 | 11820 | 11839 | TGGCAGGCCTGATACTGACG | 71 | 579 |
| 1047343 | 1637 | 1656 | 11926 | 11945 | CTTCCTCCTCATTCTAACGC | 68 | 580 |
| 1047359 | 1714 | 1733 | 12003 | 12022 | ACAGTTTCCATAACAACAGG | 137 | 581 |
| 1047375 | 1760 | 1779 | 12049 | 12068 | AAAGGCACAGTTCCCAGATA | 106 | 582 |
| 1047391 | 1814 | 1833 | 12103 | 12122 | GCCTTCCCTTTOCTGTCTGA | 34 | 583 |
| 1047407 | 2005 | 2024 | 12294 | 12313 | AGTCTAGGAGAACAACCCTC | 113 | 584 |
| 1047423 | 2138 | 2157 | 12427 | 12446 | GATGGCATCCCTGGATGGCA | 113 | 585 |
| 1047439 | 2219 | 2238 | 12508 | 12527 | GCACCTCATCCCTCTCCACG | 75 | 586 |
| 1047455 | 2244 | 2263 | 12533 | 12552 | AGGCAGCCCCCCTCTATCCC | 77 | 587 |
| 1047471 | 2343 | 2362 | 12632 | 12651 | ATCCCAATTGCCTCCTCCTC | 96 | 588 |
| 1047487 | 2414 | 2433 | 12703 | 12722 | TCCTTAATTCCCACAATCCA | 105 | 589 |

TABLE 9-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047503 | 2466 | 2485 | 12755 | 12774 | GGATACATCCCCTTTCTCTC | 48 | 590 |
| 1047519 | 2727 | 2746 | 13016 | 13035 | GCCTCAGTTTTACAATTGTA | 90 | 591 |
| 1047535 | 2844 | 2863 | 13133 | 13152 | TCTGCTCACCAGTCTGCTCA | 92 | 592 |
| 1047551 | 2880 | 2899 | 13169 | 13188 | CCTCCCAGTCCCATCTCTGG | 90 | 593 |
| 1047567 | 2937 | 2956 | 13226 | 13245 | GGAGAGGGAAGGACCCTTCT | 105 | 594 |
| 1047583 | 3048 | 3067 | 13337 | 13356 | TGTCTTTATTTTTCCTCAGC | 10 | 595 |
| 1047615 | N/A | N/A | 8851 | 8870 | GGCAGCTAACCGCGAGCCGG | 92 | 597 |
| 1047631 | N/A | N/A | 9058 | 9077 | CACCTTTACCACTAACAAGC | 105 | 598 |
| 1047647 | N/A | N/A | 9089 | 9108 | GAGCAGCTCCACTGCGCACC | 87 | 599 |
| 1047663 | N/A | N/A | 9312 | 9331 | TATTTAACATTAAGAGCAGG | 106 | 600 |
| 1047679 | N/A | N/A | 8402 | 8421 | CCAGTGCCCTTCCCACGAGG | 78 | 601 |
| 1047695 | N/A | N/A | 8469 | 8488 | TCCCTTTGCCCTGATCCTCA | 74 | 602 |
| 1047711 | N/A | N/A | 8551 | 8570 | AGCCCCACCTAGAAGTACCC | 86 | 603 |
| 1047727 | N/A | N/A | 8690 | 8709 | CAGAAAACACTCAGAAGGGC | 93 | 604 |
| 1047743 | N/A | N/A | 3974 | 3993 | TCCCCATCCCCTCCTCACTT | 92 | 605 |
| 1047759 | N/A | N/A | 4126 | 4145 | GTTTCTGGTCCCTCCCATCA | 98 | 606 |
| 1047775 | N/A | N/A | 4278 | 4297 | AGCTCGCTGCCCACAGTCAC | 170 | 607 |
| 1047791 | N/A | N/A | 4339 | 4358 | GGACATCAACCTTCTCCGCT | 98 | 608 |
| 1047807 | N/A | N/A | 4376 | 4395 | CCTCACTTTCTTCACCCCAG | 104 | 609 |
| 1047823 | N/A | N/A | 4512 | 4531 | CAGGTAACCACCTTTTGAAA | 82 | 610 |
| 1047839 | N/A | N/A | 4661 | 4680 | GCTTCTGCTCACACAGGCGC | 96 | 611 |
| 1047855 | N/A | N/A | 4713 | 4732 | GGGCTTTTGCCTTAACTCAT | 89 | 612 |
| 1047871 | N/A | N/A | 4833 | 4852 | TCAGTCTCCCTTGAGGCAGC | 87 | 613 |
| 1047887 | N/A | N/A | 4972 | 4991 | CCCCTCCACCTCCCTGACCT | 109 | 614 |
| 1047903 | N/A | N/A | 5093 | 5112 | TCAGCCTTGCCTTACCCCTC | 96 | 615 |
| 1047919 | N/A | N/A | 5286 | 5305 | GTTGAGCTTTCCTCCCTCTG | 82 | 616 |
| 1047935 | N/A | N/A | 5434 | 5453 | TCTCTTTCCGTCTCCCTTAG | 83 | 617 |
| 1047951 | N/A | N/A | 5724 | 5743 | GGCAGGGCTACCTTGGAGCG | 98 | 618 |
| 1047967 | N/A | N/A | 5814 | 5833 | AGGATATTCTCCCAGCTTCC | 74 | 619 |
| 1047983 | N/A | N/A | 5946 | 5965 | CAGAACAGTATCAGCTACTA | 76 | 620 |
| 1047999 | N/A | N/A | 6086 | 6105 | TGGAAATCCAACTCTACCAC | 122 | 621 |
| 1048015 | N/A | N/A | 6154 | 6173 | GGCTCAGTAACCCAAAACAG | 82 | 622 |
| 1048031 | N/A | N/A | 6290 | 6309 | TTCCTGGCTCCCACACTACA | 106 | 623 |
| 1048047 | N/A | N/A | 6362 | 6381 | GCCCTCCCTTCTTCTCTTCC | 84 | 624 |
| 1048063 | N/A | N/A | 6487 | 6506 | CTGCTCAGACACCAGTGGCT | 111 | 625 |

TABLE 9-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1048079 | N/A | N/A | 6569 | 6588 | TCGCCTGGCCTCACCCTGGG | 101 | 626 |
| 1048095 | N/A | N/A | 7024 | 7043 | GCTGCCAGACCTCAGCACCT | 192 | 627 |
| 1048111 | N/A | N/A | 7328 | 7347 | TGCCCTGGCCGCGCTCACCG | 82 | 628 |
| 1048127 | N/A | N/A | 7502 | 7521 | CCGCGGAGCCCCGACCCGAC | 90 | 629 |
| 1048143 | N/A | N/A | 7945 | 7964 | TGGTTGAATCCATOCATCCA | 117 | 630 |
| 1048159 | N/A | N/A | 8197 | 8216 | CTAGCTTTTTCCCCAGCAGC | 100 | 631 |
| 1048175 | N/A | N/A | 9316 | 9335 | CTAATATTTAACATTAAGAG | 128 | 632 |
| 1048191 | N/A | N/A | 9463 | 9482 | TAGTGGTCCTAAATATTCTA | 106 | 633 |
| 1048207 | N/A | N/A | 9586 | 9605 | TTCTCTCTGCCATTTATCTG | 70 | 634 |
| 1048223 | N/A | N/A | 9625 | 9644 | CACATAGGTCCCTTTCCTGT | 74 | 635 |
| 1048239 | N/A | N/A | 9800 | 9819 | CCAACTTAGCCACCAACCAG | 96 | 636 |
| 1048255 | N/A | N/A | 10577 | 10596 | TGGCTTTCTGAAAACCCAGC | 83 | 637 |
| 1048271 | N/A | N/A | 10674 | 10693 | GCCCCCAAATOCCAATAGTG | 116 | 638 |
| 1048287 | N/A | N/A | 10757 | 10776 | ATCGCACCCCCCTCCCCATC | 142 | 639 |
| 1048303 | N/A | N/A | 10928 | 10947 | CCCTCCTTACCTCTCCATCC | 117 | 640 |
| 1048319 | N/A | N/A | 10996 | 11015 | CCAGGCTTTCCTCCATGGCC | 88 | 641 |
| 1048335 | N/A | N/A | 11111 | 11130 | TTAGAACAGCCTATGGAGGG | 115 | 642 |
| 1048351 | N/A | N/A | 11301 | 11320 | AGTTTCCTTTTACCAAGCTG | 54 | 643 |
| 1048367 | N/A | N/A | 11337 | 11356 | CGGATACGCCAAATCCCCTC | 101 | 644 |
| 1048383 | N/A | N/A | 11539 | 11558 | CAGGTCCACCACCACGAGGC | 138 | 645 |

TABLE 10

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047152 | 117 | 136 | 3565 | 3584 | CCCCCACCATCATCTCCCCT | 104 | 646 |
| 1047168 | 175 | 194 | 3623 | 3642 | GGCATTCGAGCCAGGGAGAG | 90 | 647 |
| 1047184 | 435 | 454 | 3883 | 3902 | GTTGATCGAGCCGCAGCCGC | 104 | 648 |
| 1047200 | 530 | 549 | 4915 | 4934 | CAGGTTGGTTTCATCCTGGA | 56* | 649 |
| 1047216 | 621 | 640 | 5210 | 5229 | ACTCAATCTTCCTCTCCAGA | 95 | 650 |
| 1047232 | 684 | 703 | 5570 | 5589 | CCTGGAGTTCCCGAACCTCC | 126 | 651 |
| 1047248 | 946 | 965 | 7303 | 7322 | CGCAGAGACTCCAGGTCGCA | 104 | 652 |
| 1047264 | 1100 | 1119 | 7672 | 7691 | GTCCTGGTACTCCTGCAAGT | 89 | 653 |

TABLE 10-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047280 | 1273 | 1292 | 10887 | 10906 | ACGATGTTCCTCTTGAGGTG | 96 | 654 |
| 1047296 | 1320 | 1339 | N/A | N/A | TGGACTOCTTAATGACCTCT | 101 | 655 |
| 1047312 | 1372 | 1391 | 11661 | 11680 | GCAGAGGCCACCAGGTGGGT | 64 | 656 |
| 1047328 | 1580 | 1599 | 11869 | 11888 | GGTGAGTTTCTTGTTAGTTG | 29 | 657 |
| 1047344 | 1638 | 1657 | 11927 | 11946 | CCTTCCTCCTCATTCTAACG | 73 | 658 |
| 1047360 | 1715 | 1734 | 12004 | 12023 | AACAGTTTCCATAACAACAG | 115 | 659 |
| 1047376 | 1761 | 1780 | 12050 | 12069 | CAAAGGCACAGTTCCCAGAT | 94 | 660 |
| 1047392 | 1815 | 1834 | 12104 | 12123 | GGCCTTCCCTTTCCTGTCTG | 104 | 661 |
| 1047408 | 2021 | 2040 | 12310 | 12329 | TAGACTGATCAGGGTCAGTC | 125 | 662 |
| 1047424 | 2148 | 2167 | 12437 | 12456 | CGTGCCCACAGATGGCATCC | 87 | 663 |
| 1047440 | 2222 | 2241 | 12511 | 12530 | CCAGCACCTCATCCCTCTCC | 111 | 664 |
| 1047456 | 2246 | 2265 | 12535 | 12554 | CCAGGCAGCCCCCCTCTATC | 87 | 665 |
| 1047472 | 2345 | 2364 | 12634 | 12653 | CCATCCCAATTGCCTCCTCC | 76 | 666 |
| 1047488 | 2417 | 2436 | 12706 | 12725 | ACTTCCTTAATTCCCACAAT | 103 | 667 |
| 1047504 | 2468 | 2487 | 12757 | 12776 | ATGGATACATCCCCTTTCTC | 73 | 668 |
| 1047520 | 2728 | 2747 | 13017 | 13036 | TGCCTCAGTTTTACAATTGT | 109 | 669 |
| 1047536 | 2845 | 2864 | 13134 | 13153 | GTCTGCTCACCAGTCTGCTC | 110 | 670 |
| 1047552 | 2883 | 2902 | 13172 | 13191 | GGCCCTOCCAGTCCCATCTC | 85 | 671 |
| 1047568 | 2956 | 2975 | 13245 | 13264 | AAAGGACACCAAGTCTTGGG | 69 | 672 |
| 1047584 | 3049 | 3068 | 13338 | 13357 | TTGTCTTTATTTTTCCTCAG | 11 | 673 |
| 1047616 | N/A | N/A | 8852 | 8871 | AGGCAGCTAACCGCGAGCCG | 94 | 675 |
| 1047632 | N/A | V/A | 9059 | 9078 | CCACCTTTACCACTAACAAG | 89 | 676 |
| 1047648 | N/A | N/A | 9101 | 9120 | TCAGAGGCCCCAGAGCAGCT | 86 | 677 |
| 1047664 | N/A | N/A | 9314 | 9333 | AATATTTAACATTAAGAGCA | 105 | 678 |
| 1047680 | N/A | N/A | 8404 | 8423 | CTCCAGTGCCCTTCCCACGA | 86 | 679 |
| 1047696 | N/A | N/A | 8471 | 8490 | GATCCCTTTGCCCTGATCCT | 76 | 680 |
| 1047712 | N/A | N/A | 8554 | 8573 | GCAAGCCCCACCTAGAAGTA | 76 | 681 |
| 1047728 | N/A | N/A | 8691 | 8710 | ACAGAAAACACTCAGAAGGG | 92 | 682 |
| 1047744 | N/A | N/A | 3984 | 4003 | AGGCCCCCCTTCCCCATCCC | 79 | 683 |
| 1047760 | N/A | N/A | 4138 | 4157 | GGCCCTGGGCCTGTTTCTGG | 86 | 684 |
| 1047776 | N/A | N/A | 4279 | 4298 | GAGCTCGCTGCCCACAGTCA | 119 | 685 |
| 1047792 | N/A | N/A | 4340 | 4359 | TGGACATCAACCTTCTOCGC | 102 | 686 |
| 1047808 | N/A | N/A | 4377 | 4396 | CCCTCACTTTCTTCACCCCA | 71 | 687 |
| 1047824 | N/A | N/A | 4513 | 4532 | CCAGGTAACCACCTTTTGAA | 104 | 688 |
| 1047840 | N/A | N/A | 4686 | 4705 | GTGCCTTATCAGGGTTGGTG | 64 | 689 |

TABLE 10-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047856 | N/A | N/A | 4714 | 4733 | TGGGCTTTTGCCTTAACTCA | 79 | 690 |
| 1047872 | N/A | N/A | 4835 | 4854 | CCTCAGTCTCCCTTGAGGCA | 104 | 691 |
| 1047888 | N/A | N/A | 4976 | 4995 | CCCTCCCCTCCACCTCCCTG | 79 | 692 |
| 1047904 | N/A | N/A | 5094 | 5113 | CTCAGCCTTGCCTTACCCCT | 121 | 693 |
| 1047920 | N/A | N/A | 5313 | 5332 | TCTCCCTCTCTCAGTTGCAA | 80 | 694 |
| 1047936 | N/A | N/A | 5436 | 5455 | TGTCTCTTTCCGTCTCCCTT | 76 | 695 |
| 1047952 | N/A | N/A | 5738 | 5757 | CAGGCTGGCCCACAGGCAGG | 96 | 696 |
| 1047968 | N/A | V/A | 5815 | 5834 | GAGGATATTCTCCCAGCTTC | 83 | 697 |
| 1047984 | N/A | N/A | 5993 | 6012 | CACCTACTTCATAGTAAGGT | 144 | 698 |
| 1048000 | N/A | N/A | 6088 | 6107 | GTTGGAAATCCAACTCTACC | 75 | 699 |
| 1048016 | N/A | N/A | 6155 | 6174 | AGGCTCAGTAACCCAAAACA | 97 | 700 |
| 1048032 | N/A | N/A | 6298 | 6317 | CAGTGTCTTTCCTGGCTCCC | 72 | 701 |
| 1048048 | N/A | N/A | 6363 | 6382 | GGCCCTCCCTTCTTCTCTTC | 106 | 702 |
| 1048064 | N/A | N/A | 6491 | 6510 | CACCCTGCTCAGACACCAGT | 112 | 703 |
| 1048080 | N/A | N/A | 6570 | 6589 | CTCGCCTGGCCTCACCCTGG | 80 | 704 |
| 1048096 | N/A | N/A | 7028 | 7047 | GCGGGCTGCCAGACCTCAGC | 82 | 705 |
| 1048112 | N/A | V/A | 7335 | 7354 | CCCGTCCTGCCCTGGCCGCG | 92 | 706 |
| 1048128 | N/A | N/A | 7833 | 7852 | AAAAGACTCAGTCCCTGAA | 103 | 707 |
| 1048144 | N/A | N/A | 7946 | 7965 | TTGGTTGAATCCATCCATCC | 68 | 708 |
| 1048160 | N/A | N/A | 8198 | 8217 | CCTAGCTTTTTCCCCAGCAG | 71 | 709 |
| 1048176 | N/A | N/A | 9317 | 9336 | ACTAATATTTAACATTAAGA | 69 | 710 |
| 1048192 | N/A | N/A | 9465 | 9484 | TCTAGTGGTCCTAAATATTC | 108 | 711 |
| 1048208 | N/A | N/A | 9593 | 9612 | TTCCTACTTCTCTCTGCCAT | 80 | 712 |
| 1048224 | N/A | N/A | 9633 | 9652 | GCTCAATACACATAGGTCCC | 82 | 713 |
| 1048240 | N/A | N/A | 9801 | 9820 | CCCAACTTAGCCACCAACCA | 120 | 714 |
| 1048256 | N/A | N/A | 10578 | 10597 | CTGGCTTTCTGAAAACCCAG | 119 | 715 |
| 1048272 | N/A | N/A | 0675 | 10694 | AGCCCCCAAATCCCAATAGT | 116 | 716 |
| 1048288 | N/A | N/A | 10759 | 10778 | CCATCGCACCCCCCTCCCCA | 88 | 717 |
| 1048304 | N/A | N/A | 10929 | 10948 | TCCCTCCTTACCTCTCCATC | 73 | 718 |
| 1048320 | N/A | N/A | 10997 | 11016 | CCCAGGCTTTCCTCCATGGC | 113 | 719 |
| 1048336 | N/A | V/A | 11112 | 11131 | CTTAGAACAGCCTATGGAGG | 74 | 720 |
| 1048352 | N/A | N/A | 11302 | 11321 | TAGTTTCCTTTTACCAAGCT | 97 | 721 |
| 1048368 | N/A | N/A | 11338 | 11357 | GCGGATACGCCAAATCCCCT | 74 | 722 |
| 1048384 | N/A | N/A | 11541 | 11560 | CCCAGGTCCACCACCACGAG | 105 | 723 |

TABLE 11

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047153 | 119 | 138 | 356 | 3586 | GCCCCCCACCATCATCTCCC | 88 | 724 |
| 1047169 | 210 | 229 | 3658 | 3677 | CCAGGGAGAAATCCACCCGG | 81 | 725 |
| 1047185 | 440 | 459 | 3888 | 3907 | GGTGAGTTGATCGAGCCGCA | 70 | 726 |
| 1047201 | 539 | 558 | 4924 | 4943 | TTCCAGCCTCAGGTTGGTTT | 29* | 727 |
| 1047217 | 627 | 646 | 5216 | 5235 | CCAGCGACTCAATCTTCCTC | 99 | 728 |
| 1047233 | 703 | 722 | 5589 | 5608 | TGCTGTCGGGCCAGCTGCTC | 118 | 729 |
| 1047249 | 990 | 1009 | 7562 | 7581 | CCTCCTGCTCGCGCATCTGC | 93 | 730 |
| 1047265 | 1101 | 1120 | 7673 | 7692 | GGTCCTGGTACTCCTGCAAG | 129 | 731 |
| 1047281 | 1274 | 1293 | 10888 | 10907 | CACGATGTTCCTCTTGAGGT | 104 | 732 |
| 1047297 | 1321 | 1340 | N/A | N/A | TTGGACTCCTTAATGACCTC | 110 | 733 |
| 1047313 | 1393 | 1412 | 11682 | 11701 | TCGGGCCCCTCATGAGACGG | 99 | 734 |
| 1047329 | 1605 | 1624 | 11894 | 11913 | ATGCCCCTCCAGACTGCCCC | 109 | 735 |
| 1047345 | 1640 | 1659 | 11929 | 11948 | CTCCTTCCTCCTCATTCTAA | 89 | 736 |
| 1047361 | 1716 | 1735 | 12005 | 12024 | CAACAGTTTCCATAACAACA | 62 | 737 |
| 1047377 | 1770 | 1789 | 12059 | 12078 | GAGGAAACTCAAAGGCACAG | 82 | 738 |
| 1047393 | 1816 | 1835 | 12105 | 12124 | GGGCCTTCCCTTTCCTGTCT | 64 | 739 |
| 1047409 | 2024 | 2043 | 12313 | 12332 | TCTTAGACTGATCAGGGTCA | 124 | 740 |
| 1047425 | 2166 | 2185 | 12455 | 12474 | GCTCCCACCTGCCCACAGCG | 79 | 741 |
| 1047441 | 2224 | 2243 | 12513 | 12532 | TCCCAGCACCTCATCCCTCT | 109 | 742 |
| 1047457 | 2247 | 2266 | 12536 | 12555 | GCCAGGCAGCCCCCCTCTAT | 100 | 743 |
| 1047473 | 2369 | 2388 | 12658 | 12677 | CAACCCCTACTTGTATGCCT | 73 | 744 |
| 1047489 | 2429 | 2448 | 12718 | 12737 | AGAGGATGAGTCACTTCCTT | 116 | 745 |
| 1047505 | 2469 | 2488 | 12758 | 12777 | CATGGATACATCCCCTTTCT | 83 | 746 |
| 1047521 | 2748 | 2767 | 13037 | 13056 | CAGTGTCTTCACTTTGCTCG | 69 | 747 |
| 1047537 | 2846 | 2865 | 13135 | 13154 | AGTCTGCTCACCAGTCTGCT | 103 | 748 |
| 1047553 | 2884 | 2903 | 13173 | 13192 | GGGCCCTCCCAGTCCCATCT | 105 | 749 |
| 1047569 | 2957 | 2976 | 13246 | 13265 | GAAAGGACACCAAGTCTTGG | 117 | 750 |
| 1047585 | 3050 | 3069 | 13339 | 13358 | TTTGTCTTTATTTTTCCTCA | 20 | 751 |
| 1047601 | N/A | N/A | 8751 | 8770 | GATTTTCCCCGTCTTTGGTG | 38 | 752 |
| 1047617 | N/A | N/A | 8901 | 8920 | GTGAGGCTCACTOCCTGTCA | 95 | 753 |
| 1047633 | N/A | N/A | 9060 | 9079 | ACCACCTTTACCACTAACAA | 108 | 754 |
| 1047649 | N/A | N/A | 9107 | 9126 | GCTTGCTCAGAGGCCCCAGA | 59 | 755 |
| 1047665 | N/A | N/A | 9315 | 9334 | TAATATTTAACATTAAGAGC | 135 | 756 |
| 1047681 | N/A | N/A | 8406 | 8425 | GACTCCAGTGCCCTTCCCAC | 109 | 757 |
| 1047697 | N/A | N/A | 8473 | 8492 | TGGATCCCTTTGCCCTGATC | 90 | 758 |

TABLE 11-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047713 | N/A | N/A | 8557 | 8576 | GCTGCAAGCCCCACCTAGAA | 69 | 759 |
| 1047729 | N/A | N/A | 8692 | 8711 | AACAGAAAACACTCAGAAGG | 97 | 760 |
| 1047745 | N/A | N/A | 3985 | 4004 | AAGGCCCCCCTTCCCCATCC | 109 | 761 |
| 1047761 | N/A | N/A | 4158 | 4177 | TGCGGGCATCAGATCCCCGG | 138 | 762 |
| 1047777 | N/A | N/A | 4313 | 4332 | TCCTCCTTTATATGGACACA | 111 | 763 |
| 1047793 | N/A | N/A | 4341 | 4360 | ATGGACATCAACCTTCTCCG | 74 | 764 |
| 1047809 | N/A | N/A | 4378 | 4397 | TCCCTCACTTTCTTCACCCC | 100 | 765 |
| 1047825 | N/A | N/A | 4514 | 4533 | CCCAGGTAACCACCTTTTGA | 92 | 766 |
| 1047841 | N/A | N/A | 4689 | 4708 | AAGGTGCCTTATCAGGGTTG | 74 | 767 |
| 1047857 | N/A | N/A | 4716 | 4735 | TGTGGGCTTTTGCCTTAACT | 103 | 768 |
| 1047873 | N/A | N/A | 4841 | 4860 | TACCTGCCTCAGTCTCCCTT | 130 | 769 |
| 1047889 | N/A | N/A | 4998 | 5017 | AATCCTTTCCTCCCTCCCCT | 129 | 770 |
| 1047905 | N/A | N/A | 5103 | 5122 | TCCCCATTCCTCAGCCTTGC | 112 | 771 |
| 1047921 | N/A | N/A | 5317 | 5336 | TGTCTCTCCCTCTCTCAGTT | 88 | 772 |
| 1047937 | N/A | N/A | 5438 | 5457 | CTTGTCTCTTTCCGTCTCCC | 105 | 773 |
| 1047953 | N/A | N/A | 5739 | 5758 | GCAGGCTGGCCCACAGGCAG | 83 | 774 |
| 1047969 | N/A | N/A | 5816 | 5835 | AGAGGATATTCTCCCAGCTT | 80 | 775 |
| 1047985 | N/A | N/A | 5994 | 6013 | GCACCTACTTCATAGTAAGG | 65 | 776 |
| 1048001 | N/A | N/A | 6089 | 6108 | AGTTGGAAATCCAACTCTAC | 88 | 777 |
| 1048017 | N/A | N/A | 6157 | 6176 | AGAGGCTCAGTAACCCAAAA | 90 | 778 |
| 1048033 | N/A | N/A | 6306 | 6325 | CCCCTCTACAGTGTCTTTCC | 101 | 779 |
| 1048049 | N/A | N/A | 6364 | 6383 | TGGCCCTCCCTTCTTCTCTT | 89 | 780 |
| 1048065 | N/A | N/A | 6497 | 6516 | GGCCCTCACCCTGCTCAGAC | 143 | 781 |
| 104808 | N/A | N/A | 6571 | 6590 | CCTCGCCTGGCCTCACCCTG | 116 | 782 |
| 1048097 | N/A | N/A | 7056 | 7075 | ACTGTGACCCATGGATGCGG | 98 | 783 |
| 1048113 | N/A | N/A | 7343 | 7362 | CGCCCGTCCCCGTCCTGCCC | 92 | 784 |
| 1048129 | N/A | N/A | 7835 | 7854 | TGAAAAAGACTCAGTCCCTG | 103 | 785 |
| 1048145 | N/A | N/A | 7947 | 7966 | ATTGGTTGAATCCATCCATC | 106 | 786 |
| 1048161 | N/A | N/A | 8199 | 8218 | TCCTAGCTTTTTCCCCAGCA | 92 | 787 |
| 1048177 | N/A | N/A | 9318 | 9337 | CACTAATATTTAACATTAAG | 120 | 788 |
| 1048193 | N/A | N/A | 9475 | 9494 | GACATGCATATCTAGTGGTC | 64 | 789 |
| 1048209 | N/A | N/A | 9595 | 9614 | CTTTCCTACTTCTCTCTGCC | 107 | 790 |
| 1048225 | N/A | N/A | 9634 | 9653 | TGCTCAATACACATAGGTCC | 95 | 791 |
| 1048241 | N/A | N/A | 9806 | 9825 | GAAGTCCCAACTTAGCCACC | 101 | 792 |
| 1048257 | N/A | N/A | 10579 | 10598 | CCTGGCTTTCTGAAAACCCA | 70 | 793 |

TABLE 11-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1048273 | N/A | N/A | 10683 | 10702 | GGCTGGAGAGCCCCCAAATC | 144 | 794 |
| 1048289 | N/A | N/A | 10766 | 10785 | GGCTTCCCCATCGCACCCCC | 117 | 795 |
| 1048305 | N/A | N/A | 10930 | 10949 | ATCCCTCCTTACCTCTCCAT | 106 | 796 |
| 1048321 | N/A | N/A | 10998 | 11017 | CCCCAGGCTTTCCTCCATGG | 81 | 797 |
| 1048337 | N/A | N/A | 11113 | 11132 | CCTTAGAACAGCCTATGGAG | 162 | 798 |
| 1048353 | N/A | N/A | 11305 | 11324 | TGGTAGTTTCCTTTTACCAA | 89 | 799 |
| 1048369 | N/A | N/A | 11339 | 11358 | GGCGGATACGCCAAATCCCC | 93 | 800 |
| 1048385 | N/A | N/A | 11547 | 11566 | ACAGACCCCAGGTOCACCAC | 104 | 801 |

TABLE 12

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047154 | 120 | 139 | 3568 | 3587 | GGCCCCCCACCATCATCTCC | 97 | 802 |
| 1047170 | 226 | 245 | 3674 | 3693 | GCATTGAGTGCCCCAGCCAG | 128 | 803 |
| 1047186 | 471 | 490 | 3919 | 3938 | CCCTCTCAACCTCCAGCCGG | 3* | 804 |
| 1047202 | 541 | 560 | 4926 | 4945 | GCTTCCAGCCTCAGGTTGGT | 18* | 805 |
| 1047218 | 628 | 647 | 5217 | 5236 | TCCAGCGACTCAATCTTCCT | 100 | 806 |
| 1047234 | 723 | 742 | 5609 | 5628 | CGTCAAGCTCCACATGGACC | 144 | 807 |
| 1047250 | 1017 | 1036 | 7589 | 7608 | AACTGGCCGCCTCCCGCACG | 127 | 808 |
| 1047266 | 1206 | 1225 | 8355 | 8374 | GGTTGGAGAAGGTCTGCACG | 77 | 809 |
| 1047282 | 1275 | 1294 | 10889 | 10908 | CCACGATGTTCCTCTTGAGG | 157 | 810 |
| 1047298 | 1322 | 1341 | 11611 | 11630 | CTTGGACTCCTTAATGACCT | 64 | 811 |
| 1047314 | 1395 | 1414 | 11684 | 11703 | GCTCGGGCCCCTCATGAGAC | 100 | 812 |
| 1047330 | 1606 | 1625 | 11895 | 11914 | CATGCCCCTCCAGACTGCCC | 106 | 813 |
| 1047346 | 1657 | 1676 | 11946 | 11965 | CGCCCTCCTCCCCTTCTCTC | 79 | 814 |
| 1047362 | 1718 | 1737 | 12007 | 12026 | GGCAACAGTTTCCATAACAA | 31 | 815 |
| 1047378 | 1771 | 1790 | 12060 | 12079 | TGAGGAAACTCAAAGGCACA | 79 | 816 |
| 1047394 | 1835 | 1854 | 12124 | 12143 | CAGGGCTACCTTGTCTGTGG | 40 | 817 |
| 1047410 | 2025 | 2044 | 12314 | 12333 | ATCTTAGACTGATCAGGGTC | 67 | 818 |
| 1047426 | 2167 | 2186 | 12456 | 12475 | AGCTCCCACCTGCCCACAGC | 94 | 819 |
| 1047442 | 2226 | 2245 | 12515 | 12534 | CCTCCCAGCACCTCATCCCT | 97 | 820 |
| 1047458 | 2268 | 2287 | 12557 | 12576 | TCTCTGTACCCACAGCTGGG | 84 | 821 |

TABLE 12-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047474 | 2371 | 2390 | 12660 | 12679 | CACAACCCCTACTTGTATGC | 61 | 822 |
| 1047490 | 2442 | 2461 | 12731 | 12750 | TTCAGCATCTTCAAGAGGAT | 92 | 823 |
| 1047506 | 2470 | 2489 | 12759 | 12778 | CCATGGATACATCCCCTTTC | 151 | 824 |
| 1047522 | 2749 | 2768 | 13038 | 13057 | CCAGTGTCTTCACTTTGCTC | 44 | 825 |
| 1047538 | 2847 | 2866 | 13136 | 13155 | CAGTCTGCTCACCAGTCTGC | 103 | 826 |
| 1047554 | 2885 | 2904 | 13174 | 13193 | TGGGCCCTCCCAGTCCCATC | 172 | 827 |
| 1047570 | 2958 | 2977 | 13247 | 13266 | GGAAAGGACACCAAGTCTTG | 90 | 828 |
| 1047586 | 3051 | 3070 | 13340 | 13359 | ATTTGTCTTTATTTTTCCTC | 32 | 829 |
| 1047602 | N/A | N/A | 8754 | 8773 | TGTGATTTTCCCCGTCTTTG | 54 | 830 |
| 1047618 | N/A | N/A | 8902 | 8921 | GGTGAGGCTCACTCCCTGTC | 65 | 831 |
| 1047634 | N/A | N/A | 9061 | 9080 | CACCACCTTTACCACTAACA | 88 | 832 |
| 1047650 | N/A | N/A | 9109 | 9128 | CTGCTTGCTCAGAGGCCCCA | 115 | 833 |
| 1047666 | N/A | N/A | 8372 | 8391 | CTGACCTCGAATCTGCAGGT | 84 | 834 |
| 1047682 | N/A | N/A | 8412 | 8431 | GGGCAGGACTCCAGTGCCCT | 118 | 835 |
| 1047698 | N/A | N/A | 8474 | 8493 | CTGGATCCCTTTGCCCTGAT | 100 | 836 |
| 1047714 | N/A | N/A | 8626 | 8645 | CACCCAGITCTGCTGTOGAA | 94 | 837 |
| 1047730 | N/A | N/A | 8696 | 8715 | CAAAAACAGAAAACACTCAG | 160 | 838 |
| 1047746 | N/A | N/A | 3987 | 4006 | ACAAGGCCCCCCTTCCCCAT | 57 | 839 |
| 1047762 | N/A | N/A | 4215 | 4234 | CACTGCTTTCCCCAGTAGGG | 48 | 840 |
| 1047778 | N/A | N/A | 4314 | 4333 | CTCCTCCTTTATATGGACAC | 96 | 841 |
| 1047794 | N/A | N/A | 4345 | 4364 | CCTCATGGACATCAACCTTC | 92 | 842 |
| 1047810 | N/A | N/A | 4379 | 4398 | TTCCCTCACTTTCTTCACCC | 102 | 843 |
| 1047826 | N/A | N/A | 4515 | 4534 | TCCCAGGTAACCACCTTTTG | 76 | 844 |
| 1047842 | N/A | N/A | 4691 | 4710 | CTAAGGTGCCTTATCAGGGT | 78 | 845 |
| 1047858 | N/A | N/A | 4794 | 4813 | ACCCAGGACCAGTAGAGCAG | 84 | 846 |
| 1047874 | N/A | N/A | 4843 | 4862 | AATACCTGCCTCAGTCTCCC | 106 | 847 |
| 1047890 | N/A | N/A | 4999 | 5018 | CAATCCTTTCCTCCCTCCCC | 109 | 848 |
| 1047906 | N/A | N/A | 5104 | 5123 | CTCCCCATTCCTCAGCCTTG | 90 | 849 |
| 1047922 | N/A | N/A | 5334 | 5353 | CTCAGCTTCTCTGTCTCTGT | 123 | 850 |
| 1047938 | N/A | N/A | 5465 | 5484 | CCCCTCGGCCAGGAGTTCGA | 123 | 851 |
| 1047954 | N/A | N/A | 5781 | 5800 | CCCCATTCTCTTGTACAGAG | 98 | 852 |
| 1047970 | N/A | N/A | 5817 | 5836 | GAGAGGATATTCTCCCAGCT | 151 | 853 |
| 1047986 | N/A | N/A | 6001 | 6020 | AAGAACAGCACCTACTTCAT | 85 | 854 |
| 1048002 | N/A | N/A | 6090 | 6109 | GAGTTGGAAATCCAACTCTA | 97 | 855 |
| 1048018 | N/A | N/A | 6159 | 6178 | GTAGAGGCTCAGTAACCCAA | 51 | 856 |

TABLE 12-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1048034 | N/A | N/A | 6310 | 6329 | ATGCCCCCTCTACAGTGTCT | 71 | 857 |
| 1048050 | N/A | N/A | 6366 | 6385 | AATGGCCCTCCCTTCTTCTC | 177 | 858 |
| 1048066 | N/A | N/A | 6503 | 6522 | CCATCGGGCCCTCACCCTGC | 110 | 859 |
| 1048082 | N/A | N/A | 6951 | 6970 | ACCTTCCACACTGACAGCTG | 169 | 860 |
| 1048098 | N/A | N/A | 7058 | 7077 | CAACTGTGACCCATGGATGC | 78 | 861 |
| 1048114 | N/A | N/A | 7349 | 7368 | CTGCTCCGCCCGTCCCCGTC | 120 | 862 |
| 1048130 | N/A | N/A | 7836 | 7855 | CTGAAAAAGACTCAGTCCCT | 118 | 863 |
| 1048146 | N/A | N/A | 7949 | 7968 | ATATTGGTTGAATCCATCCA | 102 | 864 |
| 1048162 | N/A | N/A | 8211 | 8230 | TCTAACTCCATCTCCTAGCT | 98 | 865 |
| 1048178 | N/A | N/A | 9319 | 9338 | TCACTAATATTTAACATTAA | 84 | 866 |
| 1048194 | N/A | N/A | 9492 | 9511 | GCTGAATTAAGTCCTGAGAC | 55 | 867 |
| 1048210 | N/A | N/A | 9596 | 9615 | TCTTTCCTACTTCTCTCTGC | 82 | 868 |
| 1048226 | N/A | N/A | 9662 | 9681 | AGGCTGTTAAACATGTGGCA | 71 | 869 |
| 1048242 | N/A | N/A | 9807 | 9826 | AGAAGTCCCAACTTAGCCAC | 85 | 870 |
| 1048258 | N/A | N/A | 10580 | 10599 | ACCTGGCTTTCTGAAAACCC | 79 | 871 |
| 1048274 | N/A | N/A | 10698 | 10717 | AGGCTCTTCCAAACGGGCTG | 103 | 872 |
| 1048290 | N/A | N/A | 10768 | 10787 | CCGGCTTCCCCATCGCACCC | 81 | 873 |
| 1048306 | N/A | N/A | 10931 | 10950 | AATCCCTCCTTACCTCTCCA | 116 | 874 |
| 1048322 | N/A | N/A | 11004 | 11023 | TGCCAGCCCCAGGCTTTCCT | 66 | 875 |
| 1048338 | N/A | N/A | 11117 | 11136 | CTCCCCTTAGAACAGCCTAT | 88 | 876 |
| 1048354 | N/A | N/A | 11306 | 11325 | CTGGTAGTTTCCTTTTACCA | 113 | 877 |
| 1048370 | N/A | N/A | 11340 | 11359 | TGGCGGATACGCCAAATCCC | 75 | 878 |
| 1048386 | N/A | N/A | 11555 | 11574 | GAGTTCACACAGACCCCAGG | 85 | 879 |

TABLE 13

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047155 | 121 | 140 | 3569 | 3588 | AGGCCCCCCACCATCATCTC | 124 | 880 |
| 1047171 | 228 | 247 | 3676 | 3695 | CAGCATTGAGTGCCCCAGCC | 104 | 881 |
| 1047187 | 472 | 491 | 3920 | 3939 | TCCCTCTCAACCTCCAGCCG | 7* | 882 |
| 1047203 | 542 | 561 | 4927 | 4946 | GGCTTCCAGCCTCAGGTTGG | 18* | 883 |

TABLE 13-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047219 | 629 | 648 | 5218 | 5237 | CTCCAGCGACTCAATCTTCC | 86 | 884 |
| 1047235 | 761 | 780 | 5647 | 5666 | GATCTCTTTCAGGGCTGCGG | 51 | 885 |
| 1047251 | 1019 | 1038 | 7591 | 7610 | ATAACTGGCCGCCTCCCGCA | 143 | 886 |
| 1047267 | 1223 | 1242 | N/A | N/A | GGTTTCTCGAATCTGCAGGT | 65 | 887 |
| 1047283 | 1280 | 1299 | 10894 | 10913 | CTTCACCACGATGTTCCTCT | 73 | 888 |
| 1047299 | 1323 | 1342 | 11612 | 11631 | GCTTGGACTCCTTAATGACC | 91 | 889 |
| 1047315 | 1396 | 1415 | 11685 | 11704 | TGCTCGGGCCCCTCATGAGA | 84 | 890 |
| 1047331 | 1607 | 1626 | 11896 | 11915 | CCATGCCCCTCCAGACTGCC | 66 | 891 |
| 1047347 | 1658 | 1677 | 11947 | 11966 | CCGCCCTCCTCCCCTTCTCT | 73 | 892 |
| 1047363 | 1721 | 1740 | 12010 | 12029 | TCTGGCAACAGTTTCCATAA | 66 | 893 |
| 1047379 | 1772 | 1791 | 12061 | 12080 | CTGAGGAAACTCAAAGGCAC | 100 | 894 |
| 1047395 | 1837 | 1856 | 12126 | 12145 | GCCAGGGCTACCTTGTCTGT | 80 | 895 |
| 1047411 | 2026 | 2045 | 12315 | 12334 | CATCTTAGACTGATCAGGGT | 72 | 896 |
| 1047427 | 2169 | 2188 | 12458 | 12477 | CAAGCTCCCACCTGCCCACA | 111 | 897 |
| 1047443 | 2232 | 2251 | 12521 | 12540 | TCTATCCCTCCCAGCACCTC | 80 | 898 |
| 1047459 | 2269 | 2288 | 12558 | 12577 | CTCTCTGTACCCACAGCTGG | 85 | 899 |
| 1047475 | 2372 | 2391 | 12661 | 12680 | CCACAACCCCTACTTGTATG | 69 | 900 |
| 1047491 | 2443 | 2462 | 12732 | 12751 | TTTCAGCATCTTCAAGAGGA | 121 | 901 |
| 1047507 | 2471 | 2490 | 12760 | 12779 | CCCATGGATACATCCCCTTT | 79 | 902 |
| 1047523 | 2751 | 2770 | 13040 | 13059 | AGCCAGTGTCTTCACTTTGC | 60 | 903 |
| 1047539 | 2855 | 2874 | 13144 | 13163 | GATCCCACCAGTCTGCTCAC | 84 | 904 |
| 1047555 | 2886 | 2905 | 13175 | 13194 | GTGGGCCCTCCCAGTCCCAT | 81 | 905 |
| 1047571 | 3010 | 3029 | 13299 | 13318 | TGCCCTGAAGATTAGCAGCA | 103 | 906 |
| 1047587 | 3052 | 3071 | 13341 | 13360 | CATTTGTCTTTATTTTTCCT | 14 | 907 |
| 1047603 | N/A | N/A | 8755 | 8774 | TTGTGATTTTCCCCGTCTTT | 75 | 908 |
| 1047619 | N/A | N/A | 8969 | 8988 | ACGCAGTCCAGGCCCTTTAG | 57 | 909 |
| 1047635 | N/A | N/A | 9063 | 9082 | CTCACCACCTTTACCACTAA | 113 | 910 |
| 1047651 | N/A | N/A | 9128 | 9147 | AGAGGTGAGACAGAGGCTGC | 112 | 911 |
| 1047667 | N/A | N/A | 8374 | 8393 | TACTGACCTCGAATCTGCAG | 85 | 912 |
| 1047683 | N/A | N/A | 8432 | 8451 | CCTACAGGCCCTGGAGGAGG | 85 | 913 |
| 1047699 | N/A | N/A | 8476 | 8495 | AGCTGGATCCCTTTGCCCTG | 97 | 914 |
| 1047715 | N/A | N/A | 8630 | 8649 | CTCTCACCCAGTTCTGCTGT | 77 | 915 |
| 1047731 | N/A | N/A | 8723 | 8742 | CCCTGTAGTGACAAGCAGTT | 84 | 916 |
| 1047747 | N/A | N/A | 3997 | 4016 | CCTTCTGCTCACAAGGCCCC | 93 | 917 |
| 1047763 | N/A | N/A | 4257 | 4276 | AAGCCCAGCCATGAATGAAA | 83 | 918 |

TABLE 13-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047779 | N/A | N/A | 4316 | 4335 | AACTCCTCCTTTATATGGAC | 91 | 919 |
| 1047795 | N/A | N/A | 4353 | 4372 | CCAATCTCCCTCATGGACAT | 66 | 920 |
| 1047811 | N/A | N/A | 4386 | 4405 | CTGCTCTTTCCCTCACTTTC | 103 | 921 |
| 1047827 | N/A | N/A | 4516 | 4535 | ATCCCAGGTAACCACCTTTT | 85 | 922 |
| 1047843 | N/A | N/A | 4692 | 4711 | ACTAAGGTGCCTTATCAGGG | 117 | 923 |
| 1047859 | N/A | N/A | 4795 | 4814 | CACCCAGGACCAGTAGAGCA | 56 | 924 |
| 1047875 | N/A | N/A | 4848 | 4867 | ACTTGAATACCTGCCTCAGT | 85 | 925 |
| 1047891 | N/A | N/A | 5001 | 5020 | ATCAATCCTTTCCTCCCTCC | 102 | 926 |
| 1047907 | N/A | N/A | 5107 | 5126 | CTTCTCCCCATTCCTCAGCC | 56 | 927 |
| 1047923 | N/A | N/A | 5349 | 5368 | AGTGTCTCTCTCAGTCTCAG | 83 | 928 |
| 1047939 | N/A | N/A | 5477 | 5496 | CTCTTCTGCCTGCCCCTCGG | 101 | 929 |
| 1047955 | N/A | N/A | 5783 | 5802 | TCCCCCATTCTCTTGTACAG | 49 | 930 |
| 1047971 | N/A | N/A | 5818 | 5837 | GGAGAGGATATTCTCCCAGC | 93 | 931 |
| 1047987 | N/A | N/A | 6007 | 6026 | CTGTCAAAGAACAGCACCTA | 112 | 932 |
| 1048003 | N/A | N/A | 6091 | 6110 | AGAGTTGGAAATCCAACTCT | 92 | 933 |
| 1048019 | N/A | N/A | 6201 | 6220 | GGTCAGACACCTCTCTGTGT | 82 | 934 |
| 1048035 | N/A | N/A | 6321 | 6340 | GCCTAGCCCAAATGCCCCCT | 71 | 935 |
| 1048051 | N/A | N/A | 6384 | 6403 | GCTCTGTCCTCCACTAGGAA | 97 | 936 |
| 1048067 | N/A | N/A | 6504 | 6523 | CCCATCGGGCCCTCACCCTG | 88 | 937 |
| 1048083 | N/A | N/A | 6954 | 6973 | AGAACCTTCCACACTGACAG | 76 | 938 |
| 1048099 | N/A | N/A | 7060 | 7079 | AACAACTGTGACCCATGGAT | 74 | 939 |
| 1048115 | N/A | N/A | 7351 | 7370 | CCCTGCTCCGCCCGTCCCCG | 98 | 940 |
| 1048131 | N/A | N/A | 7837 | 7856 | GCTGAAAAAGACTCAGTOCC | 84 | 941 |
| 1048147 | N/A | N/A | 7973 | 7992 | GTCCTTGGCCTTGAGGCCTA | 95 | 942 |
| 1048163 | N/A | N/A | 8213 | 8232 | AGTCTAACTCCATCTCCTAG | 88 | 943 |
| 1048179 | N/A | N/A | 9322 | 9341 | CATTCACTAATATTTAACAT | 110 | 944 |
| 1048195 | N/A | N/A | 9507 | 9526 | GTTAGCCTTTCTGATGCTGA | 53 | 945 |
| 1048211 | N/A | N/A | 9597 | 9616 | CTCTTTCCTACTTCTCTCTG | 91 | 946 |
| 1048227 | N/A | N/A | 9708 | 9727 | GGCCTACTTCTCTAGGTGGG | 82 | 947 |
| 1048243 | N/A | N/A | 9808 | 9827 | AAGAAGTOCCAACTTAGCCA | 141 | 948 |
| 1048259 | N/A | N/A | 10602 | 10621 | CCTCTGCAAGCCCTGGCCTG | 95 | 949 |
| 1048275 | N/A | N/A | 10699 | 10718 | TAGGCTCTTCCAAACGGGCT | 89 | 950 |
| 1048291 | N/A | N/A | 10769 | 10788 | CCCGGCTTCCCCATCGCACC | 79 | 951 |
| 1048307 | N/A | N/A | 10934 | 10953 | CCAAATCCCTCCTTACCTCT | 156 | 952 |
| 1048323 | N/A | N/A | 11017 | 11036 | GGAACCTTCTATGTGCCAGC | 74 | 953 |

TABLE 13-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1048339 | N/A | N/A | 11132 | 11151 | GCTTTGGTACCAAGGCTCCC | 192 | 954 |
| 1048355 | N/A | N/A | 11307 | 11326 | CCTGGTAGTTTCCTTTTACC | 52 | 955 |
| 1048371 | N/A | N/A | 11379 | 11398 | GCTGGAGTAAGATGAGCTOC | 86 | 956 |
| 1048387 | N/A | N/A | 11570 | 11589 | CAGTGCAACAGTTAGGAGTT | 66 | 957 |

TABLE 14

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047156 | 122 | 141 | 3570 | 3589 | CAGGCCCCCCACCATCATCT | 90 | 958 |
| 1047172 | 237 | 256 | 3685 | 3704 | CCTTGAAGCCAGCATTGAGT | 89 | 959 |
| 1047188 | 473 | 492 | 3921 | 3940 | GTCCCTCTCAACCTCCAGCC | 6* | 960 |
| 1047204 | 545 | 564 | 4930 | 4949 | CTCGGCTTCCAGCCTCAGGT | 37* | 961 |
| 1047220 | 634 | 653 | 5223 | 5242 | TCCTCCTCCAGCGACTCAAT | 94 | 962 |
| 1047236 | 766 | 785 | 5652 | 5671 | GTGCGGATCTCTTTCAGGGC | 63 | 963 |
| 1047252 | 1020 | 1039 | 7592 | 7611 | GATAACTGGCCGCCTCCCGC | 113 | 964 |
| 1047268 | 1225 | 1244 | N/A | N/A | CTGGTTTCTCGAATCTGCAG | 83 | 965 |
| 1047284 | 1283 | 1302 | 10897 | 10916 | GGTCTTCACCACGATGTTCC | 94 | 966 |
| 1047300 | 1345 | 1364 | 11634 | 11653 | CACATCACATOCTTGTGCTC | 75 | 967 |
| 1047316 | 1398 | 1417 | 11687 | 11706 | TCTGCTCGGGCCCCTCATGA | 96 | 968 |
| 1047332 | 1608 | 1627 | 11897 | 11916 | GCCATGCCCCTCCAGACTGC | 73 | 969 |
| 1047348 | 1659 | 1678 | 11948 | 11967 | CCCGCCCTCCTCCCCTTCTC | 107 | 970 |
| 1047364 | 1723 | 1742 | 12012 | 12031 | TCTCTGGCAACAGTTTCCAT | 65 | 971 |
| 1047380 | 1773 | 1792 | 12062 | 12081 | CCTGAGGAAACTCAAAGGCA | 92 | 972 |
| 1047396 | 1838 | 1857 | 12127 | 12146 | GGCCAGGGCTACCTTGTCTG | 67 | 973 |
| 1047412 | 2027 | 2046 | 12316 | 12335 | CCATCTTAGACTGATCAGGG | 76 | 974 |
| 1047428 | 2170 | 2189 | 12459 | 12478 | TCAAGCTOCCACCTGCCCAC | 127 | 975 |
| 1047444 | 2233 | 2252 | 12522 | 12541 | CTCTATCCCTCCCAGCACCT | 42 | 976 |
| 1047460 | 2270 | 2289 | 12559 | 12578 | CCTCTCTGTACCCACAGCTG | 94 | 977 |
| 1047476 | 2373 | 2392 | 12662 | 12681 | CCCACAACCCCTACTTGTAT | 115 | 978 |
| 1047492 | 2449 | 2468 | 12738 | 12757 | CTCCTGTTTCAGCATCTTCA | 45 | 979 |
| 1047508 | 2472 | 2491 | 12761 | 12780 | CCCCATGGATACATCCCCTT | 86 | 980 |
| 1047524 | 2759 | 2778 | 13048 | 13067 | GGAATATGAGCCAGTGTCTT | 63 | 981 |

TABLE 14-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047540 | 2857 | 2876 | 13146 | 13165 | CAGATCCCACCAGTCTGCTC | 89 | 982 |
| 1047556 | 2889 | 2908 | 13178 | 13197 | GAAGTGGGCCCTOCCAGTCC | 113 | 983 |
| 1047572 | 3011 | 3030 | 13300 | 13319 | GTGCCCTGAAGATTAGCAGC | 85 | 984 |
| 1047588 | 3053 | 3072 | 13342 | 13361 | GCATTTGTCTTTATTTTTCC | 11 | 985 |
| 1047604 | N/A | N/A | 8756 | 8775 | CTTGTGATTTTCCCCGTCTT | 74 | 986 |
| 1047620 | N/A | N/A | 8972 | 8991 | ATGACGCAGTCCAGGCCCTT | 78 | 987 |
| 1047636 | N/A | N/A | 9064 | 9083 | ACTCACCACCTTTACCACTA | 85 | 988 |
| 1047652 | N/A | N/A | 9129 | 9148 | AAGAGGTGAGACAGAGGCTG | 66 | 989 |
| 1047668 | N/A | N/A | 8375 | 8394 | GTACTGACCTCGAATCTGCA | 96 | 990 |
| 1047684 | N/A | N/A | 8437 | 8456 | AGCAACCTACAGGCCCTGGA | 116 | 991 |
| 1047700 | N/A | N/A | 8477 | 8496 | GAGCTGGATCCCTTTGCCCT | 82 | 992 |
| 1047716 | N/A | N/A | 8631 | 8650 | GCTCTCACCCAGTTCTGCTG | 83 | 993 |
| 1047732 | N/A | N/A | 8725 | 8744 | CCCCCTGTAGTGACAAGCAG | 71 | 994 |
| 1047748 | N/A | N/A | 4051 | 4070 | GAGGTTCGGCCCCTCCCTGA | 68 | 995 |
| 1047764 | N/A | N/A | 4258 | 4277 | AAAGCCCAGCCATGAATGAA | 111 | 996 |
| 1047780 | N/A | N/A | 4317 | 4336 | CAACTCCTCCTTTATATGGA | 104 | 997 |
| 1047796 | N/A | N/A | 4355 | 4374 | ATCCAATCTCCCTCATGGAC | 78 | 998 |
| 1047812 | N/A | N/A | 4388 | 4407 | GCCTGCTCTTTCCCTCACTT | 98 | 999 |
| 1047828 | N/A | N/A | 4520 | 4539 | TCTGATCCCAGGTAACCACC | 81 | 1000 |
| 1047844 | N/A | N/A | 4693 | 4712 | TACTAAGGTGCCTTATCAGG | 92 | 1001 |
| 1047860 | N/A | N/A | 4800 | 4819 | ACCCCCACCCAGGACCAGTA | 94 | 1002 |
| 1047876 | N/A | N/A | 4851 | 4870 | GACACTTGAATACCTGCCTC | 89 | 1003 |
| 1047892 | N/A | N/A | 5002 | 5021 | CATCAATCCTTTOCTOCCTC | 79 | 1004 |
| 1047908 | N/A | N/A | 5109 | 5128 | TCCTTCTCCCCATTCCTCAG | 88 | 1005 |
| 1047924 | N/A | N/A | 5355 | 5374 | TCTCTGAGTGTCTCTCTCAG | 92 | 1006 |
| 1047940 | N/A | N/A | 5478 | 5497 | CCTCTTCTGCCTGCCCCTCG | 111 | 1007 |
| 1047956 | N/A | N/A | 5784 | 5803 | TTCCCCCATTCTCTTGTACA | 98 | 1008 |
| 1047972 | N/A | N/A | 5836 | 5855 | GGTGAAAGTCAGTCACCTGG | 90 | 1009 |
| 1047988 | N/A | N/A | 6009 | 6028 | ATCTGTCAAAGAACAGCACC | 96 | 1010 |
| 1048004 | N/A | N/A | 6092 | 6111 | TAGAGTTGGAAATCCAACTC | 92 | 1011 |
| 1048020 | N/A | N/A | 6211 | 6230 | ACACCTTCCAGGTCAGACAC | 71 | 1012 |
| 1048036 | N/A | N/A | 6322 | 6341 | TGCCTAGCCCAAATGCCCCC | 111 | 1013 |
| 1048052 | N/A | N/A | 6386 | 6405 | AGGCTCTGTCCTCCACTAGG | 87 | 1014 |
| 1048068 | N/A | N/A | 6513 | 6532 | CCTCCCAGCCCCATCGGGCC | 146 | 1015 |
| 1048084 | N/A | N/A | 6955 | 6974 | CAGAACCTTCCACACTGACA | 123 | 1016 |

TABLE 14-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1048100 | N/A | N/A | 7065 | 7084 | TTCCCAACAACTGTGACCCA | 69 | 1017 |
| 1048116 | N/A | N/A | 7387 | 7406 | TGGCCCTTCTCCCCTGGCAT | 122 | 1018 |
| 1048132 | N/A | N/A | 7840 | 7859 | AAGGCTGAAAAAGACTCAGT | 82 | 1019 |
| 1048148 | N/A | N/A | 7982 | 8001 | GTGACCCAAGTCCTTGGCCT | 85 | 1020 |
| 1048164 | N/A | N/A | 8217 | 8236 | GGAAAGTCTAACTCCATCTC | 93 | 1021 |
| 1048180 | N/A | N/A | 9323 | 9342 | ACATTCACTAATATTTAACA | 91 | 1022 |
| 1048196 | N/A | N/A | 9510 | 9529 | CTGGTTAGCCTTTCTGATGC | 51 | 1023 |
| 1048212 | N/A | N/A | 9599 | 9618 | TCCTCTTTCCTACTTCTCTC | 73 | 1024 |
| 1048228 | N/A | N/A | 9709 | 9728 | GGGCCTACTTCTCTAGGTGG | 48 | 1025 |
| 1048244 | N/A | N/A | 9813 | 9832 | AGCTCAAGAAGTCCCAACTT | 87 | 1026 |
| 1048260 | N/A | N/A | 10616 | 10635 | GCTTCATTTCAGCCCCTCTG | 82 | 1027 |
| 1048276 | N/A | N/A | 10700 | 10719 | CTAGGCTCTTCCAAACGGGC | 94 | 1028 |
| 1048292 | N/A | N/A | 10771 | 10790 | TGCCCGGCTTCCCCATCGCA | 98 | 1029 |
| 1048308 | N/A | N/A | 10936 | 10955 | GCCCAAATCCCTCCTTACCT | 95 | 1030 |
| 1048324 | N/A | N/A | 11021 | 11040 | GCTGGGAACCTTCTATGTGC | 64 | 1031 |
| 1048340 | N/A | N/A | 11133 | 11152 | GGCTTTGGTACCAAGGCTOC | 89 | 1032 |
| 1048356 | N/A | N/A | 11309 | 11328 | CCCCTGGTAGTTTCCTTTTA | 94 | 1033 |
| 1048372 | N/A | N/A | 11433 | 11452 | TGGTGAGATAACACTGGGAA | 51 | 1034 |
| 1048388 | N/A | N/A | 11571 | 11590 | ACAGTGCAACAGTTAGGAGT | 73 | 1035 |

TABLE 15

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047157 | 123 | 142 | 3571 | 3590 | CCAGGCCCCCCACCATCATC | 116 | 1036 |
| 1047173 | 239 | 258 | 3687 | 3706 | CTCCTTGAAGCCAGCATTGA | 95 | 1037 |
| 1047189 | 474 | 493 | 3922 | 3941 | TGTCCCTCTCAACCTCCAGC | 11* | 1038 |
| 1047205 | 547 | 566 | 4932 | 4951 | TTCTCGGCTTCCAGCCTCAG | 31* | 1039 |
| 1047221 | 637 | 656 | 5226 | 5245 | ATCTCCTCCTCCAGCGACTC | 83 | 1040 |
| 1047237 | 786 | 805 | 5672 | 5691 | ACGCCATTGCCTCATACTGC | 104 | 1041 |
| 1047253 | 1021 | 1040 | 7593 | 7612 | TGATAACTGGCCGCCTCCCG | 94 | 1042 |
| 1047269 | 1227 | 1246 | N/A | N/A | GGCTGGTTTCTCGAATCTGC | 92 | 1043 |

TABLE 15-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047285 | 1285 | 1304 | 10899 | 10918 | ACGGTCTTCACCACGATGTT | 86 | 1044 |
| 1047301 | 1346 | 1365 | 11635 | 11654 | TCACATCACATCCTTGTGCT | 79 | 1045 |
| 1047317 | 1406 | 1425 | 11695 | 11714 | ATCCTGCTTCTGCTCGGGCC | 98 | 1046 |
| 1047333 | 1610 | 1629 | 11899 | 11918 | TGGCCATGCCCCTCCAGACT | 74 | 1047 |
| 1047349 | 1660 | 1679 | 11949 | 11968 | CCCCGCCCTCCTCCCCTTCT | 98 | 1048 |
| 1047365 | 1724 | 1743 | 12013 | 12032 | ATCTCTGGCAACAGTTTCCA | 60 | 1049 |
| 1047381 | 1774 | 1793 | 12063 | 12082 | GCCTGAGGAAACTCAAAGGC | 91 | 1050 |
| 1047397 | 1839 | 1858 | 12128 | 12147 | TGGCCAGGGCTACCTTGTCT | 82 | 1051 |
| 1047413 | 2033 | 2052 | 12322 | 12341 | CCCCACCCATCTTAGACTGA | 84 | 1052 |
| 1047429 | 2172 | 2191 | 12461 | 12480 | AATCAAGCTCCCACCTGCCC | 45 | 1053 |
| 1047445 | 2234 | 2253 | 12523 | 12542 | CCTCTATCCCTCCCAGCACC | 104 | 1054 |
| 1047461 | 2275 | 2294 | 12564 | 12583 | CTTGACCTCTCTGTACCCAC | 67 | 1055 |
| 1047477 | 2375 | 2394 | 12664 | 12683 | CACCCACAACCCCTACTTGT | 97 | 1056 |
| 1047493 | 2450 | 2469 | 12739 | 12758 | TCTCCTGTTTCAGCATCTTC | 58 | 1057 |
| 1047509 | 2478 | 2497 | 12767 | 12786 | CCCTGCCCCCATGGATACAT | 76 | 1058 |
| 1047525 | 2765 | 2784 | 13054 | 13073 | GCTGCAGGAATATGAGCCAG | 84 | 1059 |
| 1047541 | 2858 | 2877 | 13147 | 13166 | ACAGATCCCACCAGTCTGCT | 98 | 1060 |
| 1047557 | 2890 | 2909 | 13179 | 13198 | TGAAGTGGGCCCTCCCAGTC | 87 | 1061 |
| 1047573 | 3016 | 3035 | 13305 | 13324 | CAGCAGTGCCCTGAAGATTA | 45 | 1062 |
| 1047589 | 3054 | 3073 | 13343 | 13362 | AGCATTTGTCTTTATTTTTC | 17 | 1063 |
| 1047605 | N/A | N/A | 8757 | 8776 | CCTTGTGATTTTCCCCGTCT | 64 | 1064 |
| 1047621 | N/A | N/A | 9023 | 9042 | TACAGTTACTCTGTACCACG | 118 | 1065 |
| 1047637 | N/A | N/A | 9065 | 9084 | GACTCACCACCTTTACCACT | 87 | 1066 |
| 1047653 | N/A | N/A | 9199 | 9218 | GATGAAAGAATAAAGCAGAG | 102 | 1067 |
| 1047669 | N/A | N/A | 8376 | 8395 | TGTACTGACCTCGAATCTGC | 90 | 1068 |
| 1047685 | N/A | N/A | 8439 | 8458 | GGAGCAACCTACAGGCCCTG | 104 | 1069 |
| 1047701 | N/A | N/A | 8478 | 8497 | AGAGCTGGATCCCTTTGCCC | 87 | 1070 |
| 1047717 | N/A | N/A | 8632 | 8651 | AGCTCTCACCCAGITCTGCT | 62 | 1071 |
| 1047733 | N/A | N/A | 8731 | 8750 | CTTTTGCCCCCTGTAGTGAC | 56 | 1072 |
| 1047749 | N/A | N/A | 4088 | 4107 | GTGCCCCATCAAGAGGTAGG | 147 | 1073 |
| 1047765 | N/A | N/A | 4260 | 4279 | ACAAAGCCCAGCCATGAATG | 142 | 1074 |
| 1047781 | N/A | N/A | 4318 | 4337 | CCAACTCCTCCTTTATATGG | 74 | 1075 |
| 1047797 | N/A | N/A | 4356 | 4375 | AATCCAATCTCCCTCATGGA | 93 | 1076 |
| 1047813 | N/A | N/A | 4390 | 4409 | CTGCCTGCTCTTTCCCTCAC | 99 | 1077 |
| 1047829 | N/A | N/A | 4521 | 4540 | CTCTGATCCCAGGTAACCAC | 96 | 1078 |

TABLE 15-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047845 | N/A | N/A | 4700 | 4719 | AACTCATTACTAAGGTGCCT | 101 | 1079 |
| 1047861 | N/A | N/A | 4801 | 4820 | CACCCCCACCCAGGACCAGT | 90 | 1080 |
| 1047877 | N/A | N/A | 4852 | 4871 | GGACACTTGAATACCTGCCT | 84 | 1081 |
| 1047893 | N/A | N/A | 5003 | 5022 | CCATCAATCCTTTCCTCCCT | 82 | 1082 |
| 1047909 | N/A | N/A | 5112 | 5131 | GGCTCCTTCTCCCCATTCCT | 92 | 1083 |
| 1047925 | N/A | N/A | 5368 | 5387 | TGTTTCTCTCCTCTCTCTGA | 113 | 1084 |
| 1047941 | N/A | N/A | 5484 | 5503 | TTGTGTCCTCTTCTGCCTGC | 93 | 1085 |
| 1047957 | N/A | N/A | 5786 | 5805 | CCTTCCCCCATTCTCTTGTA | 87 | 1086 |
| 1047973 | N/A | N/A | 5842 | 5861 | TTCTCTGGTGAAAGTCAGTC | 95 | 1087 |
| 1047989 | N/A | N/A | 6012 | 6031 | CTCATCTGTCAAAGAACAGC | 102 | 1088 |
| 1048005 | N/A | N/A | 6110 | 6129 | CTCCCAAGTGAGATGTGCTA | 112 | 1089 |
| 1048021 | N/A | N/A | 6212 | 6231 | CACACCTTCCAGGTCAGACA | 70 | 1090 |
| 1048037 | N/A | N/A | 6323 | 6342 | CTGCCTAGCCCAAATGCCCC | 86 | 1091 |
| 1048053 | N/A | N/A | 6396 | 6415 | TTCTGCCTCCAGGCTCTGTC | 117 | 1092 |
| 1048069 | N/A | N/A | 6519 | 6538 | GGAGGTCCTCCCAGCCCCAT | 94 | 1093 |
| 1048085 | N/A | N/A | 6956 | 6975 | CCAGAACCTTCCACACTGAC | 79 | 1094 |
| 1048101 | N/A | N/A | 7069 | 7088 | ACTTTTCCCAACAACTGTGA | 84 | 1095 |
| 1048117 | N/A | N/A | 7388 | 7407 | CTGGCCCTTCTCCCCTGGCA | 81 | 1096 |
| 1048133 | N/A | N/A | 7841 | 7860 | CAAGGCTGAAAAAGACTCAG | 121 | 1097 |
| 1048149 | N/A | N/A | 7985 | 8004 | AGGGTGACCCAAGTCCTTGG | 89 | 1098 |
| 1048165 | N/A | N/A | 8219 | 8238 | CAGGAAAGTCTAACTCCATC | 80 | 1099 |
| 1048181 | N/A | N/A | 9324 | 9343 | CACATTCACTAATATTTAAC | 93 | 21 |
| 1048197 | N/A | N/A | 9512 | 9531 | GCCTGGTTAGCCTTTCTGAT | 59 | 1100 |
| 1048213 | N/A | N/A | 9604 | 9623 | CCCTTTCCTCTTTCCTACTT | 71 | 1101 |
| 1048229 | N/A | N/A | 9727 | 9746 | TGTAAAATAAGGATGATGGG | 101 | 1102 |
| 1048245 | N/A | N/A | 9816 | 9835 | CAGAGCTCAAGAAGTCCCAA | 101 | 1103 |
| 1048261 | N/A | N/A | 10617 | 10636 | GGCTTCATTTCAGCCCCTCT | 73 | 1104 |
| 1048277 | N/A | N/A | 10702 | 10721 | GCCTAGGCTCTTCCAAACGG | 105 | 1105 |
| 1048293 | N/A | N/A | 10784 | 10803 | CCATCCTCTCCCATGCCCGG | 100 | 1106 |
| 1048309 | N/A | N/A | 10937 | 10956 | GGCCCAAATCCCTCCTTACC | 118 | 1107 |
| 1048325 | N/A | N/A | 11058 | 11077 | CTCTCCTCCAGAATTCCCTG | 76 | 1108 |
| 1048341 | N/A | N/A | 11149 | 11168 | TAGGATCCCATCTAGTGGCT | 51 | 1109 |
| 1048357 | N/A | N/A | 11316 | 11335 | TCCCATTCCCCTGGTAGTTT | 57 | 1110 |
| 1048373 | N/A | N/A | 11435 | 11454 | GGTGGTGAGATAACACTGGG | 88 | 1111 |
| 1048389 | N/A | N/A | 11608 | 11627 | GGACTCCTTAATGACCTGCA | 53 | 1112 |

TABLE 16

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047158 | 124 | 143 | 3572 | 3591 | GCCAGGCCCCCCACCATCAT | 102 | 1113 |
| 1047174 | 240 | 259 | 3688 | 3707 | TCTCCTTGAAGCCAGCATTG | 109 | 1114 |
| 1047190 | 477 | 496 | 3925 | 3944 | GATTGTCCCTCTCAACCTCC | 17* | 1115 |
| 1047206 | 563 | 582 | 4948 | 4967 | ATAGGCAGCCAGGTTGTTCT | 35* | 1116 |
| 1047222 | 638 | 657 | 5227 | 5246 | GATCTCCTCCTCCAGCGACT | 75 | 1117 |
| 1047238 | 809 | 828 | 5695 | 5714 | TTCGGCTTCATGCATGTTGC | 123 | 1118 |
| 1047254 | 1026 | 1045 | 7598 | 7617 | CCTCCTGATAACTGGCCGCC | 117 | 1119 |
| 1047270 | 1228 | 1247 | N/A | N/A | AGGCTGGTTTCTCGAATCTG | 117 | 1120 |
| 1047286 | 1286 | 1305 | 10900 | 10919 | CACGGTCTTCACCACGATGT | 89 | 1121 |
| 1047302 | 1348 | 1367 | 11637 | 11656 | CCTCACATCACATCCTTGTG | 103 | 1122 |
| 1047318 | 1413 | 1432 | 11702 | 11721 | AGCAACTATCCTGCTTCTGC | 58 | 1123 |
| 1047334 | 1612 | 1631 | 11901 | 11920 | GCTGGCCATGCCCCTCCAGA | 114 | 1124 |
| 1047350 | 1661 | 1680 | 11950 | 11969 | CCCCCGCCCTCCTCCCCTTC | 90 | 1125 |
| 1047366 | 1731 | 1750 | 12020 | 12039 | AACCTCCATCTCTGGCAACA | 59 | 1126 |
| 1047382 | 1782 | 1801 | 12071 | 12090 | CTCCAGCAGCCTGAGGAAAC | 131 | 1127 |
| 1047398 | 1844 | 863 | 12133 | 12152 | GCCTCTGGCCAGGGCTACCT | 100 | 1128 |
| 1047414 | 2034 | 2053 | 12323 | 12342 | TCCCCACCCATCTTAGACTG | 113 | 1129 |
| 1047430 | 2178 | 2197 | 12467 | 12486 | GCTGAGAATCAAGCTOCCAC | 54 | 1130 |
| 1047446 | 2235 | 2254 | 12524 | 12543 | CCCTCTATCCCTCCCAGCAC | 100 | 1131 |
| 1047462 | 2278 | 2297 | 12567 | 12586 | GGGCTTGACCTCTCTGTACC | 73 | 1132 |
| 1047478 | 2376 | 2395 | 12665 | 12684 | TCACCCACAACCCCTACTTG | 81 | 1133 |
| 1047494 | 2451 | 2470 | 12740 | 12759 | CTCTCCTGTTTCAGCATCTT | 61 | 1134 |
| 1047510 | 2481 | 2500 | 12770 | 12789 | ATGCCCTGCCCCCATGGATA | 83 | 1135 |
| 1047526 | 2777 | 2796 | 13066 | 13085 | CCCGGCCTCCAGGCTGCAGG | 89 | 1136 |
| 1047542 | 2859 | 2878 | 13148 | 13167 | CACAGATCCCACCAGTCTGC | 85 | 1137 |
| 1047558 | 2901 | 2920 | 13190 | 13209 | GAGGAGAACCCTGAAGTGGG | 95 | 1138 |
| 1047574 | 3018 | 3037 | 13307 | 13326 | AGCAGCAGTGCCCTGAAGAT | 78 | 1139 |
| 1047590 | 3055 | 3074 | 13344 | 13363 | CAGCATTTGTCTTTATTTTT | 21 | 1140 |
| 1047606 | N/A | N/A | 8758 | 8777 | ACCTTGTGATTTTCCCCGTC | 70 | 1141 |
| 1047622 | N/A | N/A | 9024 | 9043 | GTACAGTTACTCTGTACCAC | 138 | 1142 |
| 1047638 | N/A | N/A | 9066 | 9085 | GGACTCACCACCTTTACCAC | 68 | 1143 |
| 1047654 | N/A | N/A | 9200 | 9219 | GGATGAAAGAATAAAGCAGA | 85 | 1144 |
| 1047670 | N/A | N/A | 8377 | 8396 | CTGTACTGACCTCGAATCTG | 93 | 1145 |
| 1047686 | N/A | N/A | 8443 | 8462 | GTCTGGAGCAACCTACAGGC | 79 | 1146 |
| 1047702 | N/A | N/A | 8495 | 8514 | CACGAAGGCCCCCAGGGAGA | 77 | 1147 |

TABLE 16-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047718 | N/A | N/A | 8633 | 8652 | AAGCTCTCACCCAGTTCTGC | 108 | 1148 |
| 1047734 | N/A | N/A | 8733 | 8752 | TGCTTTTGCCCCCTGTAGTG | 47 | 1149 |
| 1047750 | N/A | N/A | 4090 | 4109 | TAGTGCCCCATCAAGAGGTA | 88 | 1150 |
| 1047766 | N/A | N/A | 4262 | 4281 | TCACAAAGCCCAGCCATGAA | 89 | 1151 |
| 1047782 | N/A | N/A | 4319 | 4338 | TCCAACTCCTCCTTTATATG | 85 | 1152 |
| 1047798 | N/A | N/A | 4357 | 4376 | GAATCCAATCTCCCTCATGG | 94 | 1153 |
| 1047814 | N/A | N/A | 4396 | 4415 | CCAGACCTGCCTGCTCTTTC | 89 | 1154 |
| 1047830 | N/A | N/A | 4523 | 4542 | TCCTCTGATCCCAGGTAACC | 76 | 1155 |
| 1047846 | N/A | N/A | 4701 | 4720 | TAACTCATTACTAAGGTGCC | 79 | 1156 |
| 1047862 | N/A | N/A | 4804 | 4823 | GACCACCCCCACCCAGGACC | 105 | 1157 |
| 1047878 | N/A | N/A | 4853 | 4872 | AGGACACTTGAATACCTGCC | 56 | 1158 |
| 1047894 | N/A | N/A | 5004 | 5023 | GCCATCAATCCTTTCCTCCC | 100 | 1159 |
| 1047910 | N/A | N/A | 5113 | 5132 | AGGCTOCTTCTCCCCATTCC | 90 | 1160 |
| 1047926 | N/A | N/A | 5379 | 5398 | CTGCCAATCTCTGTTTCTCT | 85 | 1161 |
| 1047942 | N/A | N/A | 5496 | 5515 | TTCCCCACGCCATTGTGTCC | 76 | 1162 |
| 1047958 | N/A | N/A | 5787 | 5806 | TCCTTCCCCCATTCTCTTGT | 121 | 1163 |
| 1047974 | N/A | N/A | 5851 | 5870 | CCATCTCACTTCTCTGGTGA | 82 | 1164 |
| 1047990 | N/A | N/A | 6019 | 6038 | CGGCTCTCTCATCTGTCAAA | 43 | 1165 |
| 1048006 | N/A | N/A | 6115 | 6134 | GCAGGCTCCCAAGTGAGATG | 99 | 1166 |
| 1048022 | N/A | N/A | 6221 | 6240 | CGTCAATATCACACCTTCCA | 96 | 1167 |
| 1048038 | N/A | N/A | 6324 | 6343 | CCTGCCTAGCCCAAATGCCC | 119 | 1168 |
| 1048054 | N/A | N/A | 6400 | 6419 | GCTTTTCTGCCTCCAGGCTC | 77 | 1169 |
| 1048070 | N/A | N/A | 6539 | 6558 | CCTTTCTCCCCTGCCTGCAG | 89 | 1170 |
| 1048086 | N/A | N/A | 6957 | 6976 | TCCAGAACCTTCCACACTGA | 82 | 1171 |
| 1048102 | N/A | N/A | 7070 | 7089 | GACTTTTCCCAACAACTGTG | 84 | 1172 |
| 1048118 | N/A | N/A | 7390 | 7409 | CCCTGGCCCTTCTCCCCTGG | 76 | 1173 |
| 1048134 | N/A | N/A | 7842 | 7861 | ACAAGGCTGAAAAAGACTCA | 83 | 1174 |
| 1048150 | N/A | N/A | 7986 | 8005 | GAGGGTGACCCAAGTCCTTG | 110 | 1175 |
| 1048166 | N/A | N/A | 8221 | 8240 | GCCAGGAAAGTCTAACTCCA | 75 | 1176 |
| 1048182 | N/A | N/A | 9326 | 9345 | GTCACATTCACTAATATTTA | 44 | 1177 |
| 1048198 | N/A | N/A | 9525 | 9544 | CCTCTACTAGTCAGCCTGGT | 65 | 1178 |
| 1048214 | N/A | N/A | 9606 | 9625 | TCCCCTTTCCTCTTTCCTAC | 75 | 1179 |
| 1048230 | N/A | N/A | 9772 | 9791 | CTCTGGGCAAGTTAATTGAC | 122 | 1180 |
| 1048246 | N/A | N/A | 9818 | 9837 | ACCAGAGCTCAAGAAGTCCC | 83 | 1181 |
| 1048262 | N/A | N/A | 10618 | 10637 | TGGCTTCATTTCAGCCCCTC | 81 | 1182 |

TABLE 16-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1048278 | N/A | N/A | 10710 | 10729 | CAGAGAGAGCCTAGGCTCTT | 95 | 1183 |
| 1048294 | N/A | N/A | 10788 | 10807 | TGAGCCATCCTCTCCCATGC | 125 | 1184 |
| 1048310 | N/A | N/A | 10940 | 10959 | CTGGGCCCAAATCCCTCCTT | 83 | 1185 |
| 1048326 | N/A | N/A | 11060 | 11079 | TGCTCTCCTCCAGAATTCCC | 123 | 1186 |
| 1048342 | N/A | N/A | 11223 | 11242 | CTAACTTTAATTCTCTTTCT | 114 | 1187 |
| 1048358 | N/A | N/A | 11317 | 11336 | TTCCCATTCCCCTGGTAGTT | 89 | 1188 |
| 1048374 | N/A | N/A | 11436 | 11455 | GGGTGGTGAGATAACACTGG | 106 | 1189 |
| 1048390 | N/A | N/A | 11609 | 11628 | TGGACTCCTTAATGACCTGC | 68 | 1190 |

TABLE 17

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047159 | 126 | 145 | 3574 | 3593 | GAGCCAGGCCCCCCACCATC | 104 | 1191 |
| 1047175 | 244 | 263 | 3692 | 3711 | CGGGTCTCCTTGAAGCCAGC | 125 | 1192 |
| 1047191 | 480 | 499 | 3928 | 3947 | CCAGATTGTCCCTCTCAACC | 15* | 1193 |
| 1047207 | 574 | 593 | N/A | N/A | GCTTCCTGTCTATAGGCAGC | 37* | 1194 |
| 1047223 | 639 | 658 | 5228 | 5247 | GGATCTCCTCCTCCAGCGAC | 79 | 1195 |
| 1047239 | 811 | 830 | 5697 | 5716 | TCTTCGGCTTCATGCATGTT | 98 | 1196 |
| 1047255 | 1028 | 1047 | 7600 | 7619 | CGCCTCCTGATAACTGGCCG | 105 | 1197 |
| 1047271 | 1241 | 1260 | 10855 | 10874 | AGACTTGGTGTCCAGGCTGG | 79 | 1198 |
| 1047287 | 1289 | 1308 | 0903 | 10922 | CTCCACGGTCTTCACCACGA | 138 | 1199 |
| 1047303 | 1349 | 1368 | 11638 | 11657 | GCCTCACATCACATCCTTGT | 113 | 1200 |
| 1047319 | 1414 | 1433 | 11703 | 11722 | GAGCAACTATCCTGCTTCTG | 68 | 1201 |
| 1047335 | 1615 | 1634 | 11904 | 11923 | GCTGCTGGCCATGCCCCTCC | 123 | 1202 |
| 1047351 | 1663 | 1682 | 11952 | 11971 | GCCCCCCGCCCTCCTCCCCT | 73 | 1203 |
| 1047367 | 1734 | 1753 | 12023 | 12042 | GAGAACCTCCATCTCTGGCA | 67 | 1204 |
| 1047383 | 1790 | 1809 | 12079 | 12098 | CAGTTTTCCTCCAGCAGCCT | 109 | 11 |
| 1047399 | 1853 | 1872 | 12142 | 12161 | ACAAAACAAGCCTCTGGCCA | 90 | 1206 |
| 1047415 | 2035 | 2054 | 12324 | 12343 | GTCCCCACCCATCTTAGACT | 76 | 1207 |
| 1047431 | 2179 | 2198 | 12468 | 12487 | TGCTGAGAATCAAGCTCCCA | 91 | 1208 |
| 1047447 | 2236 | 2255 | 12525 | 12544 | CCCCTCTATCCCTOCCAGCA | 83 | 1209 |
| 1047463 | 2279 | 2298 | 12568 | 12587 | TGGGCTTGACCTCTCTGTAC | 103 | 1210 |

TABLE 17-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1047479 | 2377 | 2396 | 12666 | 12685 | GTCACCCACAACCCCTACTT | 88 | 1211 |
| 1047495 | 2456 | 2475 | 2745 | 12764 | CCTTTCTCTCCTGTTTCAGC | 54 | 1212 |
| 1047511 | 2482 | 2501 | 12771 | 12790 | CATGCCCTGCCCCCATGGAT | 83 | 1213 |
| 1047527 | 2779 | 2798 | 13068 | 13087 | CACCCGGCCTCCAGGCTGCA | 106 | 1214 |
| 1047543 | 2860 | 2879 | 13149 | 13168 | GCACAGATCCCACCAGTCTG | 108 | 1215 |
| 1047559 | 2902 | 2921 | 13191 | 13210 | AGAGGAGAACCCTGAAGTGG | 120 | 1216 |
| 1047575 | 3034 | 3053 | 13323 | 13342 | CTCAGCGACTAAAGGCAGCA | 59 | 1217 |
| 1047591 | 3056 | 3075 | 13345 | 13364 | GCAGCATTTGTCTTTATTTT | 22 | 1218 |
| 1047607 | N/A | N/A | 8760 | 8779 | TGACCTTGTGATTTTCCCCG | 59 | 1219 |
| 1047623 | N/A | N/A | 9025 | 9044 | TGTACAGTTACTCTGTACCA | 103 | 1220 |
| 1047639 | N/A | N/A | 9067 | 9086 | AGGACTCACCACCTTTACCA | 77 | 1221 |
| 1047655 | N/A | N/A | 9201 | 9220 | GGGATGAAAGAATAAAGCAG | 67 | 1222 |
| 1047671 | N/A | N/A | 8378 | 8397 | GCTGTACTGACCTCGAATCT | 94 | 1223 |
| 1047687 | N/A | N/A | 8453 | 8472 | CTCAGTCCCAGTCTGGAGCA | 123 | 1224 |
| 1047703 | N/A | N/A | 8502 | 8521 | GCAGTGTCACGAAGGCCCCC | 89 | 1225 |
| 1047719 | N/A | N/A | 8635 | 8654 | TCAAGCTCTCACCCAGTTCT | 96 | 1226 |
| 1047735 | N/A | N/A | 8735 | 8754 | GGTGCTTTTGCCCCCTGTAG | 55 | 1227 |
| 1047751 | N/A | N/A | 4091 | 4110 | ATAGTGCCCCATCAAGAGGT | 135 | 1228 |
| 1047767 | N/A | N/A | 4263 | 4282 | GTCACAAAGCCCAGCCATGA | 122 | 1229 |
| 1047783 | N/A | N/A | 4321 | 4340 | CTTCCAACTCCTCCTTTATA | 95 | 1230 |
| 1047799 | N/A | N/A | 4358 | 4377 | AGAATCCAATCTCCCTCATG | 67 | 1231 |
| 1047815 | N/A | N/A | 4399 | 4418 | CGCCCAGACCTGCCTGCTCT | 94 | 1232 |
| 1047831 | N/A | N/A | 4524 | 4543 | TTCCTCTGATCCCAGGTAAC | 86 | 1233 |
| 1047847 | N/A | N/A | 4702 | 4721 | TTAACTCATTACTAAGGTGC | 87 | 1234 |
| 1047863 | N/A | N/A | 4805 | 4824 | AGACCACCCCCACCCAGGAC | 96 | 1235 |
| 1047879 | N/A | N/A | 4866 | 4885 | CCAGGCTCTTCTGAGGACAC | 119 | 1236 |
| 1047895 | N/A | N/A | 5005 | 5024 | GGCCATCAATCCTTTCCTCC | 81 | 1237 |
| 1047911 | N/A | N/A | 5115 | 5134 | CCAGGCTCCTTCTCCCCATT | 92 | 1238 |
| 1047927 | N/A | N/A | 5385 | 5404 | CTCTACCTGCCAATCTCTGT | 86 | 1239 |
| 1047943 | N/A | N/A | 5497 | 5516 | GTTCCCCACGCCATTGTGTC | 78 | 1240 |
| 1047959 | N/A | N/A | 5788 | 5807 | CTCCTTCCCCCATTCTCTTG | 104 | 1241 |
| 1047975 | N/A | N/A | 5933 | 5952 | GCTACTACTAATAATAGCAA | 99 | 1242 |
| 1047991 | N/A | N/A | 6021 | 6040 | TTCGGCTCTCTCATCTGTCA | 80 | 1243 |
| 1048007 | N/A | N/A | 6117 | 6136 | ATGCAGGCTCCCAAGTGAGA | 88 | 1244 |
| 1048023 | N/A | N/A | 6280 | 6299 | CCACACTACATATAAGCTCT | 163 | 1245 |

TABLE 17-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP RNA (% control) | SEQ ID NO |
|---|---|---|---|---|---|---|---|
| 1048039 | N/A | N/A | 6325 | 6344 | TCCTGCCTAGCCCAAATGCC | 100 | 1246 |
| 1048055 | N/A | N/A | 6403 | 6422 | TGTGCTTTTCTGCCTCCAGG | 52 | 1247 |
| 1048071 | N/A | N/A | 6543 | 6562 | TAGCCCTTTCTCCCCTGCCT | 77 | 1248 |
| 1048087 | N/A | N/A | 6958 | 6977 | ATCCAGAACCTTCCACACTG | 88 | 1249 |
| 1048103 | N/A | V/A | 7072 | 7091 | GGGACTTTTOCCAACAACTG | 68 | 1250 |
| 1048119 | N/A | N/A | 7393 | 7412 | CGTCCCTGGCCCTTCTCCCC | 77 | 1251 |
| 1048135 | N/A | N/A | 7843 | 7862 | CACAAGGCTGAAAAAGACTC | 94 | 1252 |
| 1048151 | N/A | N/A | 7987 | 8006 | GGAGGGTGACCCAAGTCCTT | 35 | 1253 |
| 1048167 | N/A | N/A | 8222 | 8241 | TGCCAGGAAAGTCTAACTCC | 77 | 1254 |
| 1048183 | N/A | N/A | 9362 | 9381 | TCCCCCCGCCCCGCCCGAGA | 88 | 1255 |
| 1048199 | N/A | N/A | 9533 | 9552 | CAGTATTACCTCTACTAGTC | 64 | 20 |
| 1048215 | N/A | N/A | 9609 | 9628 | CTGTCCCCTTTCCTCTTTCC | 98 | 1256 |
| 1048231 | N/A | N/A | 9788 | 9807 | CCAACCAGCCACATGACTCT | 91 | 1257 |
| 1048247 | N/A | N/A | 9825 | 9844 | TCAGGAGACCAGAGCTCAAG | 93 | 1258 |
| 1048263 | N/A | N/A | 10620 | 10639 | CCTGGCTTCATTTCAGCCCC | 87 | 1259 |
| 1048279 | N/A | N/A | 10711 | 10730 | GCAGAGAGAGCCTAGGCTCT | 143 | 1260 |
| 1048295 | N/A | N/A | 10792 | 10811 | GGCATGAGCCATCCTCTCCC | 123 | 1261 |
| 1048311 | N/A | N/A | 10941 | 10960 | ACTGGGCCCAAATCCCTCCT | 104 | 1262 |
| 1048327 | N/A | N/A | 11061 | 11080 | TTGCTCTCCTCCAGAATTCC | 97 | 1263 |
| 1048343 | N/A | N/A | 11226 | 11245 | CTACTAACTTTAATTCTCTT | 97 | 1264 |
| 1048359 | N/A | N/A | 11318 | 11337 | CTTCCCATTCCCCTGGTAGT | 86 | 1265 |
| 1048375 | N/A | N/A | 11487 | 11506 | GTCTTACTTTTCTTGATAGT | 94 | 1266 |
| 1048391 | N/A | N/A | 11610 | 11629 | TTGGACTCCTTAATGACCTG | 86 | 1267 |

Example 2: Effect of 5-10-5 MOE Gapmer Modified Oligonucleotides on Human GFAP RNA In Vitro, Single Dose Modified oligonucleotides complementary to human GFAP nucleic acid were designed and tested for their single dose effects on GFAP RNA in vitro. The modified oligonucleotides were tested in a series of experiments that had similar culture conditions.

The modified oligonucleotides in the tables below are 5-10-5 MOE gapmers with mixed PO/PS internucleoside linkages. The gapmers are 20 nucleosides in length, wherein the central gap segment consists of ten 2'-β-D-deoxynucleosides and the 5' and 3' wing segments each consists of five 2'-β-D-MOE modified nucleosides. The sugar motif for the gapmers is (from 5' to 3'): eeeeeddddddddddeeeee: wherein 'd' represents a 2'-β-D-deoxyribosyl sugar moiety, and 'e' represents a 2'-β-D-MOE sugar moiety. The internucleoside linkage motif for the gapmers is (from 5' to 3'): sooosssssssssssooss; wherein each 'o' represents a phosphodiester internucleoside linkage and each 's' represents a phosphorothioate internucleoside linkage. Each cytosine residue is a 5-methylcytosine.

"Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. Each modified oligonucleotide listed in the Tables below is 100% complementary to SEQ ID NO: 1, SEQ ID NO: 2, or SEQ ID NO: 3 (GENBANK Accession No. NM_001131019.2). 'N/A' indicates that the modified oligonucleotide is not 100% complementary to that particular gene sequence.

Cultured U251 cells were treated with modified oligonucleotide at a concentration of 4,000 nM using free uptake at a density of 10,000 cells per well. After a treatment period of approximately 48 hours, total RNA was isolated from the cells and GFAP RNA levels were measured by quantitative real-time RTPCR. Human GFAP primer probe set RTS37485, described in Example 1 above, was used to measure RNA levels. GFAP RNA levels were nominalized to total RNA content, as measured by RIBOGREEN®. Results are presented in the tables below as percent GFAP RNA levels relative to untreated control cells. The values marked with an asterisk (*) indicate that the modified oligonucleotide is complementary to the amplicon region of the primer probe set. Additional assays may be used to measure the potency and efficacy of the modified oligonucleotides complementary to the amplicon region.

TABLE 18

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 8 | 517 |
| 1072810 | 1708 | 1727 | 11997 | 12016 | TCCATAACAACAGGAATCAG | 65 | 1268 |
| 1072814 | 1719 | 1738 | 12008 | 12027 | TGGCAACAGTTTCCATAACA | 31 | 1269 |
| 1072818 | 1728 | 1747 | 12017 | 12036 | CTCCATCTCTGGCAACAGTT | 42 | 1270 |
| 1072822 | 1752 | 1771 | 12041 | 12060 | AGTTCCCAGATACTCCGAGA | 56 | 1271 |
| 1072826 | 1763 | 1782 | 12052 | 12071 | CTCAAAGGCACAGTTCCCAG | 56 | 1272 |
| 1072830 | 1786 | 1805 | 12075 | 12094 | TTTCCTCCAGCAGCCTGAGG | 79 | 1273 |
| 1072834 | 1796 | 1815 | 12085 | 12104 | GAGTCTCAGTTTTCCTCCAG | 18 | 1274 |
| 1072838 | 2173 | 2192 | 12462 | 12481 | GAATCAAGCTCCCACCTGCC | 87 | 1275 |
| 1072842 | 2177 | 2196 | 12466 | 12485 | CTGAGAATCAAGCTCCCACC | 94 | 1276 |
| 1072846 | 3039 | 3058 | 13328 | 13347 | TTTTCCTCAGCGACTAAAGG | 48 | 1277 |
| 1072850 | 3059 | 3078 | 13348 | 13367 | GGCGCAGCATTTGTCTTTAT | 45 | 1278 |
| 1072854 | N/A | N/A | 8768 | 8787 | ATATCTTGTGACCTTGTGAT | 53 | 1279 |
| 1072858 | N/A | N/A | 8774 | 8793 | TTTGAGATATCTTGTGACCT | 66 | 1280 |
| 1072862 | N/A | N/A | 8780 | 8799 | GAGGCTTTTGAGATATCTTG | 28 | 1281 |
| 1072866 | N/A | N/A | 8785 | 8804 | ATTGTGAGGCTTTTGAGATA | 66 | 1282 |
| 1072870 | N/A | N/A | 7980 | 7999 | GACCCAAGTCCTTGGCCTTG | 81 | 1283 |
| 1072874 | N/A | N/A | 7990 | 8009 | TTTGGAGGGTGACCCAAGTC | 78 | 1284 |
| 1072878 | N/A | N/A | 7997 | 8016 | CTCTTAGTTTGGAGGGTGAC | 61 | 1285 |
| 1072882 | N/A | N/A | 11296 | 11315 | CCTTTTACCAAGCTGGAAAT | 73 | 1286 |
| 1072886 | N/A | N/A | 11303 | 11322 | GTAGTTTCCTTTTACCAAGC | 34 | 1287 |
| 1072890 | N/A | N/A | 4033 | 4052 | GAGACTTCTCGGGCACTOCT | 75 | 1288 |
| 1072894 | N/A | N/A | 4133 | 4152 | TGGGCCTGTTTCTGGTCCCT | 63 | 1289 |
| 1072898 | N/A | N/A | 4208 | 4227 | TTCCCCAGTAGGGAGGTGCT | 100 | 1290 |
| 1072902 | N/A | N/A | 4285 | 4304 | ATAGGTGAGCTCGCTGCCCA | 82 | 1291 |
| 1072906 | N/A | N/A | 4297 | 4316 | CACAGGCTCAGAATAGGTGA | 68 | 1292 |
| 1072910 | N/A | N/A | 4458 | 4477 | CAAGTCAAAGTAACTTGATG | 80 | 1293 |
| 1072914 | N/A | N/A | 4492 | 4511 | TGAATTTTATTATGACCACC | 64 | 1294 |
| 1072918 | N/A | N/A | 4564 | 4583 | CATGTCCTGTCAGCTCAGTG | 61 | 1295 |
| 1072922 | N/A | N/A | 4638 | 4657 | CACAAGCATACACTCACTGT | 84 | 1296 |
| 1072926 | N/A | N/A | 4677 | 4696 | CAGGGTTGGTGCACCTGCTT | 74 | 1297 |

TABLE 18-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1072930 | N/A | N/A | 4748 | 4767 | TAGACAGAGGACTTGTCTGG | 96 | 1298 |
| 1072934 | N/A | N/A | 4826 | 4845 | CCCTTGAGGCAGCTGTCACA | 87 | 1299 |
| 1072938 | N/A | N/A | 5049 | 5068 | CATTGCTCTGGCGGGCTGAG | 89 | 1300 |
| 1072942 | N/A | N/A | 5296 | 5315 | CAATCTCTGTGTTGAGCTTT | 70 | 1301 |
| 1072946 | N/A | N/A | 5396 | 5415 | TCATTTCCTGTCTCTACCTG | 85 | 1302 |
| 1072950 | N/A | N/A | 5549 | 5568 | GACCAGGGTGAGAGAAGCGG | 78 | 1303 |
| 1072954 | N/A | N/A | 5745 | 5764 | GAGGAGGCAGGCTGGCCCAC | 84 | 1304 |
| 1072958 | N/A | N/A | 5900 | 5919 | AATAATGGGTACTTTTGAAA | 88 | 1305 |
| 1072962 | N/A | N/A | 5986 | 6005 | TTCATAGTAAGGTAATCCAT | 75 | 1306 |
| 1072966 | N/A | N/A | 6032 | 6051 | CCTCTCTGGACTTCGGCTCT | 81 | 1307 |
| 1072970 | N/A | N/A | 6240 | 6259 | GGCACTATGTTTGGGTGCAC | 85 | 1308 |
| 1072974 | N/A | N/A | 6302 | 6321 | TCTACAGTGTCTTTCCTGGC | 67 | 1309 |
| 1072978 | N/A | N/A | 6446 | 6465 | CTAGGTGCCCTGGCTAGGCT | 72 | 1310 |
| 1072982 | N/A | N/A | 6524 | 6543 | TGCAGGGAGGTCCTCCCAGC | 96 | 1311 |
| 1072986 | N/A | N/A | 6901 | 6920 | GCGAGCGGAGGCCTGGGTGT | 26 | 1312 |
| 1072990 | N/A | N/A | 6942 | 6961 | ACTGACAGCTGCATCTGCGG | 79 | 1313 |
| 1072994 | N/A | N/A | 6985 | 7004 | AAGCGAATGAATGAACAGTG | 69 | 1314 |
| 1072998 | N/A | N/A | 7079 | 7098 | CCTGGCTGGGACTTTTCCCA | 84 | 1315 |
| 1073002 | N/A | N/A | 7119 | 7138 | GGGAGGTGAGCAGCACCCCA | 84 | 1316 |
| 1073006 | N/A | N/A | 7358 | 7377 | TGGCCGTCCCTGCTCCGCCC | 96 | 1317 |
| 1073010 | N/A | N/A | 7510 | 7529 | GGCCGGTCCCGCGGAGCCCC | 86 | 1318 |
| 1073014 | N/A | N/A | 7521 | 7540 | GGGATGGAGCCGGCCGGTCC | 77 | 1319 |
| 1073018 | N/A | N/A | 7785 | 7804 | AGCAGGGAGACTTCCCCAGG | 85 | 1320 |
| 1073022 | N/A | N/A | 7827 | 7846 | ACTCAGTCCCTGAAGGGAGC | 90 | 1321 |
| 1073026 | N/A | N/A | 7898 | 7917 | CTGCTATGTGTGAGGCAGGC | 83 | 1322 |
| 1073030 | N/A | N/A | 8027 | 8046 | CAATCTTGGCTGGGAAGATG | 90 | 1323 |
| 1073034 | N/A | N/A | 8048 | 8067 | AGATGGGTGAGGTGAGGAGT | 33 | 1324 |
| 1073038 | N/A | N/A | 8231 | 8250 | CCTTTTCCTTGCCAGGAAAG | 76 | 1325 |
| 1073042 | N/A | N/A | 9380 | 9399 | AGTAATTTAGCTCCCCCCTC | 76 | 1326 |
| 1073046 | N/A | N/A | 9410 | 9429 | AGAATCATTTCAGGGCCAAT | 67 | 1327 |
| 1073050 | N/A | N/A | 9438 | 9457 | GAAGAAGAGGAATTTTGTTC | 82 | 1328 |
| 1073054 | N/A | N/A | 9486 | 9505 | TTAAGTCCTGAGACATGCAT | 55 | 1329 |
| 1073058 | N/A | N/A | 9500 | 9519 | TTTCTGATGCTGAATTAAGT | 88 | 1330 |
| 1073062 | N/A | N/A | 9543 | 9562 | TAGGATTTGGCAGTATTACC | 62 | 1331 |
| 1073066 | N/A | N/A | 9649 | 9668 | TGTGGCACATATTAGTGCTC | 76 | 1332 |
| 1073070 | N/A | N/A | 10001 | 10020 | AATCCCCTTACTCGGGAGTC | 76 | 1333 |

TABLE 18-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1073074 | N/A | N/A | 10551 | 10570 | TTGAAATCAGGAGACCAGGA | 73 | 1334 |
| 1073078 | N/A | N/A | 10567 | 10586 | AAAACCCAGCACGGTATTGA | 73 | 1335 |
| 1073082 | N/A | N/A | 10715 | 10734 | CCGAGCAGAGAGAGCCTAGG | 88 | 1336 |
| 1073086 | N/A | N/A | 10805 | 10824 | CATGGACTTTCAGGGCATGA | 90 | 1337 |
| 1073090 | N/A | N/A | 11105 | 11124 | CAGCCTATGGAGGGACTGAG | 88 | 1338 |
| 1073094 | N/A | N/A | 11165 | 11184 | AAGAGAGAGTGTGTATTAGG | 63 | 1339 |
| 1073098 | N/A | N/A | 11208 | 11227 | TTTCTCTCCCTGGCAAGCAA | 65 | 1340 |
| 1073102 | N/A | N/A | 11256 | 11275 | AACTGTGTCTGCTAGAGTTG | 66 | 1341 |
| 1073106 | N/A | N/A | 11386 | 11405 | GTAAGCTGCTGGAGTAAGAT | 45 | 1342 |
| 1073110 | N/A | N/A | 11472 | 11491 | ATAGTAACCACAGCTGOCTT | 81 | 1343 |
| 1073114 | N/A | N/A | 11516 | 11535 | GTAACCTTGGGAAGTCCCCG | 75 | 1344 |

TABLE 19

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 7 | 517 |
| 1072811 | 1711 | 1730 | 12000 | 12019 | GTTTCCATAACAACAGGAAT | 82 | 1345 |
| 1072815 | 1720 | 1739 | 12009 | 12028 | CTGGCAACAGTTTCCATAAC | 40 | 1346 |
| 1072819 | 1746 | 1765 | 12035 | 12054 | CAGATACTCCGAGAGAACCT | 75 | 1347 |
| 1072823 | 1753 | 1772 | 12042 | 12061 | CAGTTOCCAGATACTCCGAG | 65 | 1348 |
| 1072827 | 1766 | 1785 | 12055 | 12074 | AAACTCAAAGGCACAGTTCC | 99 | 1349 |
| 1072831 | 1787 | 1806 | 12076 | 12095 | TTTTCCTCCAGCAGCCTGAG | 85 | 1350 |
| 1072835 | 1797 | 1816 | 12086 | 12105 | TGAGTCTCAGTTTTCCTCCA | 18 | 1351 |
| 1072839 | 2174 | 2193 | 12463 | 12482 | AGAATCAAGCTCCCACCTGC | 82 | 1352 |
| 1072843 | 3036 | 3055 | 13325 | 13344 | TCCTCAGCGACTAAAGGCAG | 54 | 1353 |
| 1072847 | 3041 | 3060 | 13330 | 13349 | ATTTTTCCTCAGCGACTAAA | 55 | 1354 |
| 1072851 | 3061 | 3080 | 13350 | 13369 | AGGGCGCAGCATTTGTCTTT | 55 | 1355 |
| 1072855 | N/A | N/A | 8771 | 8790 | GAGATATCTTGTGACCTTGT | 37 | 1356 |
| 1072859 | N/A | N/A | 8775 | 8794 | TTTTGAGATATCTTGTGACC | 60 | 1357 |
| 1072863 | N/A | N/A | 8781 | 8800 | TGAGGCTTTTGAGATATCTT | 34 | 1358 |
| 1072867 | N/A | N/A | 8786 | 8805 | TATTGTGAGGCTTTIGAGAT | 60 | 1359 |
| 1072871 | N/A | N/A | 7983 | 8002 | GGTGACCCAAGTCCTTGGCC | 76 | 1360 |

TABLE 19-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1072875 | N/A | N/A | 7991 | 8010 | GTTTGGAGGGTGACCCAAGT | 70 | 1361 |
| 1072879 | N/A | N/A | 11290 | 11309 | ACCAAGCTGGAAATGGAAAG | 70 | 1362 |
| 1072883 | N/A | N/A | 11297 | 11316 | TCCTTTTACCAAGCTGGAAA | 83 | 1363 |
| 1072887 | N/A | N/A | 11304 | 11323 | GGTAGTTTCCTTTTACCAAG | 49 | 1364 |
| 1072891 | N/A | N/A | 4035 | 4054 | CTGAGACTTCTCGGGCACTC | 87 | 1365 |
| 1072895 | N/A | N/A | 4162 | 4181 | GGCATGCGGGCATCAGATCC | 87 | 1366 |
| 1072899 | N/A | N/A | 4221 | 4240 | CTCCTGCACTGCTTTCCCCA | 64 | 1367 |
| 1072903 | N/A | N/A | 4287 | 4306 | GAATAGGTGAGCTCGCTGCC | 89 | 1368 |
| 1072907 | N/A | N/A | 4304 | 4323 | ATATGGACACAGGCTCAGAA | 79 | 1369 |
| 1072911 | N/A | N/A | 4463 | 4482 | CTGTGCAAGTCAAAGTAACT | 76 | 1370 |
| 1072915 | N/A | N/A | 4493 | 4512 | ATGAATTTTATTATGACCAC | 67 | 1371 |
| 1072919 | N/A | N/A | 4581 | 4600 | ACTTGAAGGCACACATGCAT | 70 | 1372 |
| 1072923 | N/A | N/A | 4648 | 4667 | CAGGCGCATCCACAAGCATA | 88 | 1373 |
| 1072927 | N/A | N/A | 4732 | 4751 | CTGGAGGATGAGCAGATGTG | 57 | 1374 |
| 1072931 | N/A | N/A | 4779 | 4798 | AGCAGCAGGAGGATTAAGGG | 68 | 1375 |
| 1072935 | N/A | N/A | 4827 | 4846 | TCCCTTGAGGCAGCTGTCAC | 96 | 1376 |
| 1072939 | N/A | N/A | 5058 | 5077 | GGAGCAGCACATTGCTCTGG | 80 | 1377 |
| 1072943 | N/A | N/A | 5299 | 5318 | TTGCAATCTCTGTGTTGAGC | 55 | 1378 |
| 1072947 | N/A | N/A | 5452 | 5471 | AGTTCGAATGCTCTCTTGTC | 78 | 1379 |
| 1072951 | N/A | N/A | 5715 | 5734 | ACCTTGGAGCGGTACCACTC | 111 | 1380 |
| 1072955 | N/A | N/A | 5828 | 5847 | TCAGTCACCTGGAGAGGATA | 58 | 138 |
| 1072959 | N/A | N/A | 5918 | 5937 | AGCAATAGTAGCAGTAATAA | 82 | 1382 |
| 1072963 | N/A | N/A | 5987 | 6006 | CTTCATAGTAAGGTAATCCA | 84 | 1383 |
| 1072967 | N/A | N/A | 6122 | 6141 | ATGGAATGCAGGCTCCCAAG | 71 | 1384 |
| 1072971 | N/A | N/A | 6251 | 6270 | TGTTCTCTACGGGCACTATG | 58 | 1385 |
| 1072975 | N/A | N/A | 6374 | 6393 | CCACTAGGAATGGCCCTCCC | 61 | 1386 |
| 1072979 | N/A | N/A | 6451 | 6470 | CTCAGCTAGGTGCCCTGGCT | 80 | 1387 |
| 1072983 | N/A | N/A | 6561 | 6580 | CCTCACCCTGGGTTCTAATA | 83 | 1388 |
| 1072987 | N/A | N/A | 6903 | 6922 | AGGCGAGCGGAGGCCTGGGT | 97 | 1389 |
| 1072991 | N/A | N/A | 6944 | 6963 | ACACTGACAGCTGCATCTGC | 79 | 1390 |
| 1072995 | N/A | N/A | 6997 | 7016 | CACCTGGTCAGCAAGCGAAT | 78 | 139 |
| 1072999 | N/A | N/A | 7082 | 7101 | GGCCCTGGCTGGGACTTTTC | 79 | 1392 |
| 1073003 | N/A | N/A | 7125 | 7144 | AAATCAGGGAGGTGAGCAGC | 46 | 1393 |
| 1073007 | N/A | N/A | 7382 | 7401 | CTTCTCCCCTGGCATCTCCT | 77 | 1394 |
| 1073011 | N/A | N/A | 7517 | 7536 | TGGAGOCGGCCGGTCCCGCG | 87 | 1395 |
| 1073015 | N/A | N/A | 7757 | 7776 | TGAGGGCTCACCGGTTCTCC | 81 | 1396 |

TABLE 19-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1073019 | N/A | N/A | 7789 | 7808 | AGGCAGCAGGGAGACTTCCC | 88 | 1397 |
| 1073023 | N/A | N/A | 7855 | 7874 | AAGGGATCTGCACACAAGGC | 79 | 1398 |
| 1073027 | N/A | N/A | 7924 | 7943 | TCAGTCATCAAACATCTAGT | 78 | 1399 |
| 1073031 | N/A | N/A | 8028 | 8047 | CCAATCTTGGCTGGGAAGAT | 66 | 1400 |
| 1073035 | N/A | N/A | 8051 | 8070 | AAGAGATGGGTGAGGTGAGG | 36 | 1401 |
| 1073039 | N/A | N/A | 8274 | 8293 | TAGGCTGGGTCTTGGTGCGG | 76 | 1402 |
| 1073043 | N/A | N/A | 9381 | 9400 | AAGTAATTTAGCTCCCCCCT | 76 | 1403 |
| 1073047 | N/A | N/A | 9411 | 9430 | AAGAATCATTTCAGGGCCAA | 54 | 1404 |
| 1073051 | N/A | N/A | 9440 | 9459 | CAGAAGAAGAGGAATTTTGT | 70 | 1405 |
| 1073055 | N/A | N/A | 9487 | 9506 | ATTAAGTCCTGAGACATGCA | 64 | 1406 |
| 1073059 | N/A | N/A | 9502 | 9521 | CCTTTCTGATGCTGAATTAA | 72 | 1407 |
| 1073063 | N/A | N/A | 9552 | 9571 | GTGACTATCTAGGATTTGGC | 23 | 1408 |
| 1073067 | N/A | N/A | 9685 | 9704 | GAGGAGACAATTAACTAAAA | 64 | 1409 |
| 1073071 | N/A | N/A | 10125 | 10144 | TCGAAAGCAGGCAAGCAAGC | 99 | 1410 |
| 1073075 | N/A | N/A | 10552 | 10571 | ATTGAAATCAGGAGACCAGG | 66 | 1411 |
| 1073079 | N/A | N/A | 10612 | 10631 | CATTTCAGCCCCTCTGCAAG | 77 | 1412 |
| 1073083 | N/A | N/A | 10724 | 10743 | CCTATGCAACCGAGCAGAGA | 95 | 1413 |
| 1073087 | N/A | N/A | 10848 | 10867 | GTGTCCAGGCTGGTTTCTGC | 82 | 1414 |
| 1073091 | N/A | N/A | 11124 | 11143 | ACCAAGGCTCCCCTTAGAAC | 59 | 1415 |
| 1073095 | N/A | N/A | 11166 | 11185 | AAAGAGAGAGTGTGTATTAG | 78 | 1416 |
| 1073099 | N/A | N/A | 11210 | 11229 | TCTTTCTCTCCCTGGCAAGC | 73 | 1417 |
| 1073103 | N/A | N/A | 11283 | 11302 | TGGAAATGGAAAGCCCTCCC | 78 | 1418 |
| 1073107 | N/A | N/A | 11391 | 11410 | GAGTGGTAAGCTGCTGGAGT | 42 | 1419 |
| 1073111 | N/A | N/A | 11474 | 11493 | TGATAGTAACCACAGCTGCC | 92 | 1420 |
| 1073115 | N/A | N/A | 11518 | 11537 | GTGTAACCTTGGGAAGTCCC | 77 | 1421 |

TABLE 20

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 7 | 517 |
| 1072812 | 1713 | 1732 | 12002 | 12021 | CAGTTTCCATAACAACAGGA | 58 | 1422 |
| 1072816 | 1722 | 1741 | 12011 | 12030 | CTCTGGCAACAGTTTCCATA | 69 | 1423 |
| 1072820 | 1749 | 1768 | 12038 | 12057 | TCCCAGATACTCCGAGAGAA | 73 | 1424 |

TABLE 20-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1072824 | 1758 | 1777 | 12047 | 12066 | AGGCACAGTTCCCAGATACT | 36 | 1425 |
| 1072828 | 1784 | 1803 | 12073 | 12092 | TCCTCCAGCAGCCTGAGGAA | 71 | 1426 |
| 1072832 | 1788 | 1807 | 12077 | 12096 | GTTTTCCTCCAGCAGCCTGA | 64 | 1427 |
| 1072836 | 2168 | 2187 | 12457 | 12476 | AAGCTCCCACCTGCCCACAG | 73 | 1428 |
| 1072840 | 2175 | 2194 | 12464 | 12483 | GAGAATCAAGCTCCCACCTG | 74 | 1429 |
| 1072844 | 3037 | 3056 | 13326 | 13345 | TTCCTCAGCGACTAAAGGCA | 61 | 1430 |
| 1072848 | 3042 | 3061 | 13331 | 13350 | TATTTTTCCTCAGCGACTAA | 69 | 1431 |
| 1072852 | 3063 | 3082 | 13352 | 13371 | GAAGGGCGCAGCATTTGTCT | 57 | 1432 |
| 1072856 | N/A | N/A | 8772 | 8791 | TGAGATATCTTGTGACCTTG | 43 | 1433 |
| 1072860 | N/A | N/A | 8776 | 8795 | CTTTTGAGATATCTTGTGAC | 62 | 1434 |
| 1072864 | N/A | N/A | 8783 | 8802 | TGTGAGGCTTTTGAGATATC | 43 | 1435 |
| 1072868 | N/A | N/A | 8788 | 8807 | CGTATTGTGAGGCTTTTGAG | 20 | 1436 |
| 1072872 | N/A | N/A | 7984 | 8003 | GGGTGACCCAAGTCCTTGGC | 14 | 1437 |
| 1072876 | N/A | N/A | 7992 | 8011 | AGTTTGGAGGGTGACCCAAG | 61 | 1438 |
| 1072880 | N/A | N/A | 11293 | 11312 | TTTACCAAGCTGGAAATGGA | 83 | 1439 |
| 1072884 | N/A | N/A | 11298 | 11317 | TTCCTTTTACCAAGCTGGAA | 77 | 1440 |
| 1072888 | N/A | N/A | 11310 | 11329 | TCCCCTGGTAGTTTCCTTTT | 85 | 1441 |
| 1072892 | N/A | N/A | 4055 | 4074 | CAGGGAGGTTCGGCCCCTCC | 83 | 1442 |
| 1072896 | N/A | N/A | 4174 | 4193 | CTCCTGGCAGAAGGCATGCG | 75 | 1443 |
| 1072900 | N/A | N/A | 4231 | 4250 | GGCCCCGCTGCTCCTGCACT | 105 | 1444 |
| 1072904 | N/A | N/A | 4289 | 4308 | CAGAATAGGTGAGCTCGCTG | 83 | 1445 |
| 1072908 | N/A | N/A | 4307 | 4326 | TTTATATGGACACAGGCTCA | 83 | 1446 |
| 1072912 | N/A | N/A | 4482 | 4501 | TATGACCACCGCTTCACAGC | 95 | 1447 |
| 1072916 | N/A | N/A | 4558 | 4577 | CTGTCAGCTCAGTGAAGCGC | 86 | 1448 |
| 1072920 | N/A | N/A | 4628 | 4647 | CACTCACTGTTGCACACACA | 89 | 1449 |
| 1072924 | N/A | N/A | 4651 | 4670 | ACACAGGCGCATCCACAAGC | 98 | 1450 |
| 1072928 | N/A | N/A | 4739 | 4758 | GACTTGTCTGGAGGATGAGC | 73 | 1451 |
| 1072932 | N/A | N/A | 4785 | 4804 | CAGTAGAGCAGCAGGAGGAT | 82 | 1452 |
| 1072936 | N/A | N/A | 4882 | 4901 | GGACACATTCCTGGGTCCAG | 100 | 1453 |
| 1072940 | N/A | N/A | 5142 | 5161 | GGTGAGGAGTAGAGGGCCAC | 88 | 1454 |
| 1072944 | N/A | N/A | 5307 | 5326 | TCTCTCAGTTGCAATCTCTG | 84 | 1455 |
| 1072948 | N/A | N/A | 5453 | 5472 | GAGTTCGAATGCTCTCTTGT | 75 | 1456 |
| 1072952 | N/A | N/A | 5730 | 5749 | CCCACAGGCAGGGCTACCTT | 89 | 1457 |
| 1072956 | N/A | N/A | 5891 | 5910 | TACTTTTGAAAGCAATAGTG | 77 | 1458 |
| 1072960 | N/A | N/A | 5953 | 5972 | CTTAGAACAGAACAGTATCA | 101 | 1459 |
| 1072964 | N/A | N/A | 6028 | 6047 | TCTGGACTTCGGCTCTCTCA | 55 | 1460 |
| 1072968 | N/A | N/A | 6140 | 6159 | AAACAGACTGGCAGAGGCAT | 59 | 1461 |

TABLE 20-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1072972 | N/A | N/A | 6260 | 6279 | GAGCTGTGGTGTTCTCTACG | 58 | 1462 |
| 1072976 | N/A | N/A | 6380 | 6399 | TGTCCTCCACTAGGAATGGC | 76 | 1463 |
| 1072980 | N/A | N/A | 6459 | 6478 | TCACACTCCTCAGCTAGGTG | 32 | 1464 |
| 1072984 | N/A | N/A | 6563 | 6582 | GGCCTCACCCTGGGTTCTAA | 76 | 1465 |
| 1072988 | N/A | N/A | 6905 | 6924 | TTAGGCGAGCGGAGGCCTGG | 95 | 1466 |
| 1072992 | N/A | N/A | 6945 | 6964 | CACACTGACAGCTGCATCTG | 90 | 1467 |
| 1072996 | N/A | N/A | 7003 | 7022 | GCACAACACCTGGTCAGCAA | 73 | 1468 |
| 1073000 | N/A | N/A | 7085 | 7104 | GTTGGCCCTGGCTGGGACTT | 63 | 1469 |
| 1073004 | N/A | N/A | 7126 | 7145 | GAAATCAGGGAGGTGAGCAG | 63 | 1470 |
| 1073008 | N/A | N/A | 7475 | 7494 | GGTTTCGAGGCCCGGCCCCC | 73 | 1471 |
| 1073012 | N/A | N/A | 7518 | 7537 | ATGGAGCCGGCCGGTCCCGC | 92 | 1472 |
| 1073016 | N/A | N/A | 7762 | 7781 | TGTGATGAGGGCTCACCGGT | 65 | 1473 |
| 1073020 | N/A | N/A | 7797 | 7816 | CTACCGTGAGGCAGCAGGGA | 86 | 1474 |
| 1073024 | N/A | N/A | 7876 | 7895 | TGTGCTGGGCATTGAGGTGG | 64 | 1475 |
| 1073028 | N/A | N/A | 7967 | 7986 | GGCCTTGAGGCCTAATCAAT | 78 | 1476 |
| 1073032 | N/A | N/A | 8045 | 8064 | TGGGTGAGGTGAGGAGTCCA | 73 | 1477 |
| 1073036 | N/A | N/A | 8057 | 8076 | AGGCAGAAGAGATGGGTGAG | 67 | 1478 |
| 1073040 | N/A | N/A | 9355 | 9374 | GCCCCGCCCGAGAGAGAAAA | 92 | 1479 |
| 1073044 | N/A | N/A | 9407 | 9426 | ATCATTTCAGGGCCAATGCA | 66 | 1480 |
| 1073048 | N/A | N/A | 9423 | 9442 | TGTTCCTTAGCTAAGAATCA | 58 | 1481 |
| 1073052 | N/A | N/A | 9442 | 9461 | TCCAGAAGAAGAGGAATTTT | 94 | 1482 |
| 1073056 | N/A | N/A | 9488 | 9507 | AATTAAGTCCTGAGACATGC | 51 | 1483 |
| 1073060 | N/A | N/A | 9517 | 9536 | AGTCAGCCTGGTTAGCCTTT | 36 | 1484 |
| 1073064 | N/A | N/A | 9560 | 9579 | AGTGACCTGTGACTATCTAG | 35 | 1485 |
| 1073068 | N/A | N/A | 9889 | 9908 | TCTGCCGAAGGAAGGAAGGA | 77 | 1486 |
| 1073072 | N/A | N/A | 10129 | 10148 | TCCGTCGAAAGCAGGCAAGC | 83 | 1487 |
| 1073076 | N/A | N/A | 10555 | 10574 | GGTATTGAAATCAGGAGACC | 59 | 1488 |
| 1073080 | N/A | N/A | 10662 | 10681 | CAATAGTGCTGCTGCCAGAG | 54 | 1489 |
| 1073084 | N/A | N/A | 10727 | 10746 | GAACCTATGCAACCGAGCAG | 56 | 1490 |
| 1073088 | N/A | N/A | 11008 | 11027 | TATGTGCCAGCCCCAGGCTT | 89 | 1491 |
| 1073092 | N/A | N/A | 11128 | 11147 | TGGTACCAAGGCTCCCCTTA | 74 | 1492 |
| 1073096 | N/A | N/A | 11187 | 11206 | GCCCCCGAGTTTGAGGGTGA | 90 | 1493 |
| 1073100 | N/A | N/A | 11240 | 11259 | GTTGGAAGTGAAAGCTACTA | 58 | 1494 |
| 1073104 | N/A | N/A | 11365 | 11384 | AGCTCCCACTGTGGTTGGAG | 87 | 1495 |

TABLE 20-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1073108 | N/A | N/A | 11399 | 11418 | TGCCTGGCGAGTGGTAAGCT | 91 | 1496 |
| 1073112 | N/A | N/A | 11476 | 11495 | CTTGATAGTAACCACAGCTG | 63 | 1497 |
| 1073116 | N/A | N/A | 11561 | 11580 | AGTTAGGAGTTCACACAGAC | 72 | 1498 |

TABLE 21

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 8 | 517 |
| 1072813 | 1717 | 1736 | 12006 | 12025 | GCAACAGTTTCCATAACAAC | 32 | 1499 |
| 1072817 | 1725 | 1744 | 12014 | 12033 | CATCTCTGGCAACAGTTTCC | 62 | 1500 |
| 1072821 | 1751 | 1770 | 12040 | 12059 | GTTCCCAGATACTCCGAGAG | 53 | 1501 |
| 1072825 | 1759 | 1778 | 12048 | 12067 | AAGGCACAGTTCCCAGATAC | 51 | 1502 |
| 1072829 | 1785 | 1804 | 12074 | 12093 | TTCCTCCAGCAGCCTGAGGA | 89 | 1503 |
| 1072833 | 1789 | 1808 | 12078 | 12097 | AGTTTTCCTCCAGCAGCCTG | 46 | 1504 |
| 1072837 | 2171 | 2190 | 12460 | 12479 | ATCAAGCTCCCACCTGCCCA | 64 | 1505 |
| 1072841 | 2176 | 2195 | 12465 | 12484 | TGAGAATCAAGCTCCCACCT | 90 | 1506 |
| 1072845 | 3038 | 3057 | 13327 | 13346 | TTTCCTCAGCGACTAAAGGC | 52 | 1507 |
| 1072849 | 3057 | 3076 | 13346 | 13365 | CGCAGCATTTGTCTTTATTT | 26 | 1508 |
| 1072853 | 3064 | 3083 | 13353 | 13372 | GGAAGGGCGCAGCATTTGTC | 43 | 1509 |
| 1072857 | N/A | N/A | 8773 | 8792 | TTGAGATATCTTGTGACCTT | 32 | 1510 |
| 1072861 | N/A | N/A | 8779 | 8798 | AGGCTTTTGAGATATCTTGT | 35 | 1511 |
| 1072865 | N/A | N/A | 8784 | 8803 | TTGTGAGGCTTTTGAGATAT | 47 | 1512 |
| 1072869 | N/A | N/A | 7977 | 7996 | CCAAGTCCTTGGCCTTGAGG | 93 | 1513 |
| 1072873 | N/A | N/A | 7988 | 8007 | TGGAGGGTGACCCAAGTCCT | 107 | 1514 |
| 1072877 | N/A | N/A | 7994 | 8013 | TTAGTTTGGAGGGTGACCCA | 68 | 1515 |
| 1072881 | N/A | N/A | 11295 | 11314 | CTTTTACCAAGCTGGAAATG | 103 | 1516 |
| 1072885 | N/A | N/A | 11299 | 11318 | TTTCCTTTTACCAAGCTGGA | 80 | 1517 |
| 1072889 | N/A | N/A | 4027 | 4046 | TCTCGGGCACTCCTTCTTGG | 96 | 1518 |
| 1072893 | N/A | N/A | 4084 | 4103 | CCCATCAAGAGGTAGGGAGG | 66 | 1519 |
| 1072897 | N/A | N/A | 4183 | 4202 | GACCCTGGACTCCTGGCAGA | 83 | 1520 |
| 1072901 | N/A | N/A | 4253 | 4272 | CCAGCCATGAATGAAACACA | 82 | 1521 |
| 1072905 | N/A | N/A | 4293 | 4312 | GGCTCAGAATAGGTGAGCTC | 67 | 1522 |
| 1072909 | N/A | N/A | 4435 | 4454 | GTCACAAGCTGGTGGCAGGC | 69 | 1523 |
| 1072913 | N/A | N/A | 4487 | 4506 | TTTATTATGACCACCGCTTC | 92 | 1524 |
| 1072917 | N/A | N/A | 4563 | 4582 | ATGTCCTGTCAGCTCAGTGA | 50 | 1525 |

TABLE 21-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1072921 | N/A | N/A | 4632 | 4651 | CATACACTCACTGTTGCACA | 83 | 1526 |
| 1072925 | N/A | N/A | 4669 | 4688 | GTGCACCTGCTTCTGCTCAC | 111 | 1527 |
| 1072929 | N/A | N/A | 4741 | 4760 | AGGACTTGTCTGGAGGATGA | 47 | 1528 |
| 1072933 | N/A | N/A | 4822 | 4841 | TGAGGCAGCTGTCACAGAGA | 102 | 1529 |
| 1072937 | N/A | N/A | 4904 | 4923 | CATCCTGGAGCCTGGAGTGG | 87 | 1530 |
| 1072941 | N/A | N/A | 5295 | 5314 | AATCTCTGTGTTGAGCTTTC | 56 | 1531 |
| 1072945 | N/A | N/A | 5308 | 5327 | CTCTCTCAGTTGCAATCTCT | 75 | 1532 |
| 1072949 | N/A | N/A | 5460 | 5479 | CGGCCAGGAGTTCGAATGCT | 81 | 1533 |
| 1072953 | N/A | N/A | 5733 | 5752 | TGGCCCACAGGCAGGGCTAC | 83 | 1534 |
| 1072957 | N/A | N/A | 5895 | 5914 | TGGGTACTTTTGAAAGCAAT | 75 | 1535 |
| 1072961 | N/A | N/A | 5965 | 5984 | AAAAGCACAGGGCTTAGAAC | 76 | 1536 |
| 1072965 | N/A | N/A | 6031 | 6050 | CTCTCTGGACTTCGGCTCTC | 88 | 1537 |
| 1072969 | N/A | N/A | 6167 | 6186 | GGCATATGGTAGAGGCTCAG | 56 | 1538 |
| 1072973 | N/A | N/A | 6270 | 6289 | TATAAGCTCTGAGCTGTGGT | 37 | 1539 |
| 1072977 | N/A | N/A | 6443 | 6462 | GGTGCCCTGGCTAGGCTAGC | 77 | 1540 |
| 1072981 | N/A | N/A | 6460 | 6479 | CTCACACTCCTCAGCTAGGT | 77 | 1541 |
| 1072985 | N/A | N/A | 6897 | 6916 | GCGGAGGCCTGGGTGTTTTG | 75 | 1542 |
| 1072989 | N/A | N/A | 6908 | 6927 | GTCTTAGGCGAGCGGAGGCC | 90 | 1543 |
| 1072993 | N/A | N/A | 6972 | 6991 | AACAGTGCCACAGAATCCAG | 91 | 1544 |
| 1072997 | N/A | N/A | 7051 | 7070 | GACCCATGGATGCGGGCAGG | 68 | 1545 |
| 1073001 | N/A | N/A | 7086 | 7105 | CGTTGGCCCTGGCTGGGACT | 71 | 1546 |
| 1073005 | N/A | N/A | 7201 | 7220 | TCTGTCAGGTCTGCAAACTA | 83 | 1547 |
| 1073009 | N/A | N/A | 7479 | 7498 | GGGAGGTTTCGAGGCCCGGC | 41 | 1548 |
| 1073013 | N/A | N/A | 7520 | 7539 | GGATGGAGCCGGCCGGTCCC | 81 | 1549 |
| 1073017 | N/A | N/A | 7764 | 7783 | GCTGTGATGAGGGCTCACCG | 68 | 1550 |
| 1073021 | N/A | N/A | 7818 | 7837 | CTGAAGGGAGCAAGATGAGC | 82 | 1551 |
| 1073025 | N/A | N/A | 7878 | 7897 | ACTGTGCTGGGCATTGAGGT | 77 | 1552 |
| 1073029 | N/A | N/A | 8005 | 8024 | GAGTATGCCTCTTAGTTTGG | 63 | 1553 |
| 1073033 | N/A | N/A | 8046 | 8065 | ATGGGTGAGGTGAGGAGTCC | 36 | 1554 |
| 1073037 | N/A | N/A | 8078 | 8097 | GTGGTGAAGAAAGTTCCAAG | 88 | 1555 |
| 1073041 | N/A | N/A | 9356 | 9375 | CGCCCCGCCCGAGAGAGAAA | 64 | 1556 |
| 1073045 | N/A | N/A | 9409 | 9428 | GAATCATTTCAGGGCCAATG | 27 | 1557 |
| 1073049 | N/A | N/A | 9425 | 9444 | TTTGTTCCTTAGCTAAGAAT | 62 | 1558 |
| 1073053 | N/A | N/A | 9444 | 9463 | AGTCCAGAAGAAGAGGAATT | 68 | 1559 |
| 1073057 | N/A | N/A | 9497 | 9516 | CTGATGCTGAATTAAGTCCT | 50 | 1560 |
| 1073061 | N/A | N/A | 9519 | 9538 | CTAGTCAGCCTGGTTAGCCT | 57 | 1561 |

TABLE 21-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1073065 | N/A | N/A | 9577 | 9596 | CCATTTATCTGTGCTTTAGT | 39 | 1562 |
| 1073069 | N/A | N/A | 9892 | 9911 | CGCTCTGCCGAAGGAAGGAA | 61 | 1563 |
| 1073073 | N/A | N/A | 10548 | 10567 | AAATCAGGAGACCAGGAGGG | 59 | 1564 |
| 1073077 | N/A | N/A | 10561 | 10580 | CAGCACGGTATTGAAATCAG | 42 | 1565 |
| 1073081 | N/A | N/A | 10692 | 10711 | TTCCAAACGGGCTGGAGAGC | 84 | 1566 |
| 1073085 | N/A | N/A | 10804 | 10823 | ATGGACTTTCAGGGCATGAG | 64 | 1567 |
| 1073089 | N/A | N/A | 11097 | 11116 | GGAGGGACTGAGGAAACGGA | 68 | 1568 |
| 1073093 | N/A | N/A | 11157 | 11176 | GTGTGTATTAGGATCCCATC | 24 | 1569 |
| 1073097 | N/A | N/A | 11193 | 11212 | AGCAAGGCCCCCGAGTTTGA | 81 | 1570 |
| 1073101 | N/A | N/A | 11246 | 11265 | GCTAGAGTTGGAAGTGAAAG | 67 | 1571 |
| 1073105 | N/A | N/A | 11368 | 11387 | ATGAGCTCCCACTGTGGTTG | 72 | 1572 |
| 1073109 | N/A | N/A | 11427 | 11446 | GATAACACTGGGAAAGCATT | 91 | 1573 |
| 1073113 | N/A | N/A | 11514 | 11533 | AACCTTGGGAAGTCCCCGAC | 85 | 1574 |
| 1073117 | N/A | N/A | 11563 | 11582 | ACAGTTAGGAGTTCACACAG | 75 | 1575 |

TABLE 22

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 5 | 517 |
| 1103152 | 41 | 60 | 3489 | 3508 | CTGGCTCTGCTCGCTCCTGG | 91 | 1576 |
| 1103168 | 272 | 291 | 3720 | 3739 | CTCCATCATCTCTGCCCGCT | 106 | 1577 |
| 1103184 | 565 | 584 | 4950 | 4969 | CTATAGGCAGCCAGGTTGTT | 69* | 1578 |
| 1103200 | 760 | 779 | 5646 | 5665 | ATCTCTTTCAGGGCTGCGGT | 65 | 1579 |
| 1103216 | 1062 | 1081 | 7634 | 7653 | TGAGGCTCTGCCCCTCTTCC | 111 | 1580 |
| 1103232 | 1335 | 1354 | 11624 | 11643 | CCTTGTGCTCCTGCTTGGAC | 88 | 1581 |
| 1103248 | 1527 | 1546 | 11816 | 11835 | AGGCCTGATACTGACGGAGC | 79 | 1582 |
| 1103264 | 1669 | 1688 | 11958 | 11977 | GTAGGTGCCCCCCGCCCTCC | 90 | 1583 |
| 1103280 | 1733 | 1752 | 12022 | 12041 | AGAACCTCCATCTCTGGCAA | 62 | 1584 |
| 1103296 | 1860 | 1879 | 12149 | 12168 | CCAAAAGACAAAACAAGCCT | 75 | 1585 |
| 1103312 | 1886 | 1905 | 12175 | 12194 | CATAGGGATATCCCACCTCA | 111 | 1586 |
| 1103328 | 2094 | 2113 | 12383 | 12402 | GTCATCGCTCAGGAGGTCCT | 69 | 1587 |
| 1103344 | 2231 | 2250 | 12520 | 12539 | CTATCCCTCCCAGCACCTCA | 109 | 1588 |
| 1103360 | 2427 | 2446 | 12716 | 12735 | AGGATGAGTCACTTCCTTAA | 73 | 1589 |
| 1103376 | 2484 | 2503 | 12773 | 12792 | GTCATGCCCTGCCCCCATGG | 90 | 1590 |
| 1103392 | 2512 | 2531 | 12801 | 12820 | AGGAAGAGGCCTTTAGAAAT | 68 | 1591 |

TABLE 22-continued

| Reduction of GFAP RNA by 5-10-5 MCE gapmers with mixed PO/PS internucleoside linkages in U251 cells | | | | | | | |
|---|---|---|---|---|---|---|---|
| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
| 1103408 | 2672 | 2691 | 12961 | 12980 | GTGTGTGAGTAAGAAGGGAC | 55 | 1592 |
| 1103424 | 2724 | 2743 | 13013 | 13032 | TCAGTTTTACAATTGTAAAA | 83 | 1593 |
| 1103440 | 2899 | 2918 | 13188 | 13207 | GGAGAACCCTGAAGTGGGCC | 76 | 1594 |
| 1103472 | N/A | N/A | 8787 | 8806 | GTATTGTGAGGCTTTTGAGA | 43 | 1595 |
| 1103488 | N/A | N/A | 8899 | 8918 | GAGGCTCACTCCCTGTCAAG | 60 | 1596 |
| 1103504 | N/A | N/A | 9045 | 9064 | AACAAGCTCTGCCAGTTTAA | 66 | 1597 |
| 1103520 | N/A | N/A | 9234 | 9253 | TGAGTCAGCACTGAGCTGAG | 95 | 1598 |
| 1103536 | N/A | N/A | 9270 | 9289 | CAAGAGCTGCGGTCCTGAGG | 59 | 1599 |
| 1103552 | N/A | N/A | 9310 | 9329 | TTTAACATTAAGAGCAGGGA | 63 | 1600 |
| 1103568 | N/A | N/A | 8532 | 8551 | CTGGTATGATAGGCTCTGGC | 86 | 1601 |
| 1103584 | N/A | N/A | 8650 | 8669 | CAGACAGGGCAGATGTCAAG | 92 | 1602 |
| 1103600 | N/A | N/A | 3999 | 4018 | CCCCTTCTGCTCACAAGGCC | 121 | 1603 |
| 1103616 | N/A | N/A | 4160 | 4179 | CATGCGGGCATCAGATCCCC | 89 | 1604 |
| 1103632 | N/A | N/A | 4275 | 4294 | TCGCTGCCCACAGTCACAAA | 104 | 1605 |
| 1103648 | N/A | N/A | 4407 | 4426 | GTGCTTTGCGCCCAGACCTG | 105 | 1606 |
| 1103664 | N/A | N/A | 4496 | 4515 | GAAATGAATTTTATTATGAC | 106 | 1607 |
| 1103680 | N/A | N/A | 4640 | 4659 | TCCACAAGCATACACTCACT | 81 | 1608 |
| 1103696 | N/A | N/A | 4837 | 4856 | TGCCTCAGTCTCCCTTGAGG | 107 | 1609 |
| 1103712 | N/A | N/A | 5100 | 5119 | CCATTCCTCAGCCTTGCCTT | 98 | 1610 |
| 1103728 | N/A | N/A | 5346 | 5365 | GTCTCTCTCAGTCTCAGCTT | 78 | 1611 |
| 1103744 | N/A | N/A | 5413 | 5432 | GTCTTTCTGTTTGTCTTTCA | 57 | 1612 |
| 1103760 | N/A | N/A | 5487 | 5506 | CCATTGTGTCCTCTTCTGCC | 102 | 1613 |
| 1103776 | N/A | N/A | 5776 | 5795 | TTCTCTTGTACAGAGCAAGA | 79 | 1614 |
| 1103792 | N/A | N/A | 5860 | 5879 | CTGGGCAAGCCATCTCACTT | 86 | 1615 |
| 1103808 | N/A | N/A | 5941 | 5960 | CAGTATCAGCTACTACTAAT | 80 | 1616 |
| 1103824 | N/A | N/A | 5978 | 5997 | AAGGTAATCCATGAAAAGCA | 84 | 1617 |
| 1103840 | N/A | N/A | 6024 | 6043 | GACTTCGGCTCTCTCATCTG | 82 | 1618 |
| 1103856 | N/A | N/A | 6204 | 6223 | CCAGGTCAGACACCTCTCTG | 81 | 1619 |
| 1103872 | N/A | N/A | 6267 | 6286 | AAGCTCTGAGCTGTGGTGTT | 33 | 1620 |
| 1103888 | N/A | N/A | 6315 | 6334 | CCCAAATGCCCCCTCTACAG | 93 | 1621 |
| 1103904 | N/A | N/A | 6414 | 6433 | CCCTGCCTCTCTGTGCTTTT | 92 | 1622 |
| 1103920 | N/A | N/A | 6517 | 6536 | AGGTCCTCCCAGCCCCATCG | 108 | 1623 |
| 1103936 | N/A | N/A | 6947 | 6966 | TCCACACTGACAGCTGCATC | 92 | 1624 |
| 1103952 | N/A | N/A | 7030 | 7049 | TAGCGGGCTGCCAGACCTCA | 102 | 1625 |
| 1103968 | N/A | N/A | 7326 | 7345 | CCCTGGCCGCGCTCACCGTG | 96 | 1626 |
| 1103984 | N/A | N/A | 7421 | 7440 | TTCAGGCCCCGCCCTCGACC | 81 | 1627 |

TABLE 22-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104000 | N/A | N/A | 7814 | 7833 | AGGGAGCAAGATGAGCTCTA | 120 | 1628 |
| 1104016 | N/A | N/A | 7940 | 7959 | GAATCCATCCATCCATTCAG | 86 | 1629 |
| 1104032 | N/A | N/A | 8038 | 8057 | GGTGAGGAGTCCAATCTTGG | 76 | 1630 |
| 1104048 | N/A | N/A | 8080 | 8099 | AAGTGGTGAAGAAAGTTCCA | 108 | 1631 |
| 1104064 | N/A | N/A | 8251 | 8270 | CATCATGACAACTTGAACGC | 98 | 1632 |
| 1104080 | N/A | N/A | 9364 | 9383 | CCTCCCCCCGCCCCGCCCGA | 111 | 1633 |
| 1104096 | N/A | N/A | 9414 | 9433 | GCTAAGAATCATTTCAGGGC | 40 | 1634 |
| 1104112 | N/A | N/A | 9455 | 9474 | CTAAATATTCTAGTCCAGAA | 97 | 1635 |
| 1104128 | N/A | N/A | 9509 | 9528 | TGGTTAGCCTTTCTGATGCT | 84 | 1636 |
| 1104144 | N/A | N/A | 9535 | 9554 | GGCAGTATTACCTCTACTAG | 28 | 1637 |
| 1104160 | N/A | N/A | 9559 | 9578 | GTGACCTGTGACTATCTAGG | 47 | 1638 |
| 1104176 | N/A | N/A | 9579 | 9598 | TGCCATTTATCTGTGCTTTA | 50 | 1639 |
| 1104192 | N/A | N/A | 9665 | 9684 | TAAAGGCTGTTAAACATGTG | 51 | 1640 |
| 1104208 | N/A | N/A | 9785 | 9804 | ACCAGCCACATGACTCTGGG | 83 | 1641 |
| 1104224 | N/A | N/A | 10558 | 10577 | CACGGTATTGAAATCAGGAG | 47 | 1642 |
| 1104240 | N/A | N/A | 10654 | 10673 | CTGCTGCCAGAGTCCTGGCT | 88 | 1643 |
| 1104256 | N/A | N/A | 10753 | 10772 | CACCCCCCTCCCCATCATGA | 89 | 1644 |
| 1104272 | N/A | N/A | 10818 | 10837 | AGAGGAGGCCTCTCATGGAC | 96 | 1645 |
| 1104288 | N/A | N/A | 11083 | 11102 | AACGGAATTACATTCAGTTT | 81 | 1646 |
| 1104304 | N/A | N/A | 11152 | 11171 | TATTAGGATCCCATCTAGTG | 103 | 1647 |
| 1104320 | N/A | N/A | 11230 | 11249 | AAAGCTACTAACTTTAATTC | 81 | 1648 |
| 1104336 | N/A | N/A | 11288 | 11307 | CAAGCTGGAAATGGAAAGCC | 83 | 1649 |
| 1104352 | N/A | N/A | 11390 | 11409 | AGTGGTAAGCTGCTGGAGTA | 85 | 1650 |
| 1104368 | N/A | N/A | 11499 | 11518 | CCGACTTCCCAGGTCTTACT | 78 | 1651 |

TABLE 23

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 6 | 517 |
| 1103150 | 20 | 39 | 3468 | 3487 | ATGCGAGGGCTTTATGAAGG | 82 | 1652 |
| 1103166 | 264 | 283 | 3712 | 3731 | TCTCTGCCCGCTCACTGGCC | 126 | 1653 |
| 1103182 | 549 | 568 | 4934 | 4953 | TGTTCTCGGCTTCCAGCCTC | 40* | 1654 |
| 1103198 | 758 | 777 | 5644 | 5663 | CTCTTTCAGGGCTGCGGTGA | 35 | 1655 |
| 1103214 | 1049 | 1068 | 7621 | 7640 | CTCTTCCTCCAGCCGCGCCA | 70 | 1656 |
| 1103230 | 1327 | 1346 | 11616 | 11635 | TCCTGCTTGGACTCCTTAAT | 69 | 1657 |

TABLE 23-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103246 | 1501 | 1520 | 11790 | 11809 | CAGCAAGCTGACCTAGGGAC | 39 | 1658 |
| 1103262 | 1662 | 1681 | 11951 | 11970 | CCCCCCGCCCTCCTCCCCTT | 91 | 1659 |
| 1103278 | 1729 | 1748 | 12018 | 12037 | CCTCCATCTCTGGCAACAGT | 34 | 1660 |
| 1103294 | 1858 | 1877 | 12147 | 12166 | AAAAGACAAAACAAGCCTCT | 81 | 1661 |
| 1103310 | 1884 | 1903 | 12173 | 12192 | TAGGGATATCCCACCTCATA | 74 | 1662 |
| 1103326 | 2061 | 2080 | 12350 | 12369 | CAGGTGACTGCCCCAGGTGG | 73 | 1663 |
| 1103342 | 2228 | 2247 | 12517 | 12536 | TCCCTCCCAGCACCTCATCC | 80 | 1664 |
| 1103358 | 2424 | 2443 | 12713 | 12732 | ATGAGTCACTTCCTTAATTC | 58 | 1665 |
| 1103374 | 2467 | 2486 | 12756 | 12775 | TGGATACATCCCCTTTCTCT | 59 | 1666 |
| 1103390 | 2510 | 2529 | 12799 | 12818 | GAAGAGGCCTTTAGAAATGG | 76 | 1667 |
| 1103406 | 2668 | 2687 | 12957 | 12976 | GTGAGTAAGAAGGGACCGCA | 82 | 1668 |
| 1103422 | 2717 | 2736 | 13006 | 13025 | TACAATTGTAAAATAGGGCA | 90 | 1669 |
| 1103438 | 2849 | 2868 | 13138 | 13157 | ACCAGTCTGCTCACCAGTCT | 74 | 1670 |
| 1103470 | N/A | N/A | 8769 | 8788 | GATATCTTGTGACCTTGTGA | 34 | 1671 |
| 1103486 | N/A | N/A | 8897 | 8916 | GGCTCACTCCCTGTCAAGCT | 100 | 1672 |
| 1103502 | N/A | N/A | 9043 | 9062 | CAAGCTCTGCCAGTTTAATG | 30 | 1673 |
| 1103518 | N/A | N/A | 9224 | 9243 | CTGAGCTGAGCGATGGAGCC | 71 | 1674 |
| 1103534 | N/A | N/A | 9263 | 9282 | TGCGGTCCTGAGGGAAGAAT | 76 | 1675 |
| 1103550 | N/A | N/A | 9308 | 9327 | TAACATTAAGAGCAGGGAAC | 77 | 1676 |
| 1103566 | N/A | N/A | 8500 | 8519 | AGTGTCACGAAGGCCCCCAG | 49 | 1677 |
| 1103582 | N/A | N/A | 8584 | 8603 | GGACCAGGGCCTAGCAGGAC | 69 | 1678 |
| 1103598 | N/A | N/A | 3993 | 4012 | CTGCTCACAAGGCCCCCCTT | 92 | 1679 |
| 1103614 | N/A | N/A | 4049 | 4068 | GGTTCGGCCCCTCCCTGAGA | 69 | 1680 |
| 1103630 | N/A | N/A | 4250 | 4269 | GCCATGAATGAAACACAGGG | 66 | 1681 |
| 1103646 | N/A | N/A | 4391 | 4410 | CCTGCCTGCTCTTTCCCTCA | 76 | 1682 |
| 1103662 | N/A | N/A | 4490 | 4509 | AATTTTATTATGACCACCGC | 110 | 1683 |
| 1103678 | N/A | N/A | 4635 | 4654 | AAGCATACACTCACTGTTGC | 78 | 1684 |
| 1103694 | N/A | N/A | 4817 | 4836 | CAGCTGTCACAGAGACCACC | 100 | 1685 |
| 1103710 | N/A | N/A | 5097 | 5116 | TTCCTCAGCCTTGCCTTACC | 78 | 1686 |
| 1103726 | N/A | N/A | 5305 | 5324 | TCTCAGTTGCAATCTCTGTG | 87 | 1687 |
| 1103742 | N/A | N/A | 5398 | 5417 | TTTCATTTCCTGTCTCTACC | 89 | 1688 |
| 1103758 | N/A | N/A | 5481 | 5500 | TGTCCTCTTCTGCCTGCCCC | 94 | 1689 |
| 1103774 | N/A | N/A | 5726 | 5745 | CAGGCAGGGCTACCTTGGAG | 87 | 1690 |
| 1103790 | N/A | N/A | 5849 | 5868 | ATCTCACTTCTCTGGTGAAA | 95 | 1691 |
| 1103806 | N/A | N/A | 5923 | 5942 | ATAATAGCAATAGTAGCAGT | 103 | 1692 |
| 1103822 | N/A | N/A | 5974 | 5993 | TAATCCATGAAAAGCACAGG | 84 | 1693 |

TABLE 23-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103838 | N/A | N/A | 6020 | 6039 | TCGGCTCTCTCATCTGTCAA | 53 | 1694 |
| 1103854 | N/A | N/A | 6199 | 6218 | TCAGACACCTCTCTGTGTCC | 86 | 1695 |
| 1103870 | N/A | N/A | 6257 | 6276 | CTGTGGTGTTCTCTACGGGC | 78 | 1696 |
| 1103886 | N/A | N/A | 6313 | 6332 | CAAATGCCCCCTCTACAGTG | 105 | 1697 |
| 1103902 | N/A | N/A | 6408 | 6427 | CTCTCTGTGCTTTTCTGCCT | 71 | 1698 |
| 1103918 | N/A | N/A | 6501 | 6520 | ATCGGGCCCTCACCCTGCTC | 107 | 1699 |
| 1103934 | N/A | N/A | 6904 | 6923 | TAGGCGAGCGGAGGCCTGGG | 90 | 1700 |
| 1103950 | N/A | N/A | 7017 | 7036 | GACCTCAGCACCTAGCACAA | 82 | 1701 |
| 1103966 | N/A | N/A | 7314 | 7333 | TCACCGTGCCGCGCAGAGAC | 101 | 1702 |
| 1103982 | N/A | N/A | 7416 | 7435 | GCCCCGCCCTCGACCCAGGT | 88 | 1703 |
| 1103998 | N/A | N/A | 7805 | 7824 | GATGAGCTCTACCGTGAGGC | 71 | 1704 |
| 1104014 | N/A | N/A | 7922 | 7941 | AGTCATCAAACATCTAGTGA | 46 | 1705 |
| 1104030 | N/A | N/A | 8035 | 8054 | GAGGAGTCCAATCTTGGCTG | 67 | 1706 |
| 1104046 | N/A | N/A | 8075 | 8094 | GTGAAGAAAGTTCCAAGGAG | 93 | 1707 |
| 1104062 | N/A | N/A | 8228 | 8247 | TTTCCTTGCCAGGAAAGTCT | 81 | 1708 |
| 1104078 | N/A | N/A | 9359 | 9378 | CCCCGCCCCGCCCGAGAGAG | 36 | 1709 |
| 1104094 | N/A | N/A | 9412 | 9431 | TAAGAATCATTTCAGGGCCA | 71 | 1710 |
| 1104110 | N/A | N/A | 9452 | 9471 | AATATTCTAGTCCAGAAGAA | 103 | 1711 |
| 1104126 | N/A | N/A | 9506 | 9525 | TTAGCCTTTCTGATGCTGAA | 58 | 1712 |
| 1104142 | N/A | N/A | 9530 | 9549 | TATTACCTCTACTAGTCAGC | 65 | 1713 |
| 1104158 | N/A | N/A | 9557 | 9576 | GACCTGTGACTATCTAGGAT | 18 | 1714 |
| 1104174 | N/A | N/A | 9576 | 9595 | CATTTATCTGTGCTTTAGTG | 37 | 1715 |
| 1104190 | N/A | N/A | 9660 | 9679 | GCTGTTAAACATGTGGCACA | 74 | 1716 |
| 1104206 | N/A | N/A | 9706 | 9725 | CCTACTTCTCTAGGTGGGAG | 65 | 1717 |
| 1104222 | N/A | N/A | 10556 | 10575 | CGGTATTGAAATCAGGAGAC | 47 | 1718 |
| 1104238 | N/A | N/A | 10610 | 10629 | TTTCAGCCCCTCTGCAAGCC | 68 | 1719 |
| 1104254 | N/A | N/A | 10747 | 10766 | CCTCCCCATCATGAGTATGA | 92 | 1720 |
| 1104270 | N/A | N/A | 10816 | 10835 | AGGAGGCCTCTCATGGACTT | 93 | 172 |
| 1104286 | N/A | N/A | 11078 | 11097 | AATTACATTCAGTTTCCTTG | 88 | 1722 |
| 1104302 | N/A | N/A | 11150 | 11169 | TTAGGATCCCATCTAGTGGC | 60 | 1723 |
| 1104318 | N/A | N/A | 11225 | 11244 | TACTAACTTTAATTCTCTTT | 49 | 1724 |
| 1104334 | N/A | N/A | 11280 | 11299 | AAATGGAAAGCCCTCCCCAT | 98 | 1725 |
| 1104350 | N/A | N/A | 11388 | 11407 | TGGTAAGCTGCTGGAGTAAG | 55 | 1726 |
| 1104366 | N/A | N/A | 11494 | 11513 | TTCCCAGGTCTTACTTTTCT | 76 | 1727 |

TABLE 24

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 6 | 517 |
| 1103151 | 39 | 58 | 3487 | 3506 | GGCTCTGCTCGCTCCTGGGA | 108 | 1728 |
| 1103167 | 269 | 288 | 3717 | 3736 | CATCATCTCTGCCCGCTCAC | 93 | 1729 |
| 1103183 | 553 | 572 | 4938 | 4957 | AGGTTGTTCTCGGCTTCCAG | 55* | 1730 |
| 1103199 | 759 | 778 | 5645 | 5664 | TCTCTTTCAGGGCTGCGGTG | 54 | 1731 |
| 1103215 | 1050 | 1069 | 7622 | 7641 | CCTCTTCCTCCAGCCGCGCC | 64 | 1732 |
| 1103231 | 1334 | 1353 | 11623 | 11642 | CTTGTGCTCCTGCTTGGACT | 53 | 1733 |
| 1103247 | 1518 | 1537 | 11807 | 11826 | ACTGACGGAGCCTAGGGCAG | 61 | 1734 |
| 1103263 | 1667 | 1686 | 11956 | 11975 | AGGTGCCCCCCGCCCTCCTC | 98 | 1735 |
| 1103279 | 1730 | 1749 | 12019 | 12038 | ACCTCCATCTCTGGCAACAG | 25 | 1736 |
| 1103295 | 1859 | 1878 | 12148 | 12167 | CAAAAGACAAAACAAGCCTC | 73 | 1737 |
| 1103311 | 1885 | 1904 | 12174 | 12193 | ATAGGGATATCCCACCTCAT | 75 | 1738 |
| 1103327 | 2086 | 2105 | 12375 | 12394 | TCAGGAGGTCCTTCTGGGAT | 67 | 1739 |
| 1103343 | 2230 | 2249 | 12519 | 12538 | TATCCCTCCCAGCACCTCAT | 63 | 1740 |
| 1103359 | 2425 | 2444 | 12714 | 12733 | GATGAGTCACTTCCTTAATT | 35 | 1741 |
| 1103375 | 2483 | 2502 | 12772 | 12791 | TCATGCCCTGCCCCCATGGA | 69 | 1742 |
| 1103391 | 2511 | 2530 | 12800 | 12819 | GGAAGAGGCCTTTAGAAATG | 74 | 1743 |
| 1103407 | 2670 | 2689 | 12959 | 12978 | GTGTGAGTAAGAAGGGACCG | 46 | 1744 |
| 1103423 | 2722 | 2741 | 13011 | 13030 | AGTTTTACAATTGTAAAATA | 88 | 1745 |
| 1103439 | 2868 | 2887 | 13157 | 13176 | ATCTCTGGGCACAGATCCCA | 93 | 1746 |
| 1103471 | N/A | N/A | 8770 | 8789 | AGATATCTTGTGACCTTGTG | 35 | 1747 |
| 1103487 | N/A | N/A | 8898 | 8917 | AGGCTCACTCCCTGTCAAGC | 62 | 1748 |
| 1103503 | N/A | N/A | 9044 | 9063 | ACAAGCTCTGCCAGTTTAAT | 51 | 1749 |
| 1103519 | N/A | N/A | 9225 | 9244 | ACTGAGCTGAGCGATGGAGC | 65 | 1750 |
| 1103535 | N/A | N/A | 9266 | 9285 | AGCTGCGGTCCTGAGGGAAG | 59 | 1751 |
| 1103551 | N/A | N/A | 9309 | 9328 | TTAACATTAAGAGCAGGGAA | 68 | 1752 |
| 1103567 | N/A | N/A | 8530 | 8549 | GGTATGATAGGCTCTGGCTA | 21 | 1753 |
| 1103583 | N/A | N/A | 8649 | 8668 | AGACAGGGCAGATGTCAAGC | 90 | 1754 |
| 1103599 | N/A | N/A | 3994 | 4013 | TCTGCTCACAAGGCCCCCCT | 56 | 1755 |
| 1103615 | N/A | N/A | 4053 | 4072 | GGGAGGTTCGGCCCCTCCCT | 94 | 1756 |
| 1103631 | N/A | N/A | 4251 | 4270 | AGCCATGAATGAAACACAGG | 115 | 1757 |
| 1103647 | N/A | N/A | 4401 | 4420 | TGCGCCCAGACCTGCCTGCT | 75 | 1758 |
| 1103663 | N/A | N/A | 4495 | 4514 | AAATGAATTTTATTATGACC | 80 | 1759 |
| 1103679 | N/A | N/A | 4636 | 4655 | CAAGCATACACTCACTGTTG | 69 | 1760 |
| 1103695 | N/A | N/A | 4820 | 4839 | AGGCAGCTGTCACAGAGACC | 95 | 1761 |
| 1103711 | N/A | N/A | 5099 | 5118 | CATTCCTCAGCCTTGCCTTA | 95 | 1762 |
| 1103727 | N/A | N/A | 5311 | 5330 | TCCCTCTCTCAGTTGCAATC | 79 | 1763 |

TABLE 24-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103743 | N/A | N/A | 5412 | 5431 | TCTTTCTGTTTGTCTTTCAT | 71 | 1764 |
| 1103759 | N/A | N/A | 5482 | 5501 | GTGTCCTCTTCTGCCTGCCC | 59 | 1765 |
| 1103775 | N/A | N/A | 5775 | 5794 | TCTCTTGTACAGAGCAAGAA | 110 | 1766 |
| 1103791 | N/A | N/A | 5853 | 5872 | AGCCATCTCACTTCTCTGGT | 67 | 1767 |
| 1103807 | N/A | N/A | 5930 | 5949 | ACTACTAATAATAGCAATAG | 82 | 1768 |
| 1103823 | N/A | N/A | 5975 | 5994 | GTAATCCATGAAAAGCACAG | 97 | 1769 |
| 1103839 | N/A | N/A | 6022 | 6041 | CTTCGGCTCTCTCATCTGTC | 76 | 1770 |
| 1103855 | N/A | N/A | 6203 | 6222 | CAGGTCAGACACCTCTCTGT | 76 | 1771 |
| 1103871 | N/A | N/A | 6265 | 6284 | GCTCTGAGCTGTGGTGTTCT | 88 | 1772 |
| 1103887 | N/A | N/A | 6314 | 6333 | CCAAATGCCCCCTCTACAGT | 92 | 1773 |
| 1103903 | N/A | N/A | 6409 | 6428 | CCTCTCTGTGCTTTTCTGCC | 60 | 1774 |
| 1103919 | N/A | N/A | 6516 | 6535 | GGTCCTCCCAGCCCCATCGG | 79 | 1775 |
| 1103935 | N/A | N/A | 6906 | 6925 | CTTAGGCGAGCGGAGGCCTG | 85 | 1776 |
| 1103951 | N/A | N/A | 7021 | 7040 | GCCAGACCTCAGCACCTAGC | 65 | 1777 |
| 1103967 | N/A | N/A | 7316 | 7335 | GCTCACCGTGCCGCGCAGAG | 76 | 1778 |
| 1103983 | N/A | N/A | 7420 | 7439 | TCAGGCCCCGCCCTCGACCC | 88 | 1779 |
| 1103999 | N/A | N/A | 7806 | 7825 | AGATGAGCTCTACCGTGAGG | 66 | 1780 |
| 1104015 | N/A | N/A | 7930 | 7949 | ATCCATTCAGTCATCAAACA | 90 | 1781 |
| 1104031 | N/A | N/A | 8037 | 8056 | GTGAGGAGTCCAATCTTGGC | 77 | 1782 |
| 1104047 | N/A | N/A | 8076 | 8095 | GGTGAAGAAAGTTCCAAGGA | 59 | 1783 |
| 1104063 | N/A | N/A | 8229 | 8248 | TTTTCCTTGCCAGGAAAGTC | 76 | 1784 |
| 1104079 | N/A | N/A | 9360 | 9379 | CCCCCGCCCCGCCCGAGAGA | 103 | 1785 |
| 1104095 | N/A | N/A | 9413 | 9432 | CTAAGAATCATTTCAGGGCC | 65 | 1786 |
| 1104111 | N/A | N/A | 9454 | 9473 | TAAATATTCTAGTCCAGAAG | 87 | 1787 |
| 1104127 | N/A | N/A | 9508 | 9527 | GGTTAGCCTTTCTGATGCTG | 30 | 1788 |
| 1104143 | N/A | N/A | 9531 | 9550 | GTATTACCTCTACTAGTCAG | 56 | 1789 |
| 1104159 | N/A | N/A | 9558 | 9577 | TGACCTGTGACTATCTAGGA | 29 | 1790 |
| 1104175 | N/A | N/A | 9578 | 9597 | GCCATTTATCTGTGCTTTAG | 10 | 1791 |
| 104191 | N/A | N/A | 9664 | 9683 | AAAGGCTGTTAAACATGTGG | 39 | 1792 |
| 1104207 | N/A | N/A | 9707 | 9726 | GCCTACTTCTCTAGGTGGGA | 69 | 1793 |
| 1104223 | N/A | N/A | 10557 | 10576 | ACGGTATTGAAATCAGGAGA | 55 | 1794 |
| 1104239 | N/A | N/A | 10639 | 10658 | TGGCTGCTCTGTCTTCTGGC | 52 | 1795 |
| 1104255 | N/A | N/A | 10748 | 10767 | CCCTCCCCATCATGAGTATG | 79 | 1796 |
| 1104271 | N/A | N/A | 10817 | 10836 | GAGGAGGCCTCTCATGGACT | 95 | 1797 |
| 1104287 | N/A | N/A | 11082 | 11101 | ACGGAATTACATTCAGTTTC | 77 | 1798 |
| 1104303 | N/A | N/A | 11151 | 11170 | ATTAGGATCCCATCTAGTGG | 68 | 1799 |

TABLE 24-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104319 | N/A | N/A | 11229 | 11248 | AAGCTACTAACTTTAATTCT | 92 | 1800 |
| 1104335 | N/A | N/A | 11281 | 11300 | GAAATGGAAAGCCCTCCCCA | 113 | 1801 |
| 1104351 | N/A | N/A | 11389 | 11408 | GTGGTAAGCTGCTGGAGTAA | 60 | 1802 |
| 1104367 | N/A | N/A | 11498 | 11517 | CGACTTCCCAGGTCTTACTT | 74 | 1803 |

TABLE 25

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 7 | 517 |
| 1103153 | 44 | 63 | 3492 | 3511 | GCTCTGGCTCTGCTCGCTCC | 83 | 1804 |
| 1103169 | 354 | 373 | 3802 | 3821 | GGTTCAGCTCAGCAGCCAGC | 85 | 1805 |
| 1103185 | 566 | 585 | 4951 | 4970 | TCTATAGGCAGCCAGGTTGT | 73* | 1806 |
| 1103201 | 762 | 781 | 5648 | 5667 | GGATCTCTTTCAGGGCTGCG | 90 | 1807 |
| 1103217 | 1185 | 1204 | N/A | N/A | GAATGGTGATCCGGTTCTCC | 23 | 1808 |
| 1103233 | 1350 | 1369 | 11639 | 11658 | TGCCTCACATCACATCCTTG | 98 | 1809 |
| 1103249 | 1528 | 1547 | 11817 | 11836 | CAGGCCTGATACTGACGGAG | 103 | 1810 |
| 1103265 | 1670 | 1689 | 11959 | 11978 | AGTAGGTGCCCCCCGCCCTC | 74 | 1811 |
| 1103281 | 1750 | 1769 | 12039 | 12058 | TTCCCAGATACTCCGAGAGA | 65 | 1812 |
| 1103297 | 1861 | 1880 | 12150 | 12169 | ACCAAAAGACAAAACAAGCC | 113 | 1813 |
| 1103313 | 1887 | 1906 | 12176 | 12195 | GCATAGGGATATCCCACCTC | 95 | 1814 |
| 1103329 | 2097 | 2116 | 12386 | 12405 | TGAGTCATCGCTCAGGAGGT | 47 | 1815 |
| 1103345 | 2331 | 2350 | 12620 | 12639 | TCCTCCTCCATCTCTACCAG | 44 | 1816 |
| 1103361 | 2431 | 2450 | 12720 | 12739 | CAAGAGGATGAGTCACTTCC | 49 | 1817 |
| 1103377 | 2485 | 2504 | 12774 | 12793 | AGTCATGCCCTGCCCCCATG | 46 | 1818 |
| 1103393 | 2516 | 2535 | 12805 | 12824 | AGCAAGGAAGAGGCCTTTAG | 68 | 1819 |
| 1103409 | 2673 | 2692 | 12962 | 12981 | TGTGTGTGAGTAAGAAGGGA | 30 | 1820 |
| 1103425 | 2725 | 2744 | 13014 | 13033 | CTCAGTTTTACAATTGTAAA | 71 | 1821 |
| 1103441 | 2905 | 2924 | 13194 | 13213 | GGGAGAGGAGAACCCTGAAG | 98 | 1822 |
| 1103473 | N/A | N/A | 8813 | 8832 | CTGGTGAGCCTGTATTGGTA | 68 | 1823 |
| 1103489 | N/A | N/A | 8975 | 8994 | AAAATGACGCAGTCCAGGCC | 108 | 1824 |
| 1103505 | N/A | N/A | 9046 | 9065 | TAACAAGCTCTGCCAGTTTA | 92 | 1825 |
| 1103521 | N/A | N/A | 9238 | 9257 | GAACTGAGTCAGCACTGAGC | 124 | 1826 |
| 1103537 | N/A | N/A | 9279 | 9298 | TATTCACTGCAAGAGCTGCG | 111 | 1827 |
| 1103553 | N/A | N/A | 9313 | 9332 | ATATTTAACATTAAGAGCAG | 84 | 1828 |
| 1103569 | N/A | N/A | 8533 | 8552 | CCTGGTATGATAGGCTCTGG | 56 | 1829 |

TABLE 25-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103585 | N/A | N/A | 8655 | 8674 | ATCTGCAGACAGGGCAGATG | 113 | 1830 |
| 1103601 | N/A | N/A | 4001 | 4020 | AGCCCCTTCTGCTCACAAGG | 74 | 1831 |
| 1103617 | N/A | N/A | 4172 | 4191 | CCTGGCAGAAGGCATGCGGG | 120 | 1832 |
| 1103633 | N/A | N/A | 4295 | 4314 | CAGGCTCAGAATAGGTGAGC | 80 | 1833 |
| 1103649 | N/A | N/A | 4410 | 4429 | CCTGTGCTTTGCGCCCAGAC | 92 | 1834 |
| 1103665 | N/A | N/A | 4505 | $524 | CCACCTTTTGAAATGAATTT | 63 | 1835 |
| 1103681 | N/A | N/A | 4641 | 4660 | ATCCACAAGCATACACTCAC | 62 | 1836 |
| 1103697 | N/A | N/A | 4845 | 4864 | TGAATACCTGCCTCAGTCTC | 68 | 1837 |
| 1103713 | N/A | N/A | 5101 | 5120 | CCCATTCCTCAGCCTTGCCT | 95 | 1838 |
| 1103729 | N/A | N/A | 5351 | 5370 | TGAGTGTCTCTCTCAGTCTC | 132 | 1839 |
| 1103745 | N/A | N/A | 5420 | 5439 | CCTTAGTGTCTTTCTGTTTG | 69 | 1840 |
| 1103761 | N/A | N/A | 5489 | 5508 | CGCCATTGTGTCCTCTTCTG | 86 | 1841 |
| 1103777 | N/A | N/A | 5778 | 5797 | CATTCTCTTGTACAGAGCAA | 105 | 1842 |
| 1103793 | N/A | N/A | 5861 | 5880 | CCTGGGCAAGCCATCTCACT | 119 | 1843 |
| 1103809 | N/A | N/A | 5943 | 5962 | AACAGTATCAGCTACTACTA | 80 | 1844 |
| 1103825 | N/A | N/A | 5979 | 5998 | TAAGGTAATCCATGAAAAGC | 101 | 1845 |
| 1103841 | N/A | N/A | 6108 | 6127 | CCCAAGTGAGATGTGCTAGA | 118 | 1846 |
| 1103857 | N/A | N/A | 6205 | 6224 | TCCAGGTCAGACACCTCTCT | 97 | 1847 |
| 1103873 | N/A | N/A | 6268 | 6287 | TAAGCTCTGAGCTGTGGTGT | 51 | 1848 |
| 1103889 | N/A | N/A | 6316 | 6335 | GCCCAAATGCCCCCTCTACA | 73 | 1849 |
| 1103905 | N/A | N/A | 6415 | 6434 | GCCCTGCCTCTCTGTGCTTT | 64 | 1850 |
| 1103921 | N/A | N/A | 6522 | 6541 | CAGGGAGGTCCTCCCAGCCC | 101 | 1851 |
| 1103937 | N/A | N/A | 6948 | 6967 | TTCCACACTGACAGCTGCAT | 76 | 1852 |
| 1103953 | N/A | N/A | 7077 | 7096 | TGGCTGGGACTTTTCCCAAC | 113 | 1853 |
| 1103969 | N/A | N/A | 7330 | 7349 | CCTGCCCTGGCCGCGCTCAC | 87 | 1854 |
| 1103985 | N/A | N/A | 7423 | 7442 | CGTTCAGGCCCCGCCCTCGA | 78 | 1855 |
| 1104001 | N/A | N/A | 7815 | 7834 | AAGGGAGCAAGATGAGCTCT | 77 | 1856 |
| 1104017 | N/A | N/A | 7956 | 7975 | CTAATCAATATTGGTTGAAT | 87 | 1857 |
| 1104033 | N/A | N/A | 8039 | 8058 | AGGTGAGGAGTCCAATCTTG | 82 | 1858 |
| 1104049 | N/A | N/A | 8082 | 8101 | GAAAGTGGTGAAGAAAGTTC | 109 | 1859 |
| 1104065 | N/A | N/A | 8252 | 8271 | CCATCATGACAACTTGAACG | 110 | 1860 |
| 1104081 | N/A | N/A | 9377 | 9396 | AATTTAGCTCCCCCCTCCCC | 83 | 1861 |
| 1104097 | N/A | N/A | 9417 | 9436 | TTAGCTAAGAATCATTTCAG | 125 | 1862 |
| 1104113 | N/A | N/A | 9456 | 9475 | CCTAAATATTCTAGTCCAGA | 47 | 1863 |
| 1104129 | N/A | N/A | 9511 | 9530 | CCTGGTTAGCCTTTCTGATG | 47 | 1864 |
| 1104145 | N/A | N/A | 9537 | 9556 | TTGGCAGTATTACCTCTACT | 19 | 1865 |

TABLE 25-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104161 | N/A | N/A | 9561 | 9580 | TAGTGACCTGTGACTATCTA | 47 | 1866 |
| 1104177 | N/A | N/A | 9580 | 9599 | CTGCCATTTATCTGTGCTTT | 52 | 1867 |
| 1104193 | N/A | N/A | 9672 | 9691 | ACTAAAATAAAGGCTGTTAA | 67 | 1868 |
| 1104209 | N/A | N/A | 9786 | 9805 | AACCAGCCACATGACTCTGG | 91 | 1869 |
| 1104225 | N/A | N/A | 10559 | 10578 | GCACGGTATTGAAATCAGGA | 30 | 1870 |
| 1104241 | N/A | N/A | 10655 | 10674 | GCTGCTGCCAGAGTCCTGGC | 69 | 1871 |
| 1104257 | N/A | N/A | 10761 | 10780 | CCCCATCGCACCCCCCTCCC | 103 | 1872 |
| 1104273 | N/A | N/A | 10843 | 10862 | CAGGCTGGTTTCTGCAGATG | 92 | 1873 |
| 1104289 | N/A | N/A | 11084 | 11103 | AAACGGAATTACATTCAGTT | 67 | 1874 |
| 1104305 | N/A | N/A | 11153 | 11172 | GTATTAGGATCCCATCTAGT | 58 | 1875 |
| 1104321 | N/A | N/A | 11231 | 11250 | GAAAGCTACTAACTTTAATT | 60 | 1876 |
| 1104337 | N/A | N/A | 11308 | 11327 | CCCTGGTAGTTTCCTTTTAC | 55 | 1877 |
| 1104353 | N/A | N/A | 11392 | 11411 | CGAGTGGTAAGCTGCTGGAG | 69 | 1878 |
| 1104369 | N/A | N/A | 11512 | 11531 | CCTTGGGAAGTCCCCGACTT | 78 | 1879 |

TABLE 26

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 6 | 517 |
| 1103154 | 109 | 128 | 3557 | 3576 | ATCATCTCCCCTGAGGAGAC | 139 | 1880 |
| 1103170 | 376 | 395 | 3824 | 3843 | GTGGGCTCCTTGGCCCGCAG | 89 | 1881 |
| 1103186 | 576 | 595 | N/A | N/A | CTGCTTCCTGTCTATAGGCA | 30* | 1882 |
| 1103202 | 763 | 782 | 5649 | 5668 | CGGATCTCTTTCAGGGCTGC | 38 | 1883 |
| 1103218 | 1202 | 1221 | 8351 | 8370 | GGAGAAGGTCTGCACGGGAA | 43 | 1884 |
| 1103234 | 1355 | 1374 | 11644 | 11663 | GGTCCTGCCTCACATCACAT | 87 | 1885 |
| 1103250 | 1532 | 1551 | 11821 | 11840 | CTGGCAGGCCTGATACTGAC | 93 | 1886 |
| 1103266 | 1679 | 1698 | 11968 | 11987 | GGGCGATGTAGTAGGTGCCC | 100 | 1887 |
| 1103282 | 1762 | 1781 | 12051 | 12070 | TCAAAGGCACAGTTCCCAGA | 89 | 1888 |
| 1103298 | 1862 | 1881 | 12151 | 12170 | AACCAAAAGACAAAACAAGC | 80 | 1889 |
| 1103314 | 1889 | 1908 | 12178 | 12197 | CAGCATAGGGATATCCCACC | 86 | 1890 |
| 1103330 | 2098 | 2117 | 12387 | 12406 | TTGAGTCATCGCTCAGGAGG | 49 | 1891 |
| 1103346 | 2332 | 2351 | 12621 | 12640 | CTCCTCCTCCATCTCTACCA | 81 | 1892 |
| 1103362 | 2436 | 2455 | 12725 | 12744 | ATCTTCAAGAGGATGAGTCA | 116 | 1893 |
| 1103378 | 2487 | 2506 | 12776 | 12795 | AAAGTCATGCCCTGCCCCCA | 74 | 1894 |
| 1103394 | 2526 | 2545 | 12815 | 12834 | GGTATGACACAGCAAGGAAG | 59 | 1895 |

TABLE 26-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103410 | 2674 | 2693 | 12963 | 12982 | TTGTGTGTGAGTAAGAAGGG | 52 | 1896 |
| 1103426 | 2730 | 2749 | 13019 | 13038 | CGTGCCTCAGTTTTACAATT | 73 | 1897 |
| 1103442 | 2963 | 2982 | 13252 | 13271 | TGGAGGGAAAGGACACCAAG | 79 | 1898 |
| 1103458 | N/A | N/A | 8740 | 8759 | TCTTTGGTGCTTTTGCCCCC | 50 | 1899 |
| 1103474 | N/A | N/A | 8814 | 8833 | TCTGGTGAGCCTGTATTGGT | 66 | 1900 |
| 1103490 | N/A | N/A | 8978 | 8997 | GGGAAAATGACGCAGTCCAG | 80 | 1901 |
| 1103506 | N/A | N/A | 9076 | 9095 | GCGCACCCAAGGACTCACCA | 115 | 1902 |
| 1103522 | N/A | N/A | 9240 | 9259 | CTGAACTGAGTCAGCACTGA | 90 | 1903 |
| 1103538 | N/A | N/A | 9285 | 9304 | AAACTTTATTCACTGCAAGA | 57 | 1904 |
| 1103570 | N/A | N/A | 8537 | 8556 | GTACCCTGGTATGATAGGCT | 22 | 1905 |
| 1103586 | N/A | N/A | 8684 | 8703 | ACACTCAGAAGGGCAGTGCT | 115 | 1906 |
| 1103602 | N/A | N/A | 4002 | 4021 | CAGCCCCTTCTGCTCACAAG | 77 | 1907 |
| 1103618 | N/A | N/A | 4181 | 4200 | CCCTGGACTCCTGGCAGAAG | 98 | 1908 |
| 1103634 | N/A | N/A | 4336 | 4355 | CATCAACCTTCTCCGCTTCC | 75 | 1909 |
| 1103650 | N/A | N/A | 4411 | 4430 | ACCTGTGCTTTGCGCCCAGA | 92 | 1910 |
| 1103666 | N/A | N/A | 4566 | 4585 | TGCATGTCCTGTCAGCTCAG | 122 | 1911 |
| 1103682 | N/A | N/A | 4645 | 4664 | GCGCATCCACAAGCATACAC | 113 | 1912 |
| 1103698 | N/A | N/A | 4846 | 4865 | TTGAATACCTGCCTCAGTCT | 104 | 1913 |
| 1103714 | N/A | N/A | $140 | 5159 | TGAGGAGTAGAGGGCCACTG | 64 | 1914 |
| 1103730 | N/A | N/A | 5353 | 5372 | TCTGAGTGTCTCTCTCAGTC | 135 | 1915 |
| 1103746 | N/A | N/A | 5422 | 5441 | TCCCTTAGTGTCTTTCTGTT | 101 | 1916 |
| 1103762 | N/A | N/A | 5494 | 5513 | CCCCACGCCATTGTGTCCTC | 85 | 1917 |
| 1103778 | N/A | N/A | 5780 | 5799 | CCCATTCTCTTGTACAGAGC | 72 | 1918 |
| 1103794 | N/A | N/A | 5862 | 5881 | CCCTGGGCAAGCCATCTCAC | 80 | 1919 |
| 1103810 | N/A | N/A | 5948 | 5967 | AACAGAACAGTATCAGCTAC | 82 | 1920 |
| 1103826 | N/A | N/A | 5980 | 5999 | GTAAGGTAATCCATGAAAAG | 73 | 1921 |
| 1103842 | N/A | N/A | 6112 | 6131 | GGCTCCCAAGTGAGATGTGC | 118 | 1922 |
| 1103858 | N/A | N/A | 6207 | 6226 | CTTCCAGGTCAGACACCTCT | 75 | 1923 |
| 1103874 | N/A | N/A | 6269 | 6288 | ATAAGCTCTGAGCTGTGGTG | 50 | 1924 |
| 1103890 | N/A | N/A | 6317 | 6336 | AGCCCAAATGCCCCCTCTAC | 77 | 1925 |
| 1103906 | N/A | N/A | 6449 | 6468 | CAGCTAGGTGCCCTGGCTAG | 131 | 1926 |
| 1103922 | N/A | N/A | 6531 | 6550 | CCCTGCCTGCAGGGAGGTCC | 69 | 1927 |
| 1103938 | N/A | N/A | 6970 | 6989 | CAGTGCCACAGAATCCAGAA | 94 | 1928 |
| 1103954 | N/A | N/A | 7104 | 7123 | CCCCAGTTAACCCCAGGACG | 130 | 1929 |
| 1103970 | N/A | N/A | 7337 | 7356 | TCCCCGTCCTGCCCTGGCCG | 65 | 1930 |
| 1103986 | N/A | N/A | 7454 | 7473 | GCCCCAGGCCCCGCCTCTAG | 174 | 1931 |

TABLE 26-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104002 | N/A | N/A | 7824 | 7843 | CAGTCCCTGAAGGGAGCAAG | 113 | 1932 |
| 1104018 | N/A | N/A | 7958 | 7977 | GCCTAATCAATATTGGTTGA | 71 | 1933 |
| 1104034 | N/A | N/A | 8041 | 8060 | TGAGGTGAGGAGTCCAATCT | 69 | 1934 |
| 1104050 | N/A | N/A | 8107 | 8126 | CTGAAGGAAGATGGAAAAGG | 78 | 1935 |
| 1104066 | N/A | N/A | 8254 | 8273 | GGCCATCATGACAACTTGAA | 105 | 1936 |
| 1104082 | N/A | N/A | 9378 | 9397 | TAATTTAGCTCCCCCCTCCC | 106 | 1937 |
| 1104098 | N/A | N/A | 9418 | 9437 | CTTAGCTAAGAATCATTTCA | 96 | 1938 |
| 1104114 | N/A | N/A | 9457 | 9476 | TCCTAAATATTCTAGTCCAG | 63 | 1939 |
| 1104130 | N/A | N/A | 9513 | 9532 | AGCCTGGTTAGCCTTTCTGA | 68 | 1940 |
| 1104146 | N/A | N/A | 9538 | 9557 | TTTGGCAGTATTACCTCTAC | 73 | 1941 |
| 1104162 | N/A | N/A | 9562 | 9581 | TTAGTGACCTGTGACTATCT | 92 | 1942 |
| 1104178 | N/A | N/A | 9582 | 9601 | CTCTGCCATTTATCTGTGCT | 48 | 1943 |
| 1104194 | N/A | N/A | 9675 | 9694 | TTAACTAAAATAAAGGCTGT | 132 | 1944 |
| 1104210 | N/A | N/A | 9810 | 9829 | TCAAGAAGTCCCAACTTAGC | 74 | 1945 |
| 1104226 | N/A | N/A | 10560 | 10579 | AGCACGGTATTGAAATCAGG | 77 | 1946 |
| 1104242 | N/A | N/A | 10656 | 10675 | TGCTGCTGCCAGAGTCCTGG | 89 | 1947 |
| 1104258 | N/A | N/A | 10773 | 10792 | CATGCCCGGCTTCCCCATCG | 98 | 1948 |
| 1104274 | N/A | N/A | 10923 | 10942 | CTTACCTCTCCATCCCGCAT | 100 | 1949 |
| 1104290 | N/A | N/A | 11088 | 11107 | GAGGAAACGGAATTACATTC | 95 | 1950 |
| 1104306 | N/A | N/A | 11154 | 11173 | TGTATTAGGATCCCATCTAG | 135 | 1951 |
| 1104322 | N/A | N/A | 11232 | 11251 | TGAAAGCTACTAACTTTAAT | 75 | 1952 |
| 1104338 | N/A | N/A | 11312 | 11331 | ATTCCCCTGGTAGTTTCCTT | 97 | 1953 |
| 1104354 | N/A | N/A | 11393 | 11412 | GCGAGTGGTAAGCTGCTGGA | 57 | 1954 |
| 1104370 | N/A | N/A | 11523 | 11542 | AGGCTGTGTAACCTTGGGAA | 75 | 1955 |

TABLE 27

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 306 | 13336 | 13355 | GTCTTTATTTTTCCTCAGCG | 7 | 517 |
| 1103155 | 110 | 129 | 3558 | 3577 | CATCATCTCCCCTGAGGAGA | 90 | 1956 |
| 1103171 | 380 | 399 | 3828 | 3847 | CTTGGTGGGCTCCTTGGCCC | 103 | 1957 |
| 1103187 | 577 | 596 | N/A | N/A | TCTGCTTCCTGTCTATAGGC | 33* | 1958 |
| 1103203 | 764 | 783 | 5650 | 5669 | GCGGATCTCTTTCAGGGCTG | 65 | 1959 |
| 1103219 | 1220 | 1239 | N/A | N/A | TTCTCGAATCTGCAGGTTGG | 111 | 1960 |
| 1103235 | 1361 | 1380 | 11650 | 11669 | CAGGTGGGTCCTGCCTCACA | 147 | 1961 |

TABLE 27-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103251 | 1533 | 1552 | 11822 | 11841 | TCTGGCAGGCCTGATACTGA | 134 | 1962 |
| 1103267 | 1681 | 1700 | 11970 | 11989 | GAGGGCGATGTAGTAGGTGC | 66 | 1963 |
| 1103283 | 1768 | 1787 | 12057 | 12076 | GGAAACTCAAAGGCACAGTT | 72 | 1964 |
| 1103299 | 1870 | 1889 | 12159 | 12178 | CTCATAAAAACCAAAAGACA | 128 | 1965 |
| 1103315 | 1890 | 1909 | 12179 | 12198 | GCAGCATAGGGATATCCCAC | 89 | 1966 |
| 1103331 | 2107 | 2126 | 12396 | 12415 | CTGAGACACTTGAGTCATCG | 45 | 1967 |
| 1103347 | 2334 | 2353 | 12623 | 12642 | GCCTCCTCCTCCATCTCTAC | 53 | 1968 |
| 1103363 | 2440 | 2459 | 12729 | 12748 | CAGCATCTTCAAGAGGATGA | 109 | 1969 |
| 1103379 | 2488 | 2507 | 12777 | 12796 | CAAAGTCATGCCCTGCCCCC | 94 | 1970 |
| 1103395 | 2527 | 2546 | 12816 | 12835 | TGGTATGACACAGCAAGGAA | 48 | 1971 |
| 1103411 | 2676 | 2695 | 12965 | 12984 | TTTTGTGTGTGAGTAAGAAG | 43 | 1972 |
| 1103427 | 2750 | 2769 | 13039 | 13058 | GCCAGTGTCTTCACTTTGCT | 73 | 1973 |
| 1103443 | 3013 | 3032 | 13302 | 13321 | CAGTGCCCTGAAGATTAGCA | 68 | 1974 |
| 1103459 | N/A | N/A | 8741 | 8760 | GTCTTTGGTGCTTTTGCCCC | 51 | 1975 |
| 1103475 | N/A | N/A | 8815 | 8834 | ATCTGGTGAGCCTGTATTGG | 45 | 1976 |
| 1103491 | N/A | N/A | 8979 | 8998 | TGGGAAAATGACGCAGTCCA | 61 | 1977 |
| 1103507 | N/A | N/A | 9091 | 9110 | CAGAGCAGCTCCACTGCGCA | 127 | 1978 |
| 1103523 | N/A | N/A | 9241 | 9260 | TCTGAACTGAGTCAGCACTG | 84 | 1979 |
| 1103539 | N/A | N/A | 9286 | 9305 | AAAACTTTATTCACTGCAAG | 64 | 1980 |
| 1103555 | N/A | N/A | 8369 | 8388 | ACCTCGAATCTGCAGGTTGG | 130 | 1981 |
| 1103571 | N/A | N/A | 8538 | 8557 | AGTACCCTGGTATGATAGGC | 33 | 1982 |
| 1103587 | N/A | N/A | 8714 | 8733 | GACAAGCAGTTAAAAAAACA | 62 | 1983 |
| 1103603 | N/A | N/A | 4003 | 4022 | TCAGCCCCTTCTGCTCACAA | 58 | 1984 |
| 1103619 | N/A | N/A | 4210 | 4229 | CTTTCCCCAGTAGGGAGGTG | 86 | 1985 |
| 1103635 | N/A | N/A | 4343 | 4362 | TCATGGACATCAACCTTCTC | 87 | 1986 |
| 1103651 | N/A | N/A | 4414 | 4433 | GTCACCTGTGCTTTGCGCCC | 107 | 1987 |
| 1103667 | N/A | N/A | 4568 | 4587 | CATGCATGTCCTGTCAGCTC | 72 | 1988 |
| 1103683 | N/A | N/A | 4646 | 4665 | GGCGCATCCACAAGCATACA | 112 | 1989 |
| 1103699 | N/A | N/A | 4855 | 4874 | TGAGGACACTTGAATACCTG | 67 | 1990 |
| 1103715 | N/A | N/A | 5163 | 5182 | GCTTCCTGGAGTGGCAGGAG | 109* | 1991 |
| 1103731 | N/A | N/A | 5362 | 538 | TCTCCTCTCTCTGAGTGTCT | 69 | 1992 |
| 1103747 | N/A | N/A | 5424 | 5443 | TCTCCCTTAGTGTCTTTCTG | 65 | 1993 |
| 1103763 | N/A | N/A | 5499 | 5518 | GGGTTCCCCACGCCATTGTG | 109 | 1994 |
| 1103779 | N/A | N/A | 5782 | 5801 | CCCCCATTCTCTTGTACAGA | 136 | 1995 |
| 1103795 | N/A | N/A | 5881 | 5900 | AGCAATAGTGCCTGTGTGAC | 69 | 1996 |
| 1103811 | N/A | N/A | 5949 | 5968 | GAACAGAACAGTATCAGCTA | 91 | 1997 |

TABLE 27-continued

| Reduction of GFAP RNA by 5-10-5 MCE gapmers with mixed PO/PS internucleoside linkages in U251 cells | | | | | | | |
|---|---|---|---|---|---|---|---|
| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
| 1103827 | N/A | N/A | 5981 | 6000 | AGTAAGGTAATCCATGAAAA | 109 | 1998 |
| 1103843 | N/A | N/A | 6113 | 6132 | AGGCTCCCAAGTGAGATGTG | 89 | 1999 |
| 1103859 | N/A | N/A | 6214 | 6233 | ATCACACCTTCCAGGTCAGA | 68 | 2000 |
| 1103875 | N/A | N/A | 6271 | 6290 | ATATAAGCTCTGAGCTGTGG | 87 | 2001 |
| 1103891 | N/A | N/A | 6318 | 6337 | TAGCCCAAATGCCCCCTCTA | 101 | 2002 |
| 1103907 | N/A | N/A | 6454 | 6473 | CTCCTCAGCTAGGTGCCCTG | 66 | 2003 |
| 1103923 | N/A | N/A | 6534 | 6553 | CTCCCCTGCCTGCAGGGAGG | 124 | 2004 |
| 1103939 | N/A | N/A | 6975 | 6994 | ATGAACAGTGCCACAGAATC | 124 | 2005 |
| 1103955 | N/A | N/A | 7105 | 7124 | ACCCCAGTTAACCCCAGGAC | 90 | 2006 |
| 1103971 | N/A | N/A | 7339 | 7358 | CGTCCCCGTCCTGCCCTGGC | 93 | 2007 |
| 1103987 | N/A | N/A | 7473 | 7492 | TTTCGAGGCCCGGCCCCCGG | 78 | 2008 |
| 1104003 | N/A | N/A | 7829 | 7848 | AGACTCAGTCCCTGAAGGGA | 89 | 2009 |
| 1104019 | N/A | N/A | 7959 | 7978 | GGCCTAATCAATATTGGTTG | 80 | 2010 |
| 1104035 | N/A | N/A | 8043 | 8062 | GGTGAGGTGAGGAGTCCAAT | 62 | 2011 |
| 1104051 | N/A | N/A | 8116 | 8135 | CATGTCTATCTGAAGGAAGA | 159 | 2012 |
| 1104067 | N/A | N/A | 8283 | 8302 | GGACACCCCTAGGCTGGGTC | 121 | 2013 |
| 1104083 | N/A | N/A | 9384 | 9403 | AAAAAGTAATTTAGCTCCCC | 108 | 2014 |
| 1104099 | N/A | N/A | 9419 | 9438 | CCTTAGCTAAGAATCATTTC | 76 | 2015 |
| 1104115 | N/A | N/A | 9458 | 9477 | GTCCTAAATATTCTAGTCCA | 55 | 2016 |
| 1104131 | N/A | N/A | 9514 | 9533 | CAGCCTGGTTAGCCTTTCTG | 38 | 2017 |
| 1104147 | N/A | N/A | 9539 | 9558 | ATTTGGCAGTATTACCTCTA | 51 | 2018 |
| 1104163 | N/A | N/A | 9563 | 9582 | TTTAGTGACCTGTGACTATC | 108 | 2019 |
| 1104179 | N/A | N/A | 9583 | 9602 | TCTCTGCCATTTATCTGTGC | 48 | 2020 |
| 1104195 | N/A | N/A | 9676 | 9695 | ATTAACTAAAATAAAGGCTG | 90 | 202 |
| 1104211 | N/A | N/A | 9811 | 9830 | CTCAAGAAGTCCCAACTTAG | 83 | 2022 |
| 1104227 | N/A | N/A | 10562 | 10581 | CCAGCACGGTATTGAAATCA | 50 | 2023 |
| 1104243 | N/A | N/A | 10659 | 10678 | TAGTGCTGCTGCCAGAGTCC | 54 | 2024 |
| 1104259 | N/A | N/A | 10777 | 10796 | CTCCCATGCCCGGCTTCCCC | 147 | 2025 |
| 1104275 | N/A | N/A | 10981 | 11000 | TGGCCTGGCCTTGAGAATCC | 108 | 2026 |
| 1104291 | N/A | N/A | 11100 | 11119 | TATGGAGGGACTGAGGAAAC | 107 | 2027 |
| 1104307 | N/A | N/A | 11155 | 11174 | GTGTATTAGGATCCCATCTA | 19 | 2028 |
| 1104323 | N/A | N/A | 11233 | 11252 | GTGAAAGCTACTAACTTTAA | 51 | 2029 |
| 1104339 | N/A | N/A | 11325 | 11344 | ATCCCCTCTTCCCATTCCCC | 128 | 2030 |
| 1104355 | N/A | N/A | 11394 | 11413 | GGCGAGTGGTAAGCTGCTGG | 99 | 2031 |
| 1104371 | N/A | N/A | 11525 | 11544 | CGAGGCTGTGTAACCTTGGG | 99 | 2032 |

TABLE 28

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 14 | 517 |
| 1103156 | 142 | 161 | 3590 | 3609 | CCCAGACGGCGGCCAGGAGC | 113 | 2033 |
| 1103172 | 408 | 427 | 3856 | 3875 | GCAGCTCAGCCTGGTAGACG | 92 | 2034 |
| 1103188 | 582 | 601 | N/A | N/A | CTTCATCTGCTTCCTGTCTA | 23* | 2035 |
| 1103204 | 829 | 848 | N/A | N/A | AACTTGGAGCGGTACCACTC | 106 | 2036 |
| 1103220 | 1249 | 1268 | 10863 | 10882 | TCTGACACAGACTTGGTGTC | 110 | 2037 |
| 1103236 | 1397 | 1416 | 11686 | 11705 | CTGCTCGGGCCCCTCATGAG | 18 | 2038 |
| 1103252 | 1534 | 1553 | 11823 | 11842 | GTCTGGCAGGCCTGATACTG | 84 | 2039 |
| 1103268 | 1682 | 1701 | 11971 | 11990 | GGAGGGCGATGTAGTAGGTG | 31 | 2040 |
| 1103284 | 1798 | 1817 | 12087 | 12106 | CTGAGTCTCAGTTTTCCTCC | 48 | 2041 |
| 1103300 | 1871 | 1890 | 12160 | 12179 | CCTCATAAAAACCAAAAGAC | 76 | 2042 |
| 1103316 | 1891 | 1910 | 12180 | 12199 | GGCAGCATAGGGATATCCCA | 74 | 2043 |
| 1103332 | 2108 | 2127 | 12397 | 12416 | ACTGAGACACTTGAGTCATC | 77 | 2044 |
| 1103348 | 2339 | 2358 | 12628 | 12647 | CAATTGCCTCCTCCTCCATC | 9] | 2045 |
| 1103364 | 2444 | 2463 | 12733 | 12752 | GTTTCAGCATCTTCAAGAGG | 63 | 2046 |
| 1103380 | 2489 | 2508 | 12778 | 12797 | ACAAAGTCATGCCCTGCCCC | 89 | 2047 |
| 1103396 | 2528 | 2547 | 12817 | 12836 | CTGGTATGACACAGCAAGGA | 67 | 2048 |
| 1103412 | 2677 | 2696 | 12966 | 12985 | ATTTTGTGTGTGAGTAAGAA | 49 | 2049 |
| 1103428 | 2752 | 2771 | 13041 | 13060 | GAGCCAGTGTCTTCACTTTG | 38 | 2050 |
| 1103444 | 3014 | 3033 | 13303 | 13322 | GCAGTGCCCTGAAGATTAGC | 88 | 2051 |
| 1103460 | N/A | N/A | 8746 | 8765 | TCCCCGTCTTTGGTGCTTTT | 74 | 2052 |
| 1103476 | N/A | N/A | 8823 | 8842 | CATTTACAATCTGGTGAGCC | 103 | 2053 |
| 1103492 | N/A | N/A | 8981 | 9000 | CCTGGGAAAATGACGCAGTC | 88 | 2054 |
| 1103508 | N/A | N/A | 9103 | 9122 | GCTCAGAGGCCCCAGAGCAG | 117 | 2055 |
| 1103524 | N/A | N/A | 9242 | 9261 | CTCTGAACTGAGTCAGCACT | 93 | 2056 |
| 1103540 | N/A | N/A | 9288 | 9307 | ATAAAACTTTATTCACTGCA | 82 | 2057 |
| 1103556 | N/A | N/A | 8397 | 8416 | GCCCTTCCCACGAGGCCCTG | 102 | 2058 |
| 1103572 | N/A | N/A | 8540 | 8559 | GAAGTACCCTGGTATGATAG | 80 | 2059 |
| 1103588 | N/A | N/A | 8715 | 8734 | TGACAAGCAGTTAAAAAAAC | 98 | 2060 |
| 1103604 | N/A | N/A | 4004 | 4023 | TTCAGCCCCTTCTGCTCACA | 97 | 2061 |
| 1103620 | N/A | N/A | 4212 | 423 | TGCTTTCCCCAGTAGGGAGG | 52 | 2062 |
| 1103636 | N/A | N/A | 4351 | 4370 | AATCTCCCTCATGGACATCA | 102 | 2063 |
| 1103652 | N/A | N/A | 4421 | 4440 | GCAGGCAGTCACCTGTGCTT | 84 | 2064 |
| 1103668 | N/A | N/A | 4576 | 4595 | AAGGCACACATGCATGTCCT | 103 | 2065 |
| 1103684 | N/A | N/A | 4663 | 4682 | CTGCTTCTGCTCACACAGGC | 109 | 2066 |
| 1103700 | N/A | N/A | 4856 | 4875 | CTGAGGACACTTGAATACCT | 120 | 2067 |
| 1103716 | N/A | N/A | 5165 | 5184 | CTGCTTCCTGGAGTGGCAGG | 123* | 2068 |

TABLE 28-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103732 | N/A | N/A | 5363 | 5382 | CTCTCCTCTCTCTGAGTGTC | 100 | 2069 |
| 1103748 | N/A | N/A | 5432 | 5451 | TCTTTCCGTCTCCCTTAGTG | 94 | 2070 |
| 1103764 | N/A | N/A | 5518 | 5537 | AGGGTACAGGCCACAGCTGG | 101 | 2071 |
| 1103780 | N/A | N/A | 5785 | 5804 | CTTCCCCCATTCTCTTGTAC | 106 | 2072 |
| 1103796 | N/A | N/A | 5883 | 5902 | AAAGCAATAGTGCCTGTGTG | 80 | 2073 |
| 1103812 | N/A | N/A | 5950 | 5969 | AGAACAGAACAGTATCAGCT | 96 | 2074 |
| 1103828 | N/A | N/A | 5982 | 6001 | TAGTAAGGTAATCCATGAAA | 110 | 2075 |
| 1103844 | N/A | N/A | 6126 | 6145 | AGGCATGGAATGCAGGCTCC | 103 | 2076 |
| 1103860 | N/A | N/A | 6215 | 6234 | TATCACACCTTCCAGGTCAG | 102 | 2077 |
| 1103876 | N/A | N/A | 6272 | 6291 | CATATAAGCTCTGAGCTGTG | 91 | 2078 |
| 1103892 | N/A | N/A | 6319 | 6338 | CTAGCCCAAATGCCCCCTCT | 103 | 2079 |
| 1103908 | N/A | N/A | 6456 | 6475 | CACTCCTCAGCTAGGTGCCC | 104 | 2080 |
| 1103924 | N/A | N/A | 6535 | 6554 | TCTCCCCTGCCTGCAGGGAG | 111 | 2081 |
| 1103940 | N/A | N/A | 6977 | 6996 | GAATGAACAGTGCCACAGAA | 94 | 2082 |
| 1103956 | N/A | N/A | 7106 | 7125 | CACCCCAGTTAACCCCAGGA | 102 | 2083 |
| 1103972 | N/A | N/A | 7340 | 7359 | CCGTCCCCGTCCTGCCCTGG | 90 | 2084 |
| 1103988 | N/A | N/A | 7474 | 7493 | GTTTCGAGGCCCGGCCCCCG | 117 | 2085 |
| 1104004 | N/A | N/A | 7831 | 7850 | AAAGACTCAGTCCCTGAAGG | 119 | 2086 |
| 1104020 | N/A | N/A | 7960 | 7979 | AGGCCTAATCAATATTGGTT | 112 | 2087 |
| 1104036 | N/A | N/A | 8044 | 8063 | GGGTGAGGTGAGGAGTCCAA | 68 | 2088 |
| 1104052 | N/A | N/A | 8117 | 8136 | GCATGTCTATCTGAAGGAAG | 94 | 2089 |
| 1104068 | N/A | N/A | 8289 | 8308 | TGCCTGGGACACCCCTAGGC | 122 | 2090 |
| 1104084 | N/A | N/A | 9385 | 9404 | TAAAAAGTAATTTAGCTCCC | 91 | 2091 |
| 1104100 | N/A | N/A | 9427 | 9446 | ATTTTGTTCCTTAGCTAAGA | 96 | 2092 |
| 1104116 | N/A | N/A | 9459 | 9478 | GGTCCTAAATATTCTAGTCC | 35 | 2093 |
| 1104132 | N/A | N/A | 9515 | 9534 | TCAGCCTGGTTAGCCTTTCT | 37 | 2094 |
| 1104148 | N/A | N/A | 9540 | 9559 | GATTTGGCAGTATTACCTCT | 52 | 2095 |
| 1104164 | N/A | N/A | 9564 | 9583 | CTTTAGTGACCTGTGACTAT | 84 | 2096 |
| 1104180 | N/A | N/A | 9588 | 9607 | ACTTCTCTCTGCCATTTATC | 110 | 2097 |
| 1104196 | N/A | N/A | 9677 | 9696 | AATTAACTAAAATAAAGGCT | 108 | 2098 |
| 1104212 | N/A | N/A | 9820 | 9839 | AGACCAGAGCTCAAGAAGTC | 119 | 2099 |
| 1104228 | N/A | N/A | 10563 | 10582 | CCCAGCACGGTATTGAAATC | 84 | 2100 |
| 1104244 | N/A | N/A | 10660 | 10679 | ATAGTGCTGCTGCCAGAGTC | 88 | 2101 |
| 1104260 | N/A | N/A | 10779 | 10798 | CTCTCCCATGCCCGGCTTCC | 112 | 2102 |
| 1104276 | N/A | N/A | 10983 | 11002 | CATGGCCTGGCCTTGAGAAT | 31 | 2103 |
| 1104292 | N/A | N/A | 11115 | 11134 | CCCCTTAGAACAGCCTATGG | 111 | 2104 |

TABLE 28-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104308 | N/A | N/A | 11156 | 11175 | TGTGTATTAGGATCCCATCT | 41 | 2105 |
| 1104324 | N/A | N/A | 11234 | 11253 | AGTGAAAGCTACTAACTTTA | 78 | 2106 |
| 1104340 | N/A | N/A | 11326 | 11345 | AATCCCCTCTTCCCATTCCC | 105 | 2107 |
| 1104356 | N/A | N/A | 11396 | 11415 | CTGGCGAGTGGTAAGCTGCT | 91 | 2108 |
| 1104372 | N/A | N/A | 11535 | 11554 | TCCACCACCACGAGGCTGTG | 101 | 2109 |

TABLE 29

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 8 | 517 |
| 1103157 | 158 | 177 | 3606 | 3625 | GAGGCGGGTGCCAGGACCCA | 45 | 2110 |
| 1103173 | 409 | 428 | 3857 | 3876 | CGCAGCTCAGCCTGGTAGAC | 97 | 2111 |
| 1103189 | 636 | 655 | 5225 | 5244 | TCTCCTCCTCCAGCGACTCA | 92 | 2112 |
| 1103205 | 843 | 862 | N/A | N/A | CTGTCAGGTCTGCAAACTTG | 74 | 2113 |
| 1103221 | 1263 | 1282 | 10877 | 10896 | TCTTGAGGTGGCCTTCTGAC | 104 | 2114 |
| 1103237 | 1399 | 1418 | 11688 | 11707 | TTCTGCTCGGGCCCCTCATG | 75 | 2115 |
| 1103253 | 1544 | 1563 | 11833 | 11852 | GGTGGGTGCCGTCTGGCAGG | 34 | 2116 |
| 1103269 | 1683 | 1702 | 11972 | 11991 | TGGAGGGCGATGTAGTAGGT | 58 | 2117 |
| 1103285 | 1800 | 1819 | 12089 | 12108 | GTCTGAGTCTCAGTTTTCCT | 25 | 2118 |
| 1103301 | 1872 | 1891 | 12161 | 12180 | ACCTCATAAAAACCAAAAGA | 116 | 2119 |
| 1103317 | 1893 | 1912 | 12182 | 12201 | TAGGCAGCATAGGGATATCC | 101 | 2120 |
| 1103333 | 2110 | 2129 | 12399 | 12418 | GGACTGAGACACTTGAGTCA | 96 | 2121 |
| 1103349 | 2348 | 2367 | 12637 | 12656 | GCGCCATCCCAATTGCCTCC | 98 | 2122 |
| 1103365 | 2446 | 2465 | 12735 | 12754 | CTGTTTCAGCATCTTCAAGA | 41 | 2123 |
| 1103381 | 2493 | 2512 | 12782 | 12801 | TGGGACAAAGTCATGCCCTG | 105 | 2124 |
| 1103397 | 2530 | 2549 | 12819 | 12838 | GCCTGGTATGACACAGCAAG | 85 | 2125 |
| 1103413 | 2697 | 2716 | 12986 | 13005 | CTACCTAGAATACTGGGTAC | 110 | 2126 |
| 1103429 | 2753 | 2772 | 13042 | 13061 | TGAGCCAGTGTCTTCACTTT | 70 | 2127 |
| 1103445 | 3015 | 3034 | 13304 | 13323 | AGCAGTGCCCTGAAGATTAG | 86 | 2128 |
| 1103461 | N/A | N/A | 8748 | 8767 | TTTCCCCGTCTTTGGTGCTT | 77 | 2129 |
| 1103477 | N/A | N/A | 8824 | 8843 | CCATTTACAATCTGGTGAGC | 61 | 2130 |
| 1103493 | N/A | N/A | 8982 | 9001 | TCCTGGGAAAATGACGCAGT | 114 | 2131 |
| 1103509 | N/A | N/A | 9142 | 9161 | TCCCAGTGACAGGAAGAGGT | 105 | 2132 |
| 1103525 | N/A | N/A | 9245 | 9264 | ATCCTCTGAACTGAGTCAGC | 93 | 2133 |
| 1103541 | N/A | N/A | 9292 | 9311 | GAACATAAAACTTTATTCAC | 110 | 2134 |

TABLE 29-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103557 | N/A | N/A | 8403 | 8422 | TCCAGTGCCCTTCCCACGAG | 104 | 2135 |
| 1103573 | N/A | N/A | 8542 | 8561 | TAGAAGTACCCTGGTATGAT | 110 | 2136 |
| 1103589 | N/A | N/A | 8728 | 8747 | TTGCCCCCTGTAGTGACAAG | 103 | 2137 |
| 1103605 | N/A | N/A | 4005 | 4024 | ATTCAGCCCCTTCTGCTCAC | 106 | 2138 |
| 1103621 | V/A | N/A | 4213 | 4232 | CTGCTTTCCCCAGTAGGGAG | 94 | 2139 |
| 1103637 | N/A | N/A | 4367 | 4386 | CTTCACCCCAGAATCCAATC | 124 | 2140 |
| 1103653 | N/A | N/A | 4423 | 4442 | TGGCAGGCAGTCACCTGTGC | 130 | 2141 |
| 1103669 | N/A | N/A | 4577 | 4596 | GAAGGCACACATGCATGTCC | 103 | 2142 |
| 1103685 | N/A | N/A | 4665 | 4684 | ACCTGCTTCTGCTCACACAG | 96 | 2143 |
| 1103701 | N/A | N/A | 4858 | 4877 | TTCTGAGGACACTTGAATAC | 128 | 2144 |
| 1103717 | N/A | N/A | 5166 | 5185 | TCTGCTTCCTGGAGTGGCAG | 111* | 2145 |
| 1103733 | N/A | N/A | 5364 | 5383 | TCTCTCCTCTCTCTGAGTGT | 100 | 2146 |
| 1103749 | N/A | N/A | 5440 | 5459 | CTCTTGTCTCTTTCCGTCTC | 105 | 2147 |
| 1103765 | N/A | N/A | 5535 | 5554 | AAGCGGTACCAGGGCTCAGG | 62 | 2148 |
| 1103781 | N/A | N/A | 5810 | 5829 | TATTCTCCCAGCTTCCTCCA | 112 | 2149 |
| 1103797 | N/A | N/A | 5888 | 5907 | TTTTGAAAGCAATAGTGCCT | 94 | 2150 |
| 1103813 | N/A | N/A | 5951 | 5970 | TAGAACAGAACAGTATCAGC | 92 | 2151 |
| 1103829 | N/A | N/A | 5989 | 6008 | TACTTCATAGTAAGGTAATC | 112 | 2152 |
| 1103845 | N/A | N/A | 6144 | 6163 | CCCAAAACAGACTGGCAGAG | 79 | 2153 |
| 1103861 | N/A | N/A | 6216 | 6235 | ATATCACACCTTCCAGGTCA | 87 | 2154 |
| 1103877 | N/A | N/A | 6273 | 6292 | ACATATAAGCTCTGAGCTGT | 105 | 2155 |
| 1103893 | N/A | N/A | 6333 | 6352 | CGTGCCTGTCCTGCCTAGCC | 90 | 2156 |
| 1103909 | N/A | N/A | 6457 | 6476 | ACACTCCTCAGCTAGGTGCC | 87 | 2157 |
| 1103925 | N/A | N/A | 6536 | 6555 | TTCTCCCCTGCCTGCAGGGA | 120 | 2158 |
| 1103941 | N/A | N/A | 6978 | 6997 | TGAATGAACAGTGCCACAGA | 112 | 2159 |
| 1103957 | N/A | N/A | 7107 | 7126 | GCACCCCAGTTAACCCCAGG | 93 | 2160 |
| 1103973 | N/A | N/A | 7341 | 7360 | CCCGTCCCCGTCCTGCCCTG | 98 | 2161 |
| 1103989 | N/A | N/A | 7476 | 7495 | AGGTTTCGAGGCCCGGCCCC | 93 | 2162 |
| 1104005 | N/A | N/A | 7851 | 7870 | GATCTGCACACAAGGCTGAA | 99 | 2163 |
| 1104021 | N/A | N/A | 7961 | 7980 | GAGGCCTAATCAATATTGGT | 111 | 2164 |
| 1104037 | N/A | N/A | 8047 | 8066 | GATGGGTGAGGTGAGGAGTC | 40 | 2165 |
| 1104053 | N/A | N/A | 8118 | 8137 | CGCATGTCTATCTGAAGGAA | 90 | 2166 |
| 1104069 | N/A | N/A | 8325 | 8344 | TCCTGAAAGAAAGCAGAGGG | 114 | 2167 |
| 1104085 | N/A | N/A | 9386 | 9405 | GTAAAAAGTAATTTAGCTCC | 127 | 2168 |
| 1104101 | N/A | N/A | 9428 | 9447 | AATTTTGTTCCTTAGCTAAG | 125 | 2169 |
| 1104117 | N/A | N/A | 9460 | 9479 | TGGTCCTAAATATTCTAGTC | 74 | 2170 |

TABLE 29-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104133 | N/A | N/A | 9516 | 9535 | GTCAGCCTGGTTAGCCTTTC | 30 | 2171 |
| 1104149 | N/A | N/A | 9541 | 9560 | GGATTTGGCAGTATTACCTC | 52 | 2172 |
| 1104165 | N/A | N/A | 9565 | 9584 | GCTTTAGTGACCTGTGACTA | 43 | 2173 |
| 1104181 | N/A | N/A | 9589 | 9608 | TACTTCTCTCTGCCATTTAT | 75 | 2174 |
| 1104197 | N/A | N/A | 9678 | 9697 | CAATTAACTAAAATAAAGGC | 130 | 2175 |
| 1104213 | N/A | N/A | 9828 | 9847 | GGATCAGGAGACCAGAGCTC | 118 | 2176 |
| 1104229 | N/A | N/A | 10564 | 10583 | ACCCAGCACGGTATTGAAAT | 105 | 2177 |
| 1104245 | N/A | N/A | 10670 | 10689 | CCAAATCCCAATAGTGCTGC | 80 | 2178 |
| 1104261 | N/A | N/A | 10782 | 10801 | ATCCTCTCCCATGCCCGGCT | 87 | 2179 |
| 1104277 | N/A | N/A | 11006 | 11025 | TGTGCCAGCCCCAGGCTTTC | 125 | 2180 |
| 1104293 | N/A | N/A | 11119 | 11138 | GGCTCCCCTTAGAACAGCCT | 115 | 2181 |
| 1104309 | N/A | N/A | 11158 | 11177 | AGTGTGTATTAGGATCCCAT | 18 | 2182 |
| 1104325 | N/A | N/A | 11235 | 11254 | AAGTGAAAGCTACTAACTTT | 102 | 2183 |
| 1104341 | N/A | N/A | 11327 | 11346 | AAATCCCCTCTTCCCATTCC | 110 | 2184 |
| 1104357 | N/A | N/A | 11428 | 11447 | AGATAACACTGGGAAAGCAT | 97 | 2185 |
| 1104373 | N/A | N/A | 11537 | 11556 | GGTCCACCACCACGAGGCTG | 108 | 2186 |

TABLE 30

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 7 | 517 |
| 1103158 | 206 | 225 | 3654 | 3673 | GGAGAAATCCACCCGGGTCG | 155 | 2187 |
| 1103174 | 410 | 429 | 3858 | 3877 | TCGCAGCTCAGCCTGGTAGA | 127 | 2188 |
| 1103190 | 648 | 667 | 5237 | 5256 | TCAAGAACCGGATCTCCTCC | 63 | 2189 |
| 1103206 | 926 | 945 | 7283 | 7302 | GGTCAAGGACTGCAACTGGC | 96 | 2190 |
| 1103222 | 1270 | 1289 | 10884 | 10903 | ATGTTCCTCTTGAGGTGGCC | 86 | 2191 |
| 1103238 | 1400 | 1419 | 11689 | 11708 | CTTCTGCTCGGGCCCCTCAT | 59 | 2192 |
| 1103254 | 1573 | 1592 | 11862 | 11881 | TTCTTGTTAGTTGGAGTTGC | 33 | 2193 |
| 1103270 | 1686 | 1705 | 11975 | 11994 | ATGTGGAGGGCGATGTAGTA | 49 | 2194 |
| 1103286 | 1809 | 1828 | 12098 | 12117 | CCCTTTCCTGTCTGAGTCTC | 72 | 2195 |
| 1103302 | 1873 | 1892 | 12162 | 12181 | CACCTCATAAAAACCAAAAG | 100 | 2196 |
| 1103318 | 1996 | 2015 | 12285 | 12304 | GAACAACCCTCTGAGCTGGG | 57 | 2197 |
| 1103334 | 2124 | 2143 | 12413 | 12432 | ATGGCAGCTCAGGTGGACTG | 54 | 2198 |
| 1103350 | 2364 | 2383 | 12653 | 12672 | CCTACTTGTATGCCTAGCGC | 75 | 2199 |
| 1103366 | 2447 | 2466 | 12736 | 12755 | CCTGTTTCAGCATCTTCAAG | 42 | 2200 |

TABLE 30-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103382 | 2494 | 2513 | 12783 | 12802 | ATGGGACAAAGTCATGCCCT | 98 | 2201 |
| 1103398 | 2567 | 2586 | 12856 | 12875 | AAGAAGCAGCAGTCCCAGGG | 75 | 2202 |
| 1103414 | 2700 | 2719 | 2989 | 13008 | GCACTACCTAGAATACTGGG | 76 | 2203 |
| 1103430 | 2754 | 2773 | 13043 | 13062 | ATGAGCCAGTGTCTTCACTT | 37 | 2204 |
| 1103446 | 3017 | 3036 | 13306 | 13325 | GCAGCAGTGCCCTGAAGATT | 29 | 2205 |
| 1103462 | N/A | N/A | 8749 | 8768 | TTTTCCCCGTCTTTGGTGCT | 56 | 2206 |
| 1103478 | N/A | N/A | 8825 | 8844 | TCCATTTACAATCTGGTGAG | 41 | 2207 |
| 1103494 | N/A | N/A | 8983 | 9002 | TTCCTGGGAAAATGACGCAG | 97 | 2208 |
| 1103510 | N/A | N/A | 9144 | 9163 | CCTCCCAGTGACAGGAAGAG | 104 | 2209 |
| 1103526 | N/A | N/A | 9246 | 9265 | AATCCTCTGAACTGAGTCAG | 54 | 2210 |
| 1103542 | N/A | N/A | 9293 | 9312 | GGAACATAAAACTTTATTCA | 69 | 2211 |
| 1103558 | N/A | N/A | 8405 | 8424 | ACTCCAGTGCCCTTCCCACG | 27 | 2212 |
| 1103574 | N/A | N/A | 8543 | 8562 | CTAGAAGTACCCTGGTATGA | 95 | 2213 |
| 1103590 | N/A | N/A | 8730 | 8749 | TTTTGCCCCCTGTAGTGACA | 67 | 2214 |
| 1103606 | N/A | N/A | 4038 | 4057 | TCCCTGAGACTTCTCGGGCA | 110 | 2215 |
| 1103622 | N/A | N/A | 4214 | 4233 | ACTGCTTTCCCCAGTAGGGA | 77 | 2216 |
| 1103638 | N/A | N/A | 4371 | 4390 | CTTTCTTCACCCCAGAATCC | 139 | 2217 |
| 1103654 | N/A | N/A | 4424 | 4443 | GTGGCAGGCAGTCACCTGTG | 83 | 2218 |
| 1103670 | N/A | N/A | 4578 | 4597 | TGAAGGCACACATGCATGTC | 105 | 2219 |
| 1103686 | N/A | N/A | 4666 | 4685 | CACCTGCTTCTGCTCACACA | 158 | 2220 |
| 1103702 | N/A | N/A | 4960 | 4979 | CCTGACCTGTCTATAGGCAG | 92* | 2221 |
| 1103718 | N/A | N/A | 5167 | 5186 | ATCTGCTTCCTGGAGTGGCA | 102* | 2222 |
| 1103734 | N/A | N/A | 5365 | 5384 | TTCTCTCCTCTCTCTGAGTG | 102 | 2223 |
| 1103750 | N/A | N/A | 5442 | 5461 | CTCTCTTGTCTCTTTCCGTC | 69 | 2224 |
| 1103766 | N/A | N/A | 5536 | 5555 | GAAGCGGTACCAGGGCTCAG | 95 | 2225 |
| 1103782 | N/A | N/A | 5811 | 5830 | ATATTCTCCCAGCTTCCTCC | 92 | 2226 |
| 1103798 | N/A | N/A | 5893 | 5912 | GGTACTTTTGAAAGCAATAG | 47 | 2227 |
| 1103814 | N/A | N/A | 5955 | 5974 | GGCTTAGAACAGAACAGTAT | 87 | 2228 |
| 1103830 | N/A | N/A | 5996 | 6015 | CAGCACCTACTTCATAGTAA | 54 | 2229 |
| 1103846 | N/A | N/A | 6156 | 6175 | GAGGCTCAGTAACCCAAAAC | 60 | 2230 |
| 1103862 | N/A | N/A | 6217 | 6236 | AATATCACACCTTCCAGGTC | 130 | 2231 |
| 1103878 | N/A | N/A | 6275 | 6294 | CTACATATAAGCTCTGAGCT | 127 | 2232 |
| 1103894 | N/A | N/A | 6369 | 6388 | AGGAATGGCCCTCCCTTCTT | 93 | 2233 |
| 1103910 | N/A | N/A | 6458 | 6477 | CACACTCCTCAGCTAGGTGC | 75 | 2234 |
| 1103926 | N/A | N/A | 6541 | 6560 | GCCCTTTCTCCCCTGCCTGC | 106 | 2235 |
| 1103942 | N/A | N/A | 6980 | 6999 | AATGAATGAACAGTGCCACA | 113 | 2236 |

TABLE 30-continued

Reduction of GFAP RNA by 5-10-5 MCE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103958 | N/A | N/A | 7114 | 7133 | GTGAGCAGCACCCCAGTTAA | 117 | 2237 |
| 1103974 | N/A | N/A | 7345 | 7364 | TCCGCCCGTCCCCGTCCTGC | 119 | 2238 |
| 1103990 | N/A | N/A | 7477 | 7496 | GAGGTTTCGAGGCCCGGCCC | 129 | 2239 |
| 1104006 | N/A | N/A | 7852 | 7871 | GGATCTGCACACAAGGCTGA | 112 | 2240 |
| 1104022 | N/A | N/A | 7962 | 7981 | TGAGGCCTAATCAATATTGG | 96 | 2241 |
| 1104038 | N/A | N/A | 8050 | 8069 | AGAGATGGGTGAGGTGAGGA | 36 | 2242 |
| 1104054 | N/A | N/A | 8140 | 8159 | CTTGAGTGTTATCTGGGAGG | 61 | 2243 |
| 1104070 | N/A | N/A | 8336 | 8355 | GGGAATGGTGATCCTGAAAG | 53 | 2244 |
| 1104086 | N/A | N/A | 9388 | 9407 | AAGTAAAAAGTAATTTAGCT | 87 | 2245 |
| 1104102 | N/A | N/A | 9429 | 9448 | GAATTTTGTTCCTTAGCTAA | 80 | 2246 |
| 1104118 | N/A | N/A | 9477 | 9496 | GAGACATGCATATCTAGTGG | 23 | 2247 |
| 1104134 | N/A | N/A | 9518 | 9537 | TAGTCAGCCTGGTTAGCCTT | 63 | 2248 |
| 1104150 | N/A | N/A | 9547 | 9566 | TATCTAGGATTTGGCAGTAT | 58 | 2249 |
| 1104166 | N/A | N/A | 9567 | 9586 | GTGCTTTAGTGACCTGTGAC | 25 | 2250 |
| 1104182 | N/A | N/A | 9591 | 9610 | CCTACTTCTCTCTGCCATTT | 75 | 2251 |
| 1104198 | N/A | N/A | 9679 | 9698 | ACAATTAACTAAAATAAAGG | 95 | 2252 |
| 1104214 | N/A | N/A | 10003 | 10022 | GTAATCCCCTTACTCGGGAG | 84 | 2253 |
| 1104230 | N/A | N/A | 10565 | 10584 | AACCCAGCACGGTATTGAAA | 117 | 2254 |
| 1104246 | N/A | N/A | 10671 | 10690 | CCCAAATCCCAATAGTGCTG | 59 | 2255 |
| 1104262 | N/A | N/A | 10786 | 10805 | AGCCATCCTCTCCCATGCCC | 130 | 2256 |
| 1104278 | N/A | N/A | 11010 | 11029 | TCTATGTGCCAGCCCCAGGC | 83 | 2257 |
| 1104294 | N/A | N/A | 11120 | 11139 | AGGCTCCCCTTAGAACAGCC | 75 | 2258 |
| 1104310 | N/A | N/A | 11159 | 11178 | GAGTGTGTATTAGGATCCCA | 18 | 2259 |
| 1104326 | N/A | N/A | 11237 | 11256 | GGAAGTGAAAGCTACTAACT | 46 | 2260 |
| 1104342 | N/A | N/A | 11329 | 11348 | CCAAATCCCCTCTTCCCATT | 81 | 2261 |
| 1104358 | N/A | N/A | 11430 | 11449 | TGAGATAACACTGGGAAAGC | 89 | 2262 |
| 1104374 | N/A | N/A | 11543 | 11562 | ACCCCAGGTCCACCACCACG | 101 | 2263 |

TABLE 31

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 7 | 517 |
| 1103159 | 218 | 237 | 3666 | 3685 | TGCCCCAGCCAGGGAGAAAT | 93 | 2264 |
| 1103175 | 411 | 430 | 3859 | 3878 | CTCGCAGCTCAGCCTGGTAG | 69 | 2265 |
| 1103191 | 652 | 671 | 5241 | 5260 | TTCCTCAAGAACCGGATCTC | 79 | 2266 |

TABLE 31-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103207 | 930 | 949 | 7287 | 7306 | CGCAGGTCAAGGACTGCAAC | 84 | 2267 |
| 1103223 | 1271 | 1290 | 10885 | 10904 | GATGTTCCTCTTGAGGTGGC | 94 | 2268 |
| 1103239 | 1401 | 1420 | 11690 | 11709 | GCTTCTGCTCGGGCCCCTCA | 52 | 2269 |
| 1103255 | 1575 | 1594 | 11864 | 11883 | GTTTCTTGTTAGTTGGAGTT | 19 | 2270 |
| 1103271 | 1687 | 1706 | 11976 | 11995 | GATGTGGAGGGCGATGTAGT | 69 | 2271 |
| 1103287 | 1811 | 1830 | 12100 | 12119 | TTCCCTTTCCTGTCTGAGTC | 56 | 2272 |
| 1103303 | 1874 | 1893 | 12163 | 12182 | CCACCTCATAAAAACCAAAA | 89 | 2273 |
| 1103319 | 1997 | 2016 | 12286 | 12305 | AGAACAACCCTCTGAGCTGG | 61 | 2274 |
| 1103335 | 2183 | 2202 | 12472 | 12491 | CAAGTGCTGAGAATCAAGCT | 87 | 2275 |
| 1103351 | 2398 | 2417 | 12687 | 12706 | TCCAGAGGCCAAGTGCAACT | 57 | 2276 |
| 1103367 | 2448 | 2467 | 12737 | 12756 | TCCTGTTTCAGCATCTTCAA | 61 | 2277 |
| 1103383 | 2495 | 2514 | 12784 | 12803 | AATGGGACAAAGTCATGCCC | 88 | 2278 |
| 1103399 | 2629 | 2648 | 12918 | 12937 | AAAAGCAGCCGGTCACTATG | 100 | 2279 |
| 1103415 | 2703 | 2722 | 12992 | 13011 | AGGGCACTACCTAGAATACT | 71 | 2280 |
| 1103431 | 2789 | 2808 | 13078 | 13097 | CAGCCCTGAGCACCCGGCCT | 106 | 2281 |
| 1103447 | 3019 | 3038 | 13308 | 13327 | CAGCAGCAGTGCCCTGAAGA | 38 | 2282 |
| 1103463 | N/A | N/A | 8750 | 8769 | ATTTTCCCCGTCTTTGGTGC | 65 | 2283 |
| 1103479 | N/A | N/A | 8855 | 8874 | GGCAGGCAGCTAACCGCGAG | 80 | 2284 |
| 1103495 | N/A | N/A | 8984 | 9003 | GTTCCTGGGAAAATGACGCA | 89 | 2285 |
| 1103511 | N/A | N/A | 9146 | 9165 | GCCCTCCCAGTGACAGGAAG | 96 | 2286 |
| 1103527 | N/A | N/A | 9249 | 9268 | AAGAATCCTCTGAACTGAGT | 85 | 2287 |
| 1103543 | N/A | N/A | 9294 | 9313 | GGGAACATAAAACTTTATTC | 42 | 2288 |
| 1103559 | N/A | N/A | 8407 | 8426 | GGACTCCAGTGCCCTTCOCA | 90 | 2289 |
| 1103575 | N/A | N/A | 8544 | 8563 | CCTAGAAGTACCCTGGTATG | 64 | 2290 |
| 1103591 | N/A | N/A | 8732 | 8751 | GCTTTTGCCCCCTGTAGTGA | 36 | 2291 |
| 1103607 | N/A | N/A | 4039 | 4058 | CTCCCTGAGACTTCTCGGGC | 129 | 2292 |
| 1103623 | N/A | N/A | 4216 | 4235 | GCACTGCTTTCCCCAGTAGG | 88 | 2293 |
| 1103639 | N/A | N/A | 4372 | 4391 | ACTTTCTTCACCCCAGAATC | 101 | 2294 |
| 1103655 | N/A | N/A | 4456 | 4475 | AGTCAAAGTAACTTGATGGG | 90 | 2295 |
| 1103671 | N/A | N/A | 4579 | 4598 | TTGAAGGCACACATGCATGT | 102 | 2296 |
| 1103687 | N/A | N/A | 4728 | 4747 | AGGATGAGCAGATGTGGGCT | 77 | 2297 |
| 1103703 | N/A | N/A | 4961 | 4980 | CCCTGACCTGTCTATAGGCA | 105* | 2298 |
| 1103719 | N/A | N/A | 5169 | 5188 | TCATCTGCTTCCTGGAGTGG | 49* | 2299 |
| 1103735 | N/A | N/A | 5366 | 5385 | TTTCTCTCCTCTCTCTGAGT | 95 | 2300 |
| 1103751 | N/A | N/A | 5446 | 5465 | AATGCTCTCTTGTCTCTTTC | 83 | 2301 |
| 1103767 | N/A | N/A | 5537 | 5556 | AGAAGCGGTACCAGGGCTCA | 100 | 2302 |

TABLE 31-continued

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| Reduction of GFAP RNA by 5-10-5 MOE gapmers with mixed PO/PS internucleoside linkages in U251 cells | | | | | | | |
| 1103783 | N/A | N/A | 5830 | 5849 | AGTCAGTCACCTGGAGAGGA | 79 | 2303 |
| 1103799 | N/A | N/A | 5898 | 5917 | TAATGGGTACTTTTGAAAGC | 100 | 2304 |
| 1103815 | N/A | N/A | 5956 | 5975 | GGGCTTAGAACAGAACAGTA | 74 | 2305 |
| 1103831 | N/A | N/A | 5997 | 6016 | ACAGCACCTACTTCATAGTA | 113 | 2306 |
| 1103847 | N/A | N/A | 6158 | 6177 | TAGAGGCTCAGTAACCCAAA | 74 | 2307 |
| 1103863 | N/A | N/A | 6218 | 6237 | CAATATCACACCTTCCAGGT | 72 | 2308 |
| 1103879 | N/A | N/A | 6277 | 6296 | CACTACATATAAGCTCTGAG | 93 | 2309 |
| 1103895 | N/A | N/A | 6370 | 6389 | TAGGAATGGCCCTCCCTTCT | 91 | 2310 |
| 1103911 | N/A | N/A | 6461 | 6480 | ACTCACACTCCTCAGCTAGG | 100 | 2311 |
| 1103927 | N/A | N/A | 6546 | 6565 | TAATAGCCCTTTCTCCCCTG | 93 | 2312 |
| 1103943 | N/A | N/A | 6982 | 7001 | CGAATGAATGAACAGTGCCA | 108 | 2313 |
| 1103959 | N/A | N/A | 7120 | 7139 | AGGGAGGTGAGCAGCACCCC | 103 | 2314 |
| 1103975 | N/A | N/A | 7347 | 7366 | GCTCCGCCCGTCCCCGTCCT | 66 | 2315 |
| 1103991 | N/A | N/A | 7478 | 7497 | GGAGGTTTCGAGGCCCGGCC | 117 | 2316 |
| 1104007 | N/A | N/A | 7853 | 7872 | GGGATCTGCACACAAGGCTG | 49 | 2317 |
| 1104023 | N/A | N/A | 7963 | 7982 | TTGAGGCCTAATCAATATTG | 110 | 2318 |
| 1104039 | N/A | N/A | 8052 | 8071 | GAAGAGATGGGTGAGGTGAG | 36 | 2319 |
| 1104055 | N/A | N/A | 8193 | 8212 | CTTTTTCCCCAGCAGCCAAC | 125 | 2320 |
| 1104071 | N/A | N/A | 9325 | 9344 | TCACATTCACTAATATTTAA | 74 | 2321 |
| 1104087 | N/A | N/A | 9389 | 9408 | CAAGTAAAAAGTAATTTAGC | 120 | 2322 |
| 1104103 | N/A | N/A | 9433 | 9452 | AGAGGAATTTTGTTCCTTAG | 98 | 2323 |
| 1104119 | N/A | N/A | 9481 | 9500 | TCCTGAGACATGCATATCTA | 82 | 2324 |
| 1104135 | N/A | N/A | 9520 | 9539 | ACTAGTCAGCCTGGTTAGCC | 66 | 2325 |
| 1104151 | N/A | N/A | 9549 | 9568 | ACTATCTAGGATTTGGCAGT | 36 | 2326 |
| 1104167 | N/A | N/A | 9569 | 9588 | CTGTGCTTTAGTGACCTGTG | 42 | 2327 |
| 1104183 | N/A | N/A | 9636 | 9655 | AGTGCTCAATACACATAGGT | 58 | 2328 |
| 1104199 | N/A | N/A | 9680 | 9699 | GACAATTAACTAAAATAAAG | 87 | 2329 |
| 1104215 | N/A | N/A | 0131 | 10150 | ACTCCGTCGAAAGCAGGCAA | 91 | 2330 |
| 1104231 | N/A | N/A | 10566 | 10585 | AAACCCAGCACGGTATTGAA | 71 | 2331 |
| 1104247 | N/A | N/A | 0694 | 10713 | TCTTCCAAACGGGCTGGAGA | 98 | 2332 |
| 1104263 | N/A | N/A | 10790 | 10809 | CATGAGCCATCCTCTCCCAT | 70 | 2333 |
| 1104279 | N/A | N/A | 11023 | 11042 | TTGCTGGGAACCTTCTATGT | 97 | 2334 |
| 1104295 | N/A | N/A | 11121 | 11140 | AAGGCTCCCCTTAGAACAGC | 64 | 2335 |
| 1104311 | N/A | N/A | 11160 | 11179 | AGAGTGTGTATTAGGATCCC | 31 | 2336 |
| 1104327 | N/A | N/A | 11242 | 11261 | GAGTTGGAAGTGAAAGCTAC | 67 | 2337 |
| 1104343 | N/A | N/A | 11342 | 11361 | CGTGGCGGATACGCCAAATC | 96 | 2338 |
| 1104359 | N/A | N/A | 11431 | 11450 | GTGAGATAACACTGGGAAAG | 65 | 2339 |

TABLE 31-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104375 | N/A | N/A | 11552 | 11571 | TTCACACAGACCCCAGGTCC | 96 | 2340 |

TABLE 32

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 6 | 517 |
| 1103160 | 221 | 240 | 3669 | 3688 | GAGTGCCCCAGCCAGGGAGA | 119 | 2341 |
| 1103176 | 442 | 461 | 3890 | 3909 | GCGGTGAGTTGATCGAGCCG | 86 | 2342 |
| 1103192 | 653 | 672 | 5242 | 5261 | CTTCCTCAAGAACCGGATCT | 81 | 2343 |
| 1103208 | 932 | 951 | 7289 | 7308 | GTCGCAGGTCAAGGACTGCA | 100 | 2344 |
| 1103224 | 1293 | 1312 | 10907 | 10926 | GCATCTCCACGGTCTTCACC | 85 | 2345 |
| 1103240 | 1403 | 1422 | 11692 | 11711 | CTGCTTCTGCTCGGGCCCCT | 80 | 2346 |
| 1103256 | 1577 | 1596 | 11866 | 11885 | GAGTTTCTTGTTAGTTGGAG | 9 | 2347 |
| 1103272 | 1700 | 1719 | 11989 | 12008 | AACAGGAATCAGGGATGTGG | 35 | 2348 |
| 1103288 | 1836 | 1855 | 12125 | 12144 | CCAGGGCTACCTTGTCTGTG | 90 | 2349 |
| 1103304 | 1878 | 1897 | 12167 | 12186 | TATCCCACCTCATAAAAACC | 88 | 2350 |
| 1103320 | 2001 | 2020 | 12290 | 12309 | TAGGAGAACAACCCTCTGAG | 62 | 2351 |
| 1103336 | 2185 | 2204 | 12474 | 12493 | CCCAAGTGCTGAGAATCAAG | 53 | 2352 |
| 1103352 | 2400 | 2419 | 12689 | 12708 | AATCCAGAGGCCAAGTGCAA | 95 | 2353 |
| 1103368 | 2452 | 2471 | 12741 | 12760 | TCTCTCCTGTTTCAGCATCT | 22 | 2354 |
| 1103384 | 2496 | 2515 | 12785 | 12804 | AAATGGGACAAAGTCATGCC | 98 | 2355 |
| 1103400 | 2637 | 2656 | 12926 | 12945 | GCTTAGGGAAAAGCAGCCGG | 51 | 2356 |
| 1103416 | 2704 | 2723 | 12993 | 13012 | TAGGGCACTACCTAGAATAC | 75 | 2357 |
| 1103432 | 2791 | 2810 | 13080 | 13099 | GTCAGCCCTGAGCACCCGGC | 116 | 2358 |
| 1103448 | 3021 | 3040 | 13310 | 13329 | GGCAGCAGCAGTGCCCTGAA | 38 | 2359 |
| 1103464 | N/A | N/A | 8752 | 8771 | TGATTTTCCCCGTCTTTGGT | 58 | 2360 |
| 1103480 | N/A | N/A | 8866 | 8885 | CGTGTCTGAGAGGCAGGCAG | 76 | 2361 |
| 1103496 | N/A | N/A | 8989 | 9008 | CTGCAGTTCCTGGGAAAATG | 70 | 2362 |
| 1103512 | N/A | N/A | 9147 | 9166 | GGCCCTCCCAGTGACAGGAA | 68 | 2363 |
| 1103528 | N/A | N/A | 9250 | 9269 | GAAGAATCCTCTGAACTGAG | 64 | 2364 |
| 1103544 | N/A | N/A | 9295 | 9314 | AGGGAACATAAAACTTTATT | 57 | 2365 |
| 1103560 | N/A | N/A | 8408 | 8427 | AGGACTCCAGTGCCCTTCCC | 57 | 2366 |
| 1103576 | N/A | N/A | 8546 | 8565 | CACCTAGAAGTACCCTGGTA | 101 | 2367 |
| 1103592 | N/A | N/A | 8734 | 8753 | GTGCTTTTGCCCCCTGTAGT | 43 | 2368 |

TABLE 32-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103608 | N/A | N/A | 4040 | 4059 | CCTCCCTGAGACTTCTCGGG | 86 | 2369 |
| 1103624 | N/A | N/A | 4217 | 4236 | TGCACTGCTTTCCCCAGTAG | 102 | 2370 |
| 1103640 | N/A | N/A | 4373 | 4392 | CACTTTCTTCACCCCAGAAT | 135 | 2371 |
| 1103656 | N/A | N/A | 4465 | 4484 | AGCTGTGCAAGTCAAAGTAA | 80 | 2372 |
| 1103672 | N/A | N/A | 4584 | 4603 | TGCACTTGAAGGCACACATG | 59 | 2373 |
| 1103688 | N/A | N/A | 4729 | 4748 | GAGGATGAGCAGATGTGGGC | 65 | 2374 |
| 1103704 | N/A | N/A | 4962 | 4981 | TCCCTGACCTGTCTATAGGC | 95* | 2375 |
| 1103720 | N/A | N/A | 5170 | 5189 | TTCATCTGCTTCCTGGAGTG | 72* | 2376 |
| 1103736 | N/A | N/A | 5381 | 5400 | ACCTGCCAATCTCTGTTTCT | 94 | 2377 |
| 1103752 | N/A | N/A | 5447 | 5466 | GAATGCTCTCTTGTCTCTTT | 54 | 2378 |
| 1103768 | N/A | N/A | 5541 | 5560 | TGAGAGAAGCGGTACCAGGG | 79 | 2379 |
| 1103784 | N/A | N/A | 5832 | 5851 | AAAGTCAGTCACCTGGAGAG | 87 | 2380 |
| 1103800 | N/A | N/A | 5907 | 5926 | CAGTAATAATAATGGGTACT | 67 | 2381 |
| 1103816 | N/A | N/A | 5957 | 5976 | AGGGCTTAGAACAGAACAGT | 50 | 2382 |
| 1103832 | N/A | N/A | 6005 | 6024 | GTCAAAGAACAGCACCTACT | 121 | 2383 |
| 1103848 | N/A | N/A | 6160 | 6179 | GGTAGAGGCTCAGTAACCCA | 68 | 2384 |
| 1103864 | N/A | N/A | 6219 | 6238 | TCAATATCACACCTTCCAGG | 80 | 2385 |
| 1103880 | N/A | N/A | 6278 | 6297 | ACACTACATATAAGCTCTGA | 109 | 2386 |
| 1103896 | N/A | N/A | 6382 | 6401 | TCTGTCCTCCACTAGGAATG | 120 | 2387 |
| 1103912 | N/A | N/A | 6462 | 6481 | CACTCACACTCCTCAGCTAG | 85 | 2388 |
| 1103928 | N/A | N/A | 6554 | 6573 | CTGGGTTCTAATAGCCCTTT | 77 | 2389 |
| 1103944 | N/A | N/A | 6983 | 7002 | GCGAATGAATGAACAGTGCC | 75 | 2390 |
| 1103960 | N/A | N/A | 7122 | 7141 | TCAGGGAGGTGAGCAGCACC | 111 | 2391 |
| 1103976 | N/A | N/A | 7354 | 7373 | CGTCCCTGCTCCGCCCGTCC | 93 | 2392 |
| 1103992 | N/A | N/A | 7504 | 7523 | TCCCGCGGAGCCCCGACCCG | 90 | 2393 |
| 1104008 | N/A | N/A | 7857 | 7876 | GGAAGGGATCTGCACACAAG | 59 | 2394 |
| 1104024 | N/A | N/A | 7965 | 7984 | CCTTGAGGCCTAATCAATAT | 80 | 2395 |
| 1104040 | N/A | N/A | 8053 | 8072 | AGAAGAGATGGGTGAGGTGA | 85 | 2396 |
| 1104056 | N/A | N/A | 8201 | 8220 | TCTCCTAGCTTTTTCCCCAG | 131 | 2397 |
| 1104072 | N/A | N/A | 9327 | 9346 | CGTCACATTCACTAATATTT | 22 | 2398 |
| 1104088 | N/A | N/A | 9395 | 9414 | CCAATGCAAGTAAAAAGTAA | 92 | 2399 |
| 1104104 | N/A | N/A | 9434 | 9453 | AAGAGGAATTTTGTTCCTTA | 72 | 2400 |
| 1104120 | N/A | N/A | 9483 | 9502 | AGTCCTGAGACATGCATATC | 77 | 2401 |
| 1104136 | N/A | N/A | 9521 | 9540 | TACTAGTCAGCCTGGTTAGC | 69 | 2402 |
| 1104152 | N/A | N/A | 9550 | 9569 | GACTATCTAGGATTTGGCAG | 22 | 2403 |
| 1104168 | N/A | N/A | 9570 | 9589 | TCTGTGCTTTAGTGACCTGT | 56 | 2404 |
| 1104184 | N/A | N/A | 9637 | 9656 | TAGTGCTCAATACACATAGG | 58 | 2405 |

TABLE 32-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104200 | N/A | N/A | 9681 | 9700 | AGACAATTAACTAAAATAAA | 85 | 2406 |
| 1104216 | N/A | N/A | 10132 | 10151 | GACTCCGTCGAAAGCAGGCA | 63 | 2407 |
| 1104232 | N/A | N/A | 10570 | 10589 | CTGAAAACCCAGCACGGTAT | 142 | 2408 |
| 1104248 | N/A | N/A | 10695 | 10714 | CTCTTCCAAACGGGCTGGAG | 69 | 2409 |
| 1104264 | N/A | N/A | 10791 | 10810 | GCATGAGCCATCCTCTCCCA | 121 | 2410 |
| 1104280 | N/A | N/A | 11024 | 11043 | GTTGCTGGGAACCTTCTATG | 34 | 2411 |
| 1104296 | N/A | N/A | 11122 | 11141 | CAAGGCTCCCCTTAGAACAG | 56 | 2412 |
| 1104312 | N/A | N/A | 11162 | 11181 | AGAGAGTGTGTATTAGGATC | 37 | 2413 |
| 1104328 | N/A | N/A | 11243 | 11262 | AGAGTTGGAAGTGAAAGCTA | 73 | 2414 |
| 1104344 | N/A | N/A | 11370 | 11389 | AGATGAGCTCCCACTGTGGT | 74 | 2415 |
| 1104360 | N/A | N/A | 11432 | 11451 | GGTGAGATAACACTGGGAAA | 48 | 2416 |
| 1104376 | N/A | N/A | 11553 | 11572 | GTTCACACAGACCCCAGGTC | 96 | 2417 |

TABLE 33

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 5 | 517 |
| 1103161 | 222 | 241 | 3670 | 3689 | TGAGTGCCCCAGCCAGGGAG | 168 | 2418 |
| 1103177 | 443 | 462 | 3891 | 3910 | GGCGGTGAGTTGATCGAGCC | 101 | 2419 |
| 1103193 | 654 | 673 | 5243 | 5262 | TCTTCCTCAAGAACCGGATC | 68 | 2420 |
| 1103209 | 948 | 967 | 7305 | 7324 | CGCGCAGAGACTCCAGGTCG | 112 | 2421 |
| 1103225 | 1295 | 1314 | 10909 | 10928 | CCGCATCTCCACGGTCTTCA | 74 | 2422 |
| 1103241 | 1409 | 1428 | 11698 | 11717 | ACTATCCTGCTTCTGCTCGG | 41 | 2423 |
| 1103257 | 1578 | 1597 | 11867 | 11886 | TGAGTTTCTTGTTAGTTGGA | 24 | 2424 |
| 1103273 | 1702 | 1721 | 11991 | 12010 | ACAACAGGAATCAGGGATGT | 94 | 2425 |
| 1103289 | 1840 | 1859 | 12129 | 12148 | CTGGCCAGGGCTACCTTGTC | 95 | 2426 |
| 1103305 | 1879 | 1898 | 12168 | 12187 | ATATCCCACCTCATAAAAAC | 108 | 2427 |
| 1103321 | 2013 | 2032 | 12302 | 12321 | TCAGGGTCAGTCTAGGAGAA | 63 | 2428 |
| 1103337 | 2189 | 2208 | 12478 | 12497 | ATCCCCCAAGTGCTGAGAAT | 96 | 2429 |
| 1103353 | 2403 | 2422 | 12692 | 12711 | CACAATCCAGAGGCCAAGTG | 70 | 2430 |
| 1103369 | 2453 | 2472 | 12742 | 12761 | TTCTCTCCTGTTTCAGCATC | 32 | 2431 |
| 1103385 | 2497 | 2516 | 12786 | 12805 | GAAATGGGACAAAGTCATGC | 79 | 2432 |
| 1103401 | 2638 | 2657 | 12927 | 12946 | GGCTTAGGGAAAAGCAGCCG | 140 | 2433 |
| 1103417 | 2705 | 2724 | 12994 | 13013 | ATAGGGCACTACCTAGAATA | 117 | 2434 |

TABLE 33-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103433 | 2792 | 2811 | 13081 | 13100 | TGTCAGCCCTGAGCACCCGG | 64 | 2435 |
| 1103449 | 3031 | 3050 | 13320 | 13339 | AGCGACTAAAGGCAGCAGCA | 64 | 2436 |
| 1103465 | N/A | N/A | 8753 | 8772 | GTGATTTTCCCCGTCTTTGG | 26 | 2437 |
| 1103481 | N/A | N/A | 8892 | 8911 | ACTCCCTGTCAAGCTGGGCA | 110 | 2438 |
| 1103497 | N/A | N/A | 8991 | 9010 | CACTGCAGTTCCTGGGAAAA | 92 | 2439 |
| 1103513 | N/A | N/A | 9170 | 9189 | TCCAGGCACAGCGAGACCCA | 121 | 2440 |
| 1103529 | N/A | N/A | 9251 | 9270 | GGAAGAATCCTCTGAACTGA | 86 | 2441 |
| 1103545 | N/A | N/A | 9296 | 9315 | CAGGGAACATAAAACTTTAT | 135 | 2442 |
| 1103561 | N/A | N/A | 8409 | 8428 | CAGGACTCCAGTGCCCTTCC | 97 | 2443 |
| 1103577 | N/A | N/A | 8548 | 8567 | CCCACCTAGAAGTACCCTGG | 72 | 2444 |
| 1103593 | N/A | N/A | 8736 | 8755 | TGGTGCTTTTGCCCCCTGTA | 84 | 2445 |
| 1103609 | N/A | N/A | 4044 | 4063 | GGCCCCTCCCTGAGACTTCT | 161 | 2446 |
| 1103625 | N/A | N/A | 4218 | 4237 | CTGCACTGCTTTCCCCAGTA | 123 | 2447 |
| 1103641 | N/A | N/A | 4381 | 4400 | CTTTCCCTCACTTTCTTCAC | 135 | 2448 |
| 1103657 | N/A | N/A | 4479 | 4498 | GACCACCGCTTCACAGCTGT | 118 | 2449 |
| 1103673 | N/A | N/A | 4594 | 4613 | CATGTCCTCCTGCACTTGAA | 66 | 2450 |
| 1103689 | N/A | N/A | 4745 | 4764 | ACAGAGGACTTGTCTGGAGG | 77 | 2451 |
| 1103705 | N/A | N/A | 4963 | 4982 | CTCCCTGACCTGTCTATAGG | 97* | 2452 |
| 1103721 | N/A | N/A | 5171 | 5190 | CTTCATCTGCTTCCTGGAGT | 78* | 2453 |
| 1103737 | N/A | N/A | 5382 | 5401 | TACCTGCCAATCTCTGTTTC | 79 | 2454 |
| 1103753 | N/A | N/A | 5449 | 5468 | TCGAATGCTCTCTTGTCTCT | 92 | 2455 |
| 1103769 | N/A | N/A | 5543 | 5562 | GGTGAGAGAAGCGGTACCAG | 141 | 2456 |
| 1103785 | N/A | N/A | 5834 | 5853 | TGAAAGTCAGTCACCTGGAG | 102 | 2457 |
| 1103801 | N/A | N/A | 5908 | 5927 | GCAGTAATAATAATGGGTAC | 69 | 2458 |
| 1103817 | N/A | N/A | 5958 | 5977 | CAGGGCTTAGAACAGAACAG | 61 | 2459 |
| 1103833 | N/A | N/A | 6014 | 6033 | CTCTCATCTGTCAAAGAACA | 87 | 2460 |
| 1103849 | N/A | N/A | 6161 | 6180 | TGGTAGAGGCTCAGTAACCC | 60 | 2461 |
| 1103865 | N/A | N/A | 6246 | 6265 | TCTACGGGCACTATGTTTGG | 79 | 2462 |
| 1103881 | N/A | N/A | 6279 | 6298 | CACACTACATATAAGCTCTG | 188 | 2463 |
| 1103897 | N/A | N/A | 6398 | 6417 | TTTTCTGCCTCCAGGCTCTG | 93 | 2464 |
| 1103913 | N/A | N/A | 6469 | 6488 | CTTCTGCCACTCACACTCCT | 101 | 2465 |
| 1103929 | N/A | N/A | 6806 | 6825 | GTCAGTGGCACAATCCCGGG | 76 | 2466 |
| 1103945 | N/A | N/A | 6987 | 7006 | GCAAGCGAATGAATGAACAG | 76 | 2467 |
| 1103961 | N/A | N/A | 7123 | 7142 | ATCAGGGAGGTGAGCAGCAC | 51 | 2468 |
| 1103977 | N/A | N/A | 7360 | 7379 | GGTGGCCGTCCCTGCTCCGC | 89 | 2469 |
| 1103993 | N/A | N/A | 7760 | 7779 | TGATGAGGGCTCACCGGTTC | 77 | 2470 |
| 1104009 | N/A | N/A | 7896 | 7915 | GCTATGTGTGAGGCAGGCAC | 138 | 2471 |

TABLE 33-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104025 | N/A | N/A | 7979 | 7998 | ACCCAAGTCCTTGGCTTGA | 79 | 2472 |
| 1104041 | N/A | N/A | 8054 | 8073 | CAGAAGAGATGGGTGAGGTG | 71 | 2473 |
| 1104057 | N/A | N/A | 8202 | 8221 | ATCTCCTAGCTTTTTCCCCA | 147 | 2474 |
| 1104073 | N/A | N/A | 9345 | 9364 | AGAGAGAAAAATATAACACG | 90 | 2475 |
| 1104089 | N/A | N/A | 9401 | 9420 | TCAGGGCCAATGCAAGTAAA | 53 | 2476 |
| 1104105 | N/A | N/A | 9436 | 9455 | AGAAGAGGAATTTTGTTCCT | 68 | 2477 |
| 1104121 | N/A | N/A | 9484 | 9503 | AAGTCCTGAGACATGCATAT | 64 | 2478 |
| 1104137 | N/A | N/A | 9522 | 9541 | CTACTAGTCAGCCTGGTTAG | 68 | 2479 |
| 1104153 | N/A | N/A | 9551 | 9570 | TGACTATCTAGGATTTGGCA | 38 | 2480 |
| 1104169 | N/A | N/A | 9571 | 9590 | ATCTGTGCTTTAGTGACCTG | 80 | 2481 |
| 1104185 | N/A | N/A | 9638 | 9657 | TTAGTGCTCAATACACATAG | 75 | 2482 |
| 1104201 | N/A | N/A | 9682 | 9701 | GAGACAATTAACTAAAATAA | 86 | 2483 |
| 1104217 | N/A | N/A | 10133 | 10152 | AGACTCCGTCGAAAGCAGGC | 78 | 2484 |
| 1104233 | N/A | N/A | 10571 | 10590 | TCTGAAAACCCAGCACGGTA | 116 | 2485 |
| 1104249 | N/A | N/A | 10696 | 10715 | GCTCTTCCAAACGGGCTGGA | 116 | 2486 |
| 1104265 | N/A | N/A | 10795 | 10814 | CAGGGCATGAGCCATCCTCT | 101 | 2487 |
| 1104281 | N/A | N/A | 11056 | 11075 | CTCCTCCAGAATTCCCTGGG | 140 | 2488 |
| 1104297 | N/A | N/A | 11130 | 11149 | TTTGGTACCAAGGCTCCCCT | 72 | 2489 |
| 1104313 | N/A | N/A | 11178 | 11197 | TTTGAGGGTGAGAAAGAGAG | 82 | 2490 |
| 1104329 | N/A | N/A | 11259 | 11278 | CCCAACTGTGTCTGCTAGAG | 47 | 2491 |
| 1104345 | N/A | N/A | 11371 | 11390 | AAGATGAGCTCCCACTGTGG | 111 | 2492 |
| 1104361 | N/A | N/A | 11434 | 11453 | GTGGTGAGATAACACTGGGA | 43 | 2493 |
| 1104377 | N/A | N/A | 11557 | 11576 | AGGAGTTCACACAGACCCCA | 92 | 2494 |

TABLE 34

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 6 | 517 |
| 1103162 | 224 | 243 | 3672 | 3691 | ATTGAGTGCCCCAGCCAGGG | 94 | 2495 |
| 1103178 | 468 | 487 | 3916 | 3935 | TCTCAACCTCCAGCCGGGCG | 23* | 2496 |
| 1103194 | 687 | 706 | 5573 | 5592 | GCTCCTGGAGTTCCCGAACC | 139 | 2497 |
| 1103210 | 949 | 968 | 7306 | 7325 | CCGCGCAGAGACTCCAGGTC | 98 | 2498 |
| 1103226 | 1316 | 1335 | N/A | N/A | CTCCTTAATGACCTCTCCAT | 95 | 2499 |
| 1103242 | 1419 | 1438 | 11708 | 11727 | AGGCGGAGCAACTATCCTGC | 150 | 2500 |

TABLE 34-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103258 | 1579 | 1598 | 11868 | 11887 | GTGAGTTTCTTGTTAGTTGG | 35 | 2501 |
| 1103274 | 1706 | 1725 | 11995 | 12014 | CATAACAACAGGAATCAGGG | 49 | 2502 |
| 1103290 | 1846 | 1865 | 12135 | 12154 | AAGCCTCTGGCCAGGGCTAC | 113 | 2503 |
| 1103306 | 1880 | 1899 | 12169 | 12188 | GATATCCCACCTCATAAAAA | 98 | 2504 |
| 1103322 | 2015 | 2034 | 12304 | 12323 | GATCAGGGTCAGTCTAGGAG | 46 | 2505 |
| 1103338 | 2196 | 2215 | 12485 | 12504 | ACAACAGATCCCCCAAGTGC | 89 | 2506 |
| 1103354 | 2405 | 2424 | 12694 | 12713 | CCCACAATCCAGAGGCCAAG | 79 | 2507 |
| 1103370 | 2454 | 2473 | 12743 | 12762 | TTTCTCTCCTGTTTCAGCAT | 31 | 2508 |
| 1103386 | 2498 | 2517 | 12787 | 12806 | AGAAATGGGACAAAGTCATG | 102 | 2509 |
| 1103402 | 2643 | 2662 | 12932 | 12951 | CCCTTGGCTTAGGGAAAAGC | 102 | 2510 |
| 1103418 | 2706 | 2725 | 12995 | 13014 | AATAGGGCACTACCTAGAAT | 130 | 2511 |
| 1103434 | 2793 | 2812 | 13082 | 13101 | GTGTCAGCCCTGAGCACCCG | 73 | 2512 |
| 1103450 | 3032 | 3051 | 13321 | 13340 | CAGCGACTAAAGGCAGCAGC | 76 | 2513 |
| 1103466 | N/A | N/A | 8759 | 8778 | GACCTTGTGATTTTCCCCGT | 55 | 2514 |
| 1103482 | N/A | N/A | 8893 | 8912 | CACTCCCTGTCAAGCTGGGC | 112 | 2515 |
| 1103498 | N/A | N/A | 9028 | 9047 | TAATGTACAGTTACTCTGTA | 80 | 2516 |
| 1103514 | N/A | N/A | 9206 | 9225 | CCTCAGGGATGAAAGAATAA | 56 | 2517 |
| 1103530 | N/A | N/A | 9252 | 9271 | GGGAAGAATCCTCTGAACTG | 83 | 2518 |
| 1103546 | N/A | N/A | 9297 | 9316 | GCAGGGAACATAAAACTTTA | 132 | 2519 |
| 1103562 | N/A | N/A | 8441 | 8460 | CTGGAGCAACCTACAGGCCC | 103 | 2520 |
| 1103578 | N/A | N/A | 8550 | 8569 | GCCCCACCTAGAAGTACCCT | 83 | 2521 |
| 1103594 | N/A | N/A | 8738 | 8757 | TTTGGTGCTTTTGCCCCCTG | 76 | 2522 |
| 1103610 | N/A | N/A | 4045 | 4064 | CGGCCCCTCCCTGAGACTTC | 92 | 2523 |
| 1103626 | N/A | N/A | 4219 | 4238 | CCTGCACTGCTTTCCCCAGT | 124 | 2524 |
| 1103642 | N/A | N/A | 4384 | 4403 | GCTCTTTCCCTCACTTTCTT | 111 | 2525 |
| 1103658 | N/A | N/A | 4480 | 4499 | TGACCACCGCTTCACAGCTG | 66 | 2526 |
| 1103674 | N/A | N/A | 4598 | 4617 | CGCACATGTCCTCCTGCACT | 122 | 2527 |
| 1103690 | N/A | N/A | 4746 | 4765 | GACAGAGGACTTGTCTGGAG | 69 | 2528 |
| 1103706 | N/A | N/A | 4966 | 4985 | CACCTCCCTGACCTGTCTAT | 165* | 2529 |
| 1103722 | N/A | N/A | 5173 | 5192 | GGCTTCATCTGCTTCCTGGA | 11* | 2530 |
| 1103738 | N/A | N/A | 5390 | 5409 | CCTGTCTCTACCTGCCAATC | 93 | 2531 |
| 1103754 | N/A | N/A | 5456 | 5475 | CAGGAGTTCGAATGCTCTCT | 77 | 2532 |
| 1103770 | N/A | N/A | 5555 | 5574 | CCTCCTGACCAGGGTGAGAG | 91 | 2533 |
| 1103786 | N/A | N/A | 5838 | 5857 | CTGGTGAAAGTCAGTCACCT | 84 | 2534 |
| 1103802 | N/A | N/A | 5909 | 5928 | AGCAGTAATAATAATGGGTA | 122 | 2535 |
| 1103818 | N/A | N/A | 5960 | 5979 | CACAGGGCTTAGAACAGAAC | 101 | 2536 |
| 1103834 | N/A | N/A | 6015 | 6034 | TCTCTCATCTGTCAAAGAAC | 81 | 2537 |

TABLE 34-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103850 | N/A | N/A | 6162 | 6181 | ATGGTAGAGGCTCAGTAACC | 66 | 2538 |
| 1103866 | N/A | N/A | 6247 | 6266 | CTCTACGGGCACTATGTTTG | 72 | 2539 |
| 1103882 | N/A | N/A | 6286 | 6305 | TGGCTCCCACACTACATATA | 89 | 2540 |
| 1103898 | N/A | N/A | 6401 | 6420 | TGCTTTTCTGCCTCCAGGCT | 82 | 2541 |
| 1103914 | N/A | N/A | 6476 | 6495 | CCAGTGGCTTCTGCCACTCA | 92 | 2542 |
| 1103930 | N/A | N/A | 6898 | 6917 | AGCGGAGGCCTGGGTGTTTT | 74 | 2543 |
| 1103946 | N/A | N/A | 6988 | 7007 | AGCAAGCGAATGAATGAACA | 116 | 2544 |
| 1103962 | N/A | N/A | 7124 | 7143 | AATCAGGGAGGTGAGCAGCA | 71 | 2545 |
| 1103978 | N/A | N/A | 7384 | 7403 | CCCTTCTCCCCTGGCATCTC | 130 | 2546 |
| 1103994 | N/A | N/A | 7792 | 7811 | GTGAGGCAGCAGGGAGACTT | 80 | 2547 |
| 1104010 | N/A | N/A | 7904 | 7923 | GACTGCCTGCTATGTGTGAG | 118 | 2548 |
| 1104026 | N/A | N/A | 7981 | 8000 | TGACCCAAGTCCTTGGCCTT | 109 | 2549 |
| 1104042 | N/A | N/A | 8056 | 8075 | GGCAGAAGAGATGGGTGAGG | 75 | 2550 |
| 1104058 | N/A | N/A | 8207 | 8226 | ACTCCATCTCCTAGCTTTTT | 95 | 2551 |
| 1104074 | N/A | N/A | 9347 | 9366 | CGAGAGAGAAAAATATAACA | 129 | 2552 |
| 1104090 | N/A | N/A | 9403 | 9422 | TTTCAGGGCCAATGCAAGTA | 49 | 2553 |
| 1104106 | N/A | N/A | 9447 | 9466 | TCTAGTCCAGAAGAAGAGGA | 76 | 2554 |
| 1104122 | N/A | N/A | 9494 | 9513 | ATGCTGAATTAAGTCCTGAG | 38 | 2555 |
| 1104138 | N/A | N/A | 9523 | 9542 | TCTACTAGTCAGCCTGGTTA | 68 | 2556 |
| 1104154 | N/A | N/A | 9553 | 9572 | TGTGACTATCTAGGATTTGG | 68 | 2557 |
| 1104170 | N/A | N/A | 9572 | 9591 | TATCTGTGCTTTAGTGACCT | 53 | 2558 |
| 1104186 | N/A | N/A | 9639 | 9658 | ATTAGTGCTCAATACACATA | 101 | 2559 |
| 1104202 | N/A | N/A | 9683 | 9702 | GGAGACAATTAACTAAAATA | 94 | 2560 |
| 1104218 | N/A | N/A | 10135 | 10154 | TAAGACTCCGTCGAAAGCAG | 131 | 2561 |
| 1104234 | N/A | N/A | 10572 | 10591 | TTCTGAAAACCCAGCACGGT | 110 | 2562 |
| 1104250 | N/A | N/A | 10708 | 10727 | GAGAGAGCCTAGGCTCTTCC | 70 | 2563 |
| 1104266 | N/A | N/A | 10796 | 10815 | TCAGGGCATGAGCCATCCTC | 60 | 2564 |
| 1104282 | N/A | N/A | 11065 | 11084 | TTCCTTGCTCTCCTCCAGAA | 156 | 2565 |
| 1104298 | N/A | N/A | 11144 | 11163 | TCCCATCTAGTGGCTTTGGT | 48 | 2566 |
| 1104314 | N/A | N/A | 11212 | 11231 | TCTCTTTCTCTCCCTGGCAA | 74 | 2567 |
| 1104330 | N/A | N/A | 11264 | 11283 | CCATCCCCAACTGTGTCTGC | 64 | 2568 |
| 1104346 | N/A | N/A | 11381 | 11400 | CTGCTGGAGTAAGATGAGCT | 99 | 2569 |
| 1104362 | N/A | N/A | 11478 | 11497 | TTCTTGATAGTAACCACAGC | 53 | 2570 |
| 1104378 | N/A | N/A | 11558 | 11577 | TAGGAGTTCACACAGACCCC | 164 | 2571 |

TABLE 35

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 8 | 517 |
| 1103163 | 233 | 252 | 3681 | 3700 | GAAGCCAGCATTGAGTGCCC | 109 | 2572 |
| 1103179 | 484 | 503 | 3932 | 3951 | TGTGCCAGATTGTCCCTCTC | 13* | 2573 |
| 1103195 | 713 | 732 | 5599 | 5618 | CACATGGACCTGCTGTCGGG | 107 | 2574 |
| 1103211 | 951 | 970 | 7308 | 7327 | TGCCGCGCAGAGACTCCAGG | 90 | 2575 |
| 1103227 | 1317 | 1336 | N/A | N/A | ACTCCTTAATGACCTCTCCA | 151 | 2576 |
| 1103243 | 1434 | 1453 | 11723 | 11742 | GAAATGTGCCAGCAGAGGCG | 96 | 2577 |
| 1103259 | 1581 | 1600 | 11870 | 11889 | GGGTGAGTTTCTTGTTAGTT | 15 | 2578 |
| 1103275 | 1712 | 1731 | 12001 | 12020 | AGTTTCCATAACAACAGGAA | 91 | 2579 |
| 1103291 | 1851 | 1870 | 12140 | 12159 | AAAACAAGCCTCTGGCCAGG | 115 | 2580 |
| 1103307 | 1881 | 1900 | 12170 | 12189 | GGATATCCCACCTCATAAAA | 107 | 2581 |
| 1103323 | 2030 | 2049 | 12319 | 12338 | CACCCATCTTAGACTGATCA | 116 | 2582 |
| 1103339 | 2197 | 2216 | 12486 | 12505 | CACAACAGATCCCCCAAGTG | 110 | 2583 |
| 1103355 | 2409 | 2428 | 12698 | 12717 | AATTCCCACAATCCAGAGGC | 72 | 2584 |
| 1103371 | 2455 | 2474 | 12744 | 12763 | CTTTCTCTCCTGTTTCAGCA | 20 | 2585 |
| 1103387 | 2506 | 2525 | 12795 | 12814 | AGGCCTTTAGAAATGGGACA | 76 | 2586 |
| 1103403 | 2656 | 2675 | 12945 | 12964 | GGACCGCAAGAGGCCCTTGG | 83 | 2587 |
| 1103419 | 2707 | 2726 | 12996 | 13015 | AAATAGGGCACTACCTAGAA | 100 | 2588 |
| 1103435 | 2831 | 2850 | 13120 | 13139 | CTGCTCAGTCAAAGCAGAGT | 99 | 2589 |
| 1103467 | N/A | N/A | 8765 | 8784 | TCTTGTGACCTTGTGATTTT | 55 | 2590 |
| 1103483 | N/A | N/A | 8894 | 8913 | TCACTCCCTGTCAAGCTGGG | 130 | 2591 |
| 1103499 | N/A | N/A | 9029 | 9048 | TTAATGTACAGTTACTCTGT | 98 | 2592 |
| 1103515 | N/A | N/A | 9214 | 9233 | CGATGGAGCCTCAGGGATGA | 57 | 2593 |
| 1103531 | N/A | N/A | 9253 | 9272 | AGGGAAGAATCCTCTGAACT | 59 | 2594 |
| 1103547 | N/A | N/A | 9298 | 9317 | AGCAGGGAACATAAAACTTT | 79 | 2595 |
| 1103563 | N/A | N/A | 8458 | 8477 | TGATCCTCAGTCCCAGTCTG | 95 | 2596 |
| 1103579 | N/A | N/A | 8552 | 8571 | AAGCCCCACCTAGAAGTACC | 131 | 2597 |
| 1103595 | N/A | N/A | 3965 | 3984 | CCTCCTCACTTCTGCCTCAC | 77* | 2598 |
| 1103611 | N/A | N/A | 4046 | 4065 | TCGGCCCCTCCCTGAGACTT | 74 | 2599 |
| 1103627 | N/A | N/A | 4220 | 4239 | TCCTGCACTGCTTTCCCCAG | 80 | 2600 |
| 1103643 | N/A | N/A | 4385 | 4404 | TGCTCTTTCCCTCACTTTCT | 119 | 2601 |
| 1103659 | N/A | N/A | 4484 | 4503 | ATTATGACCACCGCTTCACA | 54 | 2602 |
| 1103675 | N/A | N/A | 4603 | 4622 | ACACACGCACATGTCCTCCT | 157 | 2603 |
| 1103691 | N/A | N/A | 4751 | 4770 | CCTTAGACAGAGGACTTGTC | 90 | 2604 |
| 1103707 | N/A | N/A | 4967 | 4986 | CCACCTCCCTGACCTGTCTA | 102* | 2605 |
| 1103723 | N/A | N/A | 5301 | 5320 | AGTTGCAATCTCTGTGTTGA | 105 | 2606 |
| 1103739 | N/A | N/A | 5391 | 5410 | TCCTGTCTCTACCTGCCAAT | 81 | 2607 |

TABLE 35-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103755 | N/A | N/A | 5457 | 5476 | CCAGGAGTTCGAATGCTCTC | 97 | 2608 |
| 1103771 | N/A | N/A | 5557 | 5576 | AACCTCCTGACCAGGGTGAG | 87 | 2609 |
| 1103787 | N/A | N/A | 5839 | 5858 | TCTGGTGAAAGTCAGTCACC | 99 | 2610 |
| 1103803 | N/A | N/A | 5910 | 5929 | TAGCAGTAATAATAATGGGT | 53 | 2611 |
| 1103819 | N/A | N/A | 5967 | 5986 | TGAAAAGCACAGGGCTTAGA | 118 | 2612 |
| 1103835 | N/A | N/A | 6016 | 6035 | CTCTCTCATCTGTCAAAGAA | 64 | 2613 |
| 1103851 | N/A | N/A | 6164 | 6183 | ATATGGTAGAGGCTCAGTAA | 70 | 2614 |
| 1103867 | N/A | N/A | 6253 | 6272 | GGTGTTCTCTACGGGCACTA | 87 | 2615 |
| 1103883 | N/A | N/A | 6289 | 6308 | TCCTGGCTCCCACACTACAT | 109 | 2616 |
| 1103899 | N/A | N/A | 6402 | 6421 | GTGCTTTTCTGCCTCCAGGC | 32 | 2617 |
| 1103915 | N/A | N/A | 6489 | 6508 | CCCTGCTCAGACACCAGTGG | 157 | 2618 |
| 1103931 | N/A | N/A | 6899 | 6918 | GAGCGGAGGCCTGGGTGTTT | 123 | 2619 |
| 1103947 | N/A | N/A | 7005 | 7024 | TAGCACAACACCTGGTCAGC | 92 | 2620 |
| 1103963 | N/A | N/A | 7127 | 7146 | GGAAATCAGGGAGGTGAGCA | 58 | 2621 |
| 1103979 | N/A | N/A | 7385 | 7404 | GCCCTTCTCCCCTGGCATCT | 83 | 2622 |
| 1103995 | N/A | N/A | 7799 | 7818 | CTCTACCGTGAGGCAGCAGG | 97 | 2623 |
| 1104011 | N/A | N/A | 7909 | 7928 | CTAGTGACTGCCTGCTATGT | 112 | 2624 |
| 1104027 | N/A | N/A | 8007 | 8026 | GGGAGTATGCCTCTTAGTTT | 55 | 2625 |
| 1104043 | N/A | N/A | 8071 | 8090 | AGAAAGTTOCAAGGAGGCAG | 112 | 2626 |
| 1104059 | N/A | N/A | 8208 | 8227 | AACTCCATCTCCTAGCTTTT | 85 | 2627 |
| 1104075 | N/A | N/A | 9348 | 9367 | CCGAGAGAGAAAAATATAAC | 66 | 2628 |
| 1104091 | N/A | N/A | 9404 | 9423 | ATTTCAGGGCCAATGCAAGT | 85 | 2629 |
| 1104107 | N/A | N/A | 9448 | 9467 | TTCTAGTCCAGAAGAAGAGG | 72 | 2630 |
| 1104123 | N/A | N/A | 9495 | 9514 | GATGCTGAATTAAGTCCTGA | 41 | 2631 |
| 1104139 | N/A | N/A | 9527 | 9546 | TACCTCTACTAGTCAGCCTG | 78 | 2632 |
| 1104155 | N/A | N/A | 9554 | 9573 | CTGTGACTATCTAGGATTTG | 70 | 2633 |
| 1104171 | N/A | N/A | 9573 | 9592 | TTATCTGTGCTTTAGTGACC | 54 | 2634 |
| 1104187 | N/A | N/A | 9642 | 9661 | CATATTAGTGCTCAATACAC | 59 | 2635 |
| 1104203 | N/A | N/A | 9703 | 9722 | ACTTCTCTAGGTGGGAGAGA | 58 | 2636 |
| 1104219 | N/A | N/A | 10136 | 10155 | GTAAGACTCCGTCGAAAGCA | 99 | 2637 |
| 1104235 | N/A | N/A | 10573 | 10592 | TTTCTGAAAACCCAGCACGG | 132 | 2638 |
| 1104251 | N/A | N/A | 10730 | 10749 | TGAGAACCTATGCAACCGAG | 62 | 2639 |
| 1104267 | N/A | N/A | 10798 | 10817 | TTTCAGGGCATGAGCCATCC | 140 | 2640 |
| 1104283 | N/A | N/A | 11070 | 11089 | TCAGTTTCCTTGCTCTCCTC | 82 | 2641 |
| 1104299 | N/A | N/A | 11146 | 11165 | GATCCCATCTAGTGGCTTTG | 39 | 2642 |
| 1104315 | N/A | N/A | 11213 | 11232 | TTCTCTTTCTCTCCCTGGCA | 85 | 2643 |

TABLE 35-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104331 | N/A | N/A | 11265 | 11284 | CCCATCCCCAACTGTGTCTG | 73 | 2644 |
| 1104347 | N/A | N/A | 11384 | 11403 | AAGCTGCTGGAGTAAGATGA | 122 | 2645 |
| 1104363 | N/A | N/A | 11483 | 11502 | TACTTTTCTTGATAGTAACC | 74 | 2646 |
| 1104379 | N/A | N/A | 11559 | 11578 | TTAGGAGTTCACACAGACCC | 85 | 2647 |

TABLE 36

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 13336 | 13355 | GTCTTTATTTTTCCTCAGCG | 10 | 517 |
| 1103164 | 254 | 273 | 3702 | 3721 | CTCACTGGCCCGGGTCTCCT | 133 | 2648 |
| 1103180 | 485 | 504 | 3933 | 3952 | CTGTGCCAGATTGTCCCTCT | 16* | 2649 |
| 1103196 | 714 | 733 | 5600 | 5619 | CCACATGGACCTGCTGTCGG | 121 | 2650 |
| 1103212 | 1046 | 1065 | 7618 | 7637 | TTCCTCCAGCCGCGCCAGCG | 135 | 2651 |
| 1103228 | 1324 | 1343 | 11613 | 11632 | TGCTTGGACTCCTTAATGAC | 97 | 2652 |
| 1103244 | 1436 | 1455 | 11725 | 11744 | GGGAAATGTGCCAGCAGAGG | 39 | 2653 |
| 1103260 | 1601 | 1620 | 11890 | 11909 | CCCTCCAGACTGCCCCTTGG | 95 | 2654 |
| 1103276 | 1726 | 1745 | 12015 | 12034 | CCATCTCTGGCAACAGTTTC | 71 | 2655 |
| 1103292 | 1856 | 1875 | 12145 | 12164 | AAGACAAAACAAGCCTCTGG | 88 | 2656 |
| 1103308 | 1882 | 1901 | 12171 | 12190 | GGGATATCCCACCTCATAAA | 88 | 2657 |
| 1103324 | 2031 | 2050 | 12320 | 12339 | CCACCCATCTTAGACTGATC | 100 | 2658 |
| 1103340 | 2198 | 2217 | 12487 | 12506 | ACACAACAGATCCCCCAAGT | 90 | 2659 |
| 1103356 | 2410 | 2429 | 12699 | 12718 | TAATTCCCACAATCCAGAGG | 115 | 2660 |
| 1103372 | 2459 | 2478 | 12748 | 12767 | TCCCCTTTCTCTCCTGTTTC | 101 | 2661 |
| 1103388 | 2508 | 2527 | 12797 | 12816 | AGAGGCCTTTAGAAATGGGA | 102 | 2662 |
| 1103404 | 2662 | 2681 | 12951 | 12970 | AAGAAGGGACCGCAAGAGGC | 83 | 2663 |
| 1103420 | 2715 | 2734 | 13004 | 13023 | CAATTGTAAAATAGGGCACT | 115 | 2664 |
| 1103436 | 2835 | 2854 | 13124 | 13143 | CAGTCTGCTCAGTCAAAGCA | 121 | 2665 |
| 1103468 | N/A | N/A | 8766 | 8785 | ATCTTGTGACCTTGTGATTT | 75 | 2666 |
| 1103484 | N/A | N/A | 8895 | 8914 | CTCACTCCCTGTCAAGCTGG | 98 | 2667 |
| 1103500 | N/A | N/A | 9033 | 9052 | CAGTTTAATGTACAGTTACT | 90 | 2668 |
| 1103516 | N/A | N/A | 9215 | 9234 | GCGATGGAGCCTCAGGGATG | 28 | 2669 |
| 1103532 | N/A | N/A | 9254 | 9273 | GAGGGAAGAATCCTCTGAAC | 86 | 2670 |
| 1103548 | N/A | N/A | 9305 | 9324 | CATTAAGAGCAGGGAACATA | 85 | 2671 |
| 1103564 | N/A | N/A | 8492 | 8511 | GAAGGCCCCCAGGGAGAGCT | 72 | 2672 |
| 1103580 | N/A | N/A | 8553 | 8572 | CAAGCCCCACCTAGAAGTAC | 107 | 2673 |

TABLE 36-continued

| Reduction of GFAP RNA by 5-10-5 MOE gapmers with mixed PO/PS internucleoside linkages in U251 cells | | | | | | | |
|---|---|---|---|---|---|---|---|
| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
| 1103596 | N/A | N/A | 3966 | 3985 | CCCTCCTCACTTCTGCCTCA | 98* | 2674 |
| 1103612 | N/A | N/A | 4047 | 4066 | TTCGGCCCCTCCCTGAGACT | 77 | 2675 |
| 1103628 | N/A | N/A | 4227 | 4246 | CCGCTGCTCCTGCACTGCTT | 123 | 2676 |
| 1103644 | N/A | N/A | 4387 | 4406 | CCTGCTCTTTCCCTCACTTT | 110 | 2677 |
| 1103660 | N/A | N/A | 4485 | 4504 | TATTATGACCACCGCTTCAC | 85 | 2678 |
| 1103676 | N/A | N/A | 4604 | 4623 | CACACACGCACATGTCCTCC | 106 | 2679 |
| 1103692 | N/A | N/A | 4754 | 4773 | GGGCCTTAGACAGAGGACTT | 97 | 2680 |
| 1103708 | N/A | N/A | 4970 | 4989 | CCTCCACCTCCCTGACCTGT | 91* | 2681 |
| 1103724 | N/A | N/A | 5302 | 5321 | CAGTTGCAATCTCTGTGTTG | 127 | 2682 |
| 1103740 | N/A | N/A | 5392 | 5411 | TTCCTGTCTCTACCTGCCAA | 153 | 2683 |
| 1103756 | N/A | N/A | 5475 | 5494 | CTTCTGCCTGCCCCTCGGCC | 109 | 2684 |
| 1103772 | N/A | N/A | 5558 | 5577 | GAACCTCCTGACCAGGGTGA | 116 | 2685 |
| 1103788 | N/A | N/A | 5840 | 5859 | CTCTGGTGAAAGTCAGTCAC | 112 | 2686 |
| 1103804 | N/A | N/A | 5911 | 5930 | GTAGCAGTAATAATAATGGG | 93 | 2687 |
| 1103820 | N/A | N/A | 5969 | 5988 | CATGAAAAGCACAGGGCTTA | 94 | 2688 |
| 1103836 | N/A | N/A | 6017 | 6036 | GCTCTCTCATCTGTCAAAGA | 59 | 2689 |
| 1103852 | N/A | N/A | 6197 | 6216 | AGACACCTCTCTGTGTCCTG | 60 | 2690 |
| 1103868 | N/A | N/A | 6255 | 6274 | GTGGTGTTCTCTACGGGCAC | 95 | 2691 |
| 1103884 | N/A | N/A | 6308 | 6327 | GCCCCCTCTACAGTGTCTTT | 85 | 2692 |
| 1103900 | N/A | N/A | 6405 | 6424 | TCTGTGCTTTTCTGCCTCCA | 59 | 2693 |
| 1103916 | N/A | N/A | 6493 | 6512 | CTCACCCTGCTCAGACACCA | 105 | 2694 |
| 1103932 | N/A | N/A | 6900 | 6919 | CGAGCGGAGGCCTGGGTGTT | 59 | 2695 |
| 1103948 | N/A | N/A | 7006 | 7025 | CTAGCACAACACCTGGTCAG | 106 | 2696 |
| 1103964 | N/A | N/A | 7195 | 7214 | AGGTCTGCAAACTAGGTGGG | 93 | 2697 |
| 1103980 | N/A | N/A | 7414 | 7433 | CCCGCCCTCGACCCAGGTCC | 121 | 2698 |
| 1103996 | N/A | N/A | 7802 | 7821 | GAGCTCTACCGTGAGGCAGC | 101 | 2699 |
| 1104012 | N/A | N/A | 7911 | 7930 | ATCTAGTGACTGCCTGCTAT | 95 | 2700 |
| 1104028 | N/A | N/A | 8031 | 8050 | AGTCCAATCTTGGCTGGGAA | 80 | 2701 |
| 1104044 | N/A | N/A | 8073 | 8092 | GAAGAAAGTTCCAAGGAGGC | 94 | 2702 |
| 1104060 | N/A | N/A | 8209 | 8228 | TAACTCCATCTCCTAGCTTT | 89 | 2703 |
| 1104076 | N/A | N/A | 9349 | 9368 | CCCGAGAGAGAAAAATATAA | 99 | 2704 |
| 1104092 | N/A | N/A | 9406 | 9425 | TCATTTCAGGGCCAATGCAA | 63 | 2705 |
| 1104108 | N/A | N/A | 9450 | 9469 | TATTCTAGTCCAGAAGAAGA | 127 | 2706 |
| 1104124 | N/A | N/A | 9504 | 9523 | AGCCTTTCTGATGCTGAATT | 52 | 2707 |
| 1104140 | N/A | N/A | 9528 | 9547 | TTACCTCTACTAGTCAGCCT | 75 | 2708 |
| 1104156 | N/A | N/A | 9555 | 9574 | CCTGTGACTATCTAGGATTT | 52 | 2709 |

TABLE 36-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104172 | N/A | N/A | 9574 | 9593 | TTTATCTGTGCTTTAGTGAC | 50 | 2710 |
| 1104188 | N/A | N/A | 9651 | 9670 | CATGTGGCACATATTAGTGC | 97 | 2711 |
| 1104204 | N/A | N/A | 9704 | 9723 | TACTTCTCTAGGTGGGAGAG | 83 | 2712 |
| 1104220 | N/A | N/A | 10137 | 10156 | AGTAAGACTCCGTCGAAAGC | 124 | 2713 |
| 1104236 | N/A | N/A | 10574 | 10593 | CTTTCTGAAAACCCAGCACG | 87 | 2714 |
| 1104252 | N/A | N/A | 10731 | 10750 | ATGAGAACCTATGCAACCGA | 68 | 2715 |
| 1104268 | N/A | N/A | 10807 | 10826 | CTCATGGACTTTCAGGGCAT | 84 | 2716 |
| 1104284 | N/A | N/A | 11076 | 11095 | TTACATTCAGTTTCCTTGCT | 108 | 2717 |
| 1104300 | N/A | N/A | 11147 | 11166 | GGATCCCATCTAGTGGCTTT | 94 | 2718 |
| 1104316 | N/A | N/A | 11222 | 11241 | TAACTTTAATTCTCTTTCTC | 135 | 2719 |
| 1104332 | N/A | N/A | 11266 | 11285 | CCCCATCCCCAACTGTGTCT | 80 | 2720 |
| 1104348 | N/A | N/A | 11385 | 11404 | TAAGCTGCTGGAGTAAGATG | 92 | 2721 |
| 1104364 | N/A | N/A | 11484 | 11503 | TTACTTTTCTTGATAGTAAC | 89 | 2722 |
| 1104380 | N/A | N/A | 11573 | 11592 | GCACAGTGCAACAGTTAGGA | 38 | 2723 |

TABLE 37

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1047582 | 3047 | 3066 | 3336 | 13355 | GTCTTTATTTTTCCTCAGCG | 6 | 517 |
| 1103165 | 261 | 280 | 3709 | 3728 | CTGCCCGCTCACTGGCCCGG | 98 | 2724 |
| 1103181 | 505 | 524 | 3953 | 3972 | TGCCTCACAGTGGCCAGGTC | 45* | 2725 |
| 1103197 | 756 | 775 | 5642 | 5661 | CTTTCAGGGCTGCGGTGAGG | 99 | 2726 |
| 1103213 | 1048 | 1067 | 7620 | 7639 | TCTTCCTCCAGCCGCGCCAG | 53 | 2727 |
| 1103229 | 1325 | 1344 | 11614 | 11633 | CTGCTTGGACTCCTTAATGA | 73 | 2728 |
| 1103245 | 1497 | 1516 | 11786 | 11805 | AAGCTGACCTAGGGACAGAG | 106 | 2729 |
| 1103261 | 1602 | 1621 | 11891 | 11910 | CCCCTCCAGACTGCCCCTTG | 73 | 2730 |
| 1103277 | 1727 | 1746 | 12016 | 12035 | TCCATCTCTGGCAACAGTTT | 48 | 2731 |
| 1103293 | 1857 | 1876 | 12146 | 12165 | AAAGACAAAACAAGCCTCTG | 71 | 2732 |
| 1103309 | 1883 | 1902 | 12172 | 12191 | AGGGATATCCCACCTCATAA | 159 | 2733 |
| 1103325 | 2057 | 2076 | 12346 | 12365 | TGACTGCCCCAGGTGGCAGG | 116 | 2734 |
| 1103341 | 2199 | 2218 | 12488 | 12507 | TACACAACAGATCCCCCAAG | 86 | 2735 |
| 1103357 | 2411 | 2430 | 12700 | 12719 | TTAATTCCCACAATCCAGAG | 104 | 2736 |
| 1103373 | 2460 | 2479 | 12749 | 12768 | ATCCCCTTTCTCTCCTGTTT | 76 | 2737 |
| 1103389 | 2509 | 2528 | 12798 | 12817 | AAGAGGCCTTTAGAAATGGG | 71 | 2738 |
| 1103405 | 2663 | 2682 | 12952 | 12971 | TAAGAAGGGACCGCAAGAGG | 81 | 2739 |

TABLE 37-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1103421 | 2716 | 2735 | 13005 | 13024 | ACAATTGTAAAATAGGGCAC | 81 | 2740 |
| 1103437 | 2837 | 2856 | 13126 | 13145 | ACCAGTCTGCTCAGTCAAAG | 90 | 2741 |
| 1103469 | N/A | N/A | 8767 | 8786 | TATCTTGTGACCTTGTGATT | 54 | 2742 |
| 1103485 | N/A | N/A | 8896 | 8915 | GCTCACTCCCTGTCAAGCTG | 76 | 2743 |
| 1103501 | N/A | N/A | 9042 | 9061 | AAGCTCTGCCAGTTTAATGT | 57 | 2744 |
| 1103517 | N/A | N/A | 9216 | 9235 | AGCGATGGAGCCTCAGGGAT | 83 | 2745 |
| 1103533 | N/A | N/A | 9255 | 9274 | TGAGGGAAGAATCCTCTGAA | 92 | 2746 |
| 1103549 | N/A | N/A | 9306 | 9325 | ACATTAAGAGCAGGGAACAT | 105 | 2747 |
| 1103565 | N/A | N/A | 8499 | 8518 | GTGTCACGAAGGCCCCCAGG | 72 | 2748 |
| 1103581 | N/A | N/A | 8556 | 8575 | CTGCAAGCCCCACCTAGAAG | 94 | 2749 |
| 1103597 | N/A | N/A | 3989 | 4008 | TCACAAGGCCCCCCTTCCCC | 98 | 2750 |
| 1103613 | N/A | N/A | 4048 | 4067 | GTTCGGCCCCTCCCTGAGAC | 90 | 2751 |
| 1103629 | N/A | N/A | 4228 | 4247 | CCCGCTGCTCCTGCACTGCT | 83 | 2752 |
| 1103645 | N/A | N/A | 4389 | 4408 | TGCCTGCTCTTTCCCTCACT | 88 | 2753 |
| 1103661 | N/A | N/A | 4489 | 4508 | ATTTTATTATGACCACCGCT | 97 | 2754 |
| 1103677 | N/A | N/A | 4625 | 4644 | TCACTGTTGCACACACACAC | 124 | 2755 |
| 1103693 | N/A | N/A | 4775 | 4794 | GCAGGAGGATTAAGGGTTGG | 76 | 2756 |
| 1103709 | N/A | N/A | 5010 | 5029 | TGGGTGGCCATCAATCCTTT | 97 | 2757 |
| 1103725 | N/A | N/A | 5303 | 5322 | TCAGTTGCAATCTCTGTGTT | 65 | 2758 |
| 1103741 | N/A | N/A | 5394 | 5413 | ATTTCCTGTCTCTACCTGCC | 95 | 2759 |
| 1103757 | N/A | N/A | 5480 | 5499 | GTCCTCTTCTGCCTGCCCCT | 90 | 2760 |
| 1103773 | N/A | N/A | 5722 | 5741 | CAGGGCTACCTTGGAGCGGT | 71 | 2761 |
| 1103789 | N/A | N/A | 5848 | 5867 | TCTCACTTCTCTGGTGAAAG | 82 | 2762 |
| 1103805 | N/A | N/A | 5912 | 5931 | AGTAGCAGTAATAATAATGG | 86 | 2763 |
| 1103821 | N/A | N/A | 5973 | 5992 | AATCCATGAAAAGCACAGGG | 88 | 2764 |
| 1103837 | N/A | N/A | 6018 | 6037 | GGCTCTCTCATCTGTCAAAG | 24 | 2765 |
| 1103853 | N/A | N/A | 6198 | 6217 | CAGACACCTCTCTGTGTOCT | 108 | 2766 |
| 1103869 | N/A | N/A | 6256 | 6275 | TGTGGTGTTCTCTACGGGCA | 62 | 2767 |
| 1103885 | N/A | N/A | 6312 | 6331 | AAATGCCCCCTCTACAGTGT | 110 | 2768 |
| 1103901 | N/A | N/A | 6406 | 6425 | CTCTGTGCTTTTCTGCCTCC | 67 | 2769 |
| 1103917 | N/A | N/A | 6500 | 6519 | TCGGGCCCTCACCCTGCTCA | 92 | 2770 |
| 1103933 | N/A | N/A | 6902 | 6921 | GGCGAGCGGAGGCCTGGGTG | 12 | 2771 |
| 1103949 | N/A | N/A | 7016 | 7035 | ACCTCAGCACCTAGCACAAC | 90 | 2772 |
| 1103965 | N/A | N/A | 7197 | 7216 | TCAGGTCTGCAAACTAGGTG | 72 | 2773 |
| 1103981 | N/A | N/A | 7415 | 7434 | CCCCGCCCTCGACCCAGGTC | 131 | 2774 |
| 1103997 | N/A | N/A | 7804 | 7823 | ATGAGCTCTACCGTGAGGCA | 88 | 2775 |

TABLE 37-continued

Reduction of GFAP RNA by 5-10-5 MOE gapmers with mixed PO/PS internucleoside linkages in U251 cells

| Compound No. | SEQ ID NO: 1 Start Site | SEQ ID NO: 1 Stop Site | SEQ ID NO: 2 Start Site | SEQ ID NO: 2 Stop Site | Sequence (5' to 3') | GFAP (% UTC) | SEQ ID NO |
|---|---|---|---|---|---|---|---|
| 1104013 | N/A | N/A | 7913 | 7932 | ACATCTAGTGACTGOCTGCT | 94 | 2776 |
| 1104029 | N/A | N/A | 8034 | 8053 | AGGAGTCCAATCTTGGCTGG | 74 | 2777 |
| 1104045 | N/A | N/A | 8074 | 8093 | TGAAGAAAGTTCCAAGGAGG | 95 | 2778 |
| 1104061 | N/A | N/A | 8215 | 8234 | AAAGTCTAACTCCATCTCCT | 131 | 2779 |
| 1104077 | N/A | N/A | 9358 | 9377 | CCCGCCCCGCCCGAGAGAGA | 83 | 2780 |
| 1104093 | N/A | N/A | 9408 | 9427 | AATCATTTCAGGGCCAATGC | 24 | 2781 |
| 1104109 | N/A | N/A | 9451 | 9470 | ATATTCTAGTCCAGAAGAAG | 123 | 2782 |
| 1104125 | N/A | N/A | 9505 | 9524 | TAGCCTTTCTGATGCTGAAT | 57 | 2783 |
| 1104141 | N/A | N/A | 9529 | 9548 | ATTACCTCTACTAGTCAGCC | 59 | 2784 |
| 1104157 | N/A | N/A | 9556 | 9575 | ACCTGTGACTATCTAGGATT | 82 | 2785 |
| 1104173 | N/A | N/A | 9575 | 9594 | ATTTATCTGTGCTTTAGTGA | 41 | 2786 |
| 1104189 | N/A | N/A | 9652 | 9671 | ACATGTGGCACATATTAGTG | 98 | 2787 |
| 1104205 | N/A | N/A | 9705 | 9724 | CTACTTCTCTAGGTGGGAGA | 79 | 2788 |
| 1104221 | N/A | N/A | 10138 | 10157 | GAGTAAGACTCCGTCGAAAG | 89 | 2789 |
| 1104237 | N/A | N/A | 10608 | 10627 | TCAGCCCCTCTGCAAGCCCT | 85 | 2790 |
| 1104253 | N/A | N/A | 10732 | 10751 | TATGAGAACCTATGCAACCG | 72 | 2791 |
| 1104269 | N/A | N/A | 10808 | 10827 | TCTCATGGACTTTCAGGGCA | 112 | 2792 |
| 1104285 | N/A | N/A | 11077 | 11096 | ATTACATTCAGTTTCCTTGC | 103 | 2793 |
| 1104301 | N/A | N/A | 11148 | 11167 | AGGATCCCATCTAGTGGCTT | 91 | 2794 |
| 1104317 | N/A | N/A | 11224 | 11243 | ACTAACTTTAATTCTCTTTC | 96 | 2795 |
| 1104333 | N/A | N/A | 11274 | 11293 | AAAGCCCTCCCCATCCCCAA | 128 | 2796 |
| 1104349 | N/A | N/A | 11387 | 11406 | GGTAAGCTGCTGGAGTAAGA | 26 | 2797 |
| 1104365 | N/A | N/A | 11485 | 11504 | CTTACTTTTCTTGATAGTAA | 36 | 2798 |
| 1104381 | N/A | N/A | 11605 | 11624 | CTCCTTAATGACCTGCAGGG | 74 | 2799 |

TABLE 38

Reduction of GFAP RNA by 5-10-5 MOE gapmers with mixed PO/PS internucleoside linkages in U251 cells

| Compound Number | SEQ ID NO: 3 Start Site | SEQ ID NO: 3 Stop Site | Sequence (5' to 3') | GFAP (% UTC) | SEQ ID NO |
|---|---|---|---|---|---|
| 1103451 | 1220 | 1239 | CCCTCGAATCTGCAGGTTGG | 94 | 2800 |
| 1103452 | 1227 | 1246 | TTTTGCCCCCTCGAATCTGC | 106 | 2801 |
| 1103453 | 1228 | 1247 | CTTTTGCCCCCTCGAATCTG | 84 | 2802 |
| 1103454 | 1229 | 1248 | GCTTTTGCCCCCTCGAATCT | 95 | 2803 |
| 1103455 | 1231 | 1250 | GTGCTTTTGCCCCCTCGAAT | 59 | 2804 |

TABLE 38-continued

Reduction of GFAP RNA by 5-10-5 MOE gapmers with mixed PO/PS internucleoside linkages in U251 cells

| Compound Number | SEQ ID NO: 3 Start Site | SEQ ID NO: 3 Stop Site | Sequence (5' to 3') | GFAP (% UTC) | SEQ ID NO |
|---|---|---|---|---|---|
| 1103456 | 1233 | 1252 | TGGTGCTTTTGCCCCCTCGA | 92 | 2805 |
| 1103457 | 1235 | 1254 | TTTGGTGCTTTTGCCCCCTC | 60 | 2806 |
| 1103554 | 1813 | 1832 | TTAATATTTAACATTAAGAG | 77 | 2807 |
| 1047595 | 1222 | 1241 | CCCCCTCGAATCTGCAGGTT | 109 | 284 |
| 1047596 | 1223 | 1242 | GCCCCCTCGAATCTGCAGGT | 107 | 362 |

TABLE 38-continued

| Reduction of GFAP RNA by 5-10-5 MOE gapmers with mixed PO/PS internucleoside linkages in U251 cells | | | | | |
|---|---|---|---|---|---|
| Compound Number | SEQ ID NO: 3 Start Site | SEQ ID NO: 3 Stop Site | Sequence (5' to 3') | GFAP (% UTC) | SEQ ID NO |
| 1047597 | 1225 | 1244 | TTGCCCCCTCGAATCTGCAG | 65 | 440 |
| 1047598 | 1230 | 1249 | TGCTTTTGCCCCCTCGAATC | 115 | 518 |
| 1047599 | 1232 | 1251 | GGTGCTTTTGCCCCCTCGAA | 43 | 596 |
| 1047600 | 1234 | 1253 | TTGGTGCTTTTGCCCCCTCG | 86 | 674 |

Example 3: Effect of Modified Oligonucleotides on Human GFAP RNA In Vitro, Multiple Doses Modified oligonucleotides selected from the examples above were tested at various doses in U251 cells. Cultured U251 cells at a density of 10,000 cells per well were treated using free uptake with various concentrations of modified oligonucleotide as specified in the tables below. After a treatment period of approximately 48 hours, total RNA was isolated from the cells and GFAP RNA levels were measured by quantitative real-time RTPCR. Human GFAP primer probe set RTS37485 was used to measure RNA levels, as described above. GFAP RNA levels were adjusted according to total RNA content, as measured by RIBOGREEN®. Results are presented as percent of GFAP RNA, relative to untreated control cells (% control). Where possible, the half maximal inhibitory concentration ($IC_{50}$) of each modified oligonucleotide was calculated using a linear regression on a log/linear plot of the data in Excel. In some cases, an $IC_{50}$ could not be reliably calculated and the data point is marked as "NC". Modified oligonucleotides marked with an asterisk (*) indicate that the modified oligonucleotide is complementary to the amplicon region of the primer probe set. Additional assays may be used to measure the potency and efficacy of the modified oligonucleotides complementary to the amplicon region.

TABLE 39

Dose-dependent percent of human GFAP RNA compared to untreated control in U251 cells by modified oligonucleotides

| Compound No. | GFAP RNA (% control) 125 nM | 500 nM | 2000 nM | 8000 nM | $IC_{50}$ (μM) |
|---|---|---|---|---|---|
| 1047225 | 76 | 57 | 47 | 42 | 2.0 |
| 1047257 | 60 | 51 | 39 | 33 | 0.5 |
| 1047258 | 51 | 50 | 38 | 29 | 0.2 |
| 1047386 | 99 | 82 | 41 | 26 | 1.9 |
| 1047387 | 109 | 73 | 33 | 13 | 1.3 |
| 1047448 | 85 | 122 | 99 | 94 | NC |
| 1047466 | 107 | 82 | 77 | 46 | 7.8 |
| 1047497 | 120 | 117 | 107 | 136 | NC |
| 1047512 | 116 | 112 | 97 | 87 | NC |
| 1047584 | 94 | 54 | 23 | 10 | 0.8 |
| 1047608 | 125 | 133 | 79 | 52 | NC |
| 1047609 | 88 | 82 | 57 | 33 | 3.0 |
| 1047610 | 92 | 75 | 43 | 19 | 1.5 |
| 1047913 | 98 | 72 | 49 | 25 | 1.9 |
| 1048203 | 120 | 95 | 57 | 31 | 3.3 |
| 1048267 | 99 | 100 | 93 | 70 | NC |
| 1048296 | 99 | 91 | 73 | 72 | NC |

TABLE 39-continued

Dose-dependent percent of human GFAP RNA compared to untreated control in U251 cells by modified oligonucleotides

| Compound No. | GFAP RNA (% control) 125 nM | 500 nM | 2000 nM | 8000 nM | $IC_{50}$ (μM) |
|---|---|---|---|---|---|
| 1048344 | 77 | 97 | 88 | 86 | NC |
| 1048361 | 92 | 115 | 85 | 109 | NC |

TABLE 40

Dose-dependent percent of human GFAP RNA compared to untreated control in U251 cells by modified oligonucleotides

| Compound No. | GFAP RNA (% control) 125 nM | 500 nM | 2000 nM | 8000 nM | $IC_{50}$ (μM) |
|---|---|---|---|---|---|
| 1047325 | 81 | 86 | 76 | 67 | NC |
| 1047357 | 74 | 63 | 47 | 22 | 1.1 |
| 1047372 | 145 | 143 | 125 | 99 | NC |
| 1047373 | 105 | 73 | 43 | 21 | 1.7 |
| 1047374 | 150 | 122 | 84 | 46 | 7.3 |
| 1047388 | 108 | 116 | 62 | 32 | 4.2 |
| 1047500 | 100 | 105 | 74 | 60 | NC |
| 1047515 | 93 | 95 | 81 | 65 | NC |
| 1047518 | 125 | 99 | 81 | 51 | NC |
| 1047579 | 92 | 113 | 81 | 53 | NC |
| 1047580 | 96 | 88 | 58 | 41 | 4.3 |
| 1047581 | 73 | 60 | 32 | 17 | 0.7 |
| 1047582 | 72 | 29 | 12 | 7 | 0.3 |
| 1047584 | 100 | 60 | 23 | 11 | 0.6 |
| 1047613 | 107 | 107 | 79 | 44 | NC |
| 1047662 | 99 | 86 | 83 | 47 | NC |
| 1047707 | 100 | 126 | 91 | 75 | NC |
| 1048027 | 82 | 83 | 59 | 56 | NC |
| 1048350 | 104 | 85 | 57 | 36 | 3.4 |

TABLE 41

Dose-dependent percent of human GFAP RNA compared to untreated control in U251 cells by modified oligonucleotides

| Compound No. | GFAP RNA (% control) 125 nM | 500 nM | 2000 nM | 8000 nM | $IC_{50}$ (μM) |
|---|---|---|---|---|---|
| 1047235 | 80 | 81 | 68 | 57 | NC |
| 1047328 | 91 | 79 | 55 | 39 | 3.5 |
| 1047362 | 110 | 77 | 52 | 20 | 2.0 |
| 1047391 | 87 | 79 | 61 | 45 | 5.5 |
| 1047394 | 78 | 74 | 52 | 36 | 2.6 |
| 1047503 | 92 | 94 | 80 | 59 | NC |
| 1047522 | 81 | 81 | 63 | 50 | NC |
| 1047583 | 97 | 54 | 19 | 12 | 0.8 |
| 1047584 | 81 | 50 | 19 | 10 | 0.6 |
| 1047585 | 85 | 73 | 38 | 18 | 1.2 |
| 1047586 | 75 | 64 | 41 | 23 | 1.1 |
| 1047587 | 92 | 66 | 41 | 19 | 1.3 |
| 1047599 | 92 | 94 | 83 | 78 | NC |
| 1047601 | 103 | 89 | 68 | 50 | NC |
| 1047762 | 99 | 84 | 70 | 71 | NC |
| 1047955 | 95 | 104 | 86 | 92 | NC |
| 1048018 | 85 | 84 | 74 | 51 | NC |
| 1048351 | 98 | 97 | 75 | 59 | NC |
| 1048355 | 114 | 114 | 90 | 61 | NC |

TABLE 42

Dose-dependent percent of human GFAP RNA compared to untreated control in U251 cells by modified oligonucleotides

| Compound | GFAP RNA (% control) | | | | $IC_{50}$ |
|---|---|---|---|---|---|
| No. | 125 nM | 500 nM | 2000 nM | 8000 nM | (μM) |
| 1047429 | 80 | 58 | 32 | 15 | 0.8 |
| 1047444 | 80 | 98 | 83 | 73 | NC |
| 1047492 | 92 | 99 | 79 | 58 | NC |
| 1047573 | 80 | 74 | 59 | 44 | 4.7 |
| 1047584 | 87 | 53 | 20 | 8 | 0.7 |
| 1047588 | 69 | 49 | 24 | 14 | 0.5 |
| 1047589 | 101 | 79 | 47 | 24 | 2.0 |
| 1047590 | 70 | 55 | 35 | 24 | 0.7 |
| 1047591 | 92 | 67 | 34 | 21 | 1.2 |
| 1047734 | 86 | 75 | 69 | 60 | NC |
| 1047990 | 75 | 75 | 58 | 40 | 4.1 |
| 1048055 | 103 | 96 | 61 | 42 | 5.0 |
| 1048151 | 94 | 76 | 23 | 16 | 1.1 |
| 1048182 | 85 | 76 | 56 | 35 | 2.9 |
| 1048195 | 105 | 104 | 87 | 87 | NC |
| 1048196 | 94 | 91 | 73 | 62 | NC |
| 1048228 | 91 | 81 | 87 | 93 | NC |
| 1048341 | 80 | 71 | 61 | 46 | 6.1 |
| 1048372 | 94 | 88 | 84 | 59 | NC |

TABLE 43

Dose-dependent percent of human GFAP RNA compared to untreated control in U251 cells by modified oligonucleotides

| Compound | GFAP RNA (% control) | | | | $IC_{50}$ |
|---|---|---|---|---|---|
| No. | 125 nM | 500 nM | 2000 nM | 8000 nM | (μM) |
| 1047321 | 94 | 91 | 84 | 79 | NC |
| 1047337 | 94 | 89 | 68 | 61 | NC |
| 1047368 | 86 | 82 | 79 | 81 | NC |
| 1047385 | 86 | 80 | 63 | 58 | NC |
| 1047432 | 89 | 84 | 75 | 89 | NC |
| 1047465 | 82 | 67 | 62 | 49 | 7.3 |
| 1047469 | 104 | 95 | 73 | 58 | NC |
| 1047513 | 106 | 100 | 96 | 80 | NC |
| 1047576 | 82 | 83 | 63 | 49 | NC |
| 1047584 | 88 | 63 | 31 | 14 | 1.0 |
| 1047625 | 86 | 80 | 73 | 55 | NC |
| 1047675 | 101 | 88 | 92 | 82 | NC |
| 1047688 | 99 | 100 | 96 | 100 | NC |
| 1047705 | 100 | 92 | 78 | 68 | NC |
| 1047866 | 90 | 81 | 71 | 78 | NC |
| 1048125 | 103 | 91 | 86 | 84 | NC |
| 1048187 | 100 | 88 | 82 | 74 | NC |
| 1048188 | 99 | 64 | 80 | 81 | NC |
| 1048201 | 80 | 65 | 41 | 23 | 1.2 |

TABLE 44

Dose-dependent percent of human GFAP RNA compared to untreated control in U251 cells by modified oligonucleotides

| Compound | GFAP RNA (% control) | | | | $IC_{50}$ |
|---|---|---|---|---|---|
| No. | 125 nM | 500 nM | 2000 nM | 8000 nM | (μM) |
| 1047298 | 87 | 83 | 74 | 75 | NC |
| 1047474 | 102 | 93 | 94 | 87 | NC |
| 1047523 | 88 | 76 | 61 | 42 | 4.6 |
| 1047582 | 79 | 37 | 18 | 12 | 0.4 |
| 1047584 | 100 | 72 | 43 | 20 | 1.6 |
| 1047607 | 92 | 85 | 68 | 56 | NC |
| 1047717 | 106 | 110 | 92 | 80 | NC |
| 1047746 | 108 | 110 | 106 | 110 | NC |
| 1047790 | 91 | 86 | 81 | 70 | NC |
| 1047799 | 104 | 100 | 95 | 93 | NC |

TABLE 44-continued

Dose-dependent percent of human GFAP RNA compared to untreated control in U251 cells by modified oligonucleotides

| Compound | GFAP RNA (% control) | | | | $IC_{50}$ |
|---|---|---|---|---|---|
| No. | 125 nM | 500 nM | 2000 nM | 8000 nM | (μM) |
| 1047840 | 92 | 88 | 75 | 58 | NC |
| 1047859 | 96 | 87 | 87 | 78 | NC |
| 1047886 | 84 | 79 | 68 | 68 | NC |
| 1047907 | 97 | 90 | 80 | 71 | NC |
| 1048093 | 97 | 89 | 93 | 90 | NC |
| 1048144 | 101 | 93 | 99 | 108 | NC |
| 1048207 | 97 | 82 | 76 | 74 | NC |
| 1048223 | 91 | 77 | 77 | 68 | NC |
| 1048350 | 104 | 80 | 57 | 44 | 4.4 |

TABLE 45

Dose-dependent percent of human GFAP RNA compared to untreated control in U251 cells by modified oligonucleotides

| Compound | GFAP RNA (% control) | | | | IC50 |
|---|---|---|---|---|---|
| No. | 370 nM | 1111 nM | 3333 nM | 10000 nM | (μM) |
| 1047582 | 25 | 11 | 7 | 5 | NC |
| 1072814 | 62 | 45 | 22 | 14 | 0.7 |
| 1072815 | 86 | 57 | 42 | 28 | 2.3 |
| 1072818 | 78 | 54 | 33 | 16 | 1.5 |
| 1072834 | 33 | 22 | 13 | 8 | NC |
| 1072835 | 54 | 30 | 15 | 9 | NC |
| 1072855 | 64 | 44 | 27 | 16 | 0.8 |
| 1072862 | 59 | 40 | 20 | 9 | 0.6 |
| 1072863 | 83 | 54 | 35 | 20 | 1.7 |
| 1072868 | 80 | 50 | 23 | 9 | 1.2 |
| 1072872 | 21 | 13 | 9 | 7 | NC |
| 1072886 | 88 | 60 | 42 | 21 | 2.2 |
| 1072986 | 84 | 68 | 22 | 11 | 1.7 |
| 1073003 | 93 | 79 | 71 | 52 | NC |
| 1073034 | 97 | 80 | 30 | 30 | 2.9 |
| 1073035 | 78 | 80 | 41 | 27 | 2.8 |
| 1073063 | 53 | 29 | 15 | 7 | NC |
| 1073106 | 87 | 76 | 57 | 39 | 5.2 |
| 1073107 | 79 | 65 | 58 | 33 | 3.7 |

TABLE 46

Dose-dependent percent of human GFAP RNA compared to untreated control in U251 cells by modified oligonucleotides

| Compound | GFAP RNA (% control) | | | | IC50 |
|---|---|---|---|---|---|
| No. | 370 nM | 1111 nM | 3333 nM | 10000 nM | (μM) |
| 1047582 | 36 | 15 | 8 | 6 | NC |
| 1072813 | 69 | 58 | 36 | 17 | 1.4 |
| 1072824 | 85 | 63 | 38 | 23 | 2.2 |
| 1072849 | 66 | 32 | 21 | 14 | 0.6 |
| 1072853 | 116 | 98 | 70 | 24 | 5.1 |
| 1072856 | 90 | 57 | 32 | 14 | 1.8 |
| 1072857 | 66 | 45 | 32 | 17 | 1.0 |
| 1072861 | 68 | 45 | 28 | 16 | 1.0 |
| 1072864 | 87 | 62 | 43 | 22 | 2.3 |
| 1072973 | 101 | 74 | 40 | 13 | 2.5 |
| 1072980 | 39 | 45 | 27 | 16 | NC |
| 1073009 | 87 | 75 | 83 | 35 | 8.2 |
| 1073033 | 87 | 44 | 19 | 24 | 1.4 |
| 1073045 | 60 | 43 | 24 | 12 | 0.7 |
| 1073060 | 68 | 43 | 28 | 16 | 0.9 |
| 1073064 | 61 | 41 | 31 | 19 | 0.7 |
| 1073065 | 69 | 61 | 36 | 18 | 1.5 |
| 1073077 | 95 | 70 | 44 | 23 | 2.8 |
| 1073093 | 57 | 33 | 20 | 10 | 0.5 |

TABLE 47

Dose-dependent percent of human GFAP RNA compared to untreated control in U251 cells by modified oligonucleotides

| Compound No. | GFAP RNA (% control) 370 nM | 1111 nM | 3333 nM | 10000 nM | IC50 (μM) |
|---|---|---|---|---|---|
| 1047582 | 70 | 30 | 9 | 5 | 0.6 |
| 1103198 | 91 | 86 | 82 | 73 | NC |
| 1103246 | 102 | 84 | 81 | 62 | NC |
| 1103278 | 89 | 96 | 72 | 51 | NC |
| 1103279 | 86 | 69 | 43 | 30 | 2.9 |
| 1103359 | 82 | 75 | 55 | 39 | 5.0 |
| 1103470 | 86 | 88 | 73 | 55 | NC |
| 1103471 | 68 | 63 | 45 | 36 | 2.6 |
| 1103502 | 104 | 93 | 75 | 51 | NC |
| 1103567 | 88 | 66 | 45 | 23 | 2.5 |
| 1104014 | 91 | 91 | 56 | 56 | NC |
| 1104078 | 92 | 100 | 103 | 92 | NC |
| 1104127 | 67 | 52 | 42 | 33 | 1.6 |
| 1104144 | 93 | 63 | 34 | 16 | 2.1 |
| 1104158 | 50 | 51 | 55 | 23 | 1.0 |
| 1104159 | 65 | 59 | 40 | 25 | 1.6 |
| 1104174 | 91 | 93 | 63 | 43 | 7.9 |
| 1104175 | 69 | 46 | 23 | 13 | 0.9 |
| 1104191 | 84 | 76 | 52 | 34 | 4.0 |

TABLE 48

Dose-dependent percent of human GFAP RNA compared to untreated control in U251 cells by modified oligonucleotides

| Compound No. | GFAP RNA (% control) 370 nM | 1111 nM | 3333 nM | 10000 nM | IC50 (μM) |
|---|---|---|---|---|---|
| 1047582 | 66 | 30 | 11 | 6 | 0.6 |
| 1103202 | 79 | 79 | 54 | 43 | 6.0 |
| 1103217 | 77 | 38 | 16 | 5 | 0.9 |
| 1103218 | 92 | 74 | 50 | 33 | 3.7 |
| 1103330 | 84 | 79 | 56 | 51 | NC |
| 1103345 | 112 | 125 | 111 | 149 | NC |
| 1103377 | 115 | 134 | 142 | 151 | NC |
| 1103409 | 82 | 93 | 70 | 45 | NC |
| 1103570 | 79 | 64 | 43 | 24 | 2.3 |
| 1103571 | 101 | 74 | 61 | 34 | 4.6 |
| 1103872 | 93 | 79 | 28 | 21 | 2.4 |
| 1103970 | 88 | 78 | 75 | 74 | NC |
| 1104096 | 109 | 112 | 65 | 47 | 9.2 |
| 1104131 | 87 | 79 | 54 | 44 | 6.1 |
| 1104145 | 99 | 89 | 65 | 39 | 6.7 |
| 1104161 | 102 | 90 | 75 | 52 | NC |
| 1104178 | 72 | 67 | 57 | 53 | NC |
| 1104225 | 87 | 82 | 57 | 39 | 5.4 |
| 1104307 | 97 | 87 | 57 | 32 | 4.7 |

TABLE 49

Dose-dependent percent of human GFAP RNA compared to untreated control in U251 cells by modified oligonucleotides

| Compound No. | GFAP RNA (% control) 370 nM | 1111 nM | 3333 nM | 10000 nM | IC50 (μM) |
|---|---|---|---|---|---|
| 1047582 | 58 | 29 | 10 | 7 | 0.4 |
| 1103236 | 81 | 62 | 27 | 12 | 1.6 |
| 1103253 | 68 | 56 | 36 | 37 | 1.8 |
| 1103268 | 86 | 62 | 37 | 30 | 2.4 |
| 1103285 | 91 | 79 | 56 | 29 | 4.0 |
| 1103300 | 100 | 98 | 83 | 81 | NC |
| 1103365 | 83 | 86 | 64 | 42 | 8.2 |
| 1103428 | 87 | 73 | 50 | 26 | 3.2 |
| 1103491 | 86 | 70 | 70 | 55 | NC |
| 1103620 | 90 | 62 | 65 | 73 | NC |

TABLE 49-continued

Dose-dependent percent of human GFAP RNA compared to untreated control in U251 cells by modified oligonucleotides

| Compound No. | GFAP RNA (% control) 370 nM | 1111 nM | 3333 nM | 10000 nM | IC50 (μM) |
|---|---|---|---|---|---|
| 1104037 | 77 | 92 | 66 | 38 | 7.8 |
| 1104116 | 85 | 63 | 42 | 23 | 2.3 |
| 1104118 | 99 | 74 | 38 | 20 | 2.6 |
| 1104132 | 107 | 79 | 53 | 35 | 4.5 |
| 1104133 | 70 | 67 | 43 | 29 | 2.3 |
| 1104165 | 91 | 86 | 59 | 32 | 4.8 |
| 1104276 | 94 | 71 | 18 | 15 | 1.9 |
| 1104309 | 73 | 60 | 36 | 20 | 1.6 |
| 1104310 | 82 | 57 | 30 | 13 | 1.6 |

TABLE 50

Dose-dependent percent of human GFAP RNA compared to untreated control in U251 cells by modified oligonucleotides

| Compound No. | GFAP RNA (% control) 370 nM | 1111 nM | 3333 nM | 10000 nM | IC50 (μM) |
|---|---|---|---|---|---|
| 1047582 | 69 | 30 | 11 | 7 | 0.6 |
| 1103241 | 87 | 71 | 60 | 50 | NC |
| 1103257 | 75 | 83 | 47 | 26 | 3.1 |
| 1103258 | 81 | 70 | 44 | 23 | 2.4 |
| 1103272 | 94 | 91 | 52 | 26 | 4.0 |
| 1103369 | 88 | 78 | 59 | 38 | 5.4 |
| 1103370 | 83 | 88 | 59 | 44 | 8.0 |
| 1103400 | 95 | 101 | 87 | 76 | NC |
| 1103448 | 91 | 73 | 49 | 32 | 3.6 |
| 1103465 | 88 | 68 | 47 | 31 | 3.1 |
| 1103592 | 96 | 111 | 75 | 48 | NC |
| 1103722* | 21 | 24 | 21 | 19 | NC |
| 1103816 | 108 | 118 | 95 | 76 | NC |
| 1104072 | 111 | 83 | 63 | 17 | 3.8 |
| 1104122 | 84 | 73 | 65 | 48 | NC |
| 1104153 | 78 | 83 | 55 | 50 | NC |
| 1104280 | 111 | 84 | 55 | 25 | 3.9 |
| 1104312 | 91 | 71 | 52 | 32 | 3.7 |
| 1104361 | 87 | 81 | 65 | 42 | 7.4 |

TABLE 51

Dose-dependent percent of human GFAP RNA compared to untreated control in U251 cells by modified oligonucleotides

| Compound No. | GFAP RNA (% control) 370 nM | 1111 nM | 3333 nM | 10000 nM | IC50 (μM) |
|---|---|---|---|---|---|
| 1047582 | 60 | 36 | 12 | 8 | 0.5 |
| 1103244 | 99 | 79 | 55 | 42 | 5.7 |
| 1103259 | 85 | 70 | 42 | 26 | 2.6 |
| 1103322 | 87 | 82 | 66 | 46 | 9.5 |
| 1103371 | 86 | 97 | 64 | 38 | 7.3 |
| 1103516 | 104 | 123 | 90 | 69 | NC |
| 1103837 | 82 | 62 | 40 | 26 | 2.2 |
| 1103899 | 94 | 87 | 68 | 48 | NC |
| 1103932 | 74 | 83 | 68 | 64 | NC |
| 1103933 | 79 | 63 | 11 | 9 | 1.3 |
| 1104093 | 90 | 61 | 33 | 24 | 2.1 |
| 1104123 | 91 | 114 | 81 | 61 | NC |
| 1104156 | 83 | 86 | 71 | 55 | NC |
| 1104173 | 87 | 89 | 60 | 42 | 7.2 |
| 1104298 | 105 | 102 | 80 | 57 | NC |
| 1104299 | 101 | 109 | 84 | 72 | NC |
| 1104349 | 104 | 71 | 57 | 35 | 4.3 |
| 1104365 | 95 | 75 | 63 | 40 | 5.8 |
| 1104380 | 95 | 83 | 61 | 45 | 7.3 |

TABLE 52

| Dose-dependent percent of human GFAP RNA compared to untreated control in U251 cells by modified oligonucleotides | | | | | |
|---|---|---|---|---|---|
| Compound | GFAP RNA (% control) | | | | IC50 |
| No. | 370 nM | 1111 nM | 3333 nM | 10000 nM | (μM) |
| 1047582 | 63 | 26 | 10 | 6 | 0.5 |
| 1103254 | 93 | 85 | 62 | 37 | 5.8 |
| 1103255 | 59 | 49 | 23 | 14 | 0.8 |
| 1103256 | 84 | 54 | 22 | 10 | 1.4 |
| 1103366 | 105 | 79 | 58 | 58 | NC |
| 1103368 | 92 | 79 | 44 | 21 | 2.9 |
| 1103430 | 97 | 86 | 60 | 42 | 6.3 |
| 1103446 | 84 | 79 | 51 | 36 | 4.3 |
| 1103447 | 88 | 79 | 49 | 32 | 3.7 |
| 1103478 | 90 | 95 | 62 | 46 | 9.1 |
| 1103558 | 82 | 92 | 59 | 32 | 5.2 |
| 1103591 | 73 | 69 | 51 | 31 | 3.0 |
| 1104038 | 68 | 51 | 31 | 36 | 1.4 |
| 1104039 | 80 | 68 | 43 | 36 | 3.1 |
| 1104151 | 80 | 65 | 46 | 28 | 2.6 |
| 1104152 | 94 | 71 | 47 | 22 | 2.8 |
| 1104166 | 94 | 70 | 45 | 27 | 3.0 |
| 1104311 | 70 | 60 | 40 | 22 | 1.7 |
| 1104326 | 97 | 85 | 64 | 52 | NC |

Example 4: Tolerability of Modified Oligonucleotides Complementary to Human GFAP in Wild-Type Mice, 3 Hour Study Modified oligonucleotides described above were tested in wild-type female C57/Bl6 mice to assess the tolerability of the oligonucleotides. Wild-type female C57/Bl6 mice each received a single ICV dose of 700 μg of modified oligonucleotide listed in the table below. Each treatment group consisted of 4 mice. A group of 4 mice received PBS as a negative control for each experiment (identified in separate tables below). At 3 hours post-injection, mice were evaluated according to seven different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not (the functional observational battery score or FOB). After all 7 criteria were evaluated, the scores were summed for each mouse and averaged within each treatment group. The results are presented in the tables below.

TABLE 53

| Tolerability scores in mice at 700 μg dose | |
|---|---|
| Compound No. | 3 hr. FOB |
| PBS | 0 |
| 1047198 | 3 |
| 1047258 | 3 |
| 1047328 | 7 |
| 1047362 | 0 |
| 1047373 | 0 |
| 1047386 | 4 |
| 1047387 | 0 |
| 1047388 | 2 |
| 1047391 | 5 |
| 1047580 | 0 |
| 1047582 | 5 |
| 1047583 | 2 |
| 1047584 | 1 |
| 1047585 | 0 |
| 1047586 | 0 |
| 1047587 | 0 |
| 1047588 | 0 |
| 1047589 | 1 |
| 1047590 | 2 |
| 1047591 | 4 |
| 1047610 | 5 |
| 1048203 | 5 |
| 1048267 | 6 |
| 1048350 | 4 |

TABLE 54

| Tolerability scores in mice at 700 μg dose | |
|---|---|
| Compound No. | 3 hr. FOB |
| PBS | 0 |
| 1047257 | 5 |
| 1047357 | 7 |
| 1047374 | 5 |
| 1047394 | 6 |
| 1047429 | 0 |
| 1047444 | 2 |
| 1047448 | 0 |
| 1047492 | 2 |
| 1047497 | 2 |
| 1047500 | 1 |
| 1047518 | 5 |
| 1047573 | 1 |
| 1047581 | 1 |
| 1047599 | 1 |
| 1047601 | 6 |
| 1047608 | 2 |
| 1047609 | 5 |
| 1047913 | 1 |
| 1047990 | 2 |
| 1048027 | 2 |
| 1048151 | 4 |
| 1048182 | 0 |
| 1048296 | 3 |
| 1048361 | 0 |

TABLE 55

| Tolerability scores in mice at 700 μg dose | |
|---|---|
| Compound No. | 3 hr. FOB |
| PBS | 0 |
| 1047211 | 2 |
| 1047223 | 0 |
| 1047225 | 1 |
| 1047298 | 0 |
| 1047306 | 0 |
| 1047316 | 2 |
| 1047352 | 4 |
| 1047353 | 2 |
| 1047402 | 2 |
| 1047432 | 0 |

TABLE 55-continued

| Tolerability scores in mice at 700 μg dose | |
|---|---|
| Compound No. | 3 hr. FOB |
| 1047522 | 0 |
| 1047523 | 2 |
| 1047532 | 2 |
| 1047579 | 2 |
| 1047598 | 4 |
| 1047602 | 5 |
| 1047662 | 4 |
| 1047679 | 2 |
| 1047711 | 2 |
| 1047811 | 0 |
| 1047884 | 3 |
| 1048201 | 1 |
| 1048204 | 0 |
| 1048227 | 1 |

TABLE 56

| Tolerability scores in mice at 700 μg dose | |
|---|---|
| Compound No. | 3 hr. FOB |
| PBS | 0 |
| 1072813 | 0 |
| 1072814 | 1 |
| 1072818 | 4 |
| 1072834 | 4 |
| 1072835 | 0 |
| 1072849 | 5 |
| 1072855 | 4 |
| 1072856 | 6 |
| 1072857 | 4 |
| 1072861 | 6 |
| 1072862 | 4 |
| 1072863 | 3 |
| 1072868 | 7 |
| 1072872 | 5 |
| 1072886 | 1 |
| 1072980 | 1 |
| 1072986 | 6 |
| 1073033 | 5 |
| 1073045 | 6 |
| 1073060 | 6 |
| 1073063 | 6 |
| 1073064 | 6 |
| 1073065 | 6 |
| 1073093 | 6 |

TABLE 57

| Tolerability scores in mice at 700 μg dose | |
|---|---|
| Compound No. | 3 hr. FOB |
| PBS | 0 |
| 1103217 | 5 |
| 1103368 | 3 |
| 1103370 | 3 |
| 1103371 | 3 |
| 1103465 | 6 |
| 1103502 | 5 |
| 1103516 | 7 |
| 1103567 | 5 |
| 1103837 | 4 |
| 1103899 | 2 |
| 1104093 | 5 |

TABLE 57-continued

| Tolerability scores in mice at 700 μg dose | |
|---|---|
| Compound No. | 3 hr. FOB |
| 1104118 | 6 |
| 1104133 | 6 |
| 1104145 | 2 |
| 1104152 | 5 |
| 1104158 | 3 |
| 1104166 | 5 |
| 1104168 | 4 |
| 1104175 | 6 |
| 1104307 | 4 |
| 1104309 | 5 |
| 1104310 | 6 |
| 1104311 | 5 |
| 1104349 | 7 |

TABLE 58

| Tolerability scores in mice at 700 μg dose | |
|---|---|
| Compound No. | 3 hr. FOB |
| PBS | 0 |
| 1103202 | 5 |
| 1103218 | 7 |
| 1103253 | 7 |
| 1103255 | 7 |
| 1103256 | 7 |
| 1103257 | 6 |
| 1103258 | 7 |
| 1103259 | 6 |
| 1103268 | 1 |
| 1103279 | 6 |
| 1103285 | 7 |
| 1103411 | 7 |
| 1103471 | 6 |
| 1103570 | 6 |
| 1103722 | 1 |
| 1103872 | 4 |
| 1103933 | 7 |
| 1104038 | 7 |
| 1104116 | 1 |
| 1104127 | 3 |
| 1104144 | 3 |
| 1104159 | 5 |
| 1104276 | 1 |

Example 5: Design of MOE Gapmer Modified Oligonucleotides with Mixed PO/PS Internucleoside Linkages Complementary to a Human GFAP Nucleic Acid Modified oligonucleotides complementary to human GFAP nucleic acid were designed. The modified oligonucleotides in the table below are 6-10-4 MOE gapmers. The gapmers are 20 nucleosides in length and have a central gap segment that consists of ten 2'-β-D-deoxynucleosides, a 5' wing segment that consists of six 2'-β-D-MOE nucleosides, and a 3' wing segment that consists of four 2'-β-D-MOE nucleosides. The sugar motif of the gapmers is (from 5' to 3): eeeeeeddddddddddeeee: wherein 'd' represents a 2'-β-D-deoxyribosyl sugar moiety, and 'e' represents a 2'-β-D-MOE sugar moiety. The gapmers have an internucleoside linkage motif of (from 5' to 3'): sooooossssssssssoss; wherein each "s" represents a phosphorothioate internucleoside linkage and each "o" represents a phosphodiester internucleoside linkage. Each cytosine nucleoside is a 5-methylcytosine.

TABLE 59

6-10-4 MOE gapmers with mixed PO/PS internucleoside linkages complementary to human GFAP

| Compound No. | SEQUENCE (5' to 3') | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1166991 | CAGCCTGGTTAGCCTTTCTG | N/A | N/A | 9514 | 9533 | 2017 |
| 1166992 | TCAGCCTGGTTAGCCTTTCT | N/A | N/A | 9515 | 9534 | 2094 |
| 1166993 | GTCAGCCTGGTTAGCCTTTC | N/A | N/A | 9516 | 9535 | 2171 |
| 1166994 | AGTCAGCCTGGTTAGCCTTT | N/A | N/A | 9517 | 9536 | 1484 |
| 1166996 | CTAGTCAGCCTGGTTAGCCT | N/A | N/A | 9519 | 9538 | 1561 |
| 1166997 | ACTAGTCAGCCTGGTTAGCC | N/A | N/A | 9520 | 9539 | 2325 |
| 1166998 | CAGTATTACCTCTACTAGTC | N/A | N/A | 9533 | 9552 | 20 |
| 1166999 | GCAGTATTACCTCTACTAGT | N/A | N/A | 9534 | 9553 | 88 |
| 1167000 | GGCAGTATTACCTCTACTAG | N/A | N/A | 9535 | 9554 | 1637 |
| 1167001 | TGGCAGTATTACCTCTACTA | N/A | N/A | 9536 | 9555 | 166 |
| 1167002 | TTGGCAGTATTACCTCTACT | N/A | N/A | 9537 | 9556 | 1865 |
| 1167003 | TTTGGCAGTATTACCTCTAC | N/A | N/A | 9538 | 9557 | 1941 |
| 1167004 | ATTTGGCAGTATTACCTCTA | N/A | N/A | 9539 | 9558 | 2018 |
| 1167024 | GTGTATTAGGATCCCATCTA | N/A | N/A | 11155 | 11174 | 2028 |
| 1167025 | TGTGTATTAGGATCCCATCT | N/A | N/A | 11156 | 11175 | 2105 |
| 1167026 | GTGTGTATTAGGATCCCATC | N/A | N/A | 11157 | 11176 | 1569 |
| 1167027 | AGTGTGTATTAGGATCCCAT | N/A | N/A | 11158 | 11177 | 2182 |
| 1167050 | CTTTATTTTTCCTCAGCGAC | 3045 | 3064 | 13334 | 13353 | 361 |
| 1167051 | TCTTTATTTTTCCTCAGCGA | 3046 | 3065 | 13335 | 13354 | 439 |
| 1167053 | TGTCTTTATTTTTCCTCAGC | 3048 | 3067 | 13337 | 13356 | 595 |
| 1167054 | TTGTCTTTATTTTTCCTCAG | 3049 | 3068 | 13338 | 13357 | 673 |
| 1167055 | TTTGTCTTTATTTTTCCTCA | 3050 | 3069 | 13339 | 13358 | 751 |
| 1167056 | ATTTGTCTTTATTTTTCCTC | 3051 | 3070 | 13340 | 13359 | 829 |
| 1166975 | TTGTGATTTTCCCCGTCTTT | N/A | N/A | 8755 | 8774 | 908 |
| 1166984 | ACATTCACTAATATTTAACA | N/A | N/A | 9323 | 9342 | 1022 |
| 1166985 | CACATTCACTAATATTTAAC | N/A | N/A | 9324 | 9343 | 21 |
| 1166986 | TCACATTCACTAATATTTAA | N/A | N/A | 9325 | 9344 | 2321 |
| 1166987 | GTCACATTCACTAATATTTA | N/A | N/A | 9326 | 9345 | 1177 |
| 1166988 | CGTCACATTCACTAATATTT | N/A | N/A | 9327 | 9346 | 2398 |
| 1166989 | ACGTCACATTCACTAATATT | N/A | N/A | 9328 | 9347 | 2808 |
| 1166990 | CACGTCACATTCACTAATAT | N/A | N/A | 9329 | 9348 | 2809 |
| 1167057 | CATTTGTCTTTATTTTTCCT | 3052 | 3071 | 13341 | 13360 | 907 |
| 1167059 | AGCATTTGTCTTTATTTTTC | 3054 | 3073 | 13343 | 13362 | 1063 |
| 1167060 | CAGCATTTGTCTTTATTTTT | 3055 | 3074 | 13344 | 13363 | 1140 |
| 1166982 | GCTTTTGAGATATCTTGTGA | N/A | N/A | 8777 | 8796 | 51 |
| 1167007 | TGACTATCTAGGATTTGGCA | N/A | N/A | 9551 | 9570 | 2480 |
| 1167011 | CCTGTGACTATCTAGGATTT | N/A | N/A | 9555 | 9574 | 2709 |

TABLE 59-continued 6-10-4 MOE gapmers with mixed PO/PS internucleoside linkages complementary to human GFAP

| Compound No. | SEQUENCE (5' to 3') | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1167012 | TTTATCTGTGCTTTAGTGAC | N/A | N/A | 9574 | 9593 | 2710 |
| 1167017 | TGCCATTTATCTGTGCTTTA | N/A | N/A | 9579 | 9598 | 1639 |
| 1167018 | CTGCCATTTATCTGTGCTTT | N/A | N/A | 9580 | 9599 | 1867 |
| 1174062 | GCTTTTGCCCCCTGTAGTGA | N/A | N/A | 8732 | 8751 | 2291 |
| 1174063 | GTGCTTTTGCCCCCTGTAGT | N/A | N/A | 8734 | 8753 | 2368 |
| 1174065 | TGGTGCTTTTGCCCCCTGTA | N/A | N/A | 8736 | 8755 | 2445 |
| 1174066 | TTGGTGCTTTTGCCCCCTGT | N/A | N/A | 8737 | 8756 | 59 |
| 1167033 | GCACAGTTCCCAGATACTOC | 1756 | 1775 | 12045 | 12064 | 426 |
| 1167034 | GGCACAGTTCCCAGATACTC | 1757 | 1776 | 12046 | 12065 | 504 |
| 1167035 | AGGCACAGTTCCCAGATACT | 1758 | 1777 | 12047 | 12066 | 1425 |
| 1167036 | AAGGCACAGTTCCCAGATAC | 1759 | 1778 | 12048 | 12067 | 1502 |
| 1167037 | AAAGGCACAGTTCCCAGATA | 1760 | 1779 | 12049 | 12068 | 582 |
| 1167040 | CTCAGTTTTCCTCCAGCAGC | 1792 | 1811 | 12081 | 12100 | 115 |
| 1167046 | GCCAGTGTCTTCACTTTGCT | 2750 | 2769 | 13039 | 13058 | 1973 |
| 1167058 | GCATTTGTCTTTATTTTTCC | 3053 | 3072 | 13342 | 13361 | 985 |

Modified oligonucleotides in the table below are 5-10-5 MOE gapmers with mixed PO/PS internucleoside linkages. The gapmers are 20 nucleosides in length, wherein the central gap segment consists of ten 2'β-D-deoxynucleosides and the 5' and 3' wing segments each consists of five 2'-β-D-MOE modified nucleosides. The sugar motif for the gapmers is (from 5' to 3'): eeeeeddddddddddeeeee; wherein 'd' represents a 2'-β-D-deoxyribose sugar moiety, and 'e' represents a 2'-β-D-MOE sugar moeity. The gapmers have an internucleoside linkage motif of (from 5' to 3'): soooossssssssssooss; wherein each "s" represents a phosphorothioate internucleoside linkage and each "o" represents a phosphodiester internucleoside linkage. Each cytosine nucleoside is a 5-methylcytosine.

TABLE 60

5-10-5 MOE gapmers with a mixed PO/PS internucleoside linkages complementary to human GFAP

| Compound No. | SEQUENCE (5' to 3') | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1166900 | CAGCCTGGTTAGCCTTTCTG | N/A | N/A | 9514 | 9533 | 2017 |
| 1166901 | TCAGCCTGGTTAGCCTTTCT | N/A | N/A | 9515 | 9534 | 2094 |
| 1166902 | GTCAGCCTGGTTAGCCTTTC | N/A | N/A | 9516 | 9535 | 2171 |
| 1166903 | AGTCAGCCTGGTTAGCCTTT | N/A | N/A | 9517 | 9536 | 1484 |
| 1166904 | TAGTCAGCCTGGTTAGCCTT | N/A | N/A | 9518 | 9537 | 2248 |
| 1166905 | CTAGTCAGCCTGGTTAGCCT | N/A | N/A | 9519 | 9538 | 1561 |
| 1166906 | ACTAGTCAGCCTGGTTAGCC | N/A | N/A | 9520 | 9539 | 2325 |
| 1166907 | CAGTATTACCTCTACTAGTC | N/A | N/A | 9533 | 9552 | 20 |
| 1166909 | GGCAGTATTACCTCTACTAG | N/A | N/A | 9535 | 9554 | 1637 |
| 1166910 | TGGCAGTATTACCTCTACTA | N/A | N/A | 9536 | 9555 | 166 |
| 1166911 | TTGGCAGTATTACCTCTACT | N/A | N/A | 9537 | 9556 | 1865 |

TABLE 60-continued 5-10-5 MOE gapmers with a mixed PO/PS internucleoside linkages complementary to human GFAP

| Compound No. | SEQUENCE (5' to 3') | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1166912 | TTTGGCAGTATTACCTCTAC | N/A | N/A | 9538 | 9557 | 1941 |
| 1166913 | ATTTGGCAGTATTACCTCTA | N/A | N/A | 9539 | 9558 | 2018 |
| 1166932 | TGTATTAGGATCCCATCTAG | N/A | N/A | 11154 | 11173 | 1951 |
| 1166933 | GTGTATTAGGATCCCATCTA | N/A | N/A | 11155 | 11174 | 2028 |
| 1166934 | TGTGTATTAGGATCCCATCT | N/A | N/A | 11156 | 11175 | 2105 |
| 1166885 | CTTGTGATTTTCCCCGTCTT | N/A | N/A | 8756 | 8775 | 986 |
| 1166886 | CCTTGTGATTTTCCCCGTCT | N/A | N/A | 8757 | 8776 | 1064 |
| 1166887 | TTGAGATATCTTGTGACCTT | N/A | N/A | 8773 | 8792 | 1510 |
| 1166888 | TTTGAGATATCTTGTGACCT | N/A | N/A | 8774 | 8793 | 1280 |
| 1166890 | CTTTTGAGATATCTTGTGAC | N/A | N/A | 8776 | 8795 | 1434 |
| 1166893 | ACATTCACTAATATTTAACA | N/A | N/A | 9323 | 9342 | 1022 |
| 1166894 | CACATTCACTAATATTTAAC | N/A | N/A | 9324 | 9343 | 21 |
| 1166895 | TCACATTCACTAATATTTAA | N/A | N/A | 9325 | 9344 | 2321 |
| 1166896 | GTCACATTCACTAATATTTA | N/A | N/A | 9326 | 9345 | 1177 |
| 1166897 | CGTCACATTCACTAATATTT | N/A | N/A | 9327 | 9346 | 2398 |
| 1166898 | ACGTCACATTCACTAATATT | N/A | N/A | 9328 | 9347 | 2808 |
| 1166899 | CACGTCACATTCACTAATAT | N/A | N/A | 9329 | 9348 | 2809 |
| 1166916 | TGACTATCTAGGATTTGGCA | N/A | N/A | 9551 | 9570 | 2480 |
| 1166920 | CCTGTGACTATCTAGGATTT | N/A | N/A | 9555 | 9574 | 2709 |
| 1166926 | TGCCATTTATCTGTGCTTTA | N/A | N/A | 9579 | 9598 | 1639 |
| 1166927 | CTGCCATTTATCTGTGCTTT | N/A | N/A | 9580 | 9599 | 1867 |
| 1166928 | TCTGCCATTTATCTGTGCTT | N/A | N/A | 9581 | 9600 | 400 |
| 1166929 | CTCTGCCATTTATCTGTGCT | N/A | N/A | 9582 | 9601 | 1943 |
| 1174056 | GCTTTTGCCCCCTGTAGTGA | N/A | N/A | 8732 | 8751 | 2291 |
| 1174058 | GGTGCTTTTGCCCCCTGTAG | N/A | N/A | 8735 | 8754 | 1227 |
| 1174059 | TGGTGCTTTTGCCCCCTGTA | N/A | N/A | 8736 | 8755 | 2445 |
| 1174060 | TTGGTGCTTTTGCCCCCTGT | N/A | N/A | 8737 | 8756 | 59 |
| 1174061 | TTTGGTGCTTTTGCCCCCTG | N/A | N/A | 8738 | 8757 | 2522 |
| 1166940 | ACAGTTCCCAGATACTCCGA | 1754 | 1773 | 12043 | 12062 | 270 |
| 1166946 | AAAGGCACAGTTCCCAGATA | 1760 | 1779 | 12049 | 12068 | 582 |
| 1166948 | TCAGTTTTCCTCCAGCAGCC | 1791 | 1810 | 12080 | 12099 | 37 |
| 1166954 | CCAGTGTCTTCACTTTGCTC | 2749 | 2768 | 13038 | 13057 | 825 |
| 1199982 | GGTCCTAAATATTCTAGTCC | N/A | N/A | 9459 | 9478 | 2093 |
| 1199983 | TGGTCCTAAATATTCTAGTC | N/A | N/A | 9460 | 9479 | 2170 |
| 1199984 | GTGGTCCTAAATATTCTAGT | N/A | N/A | 9461 | 9480 | 2813 |

The modified oligonucleotides in the table below are 4-10-6 MOE gapmers. The gapmers are 20 nucleosides in length and have a central gap segment that consists of ten 2'-β-D-deoxynucleosides, a 5' wing segment that consists of four 2'-β-D-MOE nucleosides, and a 3' wing segment that consists of six 2'-β-D-MOE nucleosides. The sugar motif of the gapmers is (from 5' to 3): eceeeddddddddddkeeecee; wherein 'd' represents a 2'-β-D-deoxyribosyl sugar moiety, and 'e' represents a 2'-β-D-MOE sugar moiety. The gapmers have an internucleoside linkage motif of (from 5' to 3'): sooosssssssssssoooss; wherein "s" represents a phosphonothioate internucleoside linkage and "o" represents a phosphodiester internucleoside linkage. Each cytosine nucleoside is a 5-methylcytosine.

TABLE 61

4-10-6 MOE gapmers with a mixed PO/PS internucleoside linkages complementary to human GFAP

| Compound No. | SEQUENCE (5' to 3') | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1166809 | CAGCCTGGTTAGCCTTTCTG | N/A | N/A | 9514 | 9533 | 2017 |
| 1166810 | TCAGCCTGGTTAGCCTTTCT | N/A | N/A | 9515 | 9534 | 2094 |
| 1166812 | AGTCAGCCTGGTTAGCCTTT | N/A | N/A | 9517 | 9536 | 1484 |
| 1166813 | TAGTCAGCCTGGTTAGCCTT | N/A | N/A | 9518 | 9537 | 2248 |
| 1166814 | CTAGTCAGCCTGGTTAGCCT | N/A | N/A | 9519 | 9538 | 1561 |
| 1166815 | ACTAGTCAGCCTGGTTAGCC | N/A | N/A | 9520 | 9539 | 2325 |
| 1166816 | CAGTATTACCTCTACTAGTC | N/A | N/A | 9533 | 9552 | 20 |
| 1166817 | GCAGTATTACCTCTACTAGT | N/A | N/A | 9534 | 9553 | 88 |
| 1166818 | GGCAGTATTACCTCTACTAG | N/A | N/A | 9535 | 9554 | 1637 |
| 1166819 | TGGCAGTATTACCTCTACTA | N/A | N/A | 9536 | 9555 | 166 |
| 1166820 | TTGGCAGTATTACCTCTACT | N/A | N/A | 9537 | 9556 | 1865 |
| 1166821 | TTTGGCAGTATTACCTCTAC | N/A | N/A | 9538 | 9557 | 1941 |
| 1166822 | ATTTGGCAGTATTACCTCTA | N/A | N/A | 9539 | 9558 | 2018 |
| 1166841 | TGTATTAGGATCCCATCTAG | N/A | N/A | 11154 | 11173 | 1951 |
| 1166842 | GTGTATTAGGATCCCATCTA | N/A | N/A | 11155 | 11174 | 2028 |
| 1166843 | TGTGTATTAGGATCCCATCT | N/A | N/A | 11156 | 11175 | 2105 |
| 1166845 | AGTGTGTATTAGGATCCCAT | N/A | N/A | 11158 | 11177 | 2182 |
| 1166846 | GAGTGTGTATTAGGATCCCA | N/A | N/A | 11159 | 11178 | 2259 |
| 1166847 | AGAGTGTGTATTAGGATCCC | N/A | N/A | 11160 | 11179 | 2336 |
| 1166869 | TCTTTATTTTTCCTCAGCGA | 3046 | 3065 | 13335 | 13354 | 439 |
| 1166870 | GTCTTTATTTTTCCTCAGCG | 3047 | 3066 | 13336 | 13355 | 517 |
| 1166871 | TGTCTTTATTTTTCCTCAGC | 3048 | 3067 | 13337 | 13356 | 595 |
| 1166872 | TTGTCTTTATTTTTCCTCAG | 3049 | 3068 | 13338 | 13357 | 673 |
| 1166873 | TTTGTCTTTATTTTTCCTCA | 3050 | 3069 | 13339 | 13358 | 751 |
| 1166874 | ATTTGTCTTTATTTTTCCTC | 3051 | 3070 | 13340 | 13359 | 829 |
| 1166793 | TTGTGATTTTCCCCGTCTTT | N/A | N/A | 8755 | 8774 | 908 |
| 1166794 | CTTGTGATTTTCCCCGTCTT | N/A | N/A | 8756 | 8775 | 986 |
| 1166795 | CCTTGTGATTTTCCCCGTCT | N/A | N/A | 8757 | 8776 | 1064 |
| 1166798 | TTTTGAGATATCTTGTGACC | N/A | N/A | 8775 | 8794 | 1357 |
| 1166799 | CTTTTGAGATATCTTGTGAC | N/A | N/A | 8776 | 8795 | 1434 |
| 1166800 | GCTTTTGAGATATCTTGTGA | N/A | N/A | 8777 | 8796 | 51 |
| 1166802 | ACATTCACTAATATTTAACA | N/A | N/A | 9323 | 9342 | 1022 |

TABLE 61-continued 4-10-6 MOE gapmers with a mixed PO/PS internucleoside linkages complementary to human GFAP

| Compound No. | SEQUENCE (5' to 3') | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1166803 | CACATTCACTAATATTTAAC | N/A | N/A | 9324 | 9343 | 21 |
| 1166804 | TCACATTCACTAATATTTAA | N/A | N/A | 9325 | 9344 | 2321 |
| 1166805 | GTCACATTCACTAATATTTA | N/A | N/A | 9326 | 9345 | 1177 |
| 1166806 | CGTCACATTCACTAATATTT | N/A | N/A | 9327 | 9346 | 2398 |
| 1166807 | ACGTCACATTCACTAATATT | N/A | N/A | 9328 | 9347 | 2808 |
| 1166808 | CACGTCACATTCACTAATAT | N/A | N/A | 9329 | 9348 | 2809 |
| 1166867 | TTTATTTTTCCTCAGCGACT | 3044 | 3063 | 13333 | 13352 | 283 |
| 1166875 | CATTTGTCTTTATTTTTCCT | 3052 | 3071 | 13341 | 13360 | 907 |
| 1166877 | AGCATTTGTCTTTATTTTTC | 3054 | 3073 | 13343 | 13362 | 1063 |
| 1166878 | CAGCATTTGTCTTTATTTTT | 3055 | 3074 | 13344 | 13363 | 1140 |
| 1166823 | ACTATCTAGGATTTGGCAGT | N/A | N/A | 9549 | 9568 | 2326 |
| 1166826 | GTGACTATCTAGGATTTGGC | N/A | N/A | 9552 | 9571 | 1408 |
| 1166831 | ATTTATCTGTGCTTTAGTGA | N/A | N/A | 9575 | 9594 | 2786 |
| 1166835 | TGCCATTTATCTGTGCTTTA | N/A | N/A | 9579 | 9598 | 1639 |
| 1174050 | GCTTTTGCCCCCTGTAGTGA | N/A | N/A | 8732 | 8751 | 2291 |
| 1174051 | GTGCTTTTGCCCCCTGTAGT | N/A | N/A | 8734 | 8753 | 2368 |
| 1174053 | TGGTGCTTTTGCCCCCTGTA | N/A | N/A | 8736 | 8755 | 2445 |
| 1174054 | TTGGTGCTTTTGCCCCCTGT | N/A | N/A | 8737 | 8756 | 59 |
| 1166852 | GGCACAGTTCCCAGATACTC | 1757 | 1776 | 12046 | 12065 | 504 |

The modified oligonucleotides in the table below are 5-8-5 MOE gapmers. The gapmers are 20 nucleosides in length and have a central gap segment that consists of eight 2'-β-D-deoxynucleosides, a 5' wing segment that consists of five 2'-β-D-MOE nucleosides, and a 3' wing segment that consists of five 2'-β-D-MOE nucleosides. The sugar motif of the gapmers is (from 5' to 3'): eeeeeddddddddeeee; wherein 'd' represents a 2'-β-D-deoxyribosyl sugar moiety, and 'e' represents a 2'-β-D-MOE sugar moiety. The gapmers have an internucleoside linkage motif of (from 5' to 3'): sooosssssssssooss; wherein each "s" represents a phosphorthioate internucleoside linkage and each "o" represents a phosphodiester internucleoside linkage. Each cytosine nucleobase is a 5-methylcytosine.

TABLE 62

5-8-5 MOE gapmers with a mixed PO/PS internucleoside linkages complementary to human GFAP

| Compound No. | SEQUENCE (5' to 3') | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1166719 | GCAGTATTACCTCTACTA | N/A | N/A | 9536 | 9553 | 2816 |
| 1166720 | GGCAGTATTACCTCTACT | N/A | N/A | 9537 | 9554 | 2817 |
| 1166721 | TGGCAGTATTACCTCTAC | N/A | N/A | 9538 | 9555 | 2818 |
| 1166749 | TCAGCCTGGTTAGCCTTT | N/A | N/A | 9517 | 9534 | 2819 |
| 1166750 | GTCAGCCTGGTTAGCCTT | N/A | N/A | 9518 | 9535 | 2820 |
| 1166751 | AGTCAGCCTGGTTAGCCT | N/A | N/A | 9519 | 9536 | 2821 |
| 1166761 | GTGTATTAGGATCCCATC | N/A | N/A | 11157 | 11174 | 2822 |

TABLE 62-continued 5-8-5 MOE gapmers with a mixed PO/PS internucleoside linkages complementary to human GFAP

| Compound No. | SEQUENCE (5' to 3') | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1166762 | TGTGTATTAGGATCCCAT | N/A | N/A | 11158 | 11175 | 2823 |
| 1166763 | GTGTGTATTAGGATCCCA | N/A | N/A | 11159 | 11176 | 2824 |
| 1166775 | TTATTTTTCCTCAGCGAC | 3045 | 3062 | 13334 | 1335} | 2825 |
| 1166776 | TTTATTTTTCCTCAGCGA | 3046 | 3063 | 13335 | 13352 | 2826 |
| 1166777 | CTTTATTTTTCCTCAGCG | 3047 | 3064 | 13336 | 13353 | 2827 |
| 1166778 | TCTTTATTTTTCCTCAGC | 3048 | 3065 | 13337 | 13354 | 2828 |
| 1166779 | GTCTTTATTTTTCCTCAG | 3049 | 3066 | 13338 | 13355 | 2829 |
| 1166780 | TGTCTTTATTTTTCCTCA | 3050 | 3067 | 13339 | 13356 | 2830 |
| 1166781 | TTGTCTTTATTTTTCCTC | 3051 | 3068 | 13340 | 13357 | 2831 |
| 1166782 | TTTGTCTTTATTTTTCCT | 3052 | 3069 | 13341 | 13358 | 2832 |
| 1166783 | ATTTGTCTTTATTTTTCC | 3053 | 3070 | 13342 | 13359 | 2833 |
| 1166738 | GTGATTTTCCCCGTCTTT | N/A | N/A | 8755 | 8772 | 2835 |
| 1166739 | TGTGATTTTCCCCGTCTT | N/A | N/A | 8756 | 8773 | 2836 |
| 1166740 | GAGATATCTTGTGACCTT | N/A | N/A | 8773 | 8790 | 2837 |
| 1166742 | TTGAGATATCTTGTGACC | N/A | N/A | 8775 | 8792 | 2839 |
| 1166746 | CACATTCACTAATATTTA | N/A | N/A | 9326 | 9343 | 2840 |
| 1166747 | TCACATTCACTAATATTT | N/A | N/A | 9327 | 9344 | 2841 |
| 1166748 | GTCACATTCACTAATATT | N/A | N/A | 9328 | 9345 | 2842 |
| 1166784 | CATTTGTCTTTATTTTTC | 3054 | 3071 | 13343 | 13360 | 2843 |
| 1166785 | GCATTTGTCTTTATTTTT | 3055 | 3072 | 13344 | 13361 | 2844 |
| 1166786 | AGCATTTGTCTTTATTTT | 3056 | 3073 | 13345 | 13362 | 2845 |
| 1166787 | CAGCATTTGTCTTTATTT | 3057 | 3074 | 13346 | 13363 | 2846 |
| 1174012 | TTGTGATTTTCCCCGTCT | N/A | N/A | 8757 | 8774 | 2850 |
| 1174013 | TTTGAGATATCTTGTGAC | N/A | N/A | 8776 | 8793 | 2851 |
| 1174015 | ATTCACTAATATTTAACA | N/A | N/A | 9323 | 9340 | 2852 |
| 1174016 | CATTCACTAATATTTAAC | N/A | N/A | 9324 | 9341 | 2853 |
| 1174018 | CGTCACATTCACTAATAT | N/A | N/A | 9329 | 9346 | 2854 |
| 1174020 | AGCCTGGTTAGCCTTTCT | N/A | N/A | 9515 | 9532 | 2856 |
| 1174024 | AGTATTACCTCTACTAGT | N/A | N/A | 9534 | 9551 | 2859 |
| 1174026 | TTGGCAGTATTACCTCTA | N/A | N/A | 9539 | 9556 | 2861 |
| 1174036 | TATTAGGATCCCATCTAG | N/A | N/A | 11154 | 11171 | 2862 |
| 1174037 | GTATTAGGATCCCATCTA | N/A | N/A | 11155 | 11172 | 2863 |
| 1166744 | GCTTTTGAGATATCTTGT | N/A | N/A | 8779 | 8796 | 2866 |
| 1166757 | CCATTTATCTGTGCTTTA | N/A | N/A | 9579 | 9596 | 2873 |
| 1166758 | TGCCATTTATCTGTGCTT | N/A | N/A | 9581 | 9598 | 2874 |
| 1166759 | CTGCCATTTATCTGTGCT | N/A | N/A | 9582 | 9599 | 2875 |

TABLE 62-continued 5-8-5 MOE gapmers with a mixed PO/PS internucleoside linkages complementary to human GFAP

| Compound No. | SEQUENCE (5' to 3') | SEQ ID No: 1 Start Site | SEQ ID No: 1 Stop Site | SEQ ID No: 2 Start Site | SEQ ID No: 2 Stop Site | SEQ ID No. |
|---|---|---|---|---|---|---|
| 1166760 | TCTGCCATTTATCTGTGC | N/A | N/A | 9583 | 9600 | 2876 |
| 1174029 | ACTATCTAGGATTTGGCA | N/A | N/A | 9551 | 9568 | 2886 |
| 1174030 | TGTGACTATCTAGGATTT | N/A | N/A | 9555 | 9572 | 2887 |
| 1174031 | TATCTGTGCTTTAGTGAC | N/A | N/A | 9574 | 9591 | 2888 |
| 1174034 | GCCATTTATCTGTGCTTT | N/A | N/A | 9580 | 9597 | 2891 |

Example 6: Tolerability of Modified Oligonucleotides Complementary to Human GFAP in Wild-Type Mice, 3 Hour Study Modified oligonucleotides described above were tested in wild-type female C57/Bl6 mice to assess the tolerability of the oligonucleotides. Wild-type female C57/Bl6 mice each received a single ICV dose of 700 μg of modified oligonucleotide listed in the table below. Each treatment group consisted of 4 mice. A group of 4 mice received PBS as a negative control for each experiment (identified in separate tables below). At 3 hours post-injection, mice were evaluated according to seven different criteria. The criteria are (1) the mouse was bright, alert, and responsive: (2) the mouse was standing or hunched without stimuli: (3) the mouse showed any movement without stimuli: (4) the mouse demonstrated forward movement after it was lifted; (5) the mouse demonstrated any movement after it was lifted; (6) the mouse responded to tail pinching: (7) regular breathing. For each of the 7 criteria, a mouse was given a subs orc of 0 if it met the criteria and 1 if it did not (the functional observational battery score or FOB). After all 7 criteria were evaluated, the scores were summed for each mouse and averaged within each treatment group. The results are presented in the tables below.

TABLE 63

Tolerability scores in mice at 700 μg dose

| Compound No. | 3 hr. FOB |
|---|---|
| PBS | 0 |
| 1166719 | 1 |
| 1166720 | 0 |
| 1166721 | 0 |
| 1166749 | 3 |
| 1166750 | 1 |
| 1166751 | 2 |
| 1166761 | 4 |
| 1166762 | 4 |
| 1166763 | 3 |
| 1166775 | 0 |
| 1166776 | 1 |
| 1166777 | 4 |
| 1166778 | 1 |
| 1166779 | 4 |
| 1166780 | 1 |
| 1166781 | 0 |
| 1166782 | 0 |
| 1166783 | 0 |
| 1166809 | 4 |

TABLE 63-continued

Tolerability scores in mice at 700 μg dose

| Compound No. | 3 hr. FOB |
|---|---|
| 1166810 | 4 |
| 1166812 | 3 |
| 1166813 | 3 |

TABLE 64

Tolerability scores in mice at 700 μg dose

| Compound No. | 3 hr. FOB |
|---|---|
| PBS | 0 |
| 1166814 | 4 |
| 1166815 | 2 |
| 1166816 | 1 |
| 1166817 | 1 |
| 1166818 | 3 |
| 1166819 | 1 |
| 1166820 | 1 |
| 1166821 | 1 |
| 1166822 | 3 |
| 1166841 | 3 |
| 1166842 | 3 |
| 1166843 | 3 |
| 1166845 | 5 |
| 1166846 | 4 |
| 1166847 | 5 |
| 1166869 | 1 |
| 1166870 | 3 |
| 1166871 | 2 |
| 1166872 | 2 |
| 1166873 | 1 |
| 1166874 | 0 |
| 1166900 | 5 |

TABLE 65

Tolerability scores in mice at 700 μg dose

| Compound No. | 3 hr. FOB |
|---|---|
| PBS | 0 |
| 1166901 | 4 |
| 1166902 | 5 |
| 1166903 | 4 |
| 1166904 | 4 |
| 1166905 | 2 |

TABLE 65-continued

| Tolerability scores in mice at 700 μg dose | |
|---|---|
| Compound No. | 3 hr. FOB |
| 1166906 | 2 |
| 1166907 | 0 |
| 1166909 | 3 |
| 1166910 | 1 |
| 1166911 | 0 |
| 1166912 | 1 |
| 1166913 | 2 |
| 1166932 | 4 |
| 1166933 | 2 |
| 1166934 | 3 |
| 1166991 | 4 |
| 1166992 | 4 |
| 1166993 | 4 |
| 1166994 | 3 |

TABLE 66

| Tolerability scores in mice at 700 μg dose | |
|---|---|
| Compound No. | 3 hr. FOB |
| PBS | 0 |
| 1166996 | 4 |
| 1166997 | 4 |
| 1166998 | 0 |
| 1166999 | 0 |
| 1167000 | 3 |
| 1167001 | 0 |
| 1167002 | 0 |
| 1167003 | 0 |
| 1167004 | 0 |
| 1167024 | 4 |
| 1167025 | 3 |
| 1167026 | 4 |
| 1167027 | 4 |
| 1167050 | 1 |
| 1167051 | 0 |
| 1167053 | 1 |
| 1167054 | 4 |
| 1167055 | 0 |
| 1167056 | 0 |

TABLE 67

| Tolerability scores in mice at 700 μg dose | |
|---|---|
| Compound No. | 3 hr. FOB |
| PBS | 0 |
| 1166738 | 0 |
| 1166739 | 0 |
| 1166740 | 4 |
| 1166742 | 3 |
| 1166746 | 0 |
| 1166747 | 0 |
| 1166748 | 0 |
| 1166784 | 0 |
| 1166785 | 1 |
| 1166786 | 3 |
| 1166787 | 3 |
| 1166793 | 0 |
| 1166794 | 0 |
| 1166795 | 1 |
| 1166797 | 4 |
| 1166798 | 3 |

TABLE 68

| Tolerability scores in mice at 700 μg dose | |
|---|---|
| Compound No. | 3 hr. FOB |
| PBS | 0 |
| 1166799 | 1 |
| 1166802 | 0 |
| 1166803 | 0 |
| 1166804 | 0 |
| 1166805 | 0 |
| 1166806 | 0 |
| 1166807 | 0 |
| 1166808 | 0 |
| 1166867 | 0 |
| 1166877 | 1 |
| 1166878 | 2 |
| 1166885 | 3 |
| 1166886 | 0 |
| 1166887 | 3 |
| 1166888 | 3 |
| 1166890 | 0 |
| 1166893 | 0 |

TABLE 69

| Tolerability scores in mice at 700 μg dose | |
|---|---|
| Compound No. | 3 hr. FOB |
| PBS | 0 |
| 1166894 | 0 |
| 1166895 | 0 |
| 1166896 | 0 |
| 1166897 | 0 |
| 1166898 | 0 |
| 1166899 | 0 |
| 1166984 | 0 |
| 1166985 | 0 |
| 1166986 | 0 |
| 1166987 | 0 |
| 1166988 | 0 |
| 1166990 | 0 |

TABLE 70

| Tolerability scores in mice at 700 μg dose | |
|---|---|
| Compound No. | 3 hr. FOB |
| PBS | 0 |
| 1167057 | 0 |
| 1167059 | 1 |
| 1167060 | 1 |
| 1174012 | 2 |
| 1174013 | 3 |
| 1174015 | 0 |
| 1174016 | 0 |
| 1174018 | 0 |
| 1174020 | 4 |
| 1174024 | 3 |
| 1174026 | 0 |
| 1174036 | 3 |
| 1174037 | 2 |

TABLE 71

| Tolerability scores in mice at 700 µg dose | |
|---|---|
| Compound No. | 3 hr. FOB |
| PBS | 0 |
| 1166744 | 3 |
| 1166757 | 4 |
| 1166758 | 3 |
| 1166759 | 1 |
| 1166760 | 3 |
| 1166800 | 1 |
| 1166823 | 2 |
| 1166826 | 3 |
| 1166831 | 2 |
| 1166875 | 0 |
| 1166975 | 4 |
| 1166989 | 0 |

TABLE 72

| Tolerability scores in mice at 700 µg dose | |
|---|---|
| Compound No. | 3 hr. FOB |
| PBS | 0 |
| 1166835 | 0 |
| 1166916 | 3 |
| 1166920 | 2 |
| 1166926 | 1 |
| 1166927 | 2 |
| 1166928 | 1 |
| 1166929 | 0 |
| 1166982 | 2 |

TABLE 73

| Tolerability scores in mice at 700 µg dose | |
|---|---|
| Compound No. | 3 hr. FOB |
| PBS | 0 |
| 1167007 | 2 |
| 1167011 | 1 |
| 1167012 | 3 |
| 1167017 | 2 |
| 1167018 | 1 |
| 1174029 | 4 |

TABLE 74

| Tolerability scores in mice at 700 µg dose | |
|---|---|
| Compound No. | 3 hr. FOB |
| PBS | 0 |
| 1174030 | 3 |
| 1174031 | 3 |
| 1174034 | 1 |
| 1174050 | 3 |
| 1174051 | 3 |
| 1174053 | 1 |
| 1174054 | 1 |
| 1174056 | 4 |
| 1174058 | 3 |
| 1174059 | 0 |
| 1174060 | 0 |
| 1174061 | 2 |
| 1174062 | 3 |
| 1174063 | 3 |

TABLE 74-continued

| Tolerability scores in mice at 700 µg dose | |
|---|---|
| Compound No. | 3 hr. FOB |
| 1174065 | 1 |
| 1174066 | 1 |

TABLE 75

| Tolerability scores in mice at 700 µg dose | |
|---|---|
| Compound No. | 3 hr. FOB |
| PBS | 0 |
| 1166852 | 1 |

TABLE 76

| Tolerability scores in mice at 700 µg dose | |
|---|---|
| Compound No. | 3 hr. FOB |
| PBS | 0 |
| 1166940 | 2 |
| 1166946 | 2 |
| 1166948 | 2 |

TABLE 77

| Tolerability scores in mice at 700 µg dose | |
|---|---|
| Compound No. | 3 hr. FOB |
| PBS | 0 |
| 1166954 | 0 |
| 1167033 | 0 |
| 1167034 | 1 |
| 1167035 | 1 |
| 1167036 | 2 |
| 1167037 | 2 |
| 1167040 | 2 |

TABLE 78

| Tolerability scores in mice at 700 µg dose | |
|---|---|
| Compound No. | 3 hr. FOB |
| PBS | 0 |
| 1167046 | 3 |
| 1167058 | 1 |

TABLE 79

| Tolerability scores in mice at 700 µg dose | |
|---|---|
| Compound No. | 3 hr. FOB |
| PBS | 0 |
| 1199982 | 1 |

TABLE 79-continued

| Tolerability scores in mice at 700 μg dose | |
|---|---|
| Compound No. | 3 hr. FOB |
| 1199983 | 1 |
| 1199984 | 1 |

Example 7: Activity of Modified Oligonucleotides Complementary to Human GFAP in Transgenic Mice Modified oligonucleotides described above were tested in human GFAP transgenic mouse model. Transgenic mice (line 73.7) was previously described in Messing A., et al., Fatal encephalopathy with astrocyte inclusions in GFAP transgenic mice, Am J Pathos, 1998, 152(2):391-398.

Treatment

The GFAP transgenic mice were divided into groups of 34 mice each. Each mouse received a single ICV bolus of 300 μg of modified oligonucleotide. A group of 34 mice received PBS as a negative control.

RNA Analysis

One week post treatment, mice were sacrificed and RNA was extracted from cortical brain tissue, and/or spinal cord for RTPCR analysis to measure amount of GFAP RNA using primer probe set RTS38621 ((forward sequence AGTTGCAGTCCTTGACCTG, designated herein as SEQ ID NO: 14; reverse sequence CAGCGCCTCCTGA-TAACTG, designated herein as SEQ ID NO: 15; probe sequence ACGAGTCCCTGGAGAGGCAGATG, designated herein as SEQ ID NO: 16), which is a human specific primer-probe set that recognizes all isoforms of GFAP. Results are presented as percent human GFAP RNA relative to PBS control, normalized to mouse peptidylprolyl isomerase A (PPIA), also known as cyclophilin A. Mouse PPIA was amplified using primer probe set m_cyclo24 (forward sequence TCGCCGCTTGCTGCA, designated herein as SEQ ID NO: 17; reverse sequence ATCGGCCGT-GATGTCGA, designated herein as SEQ ID NO: 18; probe sequence CCATGGTCAACCCCACCGTGTTC, designated herein as SEQ ID NO: 19). In some cases, RTPCR value is not defined for a certain sample, and is labeled N.D. (Not Defined).

As shown in the table below, treatment with modified oligonucleotides resulted in reduction of GFAP RNA in comparison to the PBS control.

TABLE 80

| Reduction of human GFAP RNA in transgenic mice | | |
|---|---|---|
| | GFAP RNA (% control) | |
| Compound No. | SPINAL CORD | CORTEX |
| PBS | 100 | 100 |
| 1047198 | 44 | 44 |
| 1047362 | 15 | 21 |
| 1047373 | 10 | 16 |
| 1047374 | 8 | 16 |
| 1047386 | 14 | 19 |
| 1047394 | 48 | 43 |
| 1047429 | N.D. | N.D. |
| 1047448 | 37 | 45 |
| 1047500 | 23 | 26 |
| 1047580 | 12 | 15 |
| 1047582 | 5 | 8 |

TABLE 80-continued

| Reduction of human GFAP RNA in transgenic mice | | |
|---|---|---|
| | GFAP RNA (% control) | |
| Compound No. | SPINAL CORD | CORTEX |
| 1047583 | 6 | 9 |
| 1047584 | 6 | 7 |
| 1047585 | 8 | 7 |
| 1047586 | 12 | 11 |
| 1047587 | 13 | 13 |
| 1047589 | 9 | 13 |
| 1047590 | 16 | 16 |
| 1047591 | 14 | 17 |
| 1047610 | 33 | 31 |
| 1048203 | 26 | 27 |
| 1048350 | 28 | 24 |

TABLE 81

| Reduction of human GFAP RNA in transgenic mice | | |
|---|---|---|
| | GFAP RNA (% control) | |
| Compound No. | SPINAL CORD | CORTEX |
| PBS | 100 | 100 |
| 1047211 | 71 | 66 |
| 1047225 | 65 | 61 |
| 1047298 | 34 | 27 |
| 1047316 | 29 | 24 |
| 1047402 | 30 | 25 |
| 1047432 | 28 | 29 |
| 1047518 | 49 | 34 |
| 1047522 | 23 | 19 |
| 1047532 | 40 | 30 |
| 1047579 | 27 | 17 |
| 1047581 | 11 | 10 |
| 1047598 | 77 | 50 |
| 1047599 | 21 | 15 |
| 1047601 | 47 | 30 |
| 1047602 | N.D. | N.D. |
| 1047609 | 27 | 18 |
| 1047662 | 34 | 27 |
| 1047679 | 58 | 54 |

TABLE 82

| Reduction of human GFAP RNA in transgenic mice | | |
|---|---|---|
| | GFAP RNA (% control) | |
| Compound No. | SPINAL CORD | CORTEX |
| PBS | 100 | 100 |
| 1047711 | 45 | 38 |
| 1047884 | 57 | 62 |
| 1047913 | 75 | 66 |
| 1048027 | 64 | 53 |
| 1048151 | 69 | 64 |
| 1048182 | 14 | 10 |
| 1048201 | 6 | 7 |
| 1048204 | 21 | 18 |
| 1048227 | 42 | 28 |
| 1072855 | N.D. | N.D. |
| 1072856 | N.D. | N.D. |
| 1072857 | 28 | 14 |
| 1072861 | 28 | 23 |
| 1072862 | 53 | 33 |
| 1072863 | 51 | 28 |
| 1072886 | 42 | 26 |
| 1072980 | 40 | 25 |
| 1072986 | 98 | 88 |
| 1073033 | 100 | 80 |
| 1073045 | 36 | 24 |

TABLE 82-continued

| Reduction of human GFAP RNA in transgenic mice | | |
|---|---|---|
| | GFAP RNA (% control) | |
| Compound No. | SPINAL CORD | CORTEX |
| 1073060 | 19 | 16 |
| 1073063 | 19 | 15 |
| 1073064 | 29 | 20 |
| 1073065 | 16 | 15 |
| 1073093 | 11 | 8 |

TABLE 83

| Reduction of human GFAP RNA in transgenic mice | | |
|---|---|---|
| | GFAP RNA (% control) | |
| Compound No. | SPINAL CORD | CORTEX |
| PBS | 100 | 100 |
| 1103217 | 56 | 43 |
| 1103465 | 31 | 19 |
| 1103502 | 47 | 31 |
| 1103516 | 42 | 27 |
| 1103567 | 23 | 18 |
| 1104093 | 13 | 12 |
| 1104118 | N.D. | N.D. |
| 1104145 | 8 | 6 |
| 1104152 | 27 | 17 |
| 1104166 | 17 | 13 |
| 1104175 | 15 | 8 |

TABLE 84

| Reduction of human GFAP RNA in transgenic mice | | |
|---|---|---|
| | GFAP RNA (% control) | |
| Compound No. | SPINAL CORD | CORTEX |
| PBS | 100 | 100 |
| 1072813 | 15 | 18 |
| 1072814 | 15 | 19 |
| 1103202 | 34 | 36 |
| 1103218 | 48 | 33 |
| 1103253 | 56 | 36 |
| 1103255 | N.D. | N.D. |
| 1103256 | 35 | 41 |
| 1103257 | 46 | 43 |
| 1103258 | N.D. | N.D. |
| 1103259 | 82 | 71 |
| 1103268 | N.D. | N.D. |
| 1104307 | 13 | 14 |
| 1104309 | 10 | 11 |
| 1104311 | 11 | 18 |
| 1104349 | N.D. | N.D. |

TABLE 85

| Reduction of human GFAP RNA in transgenic mice | | |
|---|---|---|
| | GFAP RNA (% control) | |
| Compound No. | SPINAL CORD | CORTEX |
| PBS | 100 | 100 |
| 1103279 | 20 | 14 |
| 1103285 | 16 | 9 |
| 1103411 | 65 | 32 |
| 1103471 | 32 | 39 |
| 1103570 | 6 | 4 |
| 1103872 | 42 | 18 |
| 1104116 | 6 | 3 |
| 1104127 | 15 | 10 |
| 1104144 | 17 | 8 |
| 1104159 | 17 | 10 |
| 1104276 | 53 | 41 |
| 1166719 | 41 | 31 |
| 1166720 | 12 | 8 |
| 1166721 | 7 | 8 |
| 1166749 | 13 | 11 |
| 1166750 | 10 | 7 |
| 1166751 | 12 | 9 |
| 1166761 | 12 | 5 |

TABLE 86

| Reduction of human GFAP RNA in transgenic mice | |
|---|---|
| Compound No. | GFAP RNA (% control) CORTEX |
| PBS | 100 |
| 1166762 | 18 |
| 1166763 | 13 |
| 1166775 | 21 |
| 1166776 | 30 |
| 1166777 | 13 |
| 1166778 | 6 |
| 1166779 | 7 |
| 1166780 | 9 |
| 1166781 | 7 |
| 1166782 | 12 |
| 1166783 | 17 |
| 1166809 | 13 |
| 1166810 | 16 |
| 1166812 | 23 |
| 1166813 | 21 |
| 1166814 | 29 |
| 1166815 | 42 |
| 1166816 | 31 |
| 1166817 | 37 |
| 1166818 | 14 |
| 1166819 | 9 |
| 1166820 | 12 |
| 1166821 | 15 |
| 1166822 | 20 |
| 1166841 | 47 |

TABLE 87

| Reduction of human GFAP RNA in transgenic mice | | |
|---|---|---|
| | GFAP RNA (% control) | |
| Compound No. | SPINAL CORD | CORTEX |
| PBS | 100 | 100 |
| 1166842 | 19 | 14 |
| 1166843 | 37 | 21 |
| 1166845 | 17 | 19 |
| 1166846 | 12 | 18 |
| 1166847 | 13 | 19 |
| 1166869 | 10 | 11 |
| 1166870 | 6 | 7 |
| 1166871 | 5 | 7 |
| 1166872 | 10 | 9 |
| 1166873 | 14 | 14 |
| 1166874 | 9 | 10 |
| 1166900 | 14 | 20 |

TABLE 87-continued

| Reduction of human GFAP RNA in transgenic mice | | |
|---|---|---|
| | GFAP RNA (% control) | |
| Compound No. | SPINAL CORD | CORTEX |
| 1166901 | 11 | 13 |
| 1166902 | 12 | 15 |
| 1166903 | 17 | 19 |
| 1166904 | 26 | 30 |
| 1166905 | 24 | 28 |
| 1166906 | 50 | 56 |
| 1166907 | 28 | 32 |

TABLE 88

| Reduction of human GFAP RNA in transgenic mice | |
|---|---|
| Compound No. | GFAP RNA (% control) CORTEX |
| PBS | 100 |
| 1166909 | 30 |
| 1166910 | 8 |
| 1166911 | 7 |
| 1166912 | 15 |
| 1166913 | 12 |
| 1166932 | 41 |
| 1166933 | 13 |
| 1166934 | 18 |
| 1166991 | 14 |
| 1166992 | 11 |
| 1166993 | 9 |
| 1166994 | 10 |
| 1166996 | 21 |
| 1166997 | 30 |
| 1166998 | 13 |
| 1166999 | 11 |
| 1167000 | 15 |

TABLE 89

| Reduction of human GFAP RNA in transgenic mice | |
|---|---|
| Compound No. | GFAP RNA (% control) CORTEX |
| PBS | 100 |
| 1167001 | 9 |
| 1167002 | 7 |
| 1167003 | 8 |
| 1167004 | 13 |
| 1167024 | 18 |
| 1167025 | 11 |
| 1167026 | 14 |
| 1167027 | 13 |
| 1167050 | 11 |
| 1167051 | 10 |
| 1167053 | 7 |
| 1167054 | 5 |
| 1167055 | 6 |
| 1167056 | 6 |

TABLE 90

| Reduction of human GFAP RNA in transgenic mice | |
|---|---|
| Compound No. | GFAP RNA (% control) CORTEX |
| PBS | 100 |
| 1166738 | 27 |
| 1166739 | 27 |
| 1166740 | 26 |
| 1166742 | 43 |
| 1166746 | 94 |
| 1166747 | 23 |
| 1166748 | 20 |
| 1166784 | 30 |
| 1166785 | 13 |
| 1166786 | 19 |
| 1166787 | 19 |
| 1166793 | 23 |
| 1166794 | 32 |
| 1166795 | 51 |
| 1166798 | 25 |
| 1166799 | 33 |
| 1166802 | 38 |
| 1166803 | 31 |
| 1166804 | 29 |
| 1166805 | 7 |
| 1166806 | 23 |
| 1166807 | 19 |
| 1166808 | 14 |
| 1166867 | 13 |
| 1166877 | 7 |
| 1166878 | 13 |
| 1166885 | 20 |
| 1166886 | 25 |

TABLE 91

| Reduction of human GFAP RNA in transgenic mice | |
|---|---|
| Compound No. | GFAP RNA (% control) CORTEX |
| PBS | 100 |
| 1166887 | 12 |
| 1166888 | 16 |
| 1166890 | 38 |
| 1166893 | 39 |
| 1166894 | 20 |
| 1166895 | 11 |
| 1166896 | 8 |
| 1166897 | 6 |
| 1166898 | 8 |
| 1166899 | 11 |
| 1166984 | 24 |
| 1166985 | 9 |
| 1166986 | 13 |
| 1166987 | 7 |
| 1166988 | 5 |
| 1166990 | 9 |
| 1167057 | 7 |
| 1167059 | 5 |
| 1167060 | 8 |
| 1174012 | 9 |
| 1174013 | 33 |
| 1174015 | 107 |

TABLE 92

| Reduction of human GFAP RNA in transgenic mice | |
|---|---|
| Compound No. | GFAP RNA (% control) CORTEX |
| PBS | 100 |
| 1166744 | 14 |
| 1166757 | 7 |
| 1166758 | 34 |
| 1166759 | 9 |
| 1166760 | 16 |
| 1166800 | 8 |
| 1166823 | 7 |
| 1166826 | 6 |
| 1166831 | 16 |
| 1166835 | 47 |
| 1166875 | 7 |
| 1166916 | 14 |
| 1166920 | 18 |
| 1166975 | 6 |
| 1166989 | 4 |
| 1174016 | 66 |
| 1174018 | 11 |
| 1174020 | 12 |
| 1174024 | 52 |
| 1174026 | 7 |
| 1174036 | 43 |
| 1174037 | 24 |

TABLE 93

| Reduction of human GFAP RNA in transgenic mice | |
|---|---|
| Compound No. | GFAP RNA (% control) CORTEX |
| PBS | 100 |
| 1166926 | 14 |
| 1166927 | 15 |
| 1166928 | 13 |
| 1166929 | 15 |
| 1166982 | 11 |
| 1167007 | 44 |
| 1167011 | 21 |
| 1167012 | 23 |
| 1167017 | 8 |
| 1167018 | 11 |
| 1174029 | 32 |
| 1174030 | 75 |
| 1174031 | 35 |
| 1174034 | 17 |
| 1174050 | 10 |
| 1174051 | 15 |
| 1174053 | 22 |
| 1174054 | 40 |
| 1174056 | 7 |
| 1174058 | 14 |
| 1174059 | 14 |
| 1174060 | 19 |
| 1174061 | 17 |
| 1174062 | 12 |
| 1174063 | 12 |

TABLE 94

| Reduction of human GFAP RNA in transgenic mice | |
|---|---|
| Compound No. | GFAP RNA (% control) CORTEX |
| PBS | 100 |
| 1166852 | 15 |
| 1166940 | 16 |
| 1166946 | 34 |
| 1166948 | 41 |
| 1166954 | 16 |
| 1167033 | 9 |
| 1167034 | 11 |
| 1167035 | 15 |
| 1167036 | 19 |
| 1167037 | 25 |
| 1167040 | 15 |

TABLE 95

| Reduction of human GFAP RNA in transgenic mice | |
|---|---|
| Compound No. | GFAP RNA (% control) CORTEX |
| PBS | 100 |
| 1167046 | 14 |
| 1167058 | 5 |
| 1174065 | 10 |
| 1174066 | 13 |
| 1199982 | 4 |
| 1199983 | 13 |
| 1199984 | 16 |

Example 8: Tolerability of Modified Oligonucleotides Complementary to Human GFAP in Rats, 3 mg Dose Modified oligonucleotides described above were tested in rats to assess the tolerability of the oligonucleotides. Sprague Dawley rats each received a single intrathecal (IT) dose of 3 mg of oligonucleotide listed in the table below. Each treatment group consisted of 24 rats. A group of 24 rats received PBS as a negative control. At 3 hours post-injection, movement in 7 different parts of the body were evaluated for each rat. The 7 body parts are (1) the rat's tail: (2) the rat's posterior posture; (3) the rat's hind limbs: (4) the rat's hind paws: (5) the rat's forepaws: (6) the rat's anterior posture; (7) the rat's head. For each of the 7 different body parts, each rat was given a sub-score of 0 if the body part was moving or 1 if the body part was paralyzed (the functional observational battery score or FOB). After each of the 7 body parts were evaluated, the sub-scores were summed for each rat and then averaged for each group. For example, if a rat's tail, head, and all other evaluated body parts were moving 3 hours after the 3 mg IT dose, it would get a summed score of 0. If another rat was not moving its tail 3 hours after the 3 mg IT dose but all other evaluated body parts were moving, it would receive a score of 1. Results are presented as the average score for each treatment group.

TABLE 96

| Tolerability scores in rats at 3 mg dose | |
|---|---|
| Compound No. | FOB 3 hr |
| PBS | 0 |
| 1047198 | 4 |
| 1047362 | 3 |
| 1047386 | 5 |
| 1047580 | 2 |
| 1047583 | 1 |
| 1047584 | 2 |
| 1047585 | 0 |
| 1047586 | 0 |
| 1047587 | 0 |
| 1047589 | 2 |
| 1047590 | 2 |
| 1047591 | 4 |
| 1048350 | 3 |

TABLE 97

| Tolerability scores in rats at 3 mg dose | |
|---|---|
| Compound No. | FOB 3 hr |
| PBS | 0 |
| 1047429 | 2 |
| 1047448 | 1 |
| 1047500 | 3 |
| 1047581 | 2 |
| 1047599 | 2 |
| 1047609 | 5 |
| 1047913 | 4 |
| 1048027 | 3 |
| 1048151 | 2 |

TABLE 98

| Tolerability scores in rats at 3 mg dose | |
|---|---|
| Compound No. | FOB 3 hr |
| PBS | 0 |
| 1047316 | 4 |
| 1047402 | 3 |
| 1047522 | 0 |
| 1047532 | 3 |
| 1047579 | 4 |
| 1048201 | 2 |
| 1048204 | 0 |

TABLE 99

| Tolerability scores in rats at 3 mg dose | |
|---|---|
| Compound No. | FOB 3 hr |
| PBS | 0 |
| 1047298 | 3 |
| 1072813 | 0 |
| 1072814 | 4 |
| 1072855 | 4 |
| 1072857 | 4 |
| 1104116 | 0 |
| 1104145 | 2 |
| 1104175 | 4 |
| 1166721 | 0 |
| 1166750 | 4 |
| 1166751 | 4 |
| 1166871 | 2 |

TABLE 100

| Tolerability scores in rats at 3 mg dose | |
|---|---|
| Compound No. | FOB 3 hr |
| PBS | 0 |
| 1166720 | 1 |
| 1166775 | 2 |
| 1166778 | 2 |
| 1166780 | 2 |
| 1166781 | 1 |
| 1166782 | 1 |
| 1166783 | 1 |
| 1166819 | 2 |
| 1166820 | 3 |
| 1166821 | 3 |
| 1166842 | 4 |
| 1166869 | 2 |
| 1166872 | 2 |
| 1166873 | 0 |
| 1166874 | 0 |

TABLE 101

| Tolerability scores in rats at 3 mg dose | |
|---|---|
| Compound No. | FOB 3 hr |
| PBS | 0 |
| 1166748 | 0 |
| 1166785 | 2 |
| 1166793 | 1 |
| 1166805 | 1 |
| 1166806 | 2 |
| 1166807 | 0 |
| 1166910 | 3 |
| 1166911 | 2 |
| 1166912 | 3 |
| 1166933 | 3 |
| 1166998 | 2 |
| 1167050 | 4 |
| 1167053 | 3 |
| 1167055 | 2 |
| 1167056 | 1 |

TABLE 102

| Tolerability scores in rats at 3 mg dose | |
|---|---|
| Compound No. | FOB 3 hr |
| PBS | 0 |
| 1166808 | 0 |
| 1166867 | 1 |

TABLE 102-continued

| Tolerability scores in rats at 3 mg dose | |
|---|---|
| Compound No. | FOB 3 hr |
| 1166877 | 2 |
| 1166878 | 3 |
| 1166894 | 1 |
| 1166895 | 0 |
| 1166896 | 2 |
| 1166897 | 2 |
| 1166898 | 0 |
| 1166899 | 0 |
| 1166985 | 0 |
| 1166990 | 0 |

TABLE 103

| Tolerability scores in rats at 3 mg dose | |
|---|---|
| Compound No. | FOB 3 hr |
| PBS | 0 |
| 1166759 | 2 |
| 1166760 | 2 |
| 1166800 | 3 |
| 1166823 | 4 |
| 1166831 | 5 |
| 1166875 | 1 |
| 1166920 | 3 |
| 1166926 | 2 |
| 1166927 | 2 |
| 1166928 | 2 |
| 1166982 | 3 |
| 1166986 | 1 |
| 1166987 | 1 |
| 1166988 | 5 |
| 1166989 | 1 |
| 1167001 | 3 |

TABLE 104

| Tolerability scores in rats at 3 mg dose | |
|---|---|
| Compound No. | FOB 3 hr |
| PBS | 0 |
| 1167002 | 2 |
| 1167003 | 3 |
| 1167017 | 3 |
| 1167018 | 3 |
| 1167057 | 1 |
| 1167059 | 2 |
| 1167060 | 2 |
| 1174012 | 3 |
| 1174018 | 3 |
| 1174026 | 2 |
| 1174034 | 3 |
| 1174059 | 1 |
| 1174060 | 1 |
| 1174061 | 4 |

TABLE 105

| Tolerability scores in rats at 3 mg dose | |
|---|---|
| Compound No. | FOB 3 hr |
| PBS | 0 |
| 1166852 | 3 |
| 1166940 | 2 |
| 1166946 | 2 |
| 1166948 | 3 |
| 1166954 | 2 |

TABLE 106

| Tolerability scores in rats at 3 mg dose | |
|---|---|
| Compound No. | FOB 3 hr |
| PBS | 0 |
| 1167033 | 4 |
| 1167034 | 3 |
| 1167035 | 3 |
| 1167036 | 2 |
| 1167037 | 2 |
| 1167040 | 3 |
| 1167046 | 3 |
| 1167058 | 2 |

TABLE 107

| Tolerability scores in rats at 3 mg dose | |
|---|---|
| Compound No. | FOB 3 hr |
| PBS | 0 |
| 1174065 | 1 |
| 1174066 | 2 |
| 1199982 | 1 |
| 1199983 | 1 |
| 1199984 | 2 |

Example 9: Potency of Modified Oligonucleotides Complementary to Human GFAP in Transgenic Mice Modified oligonucleotides described above were tested in human GFAP transgenic mouse model. Transgenic mice (line 73.7) was previously described in Messing A., et al., Fatal encephalopathy with astrocyte inclusions in GFAP transgenic mice, Am J Pathos, 1998, 152(2):391-398.

Treatment

The GFAP transgenic mice were divided into groups of 4 mice each. Each mouse received a single ICV bolus of modified oligonucleotide at the doses indicated in tables below. A group of 4-8 mice received PBS as a negative control.

RNA Analysis

Two weeks post treatment, mice were sacrificed, and RNA was extracted from the cortex, spinal cord, and brainstem for RTPCR analysis of RNA expression of GFAP using primer probe set RTS38621, described in Example 6 above. Results are presented as percent change of RNA, relative to PBS control, normalized to mouse PPIA. The half maximal effective dose ($ED_{50}$) of each modified oligonucleotide was calculated using GraphPad Prism 6 software (GraphPad Software, San Diego. CA). $ED_{50}$ values were calculated from dose and individual animal GFAP mRNA levels using custom equation Motulsky: Agonist vs response—Variable slope (four parameters) Y=Bottom+(Top−Bottom)/(1+(10^log EC50/X)^HillSlope), with the following constraints: bottom>lowest value in data set in order to compare across ASOs (3, 5, and 3 for cortex, spinal cord, and brainstem, respectively), top=100, HillSlope<−1 and >−2.

As shown in the table below, treatment with modified oligonucleotides resulted in dose-responsive reduction of GFAP RNA in comparison to the PBS control.

TABLE 108

Reduction of human GFAP RNA (all isoforms) in transgenic mice

| Compound No. | Dose (μg) | GFAP RNA (% control) CORTEX | $ED_{50}$ (μg) |
|---|---|---|---|
| PBS | N/A | 100 | N/A |
| 1104145 | 1 | 77 | 8 |
| | 3 | 74 | |
| | 10 | 53 | |
| | 30 | 19 | |
| | 100 | 8 | |

TABLE 109

Reduction of human GFAP RNA (all isoforms) in transgenic mice

| | | GFAP RNA (% control) | | | $ED_{50}$ (μg) | | |
|---|---|---|---|---|---|---|---|
| Compound No. | Dose (μg) | CORTEX | SPINAL CORD | BRAIN STEM | CORTEX | SPINAL CORD | BRAIN STEM |
| PBS | N/A | 100 | 100 | 100 | N/A | N/A | N/A |
| 1072813 | 3 | 93 | 101 | 99 | 34 | 24 | 21 |
| | 10 | 68 | 71 | 69 | | | |
| | 30 | 70 | 38 | 37 | | | |
| | 100 | 18 | 28 | 21 | | | |
| | 300 | 10 | 19 | 13 | | | |
| 1166721 | 1 | 116 | 111 | 94 | 25 | 25 | 12 |
| | 3 | 95 | 104 | 89 | | | |
| | 10 | 91 | 73 | 51 | | | |
| | 30 | 39 | 47 | 28 | | | |
| | 100 | 13 | 18 | 11 | | | |
| | 300 | 7 | 10 | 6 | | | |
| 1166874 | 1 | 81 | 102 | 78 | 27 | 11 | 7 |
| | 3 | 73 | 83 | 75 | | | |
| | 10 | 77 | 50 | 45 | | | |
| | 30 | 65 | 32 | 22 | | | |
| | 100 | 12 | 14 | 10 | | | |
| | 300 | 5 | 9 | 6 | | | |
| 1166895 | 3 | 108 | 93 | 93 | 41 | 93 | 38 |
| | 10 | 82 | 94 | 80 | | | |
| | 30 | 46 | 74 | 50 | | | |
| | 100 | 40 | 40 | 32 | | | |

TABLE 110

Reduction of human GFAP RNA (all isoforms) in transgenic mice

| | | GFAP RNA (% control) | | | ED50 (μg) | | |
|---|---|---|---|---|---|---|---|
| Compound No. | Dose (μg) | CORTEX | SPINAL CORD | BRAIN STEM | CORTEX | SPINAL CORD | BRAIN STEM |
| PBS | N/A | 100 | 100 | 100 | N/A | N/A | N/A |
| 1166895 | 300 | 16 | 45 | 27 | N/A | N/A | N/A |
| 1166926 | 3 | 103 | 77 | 77 | 47 | 32 | 17 |
| | 10 | 86 | 70 | 57 | | | |
| | 30 | 67 | 62 | 49 | | | |
| | 100 | 27 | 27 | 20 | | | |
| | 300 | 13 | 21 | 11 | | | |

TABLE 110-continued

Reduction of human GFAP RNA (all isoforms) in transgenic mice

| Compound No. | Dose (μg) | GFAP RNA (% control) CORTEX | GFAP RNA (% control) SPINAL CORD | GFAP RNA (% control) BRAIN STEM | ED50 (μg) CORTEX | ED50 (μg) SPINAL CORD | ED50 (μg) BRAIN STEM |
|---|---|---|---|---|---|---|---|
| 1166985 | 1 | 105 | 101 | 100 | 46 | 36 | 14 |
| | 3 | 96 | 90 | 78 | | | |
| | 10 | 75 | 68 | 53 | | | |
| | 30 | 79 | 58 | 40 | | | |
| | 100 | 17 | 35 | 15 | | | |
| | 300 | 8 | 23 | 10 | | | |
| 1167056 | 1 | 102 | 87 | 86 | 10 | 5 | 3 |
| | 3 | 81 | 60 | 42 | | | |
| | 10 | 54 | 35 | 20 | | | |
| | 30 | 20 | 16 | 9 | | | |
| | 100 | 5 | 8 | 5 | | | |
| | 300 | 3 | 7 | 4 | | | |
| 1167058 | 1 | 98 | 82 | 80 | 19 | 4 | 3 |
| | 3 | 79 | 59 | 44 | | | |
| | 10 | 79 | 21 | 20 | | | |

TABLE 111

Reduction of human GFAP RNA (all isoforms) in transgenic mice

| Compound No. | Dose (μg) | GFAP RNA (% control) CORTEX | GFAP RNA (% control) SPINAL CORD | GFAP RNA (% control) BRAIN STEM | ED50 (μg) CORTEX | ED50 (μg) SPINAL CORD | ED50 (μg) BRAIN STEM |
|---|---|---|---|---|---|---|---|
| PBS | N/A | 100 | 100 | 100 | N/A | N/A | N/A |
| 1166927 | 3 | 91 | 92 | 89 | 44 | 24 | 15 |
| | 10 | 98 | 62 | 57 | | | |
| | 30 | 62 | 52 | 35 | | | |
| | 100 | 25 | 26 | 14 | | | |
| | 300 | 14 | 20 | 12 | | | |
| 1166954 | 3 | 106 | 87 | 85 | 58 | 60 | 26 |
| | 10 | 79 | 80 | 68 | | | |
| | 30 | 70 | 65 | 49 | | | |
| | 100 | 36 | 46 | 27 | | | |
| | 300 | 20 | 25 | 17 | | | |
| 1166986 | 3 | 114 | 113 | 101 | 35 | 42 | 21 |
| | 10 | 87 | 88 | 66 | | | |
| | 30 | 52 | 56 | 38 | | | |
| | 100 | 23 | 30 | 20 | | | |
| | 300 | 10 | 20 | 14 | | | |
| 1166998 | 3 | 77 | 73 | 61 | 23 | 13 | 6 |
| | 10 | 90 | 63 | 42 | | | |
| | 30 | 36 | 31 | 20 | | | |
| 1167058 | 30 | 34 | 14 | 9 | N/A | N/A | N/A |
| | 100 | 9 | 7 | 6 | | | |
| | 300 | 5 | 6 | 4 | | | |

TABLE 112

Reduction of human GFAP RNA (all isoforms) in transgenic mice

| Compound No. | Dose (μg) | GFAP RNA (% control) RTS38621 CORTEX | GFAP RNA (% control) RTS38621 SPINAL CORD | GFAP RNA (% control) RTS38621 BRAIN STEM | ED50 (μg) CORTEX | ED50 (μg) SPINAL CORD | ED50 (μg) BRAIN STEM |
|---|---|---|---|---|---|---|---|
| PBS | | 100 | 100 | 100 | N/A | N/A | N/A |
| 1166998 | 100 | 11 | 18 | 17 | N/A | N/A | N/A |
| | 300 | 7 | 12 | 9 | N/A | N/A | N/A |

TABLE 112-continued

Reduction of human GFAP RNA (all isoforms) in transgenic mice

| Compound No. | Dose (μg) | GFAP RNA (% control) RTS38621 CORTEX | SPINAL CORD | BRAIN STEM | ED50 (μg) CORTEX | SPINAL CORD | BRAIN STEM |
|---|---|---|---|---|---|---|---|
| 1199983 | 3 | 75 | 83 | 71 | | | |
| | 10 | 72 | 57 | 62 | 18 | | 15 |
| | 30 | 37 | 38 | 38 | | 16 | |
| | 100 | 17 | 27 | 22 | | | |
| | 300 | 12 | 22 | 17 | | | |

Example 10: Effect of Modified Oligonucleotides on Human GFAP RNA In Vitro, Multiple Doses Modified oligonucleotides selected from the examples above were tested at various doses in U251 cells. Cultured U251 cells at a density of 30,000 cells per well were treated with electroporation with various concentrations of modified oligonucleotide as specified in the tables below. After a treatment period of approximately 24 hours, total RNA was isolated from the cells and GFAP RNA levels were measured by quantitative real-time RTPCR. Human GFAP primer probe sets RTS38621 (described herein above), RTS38024 (forward sequence AACCGGATCACCATCCC, designated herein as SEQ ID NO:2892: reverse sequence CCTTGT-GATTTTCCCCGTCT, designated herein as SEQ ID NO: 1064; probe sequence TGCTTTTGCCCCCTCGAATCTG, designated herein as SEQ ID) NO: 2894), and RTS38622 (forward sequence AACCGGATCACCATTCCC, designated herein as SEQ ID NO: 2892; reverse sequence GTCTTCACCACGATGTCCTC, designated herein as SEQ ID NO: 2896; probe sequence CAC-CAAGTCTGTGTCAGAAGGCCA, designated herein as SEQ ID NO: 2897) were used to measure RNA levels. GFAP RNA levels were normalized to total GAPDH, as measured by human primer probe set RTS104 (forward sequence GAAGGTGAAGGTCGGAGTC, designated herein as SEQ ID NO: 2898; reverse sequence GAAGATGGTGATGG-GATTTC, designated herein as SEQ ID NO: 2899; probe sequence CAAGCTTCCCGTCTCAGCC, designated herein as SEQ ID NO: 2900). Results are presented as percent of GFAP RNA, relative to untreated control cells (% UTC). The half maximal inhibitory concentration ($IC_{50}$) of each modified oligonucleotide was calculated using a linear regression on a log/linear plot of the data in Excel.

TABLE 113

Dose-dependent reduction of human GFAP RNA in U251 cells by modified oligonucleotides

| Compound No. | GFAP RNA (% UTC) RTS38621 123 nM | 370 nM | 1100 nM | 3300 nM | 10000 nM | $IC_{50}$ (μM) |
|---|---|---|---|---|---|---|
| 1072813 | 111 | 77 | 62 | 28 | 16 | 1.6 |
| 1166721 | 81 | 63 | 30 | 19 | 15 | 0.6 |
| 1166874 | 86 | 62 | 34 | 15 | 15 | 0.6 |

TABLE 113-continued

Dose-dependent reduction of human GFAP RNA in U251 cells by modified oligonucleotides

| Compound No. | GFAP RNA (% UTC) RTS38621 123 nM | 370 nM | 1100 nM | 3300 nM | 10000 nM | $IC_{50}$ (μM) |
|---|---|---|---|---|---|---|
| 1166895 | 91 | 94 | 68 | 40 | 21 | 2.5 |
| 1166954 | 69 | 52 | 35 | 14 | 12 | 0.4 |
| 1047582 | 54 | 26 | 13 | 6 | 5 | 0.1 |

TABLE 114

Dose-dependent reduction of human GFAP RNA in U251 cells by modified oligonucleotides

| Compound No. | GFAP RNA (% UTC) RTS38622 123 nM | 370 nM | 1100 nM | 3300 nM | 10000 nM | $IC_{50}$ (μM) |
|---|---|---|---|---|---|---|
| 1072813 | 84 | 70 | 34 | 20 | 9 | 0.7 |
| 1166721 | 78 | 47 | 27 | 15 | 11 | 0.4 |
| 1166874 | 80 | 49 | 27 | 9 | 7 | 0.4 |
| 1166895 | 89 | 83 | 62 | 35 | 17 | 1.8 |
| 1166954 | 68 | 50 | 27 | 9 | 5 | 0.3 |
| 1047582 | 51 | 24 | 10 | 3 | 1 | 0.1 |

TABLE 115

Dose-dependent reduction of human GFAP RNA in U251 cells by modified oligonucleotides

| Compound No. | GFAP RNA (% UTC) RTS38624 123 nM | 370 nM | 1100 nM | 3300 nM | 10000 nM | $IC_{50}$ (μM) |
|---|---|---|---|---|---|---|
| 1072813 | 98 | 86 | 78 | 61 | 54 | 10.6 |
| 1166721 | 87 | 66 | 43 | 28 | 21 | 1.0 |

TABLE 115-continued

Dose-dependent reduction of human GFAP RNA in U251 cells by modified oligonucleotides

| Compound No. | GFAP RNA (% UTC) RTS38624 123 nM | 370 nM | 1100 nM | 3300 nM | 10000 nM | $IC_{50}$ (μM) |
|---|---|---|---|---|---|---|
| 1166874 | 70 | 90 | 57 | 50 | 54 | 9.0 |
| 1166895 | 88 | 90 | 71 | 52 | 34 | 4.0 |
| 1166954 | 77 | 69 | 67 | 53 | 50 | 6.9 |
| 1047582 | 68 | 56 | 47 | 41 | 43 | 1.2 |

TABLE 116

Dose-dependent reduction of human GFAP RNA in U251 cells by modified oligonucleotides

| Compound No. | GFAP RNA (% UTC) RTS38621 123 nM | 370 nM | 1100 nM | 3300 nM | 10000 nM | $IC_{50}$ (μM) |
|---|---|---|---|---|---|---|
| 1166985 | 88 | 79 | 49 | 33 | 18 | 1.3 |
| 1166986 | 82 | 71 | 55 | 31 | 23 | 1.3 |
| 1166998 | 74 | 97 | 37 | 23 | 15 | 1.1 |
| 1167056 | 64 | 38 | 23 | 12 | 10 | 0.2 |
| 1199983 | 70 | 53 | 37 | 17 | 10 | 0.4 |
| 1048182 | 69 | 53 | 30 | 15 | 10 | 0.4 |

TABLE 117

Dose-dependent reduction of human GFAP RNA in U251 cells by modified oligonucleotides

| Compound No. | GFAP RNA (% UTC) RTS38622 123 nM | 370 nM | 1100 nM | 3300 nM | 10000 nM | $IC_{50}$ (μM) |
|---|---|---|---|---|---|---|
| 1166985 | 79 | 71 | 44 | 28 | 16 | 0.9 |
| 1166986 | 83 | 68 | 53 | 30 | 23 | 1.2 |
| 1166998 | 72 | 94 | 37 | 23 | 15 | 1.0 |
| 1167056 | 64 | 38 | 21 | 9 | 6 | 0.2 |
| 1199983 | 72 | 62 | 40 | 18 | 11 | 0.6 |
| 1048182 | 79 | 50 | 36 | 19 | 13 | 0.5 |

TABLE 118

Dose-dependent reduction of human GFAP RNA in U251 cells by modified oligonucleotides

| Compound No. | GFAP RNA (% UTC) RTS38624 123 nM | 370 nM | 1100 nM | 3300 nM | 10000 nM | $IC_{50}$ (μM) |
|---|---|---|---|---|---|---|
| 1166985 | 80 | 75 | 54 | 44 | 25 | 1.8 |
| 1166986 | 86 | 73 | 65 | 43 | 31 | 2.5 |

TABLE 118-continued

Dose-dependent reduction of human GFAP RNA in U251 cells by modified oligonucleotides

| Compound No. | GFAP RNA (% UTC) RTS38624 123 nM | 370 nM | 1100 nM | 3300 nM | 10000 nM | $IC_{50}$ (μM) |
|---|---|---|---|---|---|---|
| 1166998 | 76 | 111 | 53 | 32 | 17 | 1.8 |
| 1167056 | 80 | 72 | 62 | 53 | 55 | 10.6 |
| 1199983 | 77 | 65 | 52 | 31 | 20 | 1.0 |
| 1048182 | 92 | 69 | 52 | 33 | 20 | 1.3 |

Example 11: Effect of Modified Oligonucleotides on Human GFAP RNA Vitro, Multiple Doses Modified oligonucleotides selected from the examples above were tested at various doses in U251 cells. Cultured U251 cells at a density of 20,000 cells per well were treated using free uptake with various concentrations of modified oligonucleotide as specified in the tables below. After a treatment period of approximately 48 hours, total RNA was isolated from the cells and GFAP RNA levels were measured by quantitative real-time RTPCR. Human GFAP primer probe sets RTS37485 (described herein above) was used to measure RNA levels. GFAP RNA levels were normalized to total GAPDH, as measured by human primer probe set RTS104 (described herein above). Results are presented as percent of GFAP RNA, relative to untreated control cells (% UTC). The half maximal inhibitory concentration ($IC_{50}$) of each modified oligonucleotide was calculated using a linear regression on a log/linear plot of the data in Excel.

TABLE 113

Dose-dependent reduction of human GFAP RNA in U251 cells by modified oligonucleotides

| Compound No. | GFAP RNA (% UTC) RTS37485 250 nM | 740 nM | 2220 nM | 6670 nM | 20000 nM | $IC_{50}$ (μM) |
|---|---|---|---|---|---|---|
| 1072813 | 105 | 102 | 80 | 59 | 34 | 10 |
| 1166721 | 92 | 83 | 64 | 49 | 32 | 7 |
| 1166874 | 81 | 78 | 55 | 38 | 22 | 4 |
| 1166895 | 83 | 89 | 85 | 78 | 73 | 950 |
| 1166926 | 97 | 93 | 79 | 73 | 58 | 31 |
| 1166927 | 89 | 86 | 78 | 76 | 52 | 28 |
| 1166954 | 92 | 90 | 77 | 67 | 58 | 29 |
| 1166985 | 104 | 108 | 104 | 94 | 80 | 43 |
| 1166986 | 94 | 92 | 95 | 84 | 82 | 1063 |
| 1166998 | 91 | 91 | 77 | 59 | 42 | 12 |
| 1167056 | 77 | 55 | 32 | 17 | 12 | 1 |
| 1167058 | 85 | 59 | 41 | 18 | 15 | 1 |
| 1199983 | 94 | 88 | 73 | 62 | 49 | 17 |

SEQUENCE LISTING

The patent contains a lengthy sequence listing. A copy of the sequence listing is available in electronic form from the USPTO web site (https://seqdata.uspto.gov/docdetail?docId=US12502402B2). An electronic copy of the sequence listing will also be available from the USPTO upon request and payment of the fee set forth in 37 CFR 1.19(b)(3).

The invention claimed is:

1. A modified oligonucleotide according to the following chemical structure:

(SEQ ID NO: 21)

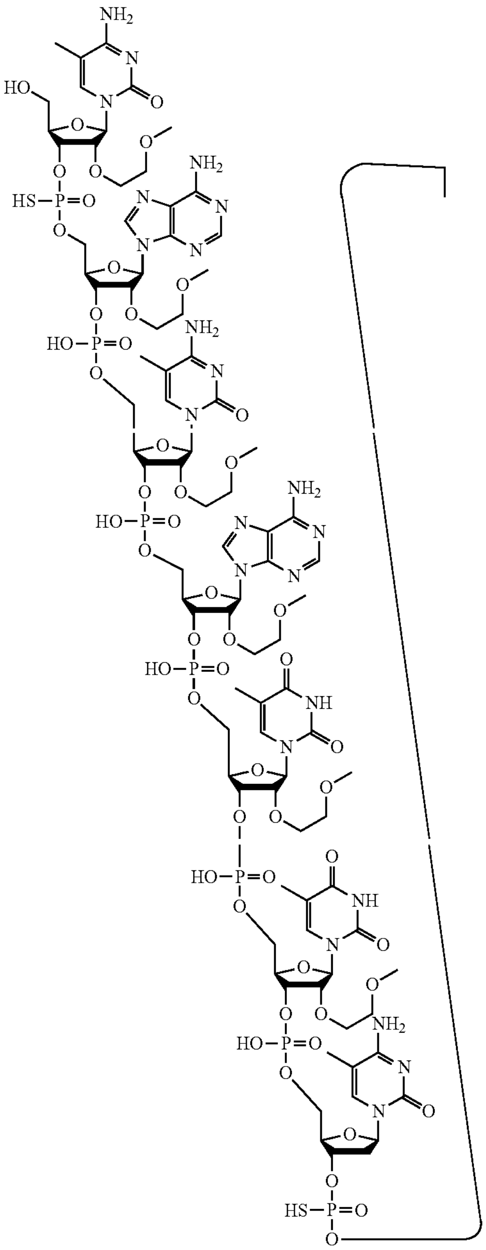

-continued

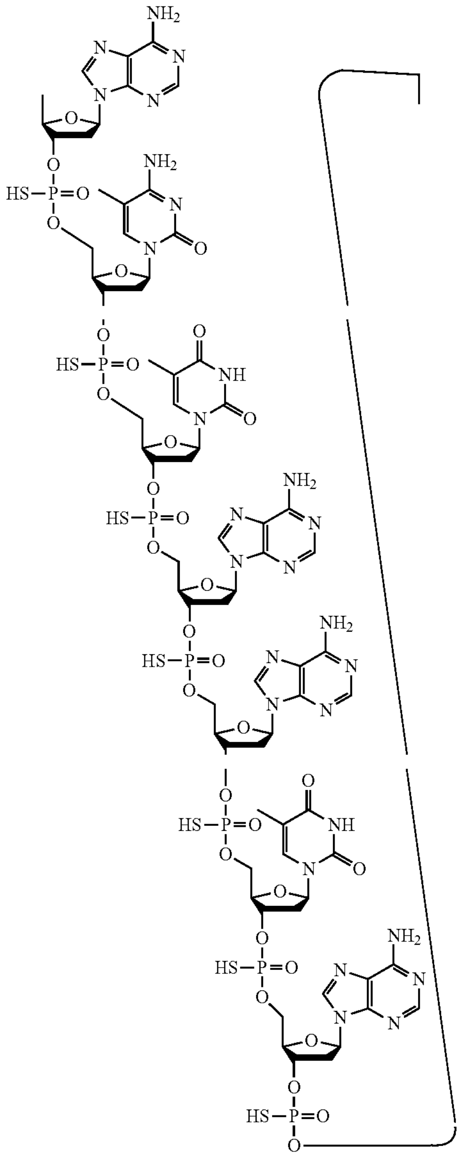

-continued
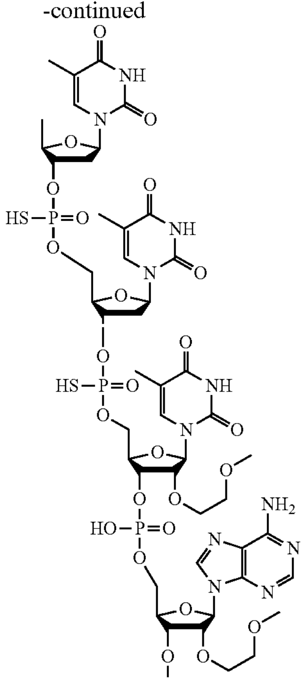
-continued
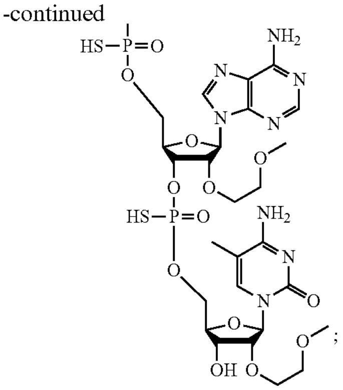
or a salt thereof.
2. A modified oligonucleotide according to the following chemical structure:
(SEQ ID NO: 21)
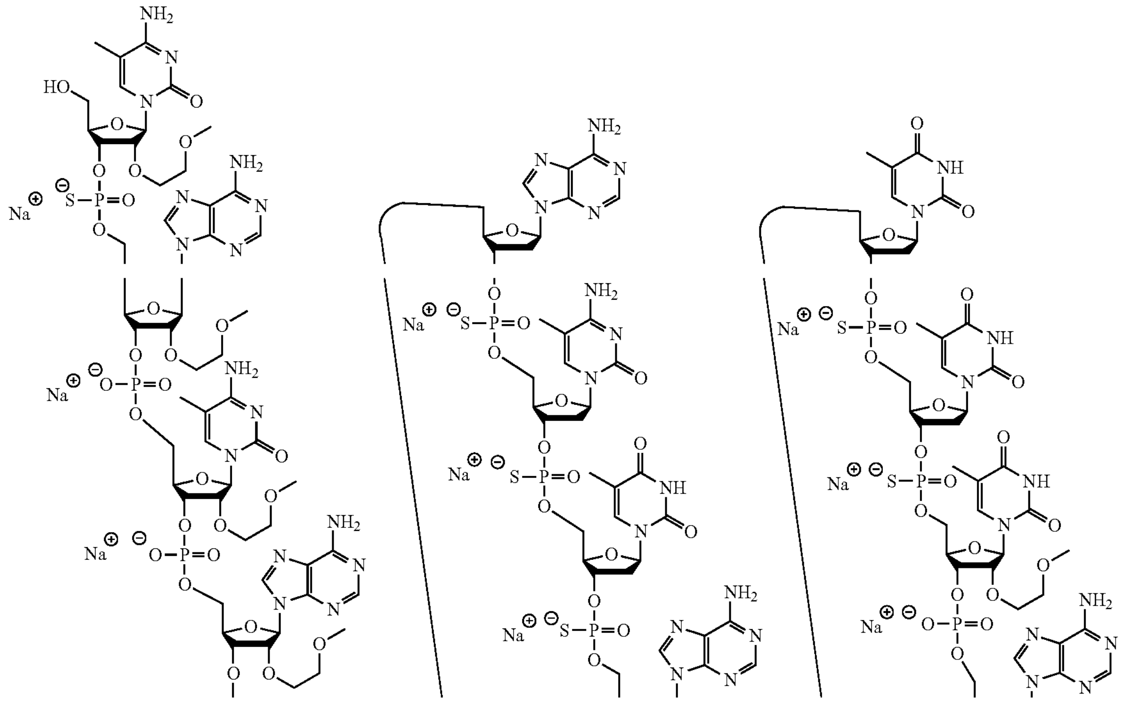

-continued

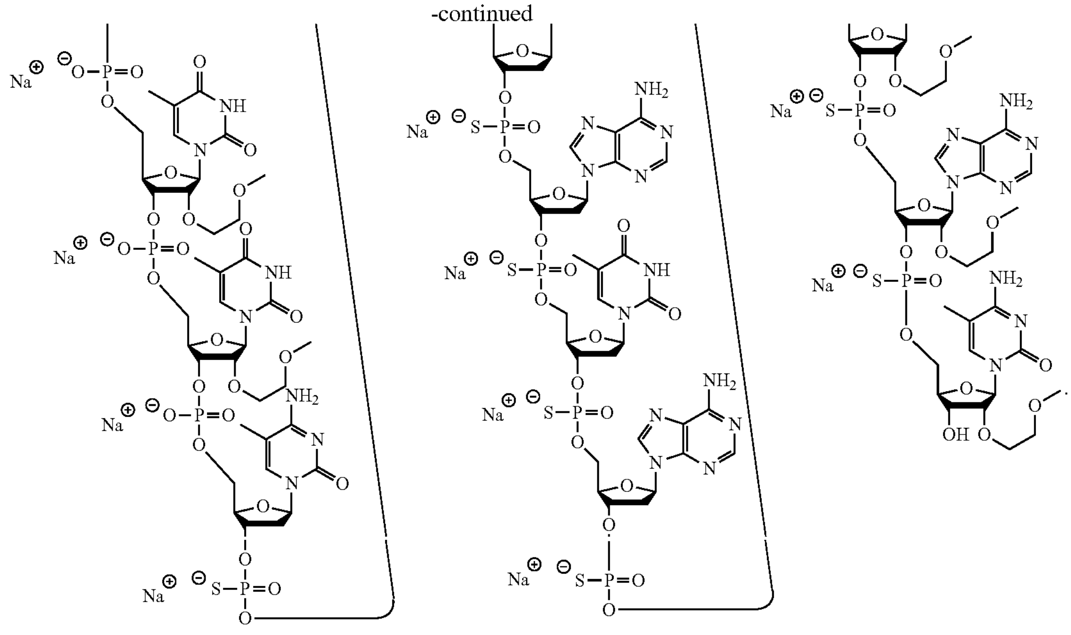

3. The modified oligonucleotide of claim 1, which is the sodium salt or the potassium salt.

4. A pharmaceutical composition comprising the modified oligonucleotide of claim 1 and a pharmaceutically acceptable diluent.

5. The pharmaceutical composition of claim 4, wherein the pharmaceutically acceptable diluent is artificial cerebrospinal fluid or phosphate-buffered saline (PBS).

6. The pharmaceutical composition of claim 5, wherein the pharmaceutical composition consists of the modified oligonucleotide and artificial cerebrospinal fluid.

7. An oligomeric compound comprising a modified oligonucleotide according to the following chemical notation:

${}^{m}C_{es}A_{eo}{}^{m}C_{eo}A_{eo}T_{eo}T_{eo}{}^{m}C_{ds}A_{ds}{}^{m}C_{ds}T_{ds}A_{ds}A_{ds}T_{ds}A_{ds}T_{ds}T_{ds}T_{eo}A_{es}A_{es}{}^{m}C_{e}$ (SEQ ID NO: 21), wherein:

A=an adenine nucleobase, ${}^{m}C$=a 5-methylcytosine nucleobase,

G=a guanine nucleobase,

T=a thymine nucleobase, e=a 2'-MOE sugar moiety, d=a 2'-deoxyribosyl sugar moiety, s=a phosphorothioate internucleoside linkage, and o=a phosphodiester internucleoside linkage.

8. The oligomeric compound of claim 7, comprising the modified oligonucleotide covalently linked to a conjugate group.

9. A pharmaceutical composition comprising the oligomeric compound of claim 7, and a pharmaceutically acceptable diluent.

10. The pharmaceutical composition of claim 9, wherein the pharmaceutically acceptable diluent is artificial cerebrospinal fluid or PBS.

11. The pharmaceutical composition of claim 10, wherein the pharmaceutical composition consists of the oligomeric compound and artificial cerebrospinal fluid.

12. A method comprising administering to an individual the pharmaceutical composition of claim 4.

13. A method of treating Alexander disease, comprising administering to an individual having or at risk of having Alexander disease a therapeutically effective amount of the pharmaceutical composition according to claim 4, thereby treating Alexander disease.

14. The method of claim 13, wherein at least one symptom or hallmark of Alexander disease is ameliorated.

15. The method of claim 14, wherein at least one symptom or hallmark is any of motor delays, cognitive delays, paroxysmal deterioration, seizures, vomiting, swallowing difficulties, ataxic gait, palatal myoclonus, autonomic dysfunction, or the presence of intra-astrocytic inclusions called Rosenthal fibers.

16. The method of claim 13, wherein the pharmaceutical composition is administered to the central nervous system or systemically.

17. The method of claim 13, wherein the pharmaceutical composition is administered to the central nervous system and systemically.

18. The pharmaceutical composition of claim 5, wherein the pharmaceutical composition consists essentially of the modified oligonucleotide and artificial cerebrospinal fluid.

19. The pharmaceutical composition of claim 10, wherein the pharmaceutical composition consists essentially of the oligomeric compound and artificial cerebrospinal fluid.

20. The pharmaceutical composition of claim 5, wherein the pharmaceutical composition consists essentially of the modified oligonucleotide and PBS.

21. The pharmaceutical composition of claim 10, wherein the pharmaceutical composition consists essentially of the oligomeric compound and PBS.

22. A pharmaceutical composition comprising the modified oligonucleotide of claim 2 and a pharmaceutically acceptable diluent.

23. The pharmaceutical composition of claim 22, wherein the pharmaceutically acceptable diluent is artificial cerebrospinal fluid or PBS.

24. The pharmaceutical composition of claim 23, wherein the pharmaceutical composition consists essentially of the modified oligonucleotide and artificial cerebrospinal fluid.

25. The pharmaceutical composition of claim 23, wherein the pharmaceutical composition consists essentially of the modified oligonucleotide and PBS.

26. A pharmaceutical composition comprising the modified oligonucleotide of claim 3 and a pharmaceutically acceptable diluent.

27. The pharmaceutical composition of claim 26, wherein the pharmaceutically acceptable diluent is artificial cerebrospinal fluid or PBS.

28. The pharmaceutical composition of claim 27, wherein the pharmaceutical composition consists essentially of the modified oligonucleotide and artificial cerebrospinal fluid.

29. The pharmaceutical composition of claim 27, wherein the pharmaceutical composition consists essentially of the modified oligonucleotide and PBS.

30. A population of modified oligonucleotides of claim 1, wherein all of the phosphorothioate internucleoside linkages of the modified oligonucleotide are stereorandom.

31. A population of modified oligonucleotides of claim 2, wherein all of the phosphorothioate internucleoside linkages of the modified oligonucleotide are stereorandom.

32. A population of modified oligonucleotides of claim 3, wherein all of the phosphorothioate internucleoside linkages of the modified oligonucleotide are stereorandom.

33. A population of oligomeric compounds of claim 7, wherein all of the phosphorothioate internucleoside linkages of the modified oligonucleotide are stereorandom.

34. A pharmaceutical composition comprising the population of modified oligonucleotides of claim 30 and a pharmaceutically acceptable diluent.

35. The pharmaceutical composition of claim 34, wherein the pharmaceutically acceptable diluent is artificial cerebrospinal fluid or PBS.

36. A pharmaceutical composition comprising the population of modified oligonucleotides of claim 31 and a pharmaceutically acceptable diluent.

37. The pharmaceutical composition of claim 36, wherein the pharmaceutically acceptable diluent is artificial cerebrospinal fluid or PBS.

38. A pharmaceutical composition comprising the population of modified oligonucleotides of claim 32 and a pharmaceutically acceptable diluent.

39. The pharmaceutical composition of claim 38, wherein the pharmaceutically acceptable diluent is artificial cerebrospinal fluid or PBS.

40. A pharmaceutical composition comprising the population of oligomeric compounds of claim 33 and a pharmaceutically acceptable diluent.

41. The pharmaceutical composition of claim 40, wherein the pharmaceutically acceptable diluent is artificial cerebrospinal fluid or PBS.

42. The method of claim 12, wherein the individual has or is at risk of having Alexander disease.

* * * * *